US006941229B1

(12) United States Patent
Elleman et al.

(10) Patent No.: US 6,941,229 B1
(45) Date of Patent: Sep. 6, 2005

(54) METHOD OF DESIGNING AGONISTS AND ANTAGONISTS TO EGF RECEPTOR FAMILY

(75) Inventors: Thomas Charles Elleman, Westmeadows (AU); Vidanagamage Chandana Epa, Parkville (AU); Thomas Peter John Garrett, Brunswick (AU); Robert Nicholas Jorissen, Keysborough (AU); Meizhen Lou, Scoresby (AU); Antony Wilks Burgess, Camberwell (AU); Neil Moreton McKern, Lilydale (AU); Herbert Rudolf Treutlein, Moonee Ponds (AU); Colin Lesley Ward, Carlton (AU)

(73) Assignees: Commonwealth Scientific and Industrial Research Organization, Campbell (AU); Ludwig Institute for Cancer Research, Parkville (AU)

( * ) Notice: Subject to any disclaimer, the term of this patent is extended or adjusted under 35 U.S.C. 154(b) by 0 days.

(21) Appl. No.: 09/701,437

(22) PCT Filed: May 31, 1999

(86) PCT No.: PCT/AU99/00420

§ 371 (c)(1),
(2), (4) Date: Mar. 2, 2001

(87) PCT Pub. No.: WO99/62955

PCT Pub. Date: Dec. 9, 1999

(30) Foreign Application Priority Data

May 29, 1998 (AU) ........................................ PP3804

(51) Int. Cl.⁷ ........................ G06F 19/00; G01N 33/48; G01N 33/50; G01N 33/53
(52) U.S. Cl. ........................... 702/27; 702/19; 702/20; 435/7.2
(58) Field of Search ............................ 702/19, 22, 20, 702/27; 435/7.2

(56) References Cited

U.S. PATENT DOCUMENTS 5,705,335 A * 1/1998 Hendry ........................... 435/6
5,708,156 A 1/1998 Ilekis

FOREIGN PATENT DOCUMENTS

WO 94/25860 11/1994

OTHER PUBLICATIONS

Kuntz et al. "A Geometric Approach to Macromolecule-Ligand Interactions". J. Mol. Biol. (1982), vol. 161, pp. 269-288.*
Goodford, P.J. "A Computational Procedure for Determining Energetically Favorable Binding Sites on Biologically Important Macromolecules", J. Med. Chem. (1985), vol. 28, pp. 8489-8857.*
"Disulfide Bond Structure of Human Epidermal Growth Factor Receptor" by Abe et al., The Journal of Biological Chemistry, vol. 273, No. 18, May 1, 1998, pp. 11150-11157.
"Modelling the ATP-Binding Site of Oncogene Products, the Epidermal Growth Factor Receptor and Related Proteins" by Sternberg et al., FEBS, vol. 175, No. 2, Oct. 1984, pp. 387-392.
"Design of a Potent Peptide Inhibitor of the Epidermal Growth Factor Receptor Tyrosine Kinase Utilizing Sequences Based on the Natural Phosphorylation Sites of Phospholipase C-γ1" by Fry et al., pp. 951-957.
"Crystal Structure of the First Three Domains of the Type-1 Insulin-Like Growth Factor Receptor" by Garrett et al., Nature, vol. 394, Jul. 23, 1998, pp. 395-399.
Singh, Juswinder., et al. "Structure-Based Design of a Patent, Selective and Irreversible Inhibitor of the Catalytic Domain of the erbB Receptor Subfamily of Protein Tyrosine Kinases," Journal of Medicinal Chemistry, American Chemical Society, vol. 40, Mar. 28, 1997, pp. 1130-1135, XP002107337.
Garrett. Thomas P., et al. "Crystal structure of the first three domains of the type-1 Insulin-like growth factor receptor," Nature (London) vol. 394, No. 6691, Jul. 23, 1998, pp. 395-399, XP002297751.
McInnes, Cambell., et al. "NMR study of the transforming growth factor-alpha (TGF-alpha)-epidermal growth factor receptor complex. Visualization of human TGF-alpha binding determinants through nuclear Overhauser enhancement analysis." Journal of Biological Chemistry, vol. 271, No. 50, 1996, pp. 32204-32211, XP002297752.
Sanchez, Roberto., et al. "Evaluation of Comparative Protein Structure Modeling by MODDELLER-3" Proteins, Structure, Function and Genetics, Suppl. Pp. 1:50-58 (1997.

* cited by examiner

Primary Examiner—Marianne P. Allen
(74) Attorney, Agent, or Firm—McDermott Will & Emery LLP

(57) ABSTRACT

The present invention relates to a method of designing compounds able to bind to a molecule of the EGF receptor family and to modulate the activity mediated by the receptor molecule based on the 3-D structure coordinates of the EGF receptor crystal of FIG. 6.

12 Claims, 72 Drawing Sheets

| | | | | | | | | |
|---|---|---|---|---|---|---|---|---|
| ATOM | 1 | N | LEU | 1 | 56.440 | 23.698 | 108.904 | 1.00 60.00 |
| ATOM | 2 | CA | LEU | 1 | 56.066 | 23.469 | 107.493 | 1.00 60.00 |
| ATOM | 3 | CB | LEU | 1 | 57.306 | 23.463 | 106.595 | 1.00 60.00 |
| ATOM | 4 | CG | LEU | 1 | 58.047 | 24.812 | 106.566 | 1.00 60.00 |
| ATOM | 5 | CD1 | LEU | 1 | 59.282 | 24.747 | 105.654 | 1.00 60.00 |
| ATOM | 6 | CD2 | LEU | 1 | 57.097 | 25.966 | 106.208 | 1.00 60.00 |
| ATOM | 7 | C | LEU | 1 | 55.390 | 22.146 | 107.356 | 1.00 60.00 |
| ATOM | 8 | O | LEU | 1 | 54.171 | 22.035 | 107.470 | 1.00 60.00 |
| ATOM | 9 | N | GLU | 2 | 56.187 | 21.094 | 107.106 | 1.00 60.00 |
| ATOM | 10 | CA | GLU | 2 | 55.622 | 19.787 | 106.953 | 1.00 60.00 |
| ATOM | 11 | CB | GLU | 2 | 56.660 | 19.710 | 106.649 | 1.00 60.00 |
| ATOM | 12 | CG | GLU | 2 | 57.348 | 18.881 | 105.282 | 1.00 60.00 |
| ATOM | 13 | CD | GLU | 2 | 58.367 | 17.763 | 105.104 | 1.00 60.00 |
| ATOM | 14 | OE1 | GLU | 2 | 57.942 | 16.580 | 105.009 | 1.00 60.00 |
| ATOM | 15 | OE2 | GLU | 2 | 59.587 | 18.080 | 105.070 | 1.00 60.00 |
| ATOM | 16 | C | GLU | 2 | 54.979 | 19.447 | 108.254 | 1.00 60.00 |
| ATOM | 17 | O | GLU | 2 | 53.886 | 18.886 | 108.286 | 1.00 60.00 |
| ATOM | 18 | N | GLU | 3 | 55.635 | 19.811 | 109.372 | 1.00 60.00 |
| ATOM | 19 | CA | GLU | 3 | 55.105 | 19.488 | 110.662 | 1.00 60.00 |
| ATOM | 20 | CB | GLU | 3 | 55.982 | 19.975 | 111.831 | 1.00 60.00 |
| ATOM | 21 | CG | GLU | 3 | 57.298 | 19.207 | 111.972 | 1.00 60.00 |
| ATOM | 22 | CD | GLU | 3 | 58.002 | 19.710 | 113.225 | 1.00 60.00 |
| ATOM | 23 | OE1 | GLU | 3 | 57.458 | 19.488 | 114.340 | 1.00 60.00 |
| ATOM | 24 | OE2 | GLU | 3 | 59.092 | 20.324 | 113.085 | 1.00 60.00 |
| ATOM | 25 | C | GLU | 3 | 53.771 | 20.141 | 110.800 | 1.00 60.00 |
| ATOM | 26 | O | GLU | 3 | 52.852 | 19.560 | 111.374 | 1.00 60.00 |
| ATOM | 27 | N | LYS | 4 | 53.621 | 21.372 | 110.272 | 1.00 60.00 |
| ATOM | 28 | CA | LYS | 4 | 52.367 | 22.054 | 110.404 | 1.00 60.00 |
| ATOM | 29 | CB | LYS | 4 | 52.277 | 23.392 | 109.653 | 1.00 60.00 |
| ATOM | 30 | CG | LYS | 4 | 53.156 | 24.512 | 110.204 | 1.00 60.00 |
| ATOM | 31 | CD | LYS | 4 | 53.178 | 25.733 | 109.282 | 1.00 60.00 |
| ATOM | 32 | CE | LYS | 4 | 53.874 | 26.957 | 109.876 | 1.00 60.00 |
| ATOM | 33 | NZ | LYS | 4 | 53.815 | 28.084 | 108.917 | 1.00 60.00 |
| ATOM | 34 | C | LYS | 4 | 51.302 | 21.193 | 109.810 | 1.00 60.00 |
| ATOM | 35 | O | LYS | 4 | 51.578 | 20.244 | 109.080 | 1.00 60.00 |
| ATOM | 36 | N | LYS | 5 | 50.037 | 21.508 | 110.135 | 1.00 40.00 |
| ATOM | 37 | CA | LYS | 5 | 48.966 | 20.748 | 109.575 | 1.00 40.00 |
| ATOM | 38 | CB | LYS | 5 | 47.573 | 21.255 | 109.989 | 1.00 40.00 |
| ATOM | 39 | CG | LYS | 5 | 47.148 | 20.806 | 111.384 | 1.00 40.00 |
| ATOM | 40 | CD | LYS | 5 | 47.058 | 19.284 | 111.511 | 1.00 40.00 |
| ATOM | 41 | CE | LYS | 5 | 46.562 | 18.804 | 112.874 | 1.00 40.00 |
| ATOM | 42 | NZ | LYS | 5 | 46.275 | 17.354 | 112.819 | 1.00 40.00 |
| ATOM | 43 | C | LYS | 5 | 49.082 | 20.925 | 108.106 | 1.00 40.00 |
| ATOM | 44 | O | LYS | 5 | 48.929 | 19.982 | 107.333 | 1.00 40.00 |
| ATOM | 45 | N | VAL | 6 | 49.383 | 22.157 | 107.664 | 1.00 40.00 |
| ATOM | 46 | CA | VAL | 6 | 49.512 | 22.339 | 106.249 | 1.00 40.00 |
| ATOM | 47 | CB | VAL | 6 | 49.637 | 23.781 | 105.851 | 1.00 40.00 |
| ATOM | 48 | CG1 | VAL | 6 | 49.792 | 23.864 | 104.325 | 1.00 40.00 |
| ATOM | 49 | CG2 | VAL | 6 | 48.415 | 24.543 | 106.390 | 1.00 40.00 |
| ATOM | 50 | C | VAL | 6 | 50.748 | 21.620 | 105.810 | 1.00 40.00 |
| ATOM | 51 | O | VAL | 6 | 51.656 | 21.379 | 106.604 | 1.00 40.00 |
| ATOM | 52 | N | CYS | 7 | 50.790 | 21.227 | 104.521 | 1.00 40.00 |
| ATOM | 53 | CA | CYS | 7 | 51.923 | 20.529 | 103.983 | 1.00 40.00 |
| ATOM | 54 | CB | CYS | 7 | 51.689 | 19.021 | 103.848 | 1.00 40.00 |
| ATOM | 55 | SG | CYS | 7 | 51.618 | 18.187 | 105.456 | 1.00 40.00 |
| ATOM | 56 | C | CYS | 7 | 52.147 | 21.055 | 102.605 | 1.00 40.00 |
| ATOM | 57 | O | CYS | 7 | 51.319 | 21.791 | 102.081 | 1.00 40.00 |
| ATOM | 58 | N | GLN | 8 | 53.347 | 20.797 | 102.055 | 1.00 40.00 |
| ATOM | 59 | CA | GLN | 8 | 53.616 | 21.165 | 100.701 | 1.00 40.00 |
| ATOM | 60 | CB | GLN | 8 | 54.351 | 22.506 | 100.524 | 1.00 40.00 |
| ATOM | 61 | CG | GLN | 8 | 53.485 | 23.727 | 100.840 | 1.00 40.00 |
| ATOM | 62 | CD | GLN | 8 | 54.294 | 24.975 | 100.513 | 1.00 40.00 |
| ATOM | 63 | OE1 | GLN | 8 | 55.306 | 25.265 | 101.151 | 1.00 40.00 |
| ATOM | 64 | NE2 | GLN | 8 | 53.838 | 25.736 | 99.482 | 1.00 40.00 |
| ATOM | 65 | C | GLN | 8 | 54.512 | 20.103 | 100.178 | 1.00 40.00 |
| ATOM | 66 | O | GLN | 8 | 55.730 | 20.163 | 100.343 | 1.00 40.00 |
| ATOM | 67 | N | GLY | 9 | 53.922 | 19.084 | 99.537 | 1.00 40.00 |
| ATOM | 68 | CA | GLY | 9 | 54.730 | 18.037 | 99.000 | 1.00 40.00 |
| ATOM | 69 | C | GLY | 9 | 55.099 | 17.129 | 100.127 | 1.00 40.00 |
| ATOM | 70 | O | GLY | 9 | 55.704 | 16.080 | 99.905 | 1.00 40.00 |
| ATOM | 71 | N | THR | 10 | 54.744 | 17.503 | 101.374 | 1.00 60.00 |
| ATOM | 72 | CA | THR | 10 | 55.074 | 16.629 | 102.460 | 1.00 60.00 |
| ATOM | 73 | CB | THR | 10 | 54.609 | 17.140 | 103.793 | 1.00 60.00 |
| ATOM | 74 | OG1 | THR | 10 | 55.222 | 18.389 | 104.079 | 1.00 60.00 |
| ATOM | 75 | CG2 | THR | 10 | 54.979 | 16.108 | 104.873 | 1.00 60.00 |
| ATOM | 76 | C | THR | 10 | 54.334 | 15.371 | 102.172 | 1.00 60.00 |
| ATOM | 77 | O | THR | 10 | 54.902 | 14.280 | 102.177 | 1.00 60.00 |

Figure 6

| | | | | | | | | |
|---|---|---|---|---|---|---|---|---|
| ATOM | 78 | N | SER | 11 | 53.031 | 15.523 | 101.874 | 1.00 60.00 |
| ATOM | 79 | CA | SER | 11 | 52.244 | 14.405 | 101.465 | 1.00 60.00 |
| ATOM | 80 | CB | SER | 11 | 50.875 | 14.310 | 102.155 | 1.00 60.00 |
| ATOM | 81 | OG | SER | 11 | 50.169 | 13.174 | 101.676 | 1.00 60.00 |
| ATOM | 82 | C | SER | 11 | 52.005 | 14.661 | 100.019 | 1.00 60.00 |
| ATOM | 83 | O | SER | 11 | 51.261 | 15.567 | 99.645 | 1.00 60.00 |
| ATOM | 84 | N | ASN | 12 | 52.663 | 13.864 | 99.165 | 1.00 40.00 |
| ATOM | 85 | CA | ASN | 12 | 52.571 | 14.073 | 97.757 | 1.00 40.00 |
| ATOM | 86 | CB | ASN | 12 | 53.837 | 14.744 | 97.194 | 1.00 40.00 |
| ATOM | 87 | CG | ASN | 12 | 53.594 | 15.173 | 95.755 | 1.00 40.00 |
| ATOM | 88 | OD1 | ASN | 12 | 52.470 | 15.141 | 95.255 | 1.00 40.00 |
| ATOM | 89 | ND2 | ASN | 12 | 54.690 | 15.585 | 95.063 | 1.00 40.00 |
| ATOM | 90 | C | ASN | 12 | 52.500 | 12.716 | 97.159 | 1.00 40.00 |
| ATOM | 91 | O | ASN | 12 | 51.561 | 11.957 | 97.390 | 1.00 40.00 |
| ATOM | 92 | N | LYS | 13 | 53.526 | 12.393 | 96.359 | 1.00 40.00 |
| ATOM | 93 | CA | LYS | 13 | 53.623 | 11.120 | 95.726 | 1.00 40.00 |
| ATOM | 94 | CB | LYS | 13 | 54.640 | 11.096 | 94.569 | 1.00 40.00 |
| ATOM | 95 | CG | LYS | 13 | 56.048 | 11.543 | 94.970 | 1.00 40.00 |
| ATOM | 96 | CD | LYS | 13 | 57.109 | 11.232 | 93.914 | 1.00 40.00 |
| ATOM | 97 | CE | LYS | 13 | 58.486 | 11.817 | 94.235 | 1.00 40.00 |
| ATOM | 98 | NZ | LYS | 13 | 58.455 | 13.291 | 94.099 | 1.00 40.00 |
| ATOM | 99 | C | LYS | 13 | 54.007 | 10.065 | 96.701 | 1.00 40.00 |
| ATOM | 100 | O | LYS | 13 | 55.183 | 9.740 | 96.853 | 1.00 40.00 |
| ATOM | 101 | N | LEU | 14 | 53.007 | 9.495 | 97.398 | 1.00 40.00 |
| ATOM | 102 | CA | LEU | 14 | 53.328 | 8.352 | 98.190 | 1.00 40.00 |
| ATOM | 103 | CB | LEU | 14 | 52.239 | 7.967 | 99.206 | 1.00 40.00 |
| ATOM | 104 | CG | LEU | 14 | 52.039 | 9.020 | 100.313 | 1.00 40.00 |
| ATOM | 105 | CD1 | LEU | 14 | 51.544 | 10.356 | 99.732 | 1.00 40.00 |
| ATOM | 106 | CD2 | LEU | 14 | 51.134 | 8.487 | 101.436 | 1.00 40.00 |
| ATOM | 107 | C | LEU | 14 | 53.428 | 7.269 | 97.171 | 1.00 40.00 |
| ATOM | 108 | O | LEU | 14 | 52.591 | 7.186 | 96.274 | 1.00 40.00 |
| ATOM | 109 | N | THR | 15 | 54.469 | 6.424 | 97.244 | 1.00 40.00 |
| ATOM | 110 | CA | THR | 15 | 54.569 | 5.441 | 96.210 | 1.00 40.00 |
| ATOM | 111 | CB | THR | 15 | 55.536 | 5.812 | 95.123 | 1.00 40.00 |
| ATOM | 112 | OG1 | THR | 15 | 56.845 | 5.948 | 95.655 | 1.00 40.00 |
| ATOM | 113 | CG2 | THR | 15 | 55.079 | 7.136 | 94.488 | 1.00 40.00 |
| ATOM | 114 | C | THR | 15 | 55.043 | 4.163 | 96.802 | 1.00 40.00 |
| ATOM | 115 | O | THR | 15 | 55.565 | 4.122 | 97.916 | 1.00 40.00 |
| ATOM | 116 | N | GLN | 16 | 54.822 | 3.059 | 96.067 | 1.00 40.00 |
| ATOM | 117 | CA | GLN | 16 | 55.300 | 1.792 | 96.521 | 1.00 40.00 |
| ATOM | 118 | CB | GLN | 16 | 54.203 | 0.712 | 96.597 | 1.00 40.00 |
| ATOM | 119 | CG | GLN | 16 | 54.696 | -0.650 | 97.095 | 1.00 40.00 |
| ATOM | 120 | CD | GLN | 16 | 53.502 | -1.591 | 97.151 | 1.00 40.00 |
| ATOM | 121 | OE1 | GLN | 16 | 52.753 | -1.725 | 96.185 | 1.00 40.00 |
| ATOM | 122 | NE2 | GLN | 16 | 53.315 | -2.259 | 98.323 | 1.00 40.00 |
| ATOM | 123 | C | GLN | 16 | 56.297 | 1.366 | 95.502 | 1.00 40.00 |
| ATOM | 124 | O | GLN | 16 | 55.946 | 1.054 | 94.365 | 1.00 40.00 |
| ATOM | 125 | N | LEU | 17 | 57.586 | 1.354 | 95.886 | 1.00 60.00 |
| ATOM | 126 | CA | LEU | 17 | 58.593 | 0.969 | 94.950 | 1.00 60.00 |
| ATOM | 127 | CB | LEU | 17 | 60.017 | 1.078 | 95.513 | 1.00 60.00 |
| ATOM | 128 | CG | LEU | 17 | 60.457 | 2.521 | 95.825 | 1.00 60.00 |
| ATOM | 129 | CD1 | LEU | 17 | 61.887 | 2.562 | 96.384 | 1.00 60.00 |
| ATOM | 130 | CD2 | LEU | 17 | 60.267 | 3.436 | 94.605 | 1.00 60.00 |
| ATOM | 131 | C | LEU | 17 | 58.338 | -0.456 | 94.601 | 1.00 60.00 |
| ATOM | 132 | O | LEU | 17 | 58.466 | -0.857 | 93.446 | 1.00 60.00 |
| ATOM | 133 | N | GLY | 18 | 57.948 | -1.256 | 95.608 | 1.00 60.00 |
| ATOM | 134 | CA | GLY | 18 | 57.715 | -2.643 | 95.367 | 1.00 60.00 |
| ATOM | 135 | C | GLY | 18 | 58.423 | -3.369 | 96.455 | 1.00 60.00 |
| ATOM | 136 | O | GLY | 18 | 58.034 | -3.308 | 97.620 | 1.00 60.00 |
| ATOM | 137 | N | THR | 19 | 59.502 | -4.079 | 96.088 | 1.00 60.00 |
| ATOM | 138 | CA | THR | 19 | 60.271 | -4.800 | 97.051 | 1.00 60.00 |
| ATOM | 139 | CB | THR | 19 | 61.451 | -5.495 | 96.444 | 1.00 60.00 |
| ATOM | 140 | OG1 | THR | 19 | 61.020 | -6.425 | 95.462 | 1.00 60.00 |
| ATOM | 141 | CG2 | THR | 19 | 62.219 | -6.222 | 97.560 | 1.00 60.00 |
| ATOM | 142 | C | THR | 19 | 60.785 | -3.785 | 98.014 | 1.00 60.00 |
| ATOM | 143 | O | THR | 19 | 60.907 | -4.051 | 99.209 | 1.00 60.00 |
| ATOM | 144 | N | PHE | 20 | 61.089 | -2.580 | 97.497 | 1.00 60.00 |
| ATOM | 145 | CA | PHE | 20 | 61.604 | -1.517 | 98.307 | 1.00 60.00 |
| ATOM | 146 | CB | PHE | 20 | 61.723 | -0.186 | 97.547 | 1.00 60.00 |
| ATOM | 147 | CG | PHE | 20 | 62.734 | -0.386 | 96.468 | 1.00 60.00 |
| ATOM | 148 | CD1 | PHE | 20 | 64.078 | -0.257 | 96.738 | 1.00 60.00 |
| ATOM | 149 | CD2 | PHE | 20 | 62.345 | -0.708 | 95.186 | 1.00 60.00 |
| ATOM | 150 | CE1 | PHE | 20 | 65.015 | -0.445 | 95.750 | 1.00 60.00 |
| ATOM | 151 | CE2 | PHE | 20 | 63.278 | -0.897 | 94.193 | 1.00 60.00 |
| ATOM | 152 | CZ | PHE | 20 | 64.617 | -0.765 | 94.473 | 1.00 60.00 |
| ATOM | 153 | C | PHE | 20 | 60.684 | -1.332 | 99.473 | 1.00 60.00 |
| ATOM | 154 | O | PHE | 20 | 59.555 | -1.819 | 99.480 | 1.00 60.00 |

Figure 6A-1

| | | | | | | | |
|---|---|---|---|---|---|---|---|
| ATOM | 155 | N | GLU | 21 | 61.184 | -0.640 100.514 | 1.00 60.00 |
| ATOM | 156 | CA | GLU | 21 | 60.471 | -0.440 101.743 | 1.00 60.00 |
| ATOM | 157 | CB | GLU | 21 | 61.314 | 0.262 102.821 | 1.00 60.00 |
| ATOM | 158 | CG | GLU | 21 | 62.418 | -0.629 103.393 | 1.00 60.00 |
| ATOM | 159 | CD | GLU | 21 | 63.461 | -0.846 102.306 | 1.00 60.00 |
| ATOM | 160 | OE1 | GLU | 21 | 63.930 | 0.172 101.730 | 1.00 60.00 |
| ATOM | 161 | OE2 | GLU | 21 | 63.798 | -2.029 102.033 | 1.00 60.00 |
| ATOM | 162 | C | GLU | 21 | 59.239 | 0.374 101.517 | 1.00 60.00 |
| ATOM | 163 | O | GLU | 21 | 58.224 | 0.142 102.170 | 1.00 60.00 |
| ATOM | 164 | N | ASP | 22 | 59.284 | 1.356 100.600 | 1.00 60.00 |
| ATOM | 165 | CA | ASP | 22 | 58.127 | 2.184 100.414 | 1.00 60.00 |
| ATOM | 166 | CB | ASP | 22 | 58.301 | 3.259 99.327 | 1.00 60.00 |
| ATOM | 167 | CG | ASP | 22 | 59.249 | 4.315 99.878 | 1.00 60.00 |
| ATOM | 168 | OD1 | ASP | 22 | 59.322 | 4.443 101.129 | 1.00 60.00 |
| ATOM | 169 | OD2 | ASP | 22 | 59.909 | 5.007 99.058 | 1.00 60.00 |
| ATOM | 170 | C | ASP | 22 | 56.961 | 1.325 100.044 | 1.00 60.00 |
| ATOM | 171 | O | ASP | 22 | 57.073 | 0.405 99.235 | 1.00 60.00 |
| ATOM | 172 | N | HIS | 23 | 55.803 | 1.615 100.670 | 1.00 40.00 |
| ATOM | 173 | CA | HIS | 23 | 54.586 | 0.892 100.442 | 1.00 40.00 |
| ATOM | 174 | ND1 | HIS | 23 | 56.474 | -1.838 101.876 | 1.00 40.00 |
| ATOM | 175 | NE2 | HIS | 23 | 56.905 | -2.977 100.017 | 1.00 40.00 |
| ATOM | 176 | CE1 | HIS | 23 | 57.266 | -2.757 101.268 | 1.00 40.00 |
| ATOM | 177 | CD2 | HIS | 23 | 55.817 | -2.148 99.817 | 1.00 40.00 |
| ATOM | 178 | CG | HIS | 23 | 55.539 | -1.442 100.947 | 1.00 40.00 |
| ATOM | 179 | CB | HIS | 23 | 54.466 | -0.431 101.225 | 1.00 40.00 |
| ATOM | 180 | C | HIS | 23 | 53.501 | 1.752 101.002 | 1.00 40.00 |
| ATOM | 181 | O | HIS | 23 | 53.574 | 2.979 100.966 | 1.00 40.00 |
| ATOM | 182 | N | PHE | 24 | 52.456 | 1.096 101.537 | 1.00 40.00 |
| ATOM | 183 | CA | PHE | 24 | 51.390 | 1.781 102.206 | 1.00 40.00 |
| ATOM | 184 | CB | PHE | 24 | 50.221 | 0.874 102.641 | 1.00 40.00 |
| ATOM | 185 | CG | PHE | 24 | 50.686 | -0.092 103.676 | 1.00 40.00 |
| ATOM | 186 | CD1 | PHE | 24 | 51.333 | -1.248 103.312 | 1.00 40.00 |
| ATOM | 187 | CD2 | PHE | 24 | 50.456 | 0.154 105.011 | 1.00 40.00 |
| ATOM | 188 | CE1 | PHE | 24 | 51.755 | -2.140 104.269 | 1.00 40.00 |
| ATOM | 189 | CE2 | PHE | 24 | 50.876 | -0.735 105.971 | 1.00 40.00 |
| ATOM | 190 | CZ | PHE | 24 | 51.528 | -1.885 105.600 | 1.00 40.00 |
| ATOM | 191 | C | PHE | 24 | 51.973 | 2.437 103.414 | 1.00 40.00 |
| ATOM | 192 | O | PHE | 24 | 51.413 | 3.393 103.945 | 1.00 40.00 |
| ATOM | 193 | N | LEU | 25 | 53.137 | 1.940 103.864 | 1.00 40.00 |
| ATOM | 194 | CA | LEU | 25 | 53.809 | 2.441 105.027 | 1.00 40.00 |
| ATOM | 195 | CB | LEU | 25 | 55.201 | 1.807 105.203 | 1.00 40.00 |
| ATOM | 196 | CG | LEU | 25 | 55.972 | 2.301 106.441 | 1.00 40.00 |
| ATOM | 197 | CD1 | LEU | 25 | 55.274 | 1.867 107.740 | 1.00 40.00 |
| ATOM | 198 | CD2 | LEU | 25 | 57.450 | 1.880 106.387 | 1.00 40.00 |
| ATOM | 199 | C | LEU | 25 | 54.004 | 3.919 104.842 | 1.00 40.00 |
| ATOM | 200 | O | LEU | 25 | 53.972 | 4.680 105.808 | 1.00 40.00 |
| ATOM | 201 | N | SER | 26 | 54.210 | 4.353 103.587 | 1.00 40.00 |
| ATOM | 202 | CA | SER | 26 | 54.437 | 5.732 103.244 | 1.00 40.00 |
| ATOM | 203 | CB | SER | 26 | 54.690 | 5.930 101.740 | 1.00 40.00 |
| ATOM | 204 | OG | SER | 26 | 55.877 | 5.257 101.350 | 1.00 40.00 |
| ATOM | 205 | C | SER | 26 | 53.231 | 6.550 103.603 | 1.00 40.00 |
| ATOM | 206 | O | SER | 26 | 53.340 | 7.745 103.875 | 1.00 40.00 |
| ATOM | 207 | N | LEU | 27 | 52.050 | 5.910 103.620 | 1.00 40.00 |
| ATOM | 208 | CA | LEU | 27 | 50.763 | 6.522 103.842 | 1.00 40.00 |
| ATOM | 209 | CB | LEU | 27 | 49.630 | 5.478 103.835 | 1.00 40.00 |
| ATOM | 210 | CG | LEU | 27 | 49.489 | 4.723 102.500 | 1.00 40.00 |
| ATOM | 211 | CD1 | LEU | 27 | 48.353 | 3.693 102.558 | 1.00 40.00 |
| ATOM | 212 | CD2 | LEU | 27 | 49.347 | 5.696 101.321 | 1.00 40.00 |
| ATOM | 213 | C | LEU | 27 | 50.727 | 7.196 105.183 | 1.00 40.00 |
| ATOM | 214 | O | LEU | 27 | 49.977 | 8.151 105.379 | 1.00 40.00 |
| ATOM | 215 | N | GLN | 28 | 51.536 | 6.712 106.139 | 1.00 40.00 |
| ATOM | 216 | CA | GLN | 28 | 51.542 | 7.178 107.498 | 1.00 40.00 |
| ATOM | 217 | CB | GLN | 28 | 52.603 | 6.451 108.345 | 1.00 40.00 |
| ATOM | 218 | CG | GLN | 28 | 54.035 | 6.691 107.858 | 1.00 40.00 |
| ATOM | 219 | CD | GLN | 28 | 54.993 | 5.910 108.749 | 1.00 40.00 |
| ATOM | 220 | OE1 | GLN | 28 | 56.205 | 5.934 108.543 | 1.00 40.00 |
| ATOM | 221 | NE2 | GLN | 28 | 54.437 | 5.195 109.764 | 1.00 40.00 |
| ATOM | 222 | C | GLN | 28 | 51.825 | 8.649 107.578 | 1.00 40.00 |
| ATOM | 223 | O | GLN | 28 | 51.263 | 9.341 108.426 | 1.00 40.00 |
| ATOM | 224 | N | ARG | 29 | 52.677 | 9.183 106.688 | 1.00 40.00 |
| ATOM | 225 | CA | ARG | 29 | 53.065 | 10.561 106.792 | 1.00 40.00 |
| ATOM | 226 | CB | ARG | 29 | 54.017 | 11.010 105.670 | 1.00 40.00 |
| ATOM | 227 | CG | ARG | 29 | 55.395 | 10.355 105.771 | 1.00 40.00 |
| ATOM | 228 | CD | ARG | 29 | 56.453 | 10.977 104.857 | 1.00 40.00 |
| ATOM | 229 | NE | ARG | 29 | 56.118 | 10.623 103.450 | 1.00 40.00 |
| ATOM | 230 | CZ | ARG | 29 | 56.967 | 10.980 102.442 | 1.00 40.00 |
| ATOM | 231 | NH1 | ARG | 29 | 58.110 | 11.670 102.726 | 1.00 40.00 |

Figure 6A-2

| | | | | | | | | |
|---|---|---|---|---|---|---|---|---|
| ATOM | 232 | NH2 | ARG | 29 | 56.677 | 10.641 | 101.152 | 1.00 40.00 |
| ATOM | 233 | C | ARG | 29 | 51.854 | 11.439 | 106.757 | 1.00 40.00 |
| ATOM | 234 | O | ARG | 29 | 51.821 | 12.487 | 107.400 | 1.00 40.00 |
| ATOM | 235 | N | MET | 30 | 50.818 | 11.033 | 106.009 | 1.00 40.00 |
| ATOM | 236 | CA | MET | 30 | 49.654 | 11.851 | 105.844 | 1.00 40.00 |
| ATOM | 237 | CB | MET | 30 | 48.583 | 11.211 | 104.944 | 1.00 40.00 |
| ATOM | 238 | CG | MET | 30 | 49.009 | 11.014 | 103.490 | 1.00 40.00 |
| ATOM | 239 | SD | MET | 30 | 47.708 | 10.321 | 102.425 | 1.00 40.00 |
| ATOM | 240 | CE | MET | 30 | 47.584 | 8.743 | 103.316 | 1.00 40.00 |
| ATOM | 241 | C | MET | 30 | 48.969 | 12.114 | 107.148 | 1.00 40.00 |
| ATOM | 242 | O | MET | 30 | 48.518 | 13.233 | 107.383 | 1.00 40.00 |
| ATOM | 243 | N | PHE | 31 | 48.880 | 11.112 | 108.042 | 1.00 40.00 |
| ATOM | 244 | CA | PHE | 31 | 48.041 | 11.271 | 109.198 | 1.00 40.00 |
| ATOM | 245 | CB | PHE | 31 | 48.099 | 10.049 | 110.136 | 1.00 40.00 |
| ATOM | 246 | CG | PHE | 31 | 47.154 | 10.272 | 111.270 | 1.00 40.00 |
| ATOM | 247 | CD1 | PHE | 31 | 47.538 | 10.974 | 112.391 | 1.00 40.00 |
| ATOM | 248 | CD2 | PHE | 31 | 45.875 | 9.770 | 111.210 | 1.00 40.00 |
| ATOM | 249 | CE1 | PHE | 31 | 46.663 | 11.173 | 113.433 | 1.00 40.00 |
| ATOM | 250 | CE2 | PHE | 31 | 44.995 | 9.964 | 112.248 | 1.00 40.00 |
| ATOM | 251 | CZ | PHE | 31 | 45.386 | 10.669 | 113.360 | 1.00 40.00 |
| ATOM | 252 | C | PHE | 31 | 48.418 | 12.473 | 110.010 | 1.00 40.00 |
| ATOM | 253 | O | PHE | 31 | 47.604 | 13.375 | 110.196 | 1.00 40.00 |
| ATOM | 254 | N | ASN | 32 | 49.662 | 12.534 | 110.513 | 1.00 40.00 |
| ATOM | 255 | CA | ASN | 32 | 50.034 | 13.638 | 111.352 | 1.00 40.00 |
| ATOM | 256 | CB | ASN | 32 | 51.367 | 13.407 | 112.087 | 1.00 40.00 |
| ATOM | 257 | CG | ASN | 32 | 51.202 | 12.237 | 113.045 | 1.00 40.00 |
| ATOM | 258 | OD1 | ASN | 32 | 50.132 | 11.639 | 113.140 | 1.00 40.00 |
| ATOM | 259 | ND2 | ASN | 32 | 52.294 | 11.903 | 113.784 | 1.00 40.00 |
| ATOM | 260 | C | ASN | 32 | 50.225 | 14.877 | 110.543 | 1.00 40.00 |
| ATOM | 261 | O | ASN | 32 | 49.758 | 15.959 | 110.898 | 1.00 40.00 |
| ATOM | 262 | N | ASN | 33 | 50.899 | 14.719 | 109.396 | 1.00 40.00 |
| ATOM | 263 | CA | ASN | 33 | 51.396 | 15.824 | 108.638 | 1.00 40.00 |
| ATOM | 264 | CB | ASN | 33 | 52.295 | 15.394 | 107.465 | 1.00 40.00 |
| ATOM | 265 | CG | ASN | 33 | 53.634 | 14.958 | 108.044 | 1.00 40.00 |
| ATOM | 266 | OD1 | ASN | 33 | 54.388 | 14.216 | 107.417 | 1.00 40.00 |
| ATOM | 267 | ND2 | ASN | 33 | 53.943 | 15.436 | 109.279 | 1.00 40.00 |
| ATOM | 268 | C | ASN | 33 | 50.355 | 16.743 | 108.089 | 1.00 40.00 |
| ATOM | 269 | O | ASN | 33 | 50.562 | 17.955 | 108.121 | 1.00 40.00 |
| ATOM | 270 | N | CYS | 34 | 49.200 | 16.267 | 107.586 | 1.00 20.00 |
| ATOM | 271 | CA | CYS | 34 | 48.544 | 17.318 | 106.866 | 1.00 20.00 |
| ATOM | 272 | CB | CYS | 34 | 48.780 | 17.152 | 105.359 | 1.00 20.00 |
| ATOM | 273 | SG | CYS | 34 | 50.474 | 16.567 | 105.052 | 1.00 20.00 |
| ATOM | 274 | C | CYS | 34 | 47.061 | 17.378 | 107.054 | 1.00 20.00 |
| ATOM | 275 | O | CYS | 34 | 46.342 | 16.441 | 106.710 | 1.00 20.00 |
| ATOM | 276 | N | GLU | 35 | 46.567 | 18.492 | 107.641 | 1.00 20.00 |
| ATOM | 277 | CA | GLU | 35 | 45.156 | 18.756 | 107.625 | 1.00 20.00 |
| ATOM | 278 | CB | GLU | 35 | 44.723 | 19.956 | 108.479 | 1.00 20.00 |
| ATOM | 279 | CG | GLU | 35 | 43.217 | 20.215 | 108.378 | 1.00 20.00 |
| ATOM | 280 | CD | GLU | 35 | 42.939 | 21.643 | 108.822 | 1.00 20.00 |
| ATOM | 281 | OE1 | GLU | 35 | 43.355 | 22.008 | 109.954 | 1.00 20.00 |
| ATOM | 282 | OE2 | GLU | 35 | 42.314 | 22.393 | 108.025 | 1.00 20.00 |
| ATOM | 283 | C | GLU | 35 | 44.854 | 19.160 | 106.224 | 1.00 20.00 |
| ATOM | 284 | O | GLU | 35 | 43.869 | 18.732 | 105.624 | 1.00 20.00 |
| ATOM | 285 | N | VAL | 36 | 45.727 | 20.030 | 105.674 | 1.00 20.00 |
| ATOM | 286 | CA | VAL | 36 | 45.545 | 20.517 | 104.342 | 1.00 20.00 |
| ATOM | 287 | CB | VAL | 36 | 45.246 | 21.986 | 104.291 | 1.00 20.00 |
| ATOM | 288 | CG1 | VAL | 36 | 45.082 | 22.406 | 102.821 | 1.00 20.00 |
| ATOM | 289 | CG2 | VAL | 36 | 44.012 | 22.268 | 105.163 | 1.00 20.00 |
| ATOM | 290 | C | VAL | 36 | 46.823 | 20.314 | 103.600 | 1.00 20.00 |
| ATOM | 291 | O | VAL | 36 | 47.828 | 20.961 | 103.884 | 1.00 20.00 |
| ATOM | 292 | N | VAL | 37 | 46.821 | 19.417 | 102.601 | 1.00 20.00 |
| ATOM | 293 | CA | VAL | 37 | 48.027 | 19.240 | 101.859 | 1.00 20.00 |
| ATOM | 294 | CB | VAL | 37 | 48.137 | 17.901 | 101.180 | 1.00 20.00 |
| ATOM | 295 | CG1 | VAL | 37 | 48.249 | 16.823 | 102.273 | 1.00 20.00 |
| ATOM | 296 | CG2 | VAL | 37 | 46.929 | 17.691 | 100.250 | 1.00 20.00 |
| ATOM | 297 | C | VAL | 37 | 48.056 | 20.322 | 100.830 | 1.00 20.00 |
| ATOM | 298 | O | VAL | 37 | 47.191 | 20.401 | 99.961 | 1.00 20.00 |
| ATOM | 299 | N | LEU | 38 | 49.052 | 21.222 | 100.926 | 1.00 20.00 |
| ATOM | 300 | CA | LEU | 38 | 49.162 | 22.282 | 99.969 | 1.00 20.00 |
| ATOM | 301 | CB | LEU | 38 | 49.882 | 23.531 | 100.528 | 1.00 20.00 |
| ATOM | 302 | CG | LEU | 38 | 49.969 | 24.782 | 99.618 | 1.00 20.00 |
| ATOM | 303 | CD1 | LEU | 38 | 50.711 | 25.914 | 100.345 | 1.00 20.00 |
| ATOM | 304 | CD2 | LEU | 38 | 50.592 | 24.502 | 98.238 | 1.00 20.00 |
| ATOM | 305 | C | LEU | 38 | 49.954 | 21.706 | 98.848 | 1.00 20.00 |
| ATOM | 306 | O | LEU | 38 | 51.182 | 21.679 | 98.886 | 1.00 20.00 |
| ATOM | 307 | N | GLY | 39 | 49.246 | 21.238 | 97.807 | 1.00 20.00 |
| ATOM | 308 | CA | GLY | 39 | 49.892 | 20.609 | 96.695 | 1.00 20.00 |

Figure 6A-3

| | | | | | | | | | |
|---|---|---|---|---|---|---|---|---|---|
| ATOM | 309 | C | GLY | 39 | 48.980 | 19.511 | 96.266 | 1.00 | 20.00 |
| ATOM | 310 | O | GLY | 39 | 47.761 | 19.640 | 96.353 | 1.00 | 20.00 |
| ATOM | 311 | N | ASN | 40 | 49.540 | 18.388 | 95.786 | 1.00 | 20.00 |
| ATOM | 312 | CA | ASN | 40 | 48.656 | 17.340 | 95.372 | 1.00 | 20.00 |
| ATOM | 313 | CB | ASN | 40 | 48.718 | 17.020 | 93.865 | 1.00 | 20.00 |
| ATOM | 314 | CG | ASN | 40 | 50.125 | 16.561 | 93.514 | 1.00 | 20.00 |
| ATOM | 315 | OD1 | ASN | 40 | 51.081 | 17.331 | 93.595 | 1.00 | 20.00 |
| ATOM | 316 | ND2 | ASN | 40 | 50.259 | 15.270 | 93.110 | 1.00 | 20.00 |
| ATOM | 317 | C | ASN | 40 | 48.984 | 16.095 | 96.124 | 1.00 | 20.00 |
| ATOM | 318 | O | ASN | 40 | 50.032 | 15.982 | 96.761 | 1.00 | 20.00 |
| ATOM | 319 | N | LEU | 41 | 48.040 | 15.135 | 96.090 | 1.00 | 20.00 |
| ATOM | 320 | CA | LEU | 41 | 48.211 | 13.866 | 96.729 | 1.00 | 20.00 |
| ATOM | 321 | CB | LEU | 41 | 47.102 | 13.532 | 97.738 | 1.00 | 20.00 |
| ATOM | 322 | CG | LEU | 41 | 47.176 | 12.079 | 98.237 | 1.00 | 20.00 |
| ATOM | 323 | CD1 | LEU | 41 | 48.519 | 11.797 | 98.922 | 1.00 | 20.00 |
| ATOM | 324 | CD2 | LEU | 41 | 45.965 | 11.721 | 99.113 | 1.00 | 20.00 |
| ATOM | 325 | C | LEU | 41 | 48.146 | 12.816 | 95.675 | 1.00 | 20.00 |
| ATOM | 326 | O | LEU | 41 | 47.188 | 12.755 | 94.907 | 1.00 | 20.00 |
| ATOM | 327 | N | GLU | 42 | 49.180 | 11.958 | 95.595 | 1.00 | 20.00 |
| ATOM | 328 | CA | GLU | 42 | 49.093 | 10.909 | 94.627 | 1.00 | 20.00 |
| ATOM | 329 | CB | GLU | 42 | 49.996 | 11.122 | 93.398 | 1.00 | 20.00 |
| ATOM | 330 | CG | GLU | 42 | 51.469 | 11.319 | 93.740 | 1.00 | 20.00 |
| ATOM | 331 | CD | GLU | 42 | 52.188 | 11.817 | 92.496 | 1.00 | 20.00 |
| ATOM | 332 | OE1 | GLU | 42 | 51.772 | 12.880 | 91.962 | 1.00 | 20.00 |
| ATOM | 333 | OE2 | GLU | 42 | 53.162 | 11.146 | 92.065 | 1.00 | 20.00 |
| ATOM | 334 | C | GLU | 42 | 49.431 | 9.626 | 95.303 | 1.00 | 20.00 |
| ATOM | 335 | O | GLU | 42 | 50.470 | 9.502 | 95.956 | 1.00 | 20.00 |
| ATOM | 336 | N | ILE | 43 | 48.523 | 8.636 | 95.195 | 1.00 | 20.00 |
| ATOM | 337 | CA | ILE | 43 | 48.778 | 7.367 | 95.806 | 1.00 | 20.00 |
| ATOM | 338 | CB | ILE | 43 | 47.667 | 6.928 | 96.716 | 1.00 | 20.00 |
| ATOM | 339 | CG2 | ILE | 43 | 47.999 | 5.514 | 97.220 | 1.00 | 20.00 |
| ATOM | 340 | CG1 | ILE | 43 | 47.473 | 7.939 | 97.859 | 1.00 | 20.00 |
| ATOM | 341 | CD1 | ILE | 43 | 48.669 | 8.039 | 98.804 | 1.00 | 20.00 |
| ATOM | 342 | C | ILE | 43 | 48.870 | 6.372 | 94.692 | 1.00 | 20.00 |
| ATOM | 343 | O | ILE | 43 | 47.857 | 5.962 | 94.131 | 1.00 | 20.00 |
| ATOM | 344 | N | THR | 44 | 50.096 | 5.931 | 94.350 | 1.00 | 20.00 |
| ATOM | 345 | CA | THR | 44 | 50.230 | 5.040 | 93.234 | 1.00 | 20.00 |
| ATOM | 346 | CB | THR | 44 | 51.275 | 5.477 | 92.252 | 1.00 | 20.00 |
| ATOM | 347 | OG1 | THR | 44 | 52.554 | 5.488 | 92.868 | 1.00 | 20.00 |
| ATOM | 348 | CG2 | THR | 44 | 50.919 | 6.887 | 91.751 | 1.00 | 20.00 |
| ATOM | 349 | C | THR | 44 | 50.627 | 3.678 | 93.719 | 1.00 | 20.00 |
| ATOM | 350 | O | THR | 44 | 51.282 | 3.535 | 94.751 | 1.00 | 20.00 |
| ATOM | 351 | N | TYR | 45 | 50.196 | 2.652 | 92.951 | 1.00 | 20.00 |
| ATOM | 352 | CA | TYR | 45 | 50.417 | 1.237 | 93.111 | 1.00 | 20.00 |
| ATOM | 353 | CB | TYR | 45 | 51.491 | 0.631 | 92.188 | 1.00 | 20.00 |
| ATOM | 354 | CG | TYR | 45 | 51.489 | -0.836 | 92.465 | 1.00 | 20.00 |
| ATOM | 355 | CD1 | TYR | 45 | 50.437 | -1.612 | 92.032 | 1.00 | 20.00 |
| ATOM | 356 | CD2 | TYR | 45 | 52.526 | -1.444 | 93.138 | 1.00 | 20.00 |
| ATOM | 357 | CE1 | TYR | 45 | 50.410 | -2.964 | 92.277 | 1.00 | 20.00 |
| ATOM | 358 | CE2 | TYR | 45 | 52.505 | -2.797 | 93.385 | 1.00 | 20.00 |
| ATOM | 359 | CZ | TYR | 45 | 51.445 | -3.559 | 92.956 | 1.00 | 20.00 |
| ATOM | 360 | OH | TYR | 45 | 51.417 | -4.947 | 93.208 | 1.00 | 20.00 |
| ATOM | 361 | C | TYR | 45 | 50.743 | 0.867 | 94.520 | 1.00 | 20.00 |
| ATOM | 362 | O | TYR | 45 | 51.894 | 0.594 | 94.854 | 1.00 | 20.00 |
| ATOM | 363 | N | VAL | 46 | 49.732 | 0.844 | 95.407 | 1.00 | 20.00 |
| ATOM | 364 | CA | VAL | 46 | 50.016 | 0.479 | 96.764 | 1.00 | 20.00 |
| ATOM | 365 | CB | VAL | 46 | 49.911 | 1.623 | 97.730 | 1.00 | 20.00 |
| ATOM | 366 | CG1 | VAL | 46 | 50.093 | 1.074 | 99.154 | 1.00 | 20.00 |
| ATOM | 367 | CG2 | VAL | 46 | 50.944 | 2.694 | 97.343 | 1.00 | 20.00 |
| ATOM | 368 | C | VAL | 46 | 49.016 | -0.541 | 97.199 | 1.00 | 20.00 |
| ATOM | 369 | O | VAL | 46 | 47.839 | -0.466 | 96.851 | 1.00 | 20.00 |
| ATOM | 370 | N | GLN | 47 | 49.477 | -1.542 | 97.975 | 1.00 | 20.00 |
| ATOM | 371 | CA | GLN | 47 | 48.569 | -2.528 | 98.483 | 1.00 | 20.00 |
| ATOM | 372 | CB | GLN | 47 | 48.926 | -3.970 | 98.083 | 1.00 | 20.00 |
| ATOM | 373 | CG | GLN | 47 | 48.819 | -4.242 | 96.583 | 1.00 | 20.00 |
| ATOM | 374 | CD | GLN | 47 | 49.200 | -5.698 | 96.348 | 1.00 | 20.00 |
| ATOM | 375 | OE1 | GLN | 47 | 48.564 | -6.618 | 96.862 | 1.00 | 20.00 |
| ATOM | 376 | NE2 | GLN | 47 | 50.278 | -5.916 | 95.548 | 1.00 | 20.00 |
| ATOM | 377 | C | GLN | 47 | 48.663 | -2.463 | 99.970 | 1.00 | 20.00 |
| ATOM | 378 | O | GLN | 47 | 49.711 | -2.745 | 100.548 | 1.00 | 20.00 |
| ATOM | 379 | N | ARG | 48 | 47.560 | -2.076 | 100.635 | 1.00 | 20.00 |
| ATOM | 380 | CA | ARG | 48 | 47.582 | -2.021 | 102.065 | 1.00 | 20.00 |
| ATOM | 381 | CB | ARG | 48 | 47.560 | -0.584 | 102.621 | 1.00 | 20.00 |
| ATOM | 382 | CG | ARG | 48 | 47.599 | -0.497 | 104.151 | 1.00 | 20.00 |
| ATOM | 383 | CD | ARG | 48 | 47.632 | 0.938 | 104.688 | 1.00 | 20.00 |
| ATOM | 384 | NE | ARG | 48 | 47.664 | 0.865 | 106.177 | 1.00 | 20.00 |
| ATOM | 385 | CZ | ARG | 48 | 48.202 | 1.890 | 106.903 | 1.00 | 20.00 |

Figure 6A-4

| | | | | | | | | |
|---|---|---|---|---|---|---|---|---|
| ATOM | 386 | NH1 | ARG | 48 | 48.705 | 2.987 | 106.265 | 1.00 20.00 |
| ATOM | 387 | NH2 | ARG | 48 | 48.230 | 1.827 | 108.266 | 1.00 20.00 |
| ATOM | 388 | C | ARG | 48 | 46.342 | -2.704 | 102.530 | 1.00 20.00 |
| ATOM | 389 | O | ARG | 48 | 45.269 | -2.511 | 101.962 | 1.00 20.00 |
| ATOM | 390 | N | ASN | 49 | 46.464 | -3.543 | 103.574 | 1.00 40.00 |
| ATOM | 391 | CA | ASN | 49 | 45.300 | -4.204 | 104.078 | 1.00 40.00 |
| ATOM | 392 | CB | ASN | 49 | 45.602 | -5.162 | 105.245 | 1.00 40.00 |
| ATOM | 393 | CG | ASN | 49 | 44.344 | -5.978 | 105.516 | 1.00 40.00 |
| ATOM | 394 | OD1 | ASN | 49 | 43.342 | -5.841 | 104.817 | 1.00 40.00 |
| ATOM | 395 | ND2 | ASN | 49 | 44.389 | -6.842 | 106.566 | 1.00 40.00 |
| ATOM | 396 | C | ASN | 49 | 44.423 | -3.124 | 104.605 | 1.00 40.00 |
| ATOM | 397 | O | ASN | 49 | 43.213 | -3.115 | 104.383 | 1.00 40.00 |
| ATOM | 398 | N | TYR | 50 | 45.046 | -2.163 | 105.310 | 1.00 40.00 |
| ATOM | 399 | CA | TYR | 50 | 44.329 | -1.062 | 105.873 | 1.00 40.00 |
| ATOM | 400 | CB | TYR | 50 | 45.065 | -0.385 | 107.039 | 1.00 40.00 |
| ATOM | 401 | CG | TYR | 50 | 45.065 | -1.389 | 108.139 | 1.00 40.00 |
| ATOM | 402 | CD1 | TYR | 50 | 43.945 | -1.550 | 108.921 | 1.00 40.00 |
| ATOM | 403 | CD2 | TYR | 50 | 46.170 | -2.169 | 108.386 | 1.00 40.00 |
| ATOM | 404 | CE1 | TYR | 50 | 43.922 | -2.473 | 109.939 | 1.00 40.00 |
| ATOM | 405 | CE2 | TYR | 50 | 46.155 | -3.095 | 109.403 | 1.00 40.00 |
| ATOM | 406 | CZ | TYR | 50 | 45.030 | -3.247 | 110.181 | 1.00 40.00 |
| ATOM | 407 | OH | TYR | 50 | 45.011 | -4.197 | 111.224 | 1.00 40.00 |
| ATOM | 408 | C | TYR | 50 | 44.098 | -0.071 | 104.787 | 1.00 40.00 |
| ATOM | 409 | O | TYR | 50 | 44.522 | -0.271 | 103.650 | 1.00 40.00 |
| ATOM | 410 | N | ASP | 51 | 43.384 | 1.022 | 105.110 | 1.00 40.00 |
| ATOM | 411 | CA | ASP | 51 | 43.064 | 1.961 | 104.081 | 1.00 40.00 |
| ATOM | 412 | CB | ASP | 51 | 41.552 | 2.120 | 103.854 | 1.00 40.00 |
| ATOM | 413 | CG | ASP | 51 | 41.029 | 0.814 | 103.272 | 1.00 40.00 |
| ATOM | 414 | OD1 | ASP | 51 | 41.865 | -0.089 | 102.997 | 1.00 40.00 |
| ATOM | 415 | OD2 | ASP | 51 | 39.787 | 0.701 | 103.095 | 1.00 40.00 |
| ATOM | 416 | C | ASP | 51 | 43.603 | 3.307 | 104.437 | 1.00 40.00 |
| ATOM | 417 | O | ASP | 51 | 44.260 | 3.501 | 105.458 | 1.00 40.00 |
| ATOM | 418 | N | LEU | 52 | 43.326 | 4.261 | 103.530 | 1.00 40.00 |
| ATOM | 419 | CA | LEU | 52 | 43.698 | 5.646 | 103.552 | 1.00 40.00 |
| ATOM | 420 | CB | LEU | 52 | 43.336 | 6.381 | 102.252 | 1.00 40.00 |
| ATOM | 421 | CG | LEU | 52 | 44.104 | 5.860 | 101.024 | 1.00 40.00 |
| ATOM | 422 | CD1 | LEU | 52 | 43.732 | 4.403 | 100.706 | 1.00 40.00 |
| ATOM | 423 | CD2 | LEU | 52 | 43.931 | 6.799 | 99.821 | 1.00 40.00 |
| ATOM | 424 | C | LEU | 52 | 42.980 | 6.329 | 104.672 | 1.00 40.00 |
| ATOM | 425 | O | LEU | 52 | 43.418 | 7.367 | 105.163 | 1.00 40.00 |
| ATOM | 426 | N | SER | 53 | 41.876 | 5.719 | 105.135 | 1.00 40.00 |
| ATOM | 427 | CA | SER | 53 | 40.953 | 6.292 | 106.070 | 1.00 40.00 |
| ATOM | 428 | CB | SER | 53 | 39.951 | 5.261 | 106.618 | 1.00 40.00 |
| ATOM | 429 | OG | SER | 53 | 40.631 | 4.269 | 107.373 | 1.00 40.00 |
| ATOM | 430 | C | SER | 53 | 41.684 | 6.865 | 107.239 | 1.00 40.00 |
| ATOM | 431 | O | SER | 53 | 41.186 | 7.794 | 107.873 | 1.00 40.00 |
| ATOM | 432 | N | PHE | 54 | 42.881 | 6.345 | 107.561 | 1.00 40.00 |
| ATOM | 433 | CA | PHE | 54 | 43.589 | 6.840 | 108.706 | 1.00 40.00 |
| ATOM | 434 | CB | PHE | 54 | 44.964 | 6.180 | 108.931 | 1.00 40.00 |
| ATOM | 435 | CG | PHE | 54 | 45.821 | 6.394 | 107.731 | 1.00 40.00 |
| ATOM | 436 | CD1 | PHE | 54 | 46.628 | 7.502 | 107.624 | 1.00 40.00 |
| ATOM | 437 | CD2 | PHE | 54 | 45.819 | 5.475 | 106.709 | 1.00 40.00 |
| ATOM | 438 | CE1 | PHE | 54 | 47.418 | 7.686 | 106.511 | 1.00 40.00 |
| ATOM | 439 | CE2 | PHE | 54 | 46.605 | 5.651 | 105.595 | 1.00 40.00 |
| ATOM | 440 | CZ | PHE | 54 | 47.407 | 6.760 | 105.494 | 1.00 40.00 |
| ATOM | 441 | C | PHE | 54 | 43.779 | 8.321 | 108.578 | 1.00 40.00 |
| ATOM | 442 | O | PHE | 54 | 43.763 | 9.023 | 109.588 | 1.00 40.00 |
| ATOM | 443 | N | LEU | 55 | 43.976 | 8.845 | 107.352 | 1.00 40.00 |
| ATOM | 444 | CA | LEU | 55 | 44.137 | 10.268 | 107.216 | 1.00 40.00 |
| ATOM | 445 | CB | LEU | 55 | 44.704 | 10.676 | 105.847 | 1.00 40.00 |
| ATOM | 446 | CG | LEU | 55 | 44.884 | 12.193 | 105.681 | 1.00 40.00 |
| ATOM | 447 | CD1 | LEU | 55 | 45.897 | 12.750 | 106.696 | 1.00 40.00 |
| ATOM | 448 | CD2 | LEU | 55 | 45.243 | 12.549 | 104.232 | 1.00 40.00 |
| ATOM | 449 | C | LEU | 55 | 42.784 | 10.895 | 107.360 | 1.00 40.00 |
| ATOM | 450 | O | LEU | 55 | 42.167 | 11.322 | 106.384 | 1.00 40.00 |
| ATOM | 451 | N | LYS | 56 | 42.295 | 10.952 | 108.613 | 1.00 40.00 |
| ATOM | 452 | CA | LYS | 56 | 41.021 | 11.494 | 108.983 | 1.00 40.00 |
| ATOM | 453 | CB | LYS | 56 | 40.684 | 11.190 | 110.451 | 1.00 40.00 |
| ATOM | 454 | CG | LYS | 56 | 39.337 | 11.745 | 110.910 | 1.00 40.00 |
| ATOM | 455 | CD | LYS | 56 | 38.977 | 11.337 | 112.341 | 1.00 40.00 |
| ATOM | 456 | CE | LYS | 56 | 39.847 | 12.023 | 113.398 | 1.00 40.00 |
| ATOM | 457 | NZ | LYS | 56 | 39.445 | 11.587 | 114.754 | 1.00 40.00 |
| ATOM | 458 | C | LYS | 56 | 41.024 | 12.987 | 108.854 | 1.00 40.00 |
| ATOM | 459 | O | LYS | 56 | 40.057 | 13.582 | 108.382 | 1.00 40.00 |
| ATOM | 460 | N | THR | 57 | 42.138 | 13.618 | 109.273 | 1.00 20.00 |
| ATOM | 461 | CA | THR | 57 | 42.263 | 15.045 | 109.401 | 1.00 20.00 |
| ATOM | 462 | CB | THR | 57 | 43.574 | 15.452 | 110.004 | 1.00 20.00 |

Figure 6A-5

```
ATOM    463  OG1 THR    57      43.716  14.887 111.300  1.00 20.00
ATOM    464  CG2 THR    57      43.618  16.986 110.088  1.00 20.00
ATOM    465  C   THR    57      42.147  15.766 108.095  1.00 20.00
ATOM    466  O   THR    57      41.559  16.845 108.044  1.00 20.00
ATOM    467  N   ILE    58      42.691  15.207 107.001  1.00 20.00
ATOM    468  CA  ILE    58      42.752  15.953 105.774  1.00 20.00
ATOM    469  CB  ILE    58      43.416  15.202 104.651  1.00 20.00
ATOM    470  CG2 ILE    58      42.628  13.911 104.365  1.00 20.00
ATOM    471  CG1 ILE    58      43.605  16.125 103.437  1.00 20.00
ATOM    472  CD1 ILE    58      44.543  15.551 102.377  1.00 20.00
ATOM    473  C   ILE    58      41.407  16.442 105.323  1.00 20.00
ATOM    474  O   ILE    58      40.596  15.695 104.777  1.00 20.00
ATOM    475  N   GLN    59      41.124  17.731 105.614  1.00 20.00
ATOM    476  CA  GLN    59      39.940  18.413 105.171  1.00 20.00
ATOM    477  CB  GLN    59      39.586  19.650 106.016  1.00 20.00
ATOM    478  CG  GLN    59      39.114  19.318 107.433  1.00 20.00
ATOM    479  CD  GLN    59      38.798  20.630 108.139  1.00 20.00
ATOM    480  OE1 GLN    59      37.646  20.908 108.470  1.00 20.00
ATOM    481  NE2 GLN    59      39.846  21.464 108.372  1.00 20.00
ATOM    482  C   GLN    59      40.087  18.883 103.753  1.00 20.00
ATOM    483  O   GLN    59      39.119  18.885 102.994  1.00 20.00
ATOM    484  N   GLU    60      41.302  19.315 103.351  1.00 20.00
ATOM    485  CA  GLU    60      41.406  19.919 102.052  1.00 20.00
ATOM    486  CB  GLU    60      41.582  21.445 102.130  1.00 20.00
ATOM    487  CG  GLU    60      40.426  22.179 102.808  1.00 20.00
ATOM    488  CD  GLU    60      40.902  23.592 103.121  1.00 20.00
ATOM    489  OE1 GLU    60      42.013  23.957 102.650  1.00 20.00
ATOM    490  OE2 GLU    60      40.168  24.323 103.840  1.00 20.00
ATOM    491  C   GLU    60      42.625  19.426 101.339  1.00 20.00
ATOM    492  O   GLU    60      43.535  18.854 101.933  1.00 20.00
ATOM    493  N   VAL    61      42.623  19.617 100.003  1.00 20.00
ATOM    494  CA  VAL    61      43.739  19.371  99.139  1.00 20.00
ATOM    495  CB  VAL    61      43.618  18.104  98.346  1.00 20.00
ATOM    496  CG1 VAL    61      44.815  18.008  97.386  1.00 20.00
ATOM    497  CG2 VAL    61      43.510  16.923  99.326  1.00 20.00
ATOM    498  C   VAL    61      43.663  20.512  98.175  1.00 20.00
ATOM    499  O   VAL    61      42.629  20.706  97.541  1.00 20.00
ATOM    500  N   ALA    62      44.739  21.307  98.028  1.00 20.00
ATOM    501  CA  ALA    62      44.601  22.467  97.194  1.00 20.00
ATOM    502  CB  ALA    62      45.522  23.621  97.628  1.00 20.00
ATOM    503  C   ALA    62      44.949  22.139  95.778  1.00 20.00
ATOM    504  O   ALA    62      45.261  23.037  94.998  1.00 20.00
ATOM    505  N   GLY    63      44.913  20.849  95.400  1.00 20.00
ATOM    506  CA  GLY    63      45.218  20.512  94.039  1.00 20.00
ATOM    507  C   GLY    63      44.232  19.500  93.561  1.00 20.00
ATOM    508  O   GLY    63      43.030  19.748  93.502  1.00 20.00
ATOM    509  N   TYR    64      44.743  18.311  93.190  1.00 20.00
ATOM    510  CA  TYR    64      43.878  17.267  92.734  1.00 20.00
ATOM    511  CB  TYR    64      43.952  17.027  91.216  1.00 20.00
ATOM    512  CG  TYR    64      45.282  16.458  90.869  1.00 20.00
ATOM    513  CD1 TYR    64      46.437  17.086  91.257  1.00 20.00
ATOM    514  CD2 TYR    64      45.375  15.321  90.104  1.00 20.00
ATOM    515  CE1 TYR    64      47.666  16.569  90.923  1.00 20.00
ATOM    516  CE2 TYR    64      46.603  14.803  89.766  1.00 20.00
ATOM    517  CZ  TYR    64      47.754  15.422  90.178  1.00 20.00
ATOM    518  OH  TYR    64      49.014  14.890  89.831  1.00 20.00
ATOM    519  C   TYR    64      44.285  16.029  93.455  1.00 20.00
ATOM    520  O   TYR    64      45.341  15.991  94.083  1.00 20.00
ATOM    521  N   VAL    65      43.422  14.996  93.431  1.00 20.00
ATOM    522  CA  VAL    65      43.773  13.787  94.112  1.00 20.00
ATOM    523  CB  VAL    65      42.806  13.411  95.195  1.00 20.00
ATOM    524  CG1 VAL    65      41.422  13.221  94.564  1.00 20.00
ATOM    525  CG2 VAL    65      43.342  12.159  95.910  1.00 20.00
ATOM    526  C   VAL    65      43.821  12.671  93.113  1.00 20.00
ATOM    527  O   VAL    65      42.893  12.479  92.329  1.00 20.00
ATOM    528  N   LEU    66      44.934  11.906  93.110  1.00 20.00
ATOM    529  CA  LEU    66      45.043  10.791  92.210  1.00 20.00
ATOM    530  CB  LEU    66      46.320  10.774  91.355  1.00 20.00
ATOM    531  CG  LEU    66      46.450  11.929  90.359  1.00 20.00
ATOM    532  CD1 LEU    66      47.728  11.779  89.521  1.00 20.00
ATOM    533  CD2 LEU    66      45.187  12.092  89.499  1.00 20.00
ATOM    534  C   LEU    66      45.142   9.553  93.039  1.00 20.00
ATOM    535  O   LEU    66      45.964   9.471  93.951  1.00 20.00
ATOM    536  N   ILE    67      44.301   8.544  92.747  1.00 20.00
ATOM    537  CA  ILE    67      44.414   7.352  93.528  1.00 20.00
ATOM    538  CB  ILE    67      43.344   7.223  94.576  1.00 20.00
ATOM    539  CG2 ILE    67      41.980   7.108  93.873  1.00 20.00
```

Figure 6A-6

| | | | | | | | | |
|---|---|---|---|---|---|---|---|---|
| ATOM | 540 | CG1 | ILE | 67 | 43.670 | 6.062 | 95.530 | 1.00 20.00 |
| ATOM | 541 | CD1 | ILE | 67 | 42.805 | 6.050 | 96.789 | 1.00 20.00 |
| ATOM | 542 | C | ILE | 67 | 44.326 | 6.156 | 92.637 | 1.00 20.00 |
| ATOM | 543 | O | ILE | 67 | 43.429 | 6.036 | 91.805 | 1.00 20.00 |
| ATOM | 544 | N | ALA | 68 | 45.306 | 5.248 | 92.781 | 1.00 40.00 |
| ATOM | 545 | CA | ALA | 68 | 45.292 | 3.994 | 92.090 | 1.00 40.00 |
| ATOM | 546 | CB | ALA | 68 | 46.147 | 3.983 | 90.811 | 1.00 40.00 |
| ATOM | 547 | C | ALA | 68 | 45.906 | 3.023 | 93.057 | 1.00 40.00 |
| ATOM | 548 | O | ALA | 68 | 47.087 | 3.150 | 93.373 | 1.00 40.00 |
| ATOM | 549 | N | LEU | 69 | 45.135 | 2.029 | 93.551 | 1.00 40.00 |
| ATOM | 550 | CA | LEU | 69 | 45.680 | 1.141 | 94.543 | 1.00 40.00 |
| ATOM | 551 | CB | LEU | 69 | 45.501 | 1.657 | 95.981 | 1.00 40.00 |
| ATOM | 552 | CG | LEU | 69 | 46.280 | 2.945 | 96.317 | 1.00 40.00 |
| ATOM | 553 | CD1 | LEU | 69 | 46.035 | 3.378 | 97.774 | 1.00 40.00 |
| ATOM | 554 | CD2 | LEU | 69 | 47.775 | 2.793 | 96.000 | 1.00 40.00 |
| ATOM | 555 | C | LEU | 69 | 44.949 | -0.160 | 94.495 | 1.00 40.00 |
| ATOM | 556 | O | LEU | 69 | 44.091 | -0.387 | 93.643 | 1.00 40.00 |
| ATOM | 557 | N | ASN | 70 | 45.312 | -1.065 | 95.430 | 1.00 40.00 |
| ATOM | 558 | CA | ASN | 70 | 44.673 | -2.342 | 95.543 | 1.00 40.00 |
| ATOM | 559 | CB | ASN | 70 | 45.584 | -3.527 | 95.185 | 1.00 40.00 |
| ATOM | 560 | CG | ASN | 70 | 45.968 | -3.425 | 93.715 | 1.00 40.00 |
| ATOM | 561 | OD1 | ASN | 70 | 45.513 | -2.541 | 92.992 | 1.00 40.00 |
| ATOM | 562 | ND2 | ASN | 70 | 46.838 | -4.367 | 93.259 | 1.00 40.00 |
| ATOM | 563 | C | ASN | 70 | 44.318 | -2.510 | 96.984 | 1.00 40.00 |
| ATOM | 564 | O | ASN | 70 | 44.758 | -1.736 | 97.832 | 1.00 40.00 |
| ATOM | 565 | N | THR | 71 | 43.470 | -3.517 | 97.280 | 1.00 20.00 |
| ATOM | 566 | CA | THR | 71 | 43.052 | -3.866 | 98.612 | 1.00 20.00 |
| ATOM | 567 | CB | THR | 71 | 44.152 | -4.465 | 99.444 | 1.00 20.00 |
| ATOM | 568 | OG1 | THR | 71 | 45.227 | -3.551 | 99.595 | 1.00 20.00 |
| ATOM | 569 | CG2 | THR | 71 | 44.640 | -5.747 | 98.748 | 1.00 20.00 |
| ATOM | 570 | C | THR | 71 | 42.444 | -2.701 | 99.332 | 1.00 20.00 |
| ATOM | 571 | O | THR | 71 | 42.100 | -2.811 | 100.509 | 1.00 20.00 |
| ATOM | 572 | N | VAL | 72 | 42.258 | -1.558 | 98.649 | 1.00 20.00 |
| ATOM | 573 | CA | VAL | 72 | 41.644 | -0.442 | 99.303 | 1.00 20.00 |
| ATOM | 574 | CB | VAL | 72 | 42.202 | 0.880 | 98.865 | 1.00 20.00 |
| ATOM | 575 | CG1 | VAL | 72 | 41.433 | 2.002 | 99.581 | 1.00 20.00 |
| ATOM | 576 | CG2 | VAL | 72 | 43.713 | 0.883 | 99.152 | 1.00 20.00 |
| ATOM | 577 | C | VAL | 72 | 40.201 | -0.486 | 98.919 | 1.00 20.00 |
| ATOM | 578 | O | VAL | 72 | 39.857 | -0.358 | 97.746 | 1.00 20.00 |
| ATOM | 579 | N | GLU | 73 | 39.327 | -0.717 | 99.915 | 1.00 20.00 |
| ATOM | 580 | CA | GLU | 73 | 37.915 | -0.843 | 99.701 | 1.00 20.00 |
| ATOM | 581 | CB | GLU | 73 | 37.194 | -1.339 | 100.963 | 1.00 20.00 |
| ATOM | 582 | CG | GLU | 73 | 37.640 | -2.744 | 101.372 | 1.00 20.00 |
| ATOM | 583 | CD | GLU | 73 | 36.928 | -3.110 | 102.666 | 1.00 20.00 |
| ATOM | 584 | OE1 | GLU | 73 | 36.063 | -2.311 | 103.113 | 1.00 20.00 |
| ATOM | 585 | OE2 | GLU | 73 | 37.239 | -4.194 | 103.228 | 1.00 20.00 |
| ATOM | 586 | C | GLU | 73 | 37.316 | 0.470 | 99.306 | 1.00 20.00 |
| ATOM | 587 | O | GLU | 73 | 36.516 | 0.533 | 98.375 | 1.00 20.00 |
| ATOM | 588 | N | ARG | 74 | 37.683 | 1.567 | 99.997 | 1.00 20.00 |
| ATOM | 589 | CA | ARG | 74 | 37.070 | 2.827 | 99.685 | 1.00 20.00 |
| ATOM | 590 | CB | ARG | 74 | 35.789 | 3.070 | 100.496 | 1.00 20.00 |
| ATOM | 591 | CG | ARG | 74 | 36.045 | 3.117 | 102.003 | 1.00 20.00 |
| ATOM | 592 | CD | ARG | 74 | 34.812 | 2.787 | 102.845 | 1.00 20.00 |
| ATOM | 593 | NE | ARG | 74 | 34.771 | 1.303 | 102.979 | 1.00 20.00 |
| ATOM | 594 | CZ | ARG | 74 | 33.882 | 0.711 | 103.828 | 1.00 20.00 |
| ATOM | 595 | NH1 | ARG | 74 | 32.999 | 1.476 | 104.533 | 1.00 20.00 |
| ATOM | 596 | NH2 | ARG | 74 | 33.879 | -0.646 | 103.970 | 1.00 20.00 |
| ATOM | 597 | C | ARG | 74 | 38.041 | 3.891 | 100.057 | 1.00 20.00 |
| ATOM | 598 | O | ARG | 74 | 39.121 | 3.600 | 100.564 | 1.00 20.00 |
| ATOM | 599 | N | ILE | 75 | 37.703 | 5.166 | 99.786 | 1.00 20.00 |
| ATOM | 600 | CA | ILE | 75 | 38.585 | 6.208 | 100.225 | 1.00 20.00 |
| ATOM | 601 | CB | ILE | 75 | 39.043 | 7.136 | 99.134 | 1.00 20.00 |
| ATOM | 602 | CG2 | ILE | 75 | 37.817 | 7.775 | 98.460 | 1.00 20.00 |
| ATOM | 603 | CG1 | ILE | 75 | 40.071 | 8.131 | 99.702 | 1.00 20.00 |
| ATOM | 604 | CD1 | ILE | 75 | 40.836 | 8.911 | 98.634 | 1.00 20.00 |
| ATOM | 605 | C | ILE | 75 | 37.853 | 7.001 | 101.261 | 1.00 20.00 |
| ATOM | 606 | O | ILE | 75 | 37.671 | 8.211 | 101.160 | 1.00 20.00 |
| ATOM | 607 | N | PRO | 76 | 37.535 | 6.301 | 102.310 | 1.00 20.00 |
| ATOM | 608 | CA | PRO | 76 | 36.674 | 6.739 | 103.368 | 1.00 20.00 |
| ATOM | 609 | CD | PRO | 76 | 38.383 | 5.207 | 102.753 | 1.00 20.00 |
| ATOM | 610 | CB | PRO | 76 | 36.562 | 5.541 | 104.303 | 1.00 20.00 |
| ATOM | 611 | CG | PRO | 76 | 37.957 | 4.907 | 104.199 | 1.00 20.00 |
| ATOM | 612 | C | PRO | 76 | 37.213 | 7.895 | 104.144 | 1.00 20.00 |
| ATOM | 613 | O | PRO | 76 | 36.616 | 8.128 | 105.194 | 1.00 20.00 |
| ATOM | 614 | N | LEU | 77 | 38.343 | 8.534 | 103.731 | 1.00 20.00 |
| ATOM | 615 | CA | LEU | 77 | 38.864 | 9.725 | 104.379 | 1.00 20.00 |
| ATOM | 616 | CB | LEU | 77 | 39.775 | 10.571 | 103.467 | 1.00 20.00 |

Figure 6A-7

| | | | | | | | | |
|---|---|---|---|---|---|---|---|---|
| ATOM | 617 | CG | LEU | 77 | 41.107 | 9.897 | 103.114 | 1.00 20.00 |
| ATOM | 618 | CD1 | LEU | 77 | 41.968 | 10.791 | 102.207 | 1.00 20.00 |
| ATOM | 619 | CD2 | LEU | 77 | 41.848 | 9.468 | 104.385 | 1.00 20.00 |
| ATOM | 620 | C | LEU | 77 | 37.678 | 10.573 | 104.701 | 1.00 20.00 |
| ATOM | 621 | O | LEU | 77 | 37.135 | 11.270 | 103.847 | 1.00 20.00 |
| ATOM | 622 | N | GLU | 78 | 37.263 | 10.523 | 105.980 | 1.00 20.00 |
| ATOM | 623 | CA | GLU | 78 | 36.010 | 11.071 | 106.401 | 1.00 20.00 |
| ATOM | 624 | CB | GLU | 78 | 35.733 | 10.830 | 107.895 | 1.00 20.00 |
| ATOM | 625 | CG | GLU | 78 | 35.522 | 9.357 | 108.252 | 1.00 20.00 |
| ATOM | 626 | CD | GLU | 78 | 35.263 | 9.275 | 109.750 | 1.00 20.00 |
| ATOM | 627 | OE1 | GLU | 78 | 35.743 | 10.178 | 110.485 | 1.00 20.00 |
| ATOM | 628 | OE2 | GLU | 78 | 34.577 | 8.308 | 110.180 | 1.00 20.00 |
| ATOM | 629 | C | GLU | 78 | 35.939 | 12.545 | 106.181 | 1.00 20.00 |
| ATOM | 630 | O | GLU | 78 | 34.935 | 13.043 | 105.683 | 1.00 20.00 |
| ATOM | 631 | N | ASN | 79 | 37.005 | 13.274 | 106.548 | 1.00 20.00 |
| ATOM | 632 | CA | ASN | 79 | 37.018 | 14.711 | 106.554 | 1.00 20.00 |
| ATOM | 633 | CB | ASN | 79 | 38.156 | 15.300 | 107.401 | 1.00 20.00 |
| ATOM | 634 | CG | ASN | 79 | 37.761 | 15.120 | 108.858 | 1.00 20.00 |
| ATOM | 635 | OD1 | ASN | 79 | 37.588 | 14.003 | 109.343 | 1.00 20.00 |
| ATOM | 636 | ND2 | ASN | 79 | 37.601 | 16.260 | 109.581 | 1.00 20.00 |
| ATOM | 637 | C | ASN | 79 | 37.063 | 15.387 | 105.216 | 1.00 20.00 |
| ATOM | 638 | O | ASN | 79 | 36.550 | 16.500 | 105.119 | 1.00 20.00 |
| ATOM | 639 | N | LEU | 80 | 37.681 | 14.769 | 104.183 | 1.00 20.00 |
| ATOM | 640 | CA | LEU | 80 | 37.952 | 15.381 | 102.896 | 1.00 20.00 |
| ATOM | 641 | CB | LEU | 80 | 38.244 | 14.333 | 101.805 | 1.00 20.00 |
| ATOM | 642 | CG | LEU | 80 | 38.538 | 14.936 | 100.420 | 1.00 20.00 |
| ATOM | 643 | CD1 | LEU | 80 | 39.837 | 15.762 | 100.442 | 1.00 20.00 |
| ATOM | 644 | CD2 | LEU | 80 | 38.542 | 13.854 | 99.330 | 1.00 20.00 |
| ATOM | 645 | C | LEU | 80 | 36.792 | 16.221 | 102.430 | 1.00 20.00 |
| ATOM | 646 | O | LEU | 80 | 35.806 | 15.703 | 101.910 | 1.00 20.00 |
| ATOM | 647 | N | GLN | 81 | 36.880 | 17.544 | 102.714 | 1.00 20.00 |
| ATOM | 648 | CA | GLN | 81 | 35.908 | 18.567 | 102.408 | 1.00 20.00 |
| ATOM | 649 | CB | GLN | 81 | 36.105 | 19.797 | 103.309 | 1.00 20.00 |
| ATOM | 650 | CG | GLN | 81 | 36.195 | 19.478 | 104.804 | 1.00 20.00 |
| ATOM | 651 | CD | GLN | 81 | 34.852 | 18.957 | 105.288 | 1.00 20.00 |
| ATOM | 652 | OE1 | GLN | 81 | 34.703 | 18.599 | 106.455 | 1.00 20.00 |
| ATOM | 653 | NE2 | GLN | 81 | 33.847 | 18.914 | 104.373 | 1.00 20.00 |
| ATOM | 654 | C | GLN | 81 | 35.951 | 19.113 | 101.000 | 1.00 20.00 |
| ATOM | 655 | O | GLN | 81 | 34.917 | 19.216 | 100.342 | 1.00 20.00 |
| ATOM | 656 | N | ILE | 82 | 37.144 | 19.517 | 100.500 | 1.00 20.00 |
| ATOM | 657 | CA | ILE | 82 | 37.179 | 20.183 | 99.221 | 1.00 20.00 |
| ATOM | 658 | CB | ILE | 82 | 37.036 | 21.674 | 99.331 | 1.00 20.00 |
| ATOM | 659 | CG2 | ILE | 82 | 38.255 | 22.209 | 100.098 | 1.00 20.00 |
| ATOM | 660 | CG1 | ILE | 82 | 36.846 | 22.303 | 97.941 | 1.00 20.00 |
| ATOM | 661 | CD1 | ILE | 82 | 36.418 | 23.770 | 97.983 | 1.00 20.00 |
| ATOM | 662 | C | ILE | 82 | 38.488 | 19.931 | 98.535 | 1.00 20.00 |
| ATOM | 663 | O | ILE | 82 | 39.512 | 19.721 | 99.182 | 1.00 20.00 |
| ATOM | 664 | N | ILE | 83 | 38.463 | 19.933 | 97.183 | 1.00 20.00 |
| ATOM | 665 | CA | ILE | 83 | 39.639 | 19.776 | 96.369 | 1.00 20.00 |
| ATOM | 666 | CB | ILE | 83 | 39.580 | 18.550 | 95.503 | 1.00 20.00 |
| ATOM | 667 | CG2 | ILE | 83 | 40.815 | 18.541 | 94.587 | 1.00 20.00 |
| ATOM | 668 | CG1 | ILE | 83 | 39.446 | 17.289 | 96.373 | 1.00 20.00 |
| ATOM | 669 | CD1 | ILE | 83 | 39.047 | 16.047 | 95.580 | 1.00 20.00 |
| ATOM | 670 | C | ILE | 83 | 39.638 | 20.964 | 95.451 | 1.00 20.00 |
| ATOM | 671 | O | ILE | 83 | 38.949 | 20.969 | 94.436 | 1.00 20.00 |
| ATOM | 672 | N | ARG | 84 | 40.475 | 21.974 | 95.739 | 1.00 20.00 |
| ATOM | 673 | CA | ARG | 84 | 40.438 | 23.237 | 95.051 | 1.00 20.00 |
| ATOM | 674 | CB | ARG | 84 | 41.379 | 24.292 | 95.663 | 1.00 20.00 |
| ATOM | 675 | CG | ARG | 84 | 41.056 | 24.532 | 97.144 | 1.00 20.00 |
| ATOM | 676 | CD | ARG | 84 | 41.813 | 25.688 | 97.804 | 1.00 20.00 |
| ATOM | 677 | NE | ARG | 84 | 41.337 | 26.957 | 97.179 | 1.00 20.00 |
| ATOM | 678 | CZ | ARG | 84 | 40.267 | 27.637 | 97.693 | 1.00 20.00 |
| ATOM | 679 | NH1 | ARG | 84 | 39.610 | 27.185 | 98.804 | 1.00 20.00 |
| ATOM | 680 | NH2 | ARG | 84 | 39.851 | 28.788 | 97.090 | 1.00 20.00 |
| ATOM | 681 | C | ARG | 84 | 40.670 | 23.120 | 93.575 | 1.00 20.00 |
| ATOM | 682 | O | ARG | 84 | 40.120 | 23.909 | 92.809 | 1.00 20.00 |
| ATOM | 683 | N | GLY | 85 | 41.524 | 22.192 | 93.117 | 1.00 20.00 |
| ATOM | 684 | CA | GLY | 85 | 41.729 | 22.083 | 91.698 | 1.00 20.00 |
| ATOM | 685 | C | GLY | 85 | 42.603 | 23.201 | 91.212 | 1.00 20.00 |
| ATOM | 686 | O | GLY | 85 | 42.529 | 23.592 | 90.048 | 1.00 20.00 |
| ATOM | 687 | N | ASN | 86 | 43.476 | 23.734 | 92.087 | 1.00 20.00 |
| ATOM | 688 | CA | ASN | 86 | 44.351 | 24.804 | 91.696 | 1.00 20.00 |
| ATOM | 689 | CB | ASN | 86 | 45.378 | 25.141 | 92.790 | 1.00 20.00 |
| ATOM | 690 | CG | ASN | 86 | 46.262 | 26.275 | 92.294 | 1.00 20.00 |
| ATOM | 691 | OD1 | ASN | 86 | 45.903 | 26.998 | 91.366 | 1.00 20.00 |
| ATOM | 692 | ND2 | ASN | 86 | 47.457 | 26.429 | 92.924 | 1.00 20.00 |
| ATOM | 693 | C | ASN | 86 | 45.130 | 24.312 | 90.520 | 1.00 20.00 |

Figure 6A-8

| ATOM | 694 | O | ASN | 86 | 45.319 | 25.026 | 89.535 | 1.00 | 20.00 |
|------|-----|-----|-----|----|--------|--------|--------|------|-------|
| ATOM | 695 | N | MET | 87 | 45.617 | 23.064 | 90.609 | 1.00 | 20.00 |
| ATOM | 696 | CA | MET | 87 | 46.314 | 22.475 | 89.508 | 1.00 | 20.00 |
| ATOM | 697 | CB | MET | 87 | 47.798 | 22.195 | 89.796 | 1.00 | 20.00 |
| ATOM | 698 | CG | MET | 87 | 48.622 | 23.467 | 89.999 | 1.00 | 20.00 |
| ATOM | 699 | SD | MET | 87 | 50.375 | 23.181 | 90.389 | 1.00 | 20.00 |
| ATOM | 700 | CE | MET | 87 | 50.052 | 22.614 | 92.089 | 1.00 | 20.00 |
| ATOM | 701 | C | MET | 87 | 45.644 | 21.165 | 89.286 | 1.00 | 20.00 |
| ATOM | 702 | O | MET | 87 | 45.346 | 20.450 | 90.240 | 1.00 | 20.00 |
| ATOM | 703 | N | TYR | 88 | 45.386 | 20.807 | 88.016 | 1.00 | 20.00 |
| ATOM | 704 | CA | TYR | 88 | 44.662 | 19.593 | 87.805 | 1.00 | 20.00 |
| ATOM | 705 | CB | TYR | 88 | 43.276 | 19.806 | 87.169 | 1.00 | 20.00 |
| ATOM | 706 | CG | TYR | 88 | 43.437 | 20.643 | 85.946 | 1.00 | 20.00 |
| ATOM | 707 | CD1 | TYR | 88 | 43.781 | 20.077 | 84.712 | 1.00 | 20.00 |
| ATOM | 708 | CD2 | TYR | 88 | 43.258 | 22.005 | 86.011 | 1.00 | 20.00 |
| ATOM | 709 | CE1 | TYR | 88 | 43.928 | 20.850 | 83.615 | 1.00 | 20.00 |
| ATOM | 710 | CE2 | TYR | 88 | 43.403 | 22.787 | 84.868 | 1.00 | 20.00 |
| ATOM | 711 | CZ | TYR | 88 | 43.737 | 22.207 | 83.667 | 1.00 | 20.00 |
| ATOM | 712 | OH | TYR | 88 | 43.865 | 23.004 | 82.532 | 1.00 | 20.00 |
| ATOM | 713 | C | TYR | 88 | 45.425 | 18.639 | 86.950 | 1.00 | 20.00 |
| ATOM | 714 | O | TYR | 88 | 46.402 | 18.994 | 86.293 | 1.00 | 20.00 |
| ATOM | 715 | N | TYR | 89 | 44.984 | 17.364 | 86.998 | 1.00 | 20.00 |
| ATOM | 716 | CA | TYR | 89 | 45.547 | 16.309 | 86.214 | 1.00 | 20.00 |
| ATOM | 717 | CB | TYR | 89 | 44.896 | 14.946 | 86.509 | 1.00 | 20.00 |
| ATOM | 718 | CG | TYR | 89 | 45.687 | 13.873 | 85.844 | 1.00 | 20.00 |
| ATOM | 719 | CD1 | TYR | 89 | 46.827 | 13.387 | 86.441 | 1.00 | 20.00 |
| ATOM | 720 | CD2 | TYR | 89 | 45.290 | 13.343 | 84.638 | 1.00 | 20.00 |
| ATOM | 721 | CE1 | TYR | 89 | 47.566 | 12.394 | 85.844 | 1.00 | 20.00 |
| ATOM | 722 | CE2 | TYR | 89 | 46.025 | 12.348 | 84.036 | 1.00 | 20.00 |
| ATOM | 723 | CZ | TYR | 89 | 47.165 | 11.873 | 84.639 | 1.00 | 20.00 |
| ATOM | 724 | OH | TYR | 89 | 47.920 | 10.853 | 84.022 | 1.00 | 20.00 |
| ATOM | 725 | C | TYR | 89 | 45.244 | 16.696 | 84.806 | 1.00 | 20.00 |
| ATOM | 726 | O | TYR | 89 | 44.261 | 17.387 | 84.555 | 1.00 | 20.00 |
| ATOM | 727 | N | GLU | 90 | 46.051 | 16.198 | 83.856 | 1.00 | 20.00 |
| ATOM | 728 | CA | GLU | 90 | 46.054 | 16.661 | 82.499 | 1.00 | 20.00 |
| ATOM | 729 | CB | GLU | 90 | 46.848 | 15.747 | 81.554 | 1.00 | 20.00 |
| ATOM | 730 | CG | GLU | 90 | 47.131 | 16.399 | 80.202 | 1.00 | 20.00 |
| ATOM | 731 | CD | GLU | 90 | 48.086 | 17.557 | 80.456 | 1.00 | 20.00 |
| ATOM | 732 | OE1 | GLU | 90 | 48.382 | 17.828 | 81.651 | 1.00 | 20.00 |
| ATOM | 733 | OE2 | GLU | 90 | 48.535 | 18.189 | 79.462 | 1.00 | 20.00 |
| ATOM | 734 | C | GLU | 90 | 44.696 | 16.847 | 81.911 | 1.00 | 20.00 |
| ATOM | 735 | O | GLU | 90 | 44.369 | 17.952 | 81.480 | 1.00 | 20.00 |
| ATOM | 736 | N | ASN | 91 | 43.842 | 15.807 | 81.891 | 1.00 | 20.00 |
| ATOM | 737 | CA | ASN | 91 | 42.583 | 15.998 | 81.226 | 1.00 | 20.00 |
| ATOM | 738 | CB | ASN | 91 | 41.895 | 14.683 | 80.822 | 1.00 | 20.00 |
| ATOM | 739 | CG | ASN | 91 | 40.821 | 15.007 | 79.790 | 1.00 | 20.00 |
| ATOM | 740 | OD1 | ASN | 91 | 40.502 | 16.168 | 79.540 | 1.00 | 20.00 |
| ATOM | 741 | ND2 | ASN | 91 | 40.244 | 13.944 | 79.168 | 1.00 | 20.00 |
| ATOM | 742 | C | ASN | 91 | 41.654 | 16.782 | 82.103 | 1.00 | 20.00 |
| ATOM | 743 | O | ASN | 91 | 40.436 | 16.618 | 82.040 | 1.00 | 20.00 |
| ATOM | 744 | N | SER | 92 | 42.217 | 17.685 | 82.928 | 1.00 | 20.00 |
| ATOM | 745 | CA | SER | 92 | 41.458 | 18.550 | 83.771 | 1.00 | 20.00 |
| ATOM | 746 | CB | SER | 92 | 40.411 | 19.377 | 83.005 | 1.00 | 20.00 |
| ATOM | 747 | OG | SER | 92 | 41.053 | 20.266 | 82.105 | 1.00 | 20.00 |
| ATOM | 748 | C | SER | 92 | 40.740 | 17.743 | 84.795 | 1.00 | 20.00 |
| ATOM | 749 | O | SER | 92 | 39.548 | 17.946 | 85.011 | 1.00 | 20.00 |
| ATOM | 750 | N | TYR | 93 | 41.445 | 16.816 | 85.473 | 1.00 | 20.00 |
| ATOM | 751 | CA | TYR | 93 | 40.754 | 16.048 | 86.465 | 1.00 | 20.00 |
| ATOM | 752 | CB | TYR | 93 | 40.931 | 14.526 | 86.323 | 1.00 | 20.00 |
| ATOM | 753 | CG | TYR | 93 | 40.207 | 14.111 | 85.087 | 1.00 | 20.00 |
| ATOM | 754 | CD1 | TYR | 93 | 38.833 | 14.096 | 85.062 | 1.00 | 20.00 |
| ATOM | 755 | CD2 | TYR | 93 | 40.892 | 13.724 | 83.959 | 1.00 | 20.00 |
| ATOM | 756 | CE1 | TYR | 93 | 38.150 | 13.713 | 83.933 | 1.00 | 20.00 |
| ATOM | 757 | CE2 | TYR | 93 | 40.211 | 13.339 | 82.828 | 1.00 | 20.00 |
| ATOM | 758 | CZ | TYR | 93 | 38.839 | 13.335 | 82.808 | 1.00 | 20.00 |
| ATOM | 759 | OH | TYR | 93 | 38.146 | 12.941 | 81.645 | 1.00 | 20.00 |
| ATOM | 760 | C | TYR | 93 | 41.222 | 16.439 | 87.832 | 1.00 | 20.00 |
| ATOM | 761 | O | TYR | 93 | 42.414 | 16.457 | 88.129 | 1.00 | 20.00 |
| ATOM | 762 | N | ALA | 94 | 40.261 | 16.855 | 88.676 | 1.00 | 20.00 |
| ATOM | 763 | CA | ALA | 94 | 40.483 | 17.180 | 90.055 | 1.00 | 20.00 |
| ATOM | 764 | CB | ALA | 94 | 39.342 | 18.012 | 90.662 | 1.00 | 20.00 |
| ATOM | 765 | C | ALA | 94 | 40.581 | 15.919 | 90.851 | 1.00 | 20.00 |
| ATOM | 766 | O | ALA | 94 | 41.329 | 15.847 | 91.824 | 1.00 | 20.00 |
| ATOM | 767 | N | LEU | 95 | 39.774 | 14.906 | 90.473 | 1.00 | 20.00 |
| ATOM | 768 | CA | LEU | 95 | 39.719 | 13.653 | 91.173 | 1.00 | 20.00 |
| ATOM | 769 | CB | LEU | 95 | 38.354 | 13.459 | 91.861 | 1.00 | 20.00 |
| ATOM | 770 | CG | LEU | 95 | 38.094 | 12.070 | 92.472 | 1.00 | 20.00 |

Figure 6A-9

| | | | | | | | | |
|---|---|---|---|---|---|---|---|---|
| ATOM | 771 | CD1 | LEU | 95 | 39.069 | 11.743 | 93.609 | 1.00 20.00 |
| ATOM | 772 | CD2 | LEU | 95 | 36.623 | 11.933 | 92.905 | 1.00 20.00 |
| ATOM | 773 | C | LEU | 95 | 39.870 | 12.559 | 90.167 | 1.00 20.00 |
| ATOM | 774 | O | LEU | 95 | 38.961 | 12.291 | 89.383 | 1.00 20.00 |
| ATOM | 775 | N | ALA | 96 | 41.031 | 11.882 | 90.164 | 1.00 20.00 |
| ATOM | 776 | CA | ALA | 96 | 41.200 | 10.812 | 89.228 | 1.00 20.00 |
| ATOM | 777 | CB | ALA | 96 | 42.470 | 10.941 | 88.368 | 1.00 20.00 |
| ATOM | 778 | C | ALA | 96 | 41.329 | 9.551 | 90.013 | 1.00 20.00 |
| ATOM | 779 | O | ALA | 96 | 42.199 | 9.438 | 90.874 | 1.00 20.00 |
| ATOM | 780 | N | VAL | 97 | 40.424 | 8.584 | 89.761 | 1.00 20.00 |
| ATOM | 781 | CA | VAL | 97 | 40.531 | 7.299 | 90.381 | 1.00 20.00 |
| ATOM | 782 | CB | VAL | 97 | 39.363 | 6.955 | 91.271 | 1.00 20.00 |
| ATOM | 783 | CG1 | VAL | 97 | 39.424 | 7.874 | 92.503 | 1.00 20.00 |
| ATOM | 784 | CG2 | VAL | 97 | 38.046 | 7.115 | 90.490 | 1.00 20.00 |
| ATOM | 785 | C | VAL | 97 | 40.626 | 6.319 | 89.253 | 1.00 20.00 |
| ATOM | 786 | O | VAL | 97 | 39.652 | 6.044 | 88.555 | 1.00 20.00 |
| ATOM | 787 | N | LEU | 98 | 41.820 | 5.743 | 89.036 | 1.00 20.00 |
| ATOM | 788 | CA | LEU | 98 | 41.928 | 4.905 | 87.883 | 1.00 20.00 |
| ATOM | 789 | CB | LEU | 98 | 42.951 | 5.434 | 86.864 | 1.00 20.00 |
| ATOM | 790 | CG | LEU | 98 | 42.656 | 6.870 | 86.390 | 1.00 20.00 |
| ATOM | 791 | CD1 | LEU | 98 | 43.675 | 7.332 | 85.335 | 1.00 20.00 |
| ATOM | 792 | CD2 | LEU | 98 | 41.199 | 7.031 | 85.934 | 1.00 20.00 |
| ATOM | 793 | C | LEU | 98 | 42.392 | 3.552 | 88.296 | 1.00 20.00 |
| ATOM | 794 | O | LEU | 98 | 43.270 | 3.424 | 89.148 | 1.00 20.00 |
| ATOM | 795 | N | SER | 99 | 41.794 | 2.516 | 87.669 | 1.00 20.00 |
| ATOM | 796 | CA | SER | 99 | 42.134 | 1.136 | 87.873 | 1.00 20.00 |
| ATOM | 797 | CB | SER | 99 | 43.417 | 0.713 | 87.138 | 1.00 20.00 |
| ATOM | 798 | OG | SER | 99 | 43.242 | 0.839 | 85.735 | 1.00 20.00 |
| ATOM | 799 | C | SER | 99 | 42.335 | 0.871 | 89.327 | 1.00 20.00 |
| ATOM | 800 | O | SER | 99 | 43.443 | 0.555 | 89.755 | 1.00 20.00 |
| ATOM | 801 | N | ASN | 100 | 41.270 | 1.019 | 90.134 | 1.00 40.00 |
| ATOM | 802 | CA | ASN | 100 | 41.424 | 0.743 | 91.529 | 1.00 40.00 |
| ATOM | 803 | CB | ASN | 100 | 40.691 | 1.735 | 92.448 | 1.00 40.00 |
| ATOM | 804 | CG | ASN | 100 | 41.518 | 3.011 | 92.524 | 1.00 40.00 |
| ATOM | 805 | OD1 | ASN | 100 | 41.325 | 3.950 | 91.753 | 1.00 40.00 |
| ATOM | 806 | ND2 | ASN | 100 | 42.469 | 3.050 | 93.495 | 1.00 40.00 |
| ATOM | 807 | C | ASN | 100 | 40.850 | -0.608 | 91.768 | 1.00 40.00 |
| ATOM | 808 | O | ASN | 100 | 39.636 | -0.793 | 91.798 | 1.00 40.00 |
| ATOM | 809 | N | TYR | 101 | 41.744 | -1.602 | 91.912 | 1.00 40.00 |
| ATOM | 810 | CA | TYR | 101 | 41.306 | -2.957 | 92.024 | 1.00 40.00 |
| ATOM | 811 | CB | TYR | 101 | 41.928 | -3.882 | 90.963 | 1.00 40.00 |
| ATOM | 812 | CG | TYR | 101 | 41.573 | -3.386 | 89.604 | 1.00 40.00 |
| ATOM | 813 | CD1 | TYR | 101 | 42.196 | -2.271 | 89.092 | 1.00 40.00 |
| ATOM | 814 | CD2 | TYR | 101 | 40.643 | -4.043 | 88.832 | 1.00 40.00 |
| ATOM | 815 | CE1 | TYR | 101 | 41.885 | -1.805 | 87.837 | 1.00 40.00 |
| ATOM | 816 | CE2 | TYR | 101 | 40.330 | -3.583 | 87.574 | 1.00 40.00 |
| ATOM | 817 | CZ | TYR | 101 | 40.949 | -2.462 | 87.076 | 1.00 40.00 |
| ATOM | 818 | OH | TYR | 101 | 40.628 | -1.989 | 85.786 | 1.00 40.00 |
| ATOM | 819 | C | TYR | 101 | 41.795 | -3.497 | 93.322 | 1.00 40.00 |
| ATOM | 820 | O | TYR | 101 | 42.252 | -2.770 | 94.202 | 1.00 40.00 |
| ATOM | 821 | N | ASP | 102 | 41.681 | -4.830 | 93.440 | 1.00 60.00 |
| ATOM | 822 | CA | ASP | 102 | 42.123 | -5.594 | 94.562 | 1.00 60.00 |
| ATOM | 823 | CB | ASP | 102 | 40.964 | -6.200 | 95.376 | 1.00 60.00 |
| ATOM | 824 | CG | ASP | 102 | 41.496 | -6.734 | 96.697 | 1.00 60.00 |
| ATOM | 825 | OD1 | ASP | 102 | 42.710 | -6.541 | 96.970 | 1.00 60.00 |
| ATOM | 826 | OD2 | ASP | 102 | 40.693 | -7.345 | 97.452 | 1.00 60.00 |
| ATOM | 827 | C | ASP | 102 | 42.861 | -6.724 | 93.928 | 1.00 60.00 |
| ATOM | 828 | O | ASP | 102 | 43.134 | -6.686 | 92.729 | 1.00 60.00 |
| ATOM | 829 | N | ALA | 103 | 43.225 | -7.756 | 94.709 | 1.00 60.00 |
| ATOM | 830 | CA | ALA | 103 | 43.893 | -8.865 | 94.104 | 1.00 60.00 |
| ATOM | 831 | CB | ALA | 103 | 44.202 | -9.996 | 95.099 | 1.00 60.00 |
| ATOM | 832 | C | ALA | 103 | 42.923 | -9.393 | 93.102 | 1.00 60.00 |
| ATOM | 833 | O | ALA | 103 | 43.286 | -9.729 | 91.976 | 1.00 60.00 |
| ATOM | 834 | N | ASN | 104 | 41.641 | -9.448 | 93.502 | 1.00 60.00 |
| ATOM | 835 | CA | ASN | 104 | 40.604 | -9.896 | 92.625 | 1.00 60.00 |
| ATOM | 836 | CB | ASN | 104 | 39.414 | -10.537 | 93.359 | 1.00 60.00 |
| ATOM | 837 | CG | ASN | 104 | 39.898 | -11.855 | 93.949 | 1.00 60.00 |
| ATOM | 838 | OD1 | ASN | 104 | 40.883 | -12.429 | 93.485 | 1.00 60.00 |
| ATOM | 839 | ND2 | ASN | 104 | 39.189 | -12.352 | 94.997 | 1.00 60.00 |
| ATOM | 840 | C | ASN | 104 | 40.102 | -8.702 | 91.880 | 1.00 60.00 |
| ATOM | 841 | O | ASN | 104 | 40.658 | -7.610 | 91.981 | 1.00 60.00 |
| ATOM | 842 | N | LYS | 105 | 39.031 | -8.901 | 91.090 | 1.00 60.00 |
| ATOM | 843 | CA | LYS | 105 | 38.458 | -7.851 | 90.301 | 1.00 60.00 |
| ATOM | 844 | CB | LYS | 105 | 37.253 | -8.323 | 89.471 | 1.00 60.00 |
| ATOM | 845 | CG | LYS | 105 | 37.606 | -9.373 | 88.415 | 1.00 60.00 |
| ATOM | 846 | CD | LYS | 105 | 38.031 | -10.717 | 89.010 | 1.00 60.00 |
| ATOM | 847 | CE | LYS | 105 | 38.386 | -11.771 | 87.958 | 1.00 60.00 |

Figure 6A-10

| | | | | | | | | |
|---|---|---|---|---|---|---|---|---|
| ATOM | 848 | NZ | LYS | 105 | 37.175 | -12.149 | 87.195 | 1.00 60.00 |
| ATOM | 849 | C | LYS | 105 | 37.972 | -6.794 | 91.237 | 1.00 60.00 |
| ATOM | 850 | O | LYS | 105 | 38.074 | -5.601 | 90.953 | 1.00 60.00 |
| ATOM | 851 | N | THR | 106 | 37.438 | -7.217 | 92.397 | 1.00 60.00 |
| ATOM | 852 | CA | THR | 106 | 36.902 | -6.318 | 93.378 | 1.00 60.00 |
| ATOM | 853 | CB | THR | 106 | 36.226 | -7.076 | 94.496 | 1.00 60.00 |
| ATOM | 854 | OG1 | THR | 106 | 35.283 | -7.980 | 93.939 | 1.00 60.00 |
| ATOM | 855 | CG2 | THR | 106 | 35.461 | -6.112 | 95.423 | 1.00 60.00 |
| ATOM | 856 | C | THR | 106 | 38.064 | -5.520 | 93.910 | 1.00 60.00 |
| ATOM | 857 | O | THR | 106 | 39.174 | -5.602 | 93.387 | 1.00 60.00 |
| ATOM | 858 | N | GLY | 107 | 37.841 | -4.704 | 94.959 | 1.00 60.00 |
| ATOM | 859 | CA | GLY | 107 | 38.890 | -3.902 | 95.515 | 1.00 60.00 |
| ATOM | 860 | C | GLY | 107 | 38.297 | -2.600 | 95.946 | 1.00 60.00 |
| ATOM | 861 | O | GLY | 107 | 38.185 | -2.344 | 97.144 | 1.00 60.00 |
| ATOM | 862 | N | LEU | 108 | 37.892 | -1.730 | 95.002 | 1.00 20.00 |
| ATOM | 863 | CA | LEU | 108 | 37.286 | -0.514 | 95.481 | 1.00 20.00 |
| ATOM | 864 | CB | LEU | 108 | 37.761 | 0.736 | 94.725 | 1.00 20.00 |
| ATOM | 865 | CG | LEU | 108 | 37.132 | 2.051 | 95.223 | 1.00 20.00 |
| ATOM | 866 | CD1 | LEU | 108 | 37.587 | 2.382 | 96.651 | 1.00 20.00 |
| ATOM | 867 | CD2 | LEU | 108 | 37.392 | 3.199 | 94.236 | 1.00 20.00 |
| ATOM | 868 | C | LEU | 108 | 35.808 | -0.622 | 95.296 | 1.00 20.00 |
| ATOM | 869 | O | LEU | 108 | 35.310 | -0.562 | 94.175 | 1.00 20.00 |
| ATOM | 870 | N | LYS | 109 | 35.080 | -0.834 | 96.407 | 1.00 20.00 |
| ATOM | 871 | CA | LYS | 109 | 33.652 | -0.972 | 96.422 | 1.00 20.00 |
| ATOM | 872 | CB | LYS | 109 | 33.177 | -1.588 | 97.746 | 1.00 20.00 |
| ATOM | 873 | CG | LYS | 109 | 33.781 | -2.980 | 97.942 | 1.00 20.00 |
| ATOM | 874 | CD | LYS | 109 | 33.705 | -3.514 | 99.371 | 1.00 20.00 |
| ATOM | 875 | CE | LYS | 109 | 34.435 | -4.847 | 99.554 | 1.00 20.00 |
| ATOM | 876 | NZ | LYS | 109 | 35.900 | -4.636 | 99.510 | 1.00 20.00 |
| ATOM | 877 | C | LYS | 109 | 32.969 | 0.346 | 96.216 | 1.00 20.00 |
| ATOM | 878 | O | LYS | 109 | 31.967 | 0.426 | 95.508 | 1.00 20.00 |
| ATOM | 879 | N | GLU | 110 | 33.479 | 1.425 | 96.838 | 1.00 20.00 |
| ATOM | 880 | CA | GLU | 110 | 32.817 | 2.691 | 96.712 | 1.00 20.00 |
| ATOM | 881 | CB | GLU | 110 | 31.570 | 2.777 | 97.609 | 1.00 20.00 |
| ATOM | 882 | CG | GLU | 110 | 31.790 | 2.191 | 99.006 | 1.00 20.00 |
| ATOM | 883 | CD | GLU | 110 | 30.514 | 2.388 | 99.813 | 1.00 20.00 |
| ATOM | 884 | OE1 | GLU | 110 | 29.628 | 3.150 | 99.342 | 1.00 20.00 |
| ATOM | 885 | OE2 | GLU | 110 | 30.409 | 1.781 | 100.912 | 1.00 20.00 |
| ATOM | 886 | C | GLU | 110 | 33.783 | 3.774 | 97.071 | 1.00 20.00 |
| ATOM | 887 | O | GLU | 110 | 34.925 | 3.502 | 97.431 | 1.00 20.00 |
| ATOM | 888 | N | LEU | 111 | 33.352 | 5.041 | 96.877 | 1.00 20.00 |
| ATOM | 889 | CA | LEU | 111 | 34.081 | 6.238 | 97.206 | 1.00 20.00 |
| ATOM | 890 | CB | LEU | 111 | 33.635 | 7.452 | 96.373 | 1.00 20.00 |
| ATOM | 891 | CG | LEU | 111 | 33.957 | 7.309 | 94.874 | 1.00 20.00 |
| ATOM | 892 | CD1 | LEU | 111 | 33.534 | 8.562 | 94.088 | 1.00 20.00 |
| ATOM | 893 | CD2 | LEU | 111 | 35.433 | 6.938 | 94.658 | 1.00 20.00 |
| ATOM | 894 | C | LEU | 111 | 34.016 | 6.650 | 98.671 | 1.00 20.00 |
| ATOM | 895 | O | LEU | 111 | 35.004 | 7.215 | 99.134 | 1.00 20.00 |
| ATOM | 896 | N | PRO | 112 | 32.985 | 6.311 | 99.441 | 1.00 20.00 |
| ATOM | 897 | CA | PRO | 112 | 32.657 | 7.027 | 100.668 | 1.00 20.00 |
| ATOM | 898 | CD | PRO | 112 | 32.920 | 4.888 | 99.729 | 1.00 20.00 |
| ATOM | 899 | CB | PRO | 112 | 32.502 | 6.009 | 101.799 | 1.00 20.00 |
| ATOM | 900 | CG | PRO | 112 | 33.114 | 4.728 | 101.239 | 1.00 20.00 |
| ATOM | 901 | C | PRO | 112 | 33.422 | 8.238 | 101.103 | 1.00 20.00 |
| ATOM | 902 | O | PRO | 112 | 33.888 | 8.320 | 102.236 | 1.00 20.00 |
| ATOM | 903 | N | MET | 113 | 33.441 | 9.227 | 100.204 | 1.00 20.00 |
| ATOM | 904 | CA | MET | 113 | 33.992 | 10.547 | 100.278 | 1.00 20.00 |
| ATOM | 905 | CB | MET | 113 | 34.370 | 11.152 | 98.914 | 1.00 20.00 |
| ATOM | 906 | CG | MET | 113 | 35.593 | 10.495 | 98.271 | 1.00 20.00 |
| ATOM | 907 | SD | MET | 113 | 36.060 | 11.195 | 96.659 | 1.00 20.00 |
| ATOM | 908 | CE | MET | 113 | 37.578 | 10.213 | 96.488 | 1.00 20.00 |
| ATOM | 909 | C | MET | 113 | 32.967 | 11.442 | 100.897 | 1.00 20.00 |
| ATOM | 910 | O | MET | 113 | 32.986 | 12.634 | 100.634 | 1.00 20.00 |
| ATOM | 911 | N | ARG | 114 | 32.006 | 10.898 | 101.670 | 1.00 20.00 |
| ATOM | 912 | CA | ARG | 114 | 30.791 | 11.572 | 102.067 | 1.00 20.00 |
| ATOM | 913 | CB | ARG | 114 | 30.082 | 10.907 | 103.264 | 1.00 20.00 |
| ATOM | 914 | CG | ARG | 114 | 30.878 | 10.927 | 104.569 | 1.00 20.00 |
| ATOM | 915 | CD | ARG | 114 | 30.118 | 10.306 | 105.744 | 1.00 20.00 |
| ATOM | 916 | NE | ARG | 114 | 28.888 | 11.122 | 105.958 | 1.00 20.00 |
| ATOM | 917 | CZ | ARG | 114 | 28.896 | 12.171 | 106.832 | 1.00 20.00 |
| ATOM | 918 | NH1 | ARG | 114 | 30.027 | 12.467 | 107.538 | 1.00 20.00 |
| ATOM | 919 | NH2 | ARG | 114 | 27.770 | 12.923 | 107.000 | 1.00 20.00 |
| ATOM | 920 | C | ARG | 114 | 30.943 | 13.031 | 102.415 | 1.00 20.00 |
| ATOM | 921 | O | ARG | 114 | 30.010 | 13.792 | 102.177 | 1.00 20.00 |
| ATOM | 922 | N | ASN | 115 | 32.050 | 13.477 | 103.024 | 1.00 20.00 |
| ATOM | 923 | CA | ASN | 115 | 32.208 | 14.868 | 103.374 | 1.00 20.00 |
| ATOM | 924 | CB | ASN | 115 | 33.263 | 15.108 | 104.462 | 1.00 20.00 |

Figure 6A-11

| | | | | | | | | |
|---|---|---|---|---|---|---|---|---|
| ATOM | 925 | CG | ASN | 115 | 32.622 | 14.667 | 105.771 | 1.00 20.00 |
| ATOM | 926 | OD1 | ASN | 115 | 31.474 | 14.228 | 105.797 | 1.00 20.00 |
| ATOM | 927 | ND2 | ASN | 115 | 33.369 | 14.812 | 106.896 | 1.00 20.00 |
| ATOM | 928 | C | ASN | 115 | 32.512 | 15.762 | 102.193 | 1.00 20.00 |
| ATOM | 929 | O | ASN | 115 | 32.475 | 16.985 | 102.326 | 1.00 20.00 |
| ATOM | 930 | N | LEU | 116 | 32.874 | 15.197 | 101.027 | 1.00 20.00 |
| ATOM | 931 | CA | LEU | 116 | 33.324 | 15.949 | 99.887 | 1.00 20.00 |
| ATOM | 932 | CB | LEU | 116 | 33.891 | 15.048 | 98.774 | 1.00 20.00 |
| ATOM | 933 | CG | LEU | 116 | 34.406 | 15.807 | 97.541 | 1.00 20.00 |
| ATOM | 934 | CD1 | LEU | 116 | 35.587 | 16.720 | 97.907 | 1.00 20.00 |
| ATOM | 935 | CD2 | LEU | 116 | 34.751 | 14.836 | 96.401 | 1.00 20.00 |
| ATOM | 936 | C | LEU | 116 | 32.208 | 16.778 | 99.318 | 1.00 20.00 |
| ATOM | 937 | O | LEU | 116 | 31.331 | 16.276 | 98.617 | 1.00 20.00 |
| ATOM | 938 | N | GLN | 117 | 32.201 | 18.074 | 99.699 | 1.00 20.00 |
| ATOM | 939 | CA | GLN | 117 | 31.258 | 19.080 | 99.298 | 1.00 20.00 |
| ATOM | 940 | CB | GLN | 117 | 31.161 | 20.221 | 100.327 | 1.00 20.00 |
| ATOM | 941 | CG | GLN | 117 | 30.430 | 19.854 | 101.620 | 1.00 20.00 |
| ATOM | 942 | CD | GLN | 117 | 28.941 | 20.045 | 101.368 | 1.00 20.00 |
| ATOM | 943 | OE1 | GLN | 117 | 28.107 | 19.776 | 102.231 | 1.00 20.00 |
| ATOM | 944 | NE2 | GLN | 117 | 28.594 | 20.532 | 100.146 | 1.00 20.00 |
| ATOM | 945 | C | GLN | 117 | 31.549 | 19.738 | 97.980 | 1.00 20.00 |
| ATOM | 946 | O | GLN | 117 | 30.616 | 20.069 | 97.255 | 1.00 20.00 |
| ATOM | 947 | N | GLU | 118 | 32.825 | 20.024 | 97.640 | 1.00 20.00 |
| ATOM | 948 | CA | GLU | 118 | 32.991 | 20.755 | 96.414 | 1.00 20.00 |
| ATOM | 949 | CB | GLU | 118 | 32.814 | 22.274 | 96.583 | 1.00 20.00 |
| ATOM | 950 | CG | GLU | 118 | 31.386 | 22.711 | 96.912 | 1.00 20.00 |
| ATOM | 951 | CD | GLU | 118 | 31.397 | 24.228 | 97.045 | 1.00 20.00 |
| ATOM | 952 | OE1 | GLU | 118 | 32.502 | 24.820 | 96.919 | 1.00 20.00 |
| ATOM | 953 | OE2 | GLU | 118 | 30.306 | 24.815 | 97.280 | 1.00 20.00 |
| ATOM | 954 | C | GLU | 118 | 34.359 | 20.564 | 95.847 | 1.00 20.00 |
| ATOM | 955 | O | GLU | 118 | 35.346 | 20.459 | 96.573 | 1.00 20.00 |
| ATOM | 956 | N | ILE | 119 | 34.430 | 20.506 | 94.501 | 1.00 20.00 |
| ATOM | 957 | CA | ILE | 119 | 35.680 | 20.480 | 93.804 | 1.00 20.00 |
| ATOM | 958 | CB | ILE | 119 | 35.809 | 19.351 | 92.818 | 1.00 20.00 |
| ATOM | 959 | CG2 | ILE | 119 | 37.074 | 19.581 | 91.976 | 1.00 20.00 |
| ATOM | 960 | CG1 | ILE | 119 | 35.802 | 18.001 | 93.555 | 1.00 20.00 |
| ATOM | 961 | CD1 | ILE | 119 | 35.706 | 16.791 | 92.626 | 1.00 20.00 |
| ATOM | 962 | C | ILE | 119 | 35.709 | 21.770 | 93.052 | 1.00 20.00 |
| ATOM | 963 | O | ILE | 119 | 35.224 | 21.861 | 91.926 | 1.00 20.00 |
| ATOM | 964 | N | LEU | 120 | 36.396 | 22.773 | 93.625 | 1.00 20.00 |
| ATOM | 965 | CA | LEU | 120 | 36.373 | 24.132 | 93.162 | 1.00 20.00 |
| ATOM | 966 | CB | LEU | 120 | 37.433 | 25.005 | 93.855 | 1.00 20.00 |
| ATOM | 967 | CG | LEU | 120 | 37.439 | 26.469 | 93.379 | 1.00 20.00 |
| ATOM | 968 | CD1 | LEU | 120 | 36.125 | 27.179 | 93.746 | 1.00 20.00 |
| ATOM | 969 | CD2 | LEU | 120 | 38.685 | 27.215 | 93.877 | 1.00 20.00 |
| ATOM | 970 | C | LEU | 120 | 36.652 | 24.185 | 91.695 | 1.00 20.00 |
| ATOM | 971 | O | LEU | 120 | 36.082 | 25.024 | 90.999 | 1.00 20.00 |
| ATOM | 972 | N | HIS | 121 | 37.550 | 23.334 | 91.164 | 1.00 20.00 |
| ATOM | 973 | CA | HIS | 121 | 37.743 | 23.442 | 89.747 | 1.00 20.00 |
| ATOM | 974 | ND1 | HIS | 121 | 37.979 | 25.853 | 87.395 | 1.00 20.00 |
| ATOM | 975 | NE2 | HIS | 121 | 39.013 | 24.938 | 85.652 | 1.00 20.00 |
| ATOM | 976 | CE1 | HIS | 121 | 38.173 | 25.875 | 86.053 | 1.00 20.00 |
| ATOM | 977 | CD2 | HIS | 121 | 39.379 | 24.279 | 86.812 | 1.00 20.00 |
| ATOM | 978 | CG | HIS | 121 | 38.754 | 24.827 | 87.891 | 1.00 20.00 |
| ATOM | 979 | CB | HIS | 121 | 38.820 | 24.461 | 89.344 | 1.00 20.00 |
| ATOM | 980 | C | HIS | 121 | 38.157 | 22.111 | 89.206 | 1.00 20.00 |
| ATOM | 981 | O | HIS | 121 | 38.717 | 21.281 | 89.920 | 1.00 20.00 |
| ATOM | 982 | N | GLY | 122 | 37.876 | 21.878 | 87.907 | 1.00 20.00 |
| ATOM | 983 | CA | GLY | 122 | 38.266 | 20.659 | 87.263 | 1.00 20.00 |
| ATOM | 984 | C | GLY | 122 | 37.146 | 19.672 | 87.386 | 1.00 20.00 |
| ATOM | 985 | O | GLY | 122 | 36.209 | 19.872 | 88.158 | 1.00 20.00 |
| ATOM | 986 | N | ALA | 123 | 37.239 | 18.576 | 86.599 | 1.00 20.00 |
| ATOM | 987 | CA | ALA | 123 | 36.262 | 17.523 | 86.553 | 1.00 20.00 |
| ATOM | 988 | CB | ALA | 123 | 35.947 | 17.049 | 85.122 | 1.00 20.00 |
| ATOM | 989 | C | ALA | 123 | 36.781 | 16.328 | 87.296 | 1.00 20.00 |
| ATOM | 990 | O | ALA | 123 | 37.767 | 16.415 | 88.023 | 1.00 20.00 |
| ATOM | 991 | N | VAL | 124 | 36.091 | 15.174 | 87.150 | 1.00 20.00 |
| ATOM | 992 | CA | VAL | 124 | 36.495 | 13.953 | 87.799 | 1.00 20.00 |
| ATOM | 993 | CB | VAL | 124 | 35.513 | 13.479 | 88.830 | 1.00 20.00 |
| ATOM | 994 | CG1 | VAL | 124 | 36.036 | 12.172 | 89.447 | 1.00 20.00 |
| ATOM | 995 | CG2 | VAL | 124 | 35.297 | 14.606 | 89.854 | 1.00 20.00 |
| ATOM | 996 | C | VAL | 124 | 36.598 | 12.871 | 86.761 | 1.00 20.00 |
| ATOM | 997 | O | VAL | 124 | 35.978 | 12.958 | 85.704 | 1.00 20.00 |
| ATOM | 998 | N | ARG | 125 | 37.431 | 11.834 | 87.011 | 1.00 20.00 |
| ATOM | 999 | CA | ARG | 125 | 37.499 | 10.738 | 86.083 | 1.00 20.00 |
| ATOM | 1000 | CB | ARG | 125 | 38.785 | 10.700 | 85.246 | 1.00 20.00 |
| ATOM | 1001 | CG | ARG | 125 | 38.867 | 9.479 | 84.329 | 1.00 20.00 |

Figure 6A-12

| | | | | | | | | |
|---|---|---|---|---|---|---|---|---|
| ATOM | 1002 | CD | ARG | 125 | 39.979 | 9.589 | 83.289 | 1.00 20.00 |
| ATOM | 1003 | NE | ARG | 125 | 41.137 | 10.238 | 83.961 | 1.00 20.00 |
| ATOM | 1004 | CZ | ARG | 125 | 42.061 | 10.906 | 83.213 | 1.00 20.00 |
| ATOM | 1005 | NH1 | ARG | 125 | 41.961 | 10.909 | 81.852 | 1.00 20.00 |
| ATOM | 1006 | NH2 | ARG | 125 | 43.075 | 11.584 | 83.824 | 1.00 20.00 |
| ATOM | 1007 | C | ARG | 125 | 37.433 | 9.452 | 86.847 | 1.00 20.00 |
| ATOM | 1008 | O | ARG | 125 | 38.360 | 9.097 | 87.572 | 1.00 20.00 |
| ATOM | 1009 | N | PHE | 126 | 36.329 | 8.698 | 86.690 | 1.00 20.00 |
| ATOM | 1010 | CA | PHE | 126 | 36.228 | 7.446 | 87.385 | 1.00 20.00 |
| ATOM | 1011 | CB | PHE | 126 | 34.851 | 7.195 | 88.031 | 1.00 20.00 |
| ATOM | 1012 | CG | PHE | 126 | 34.507 | 8.261 | 89.012 | 1.00 20.00 |
| ATOM | 1013 | CD1 | PHE | 126 | 34.990 | 8.228 | 90.299 | 1.00 20.00 |
| ATOM | 1014 | CD2 | PHE | 126 | 33.671 | 9.287 | 88.639 | 1.00 20.00 |
| ATOM | 1015 | CE1 | PHE | 126 | 34.653 | 9.216 | 91.194 | 1.00 20.00 |
| ATOM | 1016 | CE2 | PHE | 126 | 33.330 | 10.277 | 89.530 | 1.00 20.00 |
| ATOM | 1017 | CZ | PHE | 126 | 33.824 | 10.243 | 90.811 | 1.00 20.00 |
| ATOM | 1018 | C | PHE | 126 | 36.313 | 6.375 | 86.337 | 1.00 20.00 |
| ATOM | 1019 | O | PHE | 126 | 35.314 | 6.051 | 85.695 | 1.00 20.00 |
| ATOM | 1020 | N | SER | 127 | 37.491 | 5.752 | 86.157 | 1.00 20.00 |
| ATOM | 1021 | CA | SER | 127 | 37.559 | 4.790 | 85.099 | 1.00 20.00 |
| ATOM | 1022 | CB | SER | 127 | 38.463 | 5.222 | 83.931 | 1.00 20.00 |
| ATOM | 1023 | OG | SER | 127 | 39.823 | 5.213 | 84.338 | 1.00 20.00 |
| ATOM | 1024 | C | SER | 127 | 38.093 | 3.484 | 85.593 | 1.00 20.00 |
| ATOM | 1025 | O | SER | 127 | 38.762 | 3.399 | 86.622 | 1.00 20.00 |
| ATOM | 1026 | N | ASN | 128 | 37.773 | 2.419 | 84.830 | 1.00 20.00 |
| ATOM | 1027 | CA | ASN | 128 | 38.272 | 1.090 | 85.056 | 1.00 20.00 |
| ATOM | 1028 | CB | ASN | 128 | 39.735 | 0.895 | 84.611 | 1.00 20.00 |
| ATOM | 1029 | CG | ASN | 128 | 39.832 | 1.046 | 83.097 | 1.00 20.00 |
| ATOM | 1030 | OD1 | ASN | 128 | 40.440 | 1.995 | 82.604 | 1.00 20.00 |
| ATOM | 1031 | ND2 | ASN | 128 | 39.233 | 0.089 | 82.337 | 1.00 20.00 |
| ATOM | 1032 | C | ASN | 128 | 38.197 | 0.700 | 86.497 | 1.00 20.00 |
| ATOM | 1033 | O | ASN | 128 | 39.228 | 0.550 | 87.153 | 1.00 20.00 |
| ATOM | 1034 | N | ASN | 129 | 36.977 | 0.539 | 87.046 | 1.00 20.00 |
| ATOM | 1035 | CA | ASN | 129 | 36.919 | 0.066 | 88.402 | 1.00 20.00 |
| ATOM | 1036 | CB | ASN | 129 | 36.561 | 1.183 | 89.392 | 1.00 20.00 |
| ATOM | 1037 | CG | ASN | 129 | 37.695 | 2.197 | 89.370 | 1.00 20.00 |
| ATOM | 1038 | OD1 | ASN | 129 | 38.830 | 1.889 | 89.731 | 1.00 20.00 |
| ATOM | 1039 | ND2 | ASN | 129 | 37.381 | 3.442 | 88.922 | 1.00 20.00 |
| ATOM | 1040 | C | ASN | 129 | 35.824 | -0.953 | 88.478 | 1.00 20.00 |
| ATOM | 1041 | O | ASN | 129 | 34.736 | -0.657 | 88.969 | 1.00 20.00 |
| ATOM | 1042 | N | PRO | 130 | 36.113 | -2.167 | 88.094 | 1.00 20.00 |
| ATOM | 1043 | CA | PRO | 130 | 35.133 | -3.218 | 87.967 | 1.00 20.00 |
| ATOM | 1044 | CD | PRO | 130 | 37.477 | -2.650 | 87.977 | 1.00 20.00 |
| ATOM | 1045 | CB | PRO | 130 | 35.928 | -4.509 | 87.765 | 1.00 20.00 |
| ATOM | 1046 | CG | PRO | 130 | 37.329 | -4.036 | 87.327 | 1.00 20.00 |
| ATOM | 1047 | C | PRO | 130 | 34.166 | -3.318 | 89.118 | 1.00 20.00 |
| ATOM | 1048 | O | PRO | 130 | 32.965 | -3.409 | 88.870 | 1.00 20.00 |
| ATOM | 1049 | N | ALA | 131 | 34.670 | -3.327 | 90.365 | 1.00 20.00 |
| ATOM | 1050 | CA | ALA | 131 | 33.926 | -3.463 | 91.592 | 1.00 20.00 |
| ATOM | 1051 | CB | ALA | 131 | 34.809 | -3.930 | 92.762 | 1.00 20.00 |
| ATOM | 1052 | C | ALA | 131 | 33.247 | -2.196 | 92.045 | 1.00 20.00 |
| ATOM | 1053 | O | ALA | 131 | 32.352 | -2.253 | 92.884 | 1.00 20.00 |
| ATOM | 1054 | N | LEU | 132 | 33.686 | -1.015 | 91.574 | 1.00 20.00 |
| ATOM | 1055 | CA | LEU | 132 | 33.213 | 0.222 | 92.140 | 1.00 20.00 |
| ATOM | 1056 | CB | LEU | 132 | 33.939 | 1.453 | 91.558 | 1.00 20.00 |
| ATOM | 1057 | CG | LEU | 132 | 33.469 | 2.799 | 92.139 | 1.00 20.00 |
| ATOM | 1058 | CD1 | LEU | 132 | 33.739 | 2.881 | 93.647 | 1.00 20.00 |
| ATOM | 1059 | CD2 | LEU | 132 | 34.091 | 3.978 | 91.369 | 1.00 20.00 |
| ATOM | 1060 | C | LEU | 132 | 31.745 | 0.413 | 91.960 | 1.00 20.00 |
| ATOM | 1061 | O | LEU | 132 | 31.198 | 0.282 | 90.868 | 1.00 20.00 |
| ATOM | 1062 | N | CYS | 133 | 31.068 | 0.757 | 93.071 | 1.00 20.00 |
| ATOM | 1063 | CA | CYS | 133 | 29.663 | 0.994 | 93.024 | 1.00 20.00 |
| ATOM | 1064 | CB | CYS | 133 | 28.845 | -0.167 | 93.563 | 1.00 20.00 |
| ATOM | 1065 | SG | CYS | 133 | 28.793 | -1.500 | 92.338 | 1.00 20.00 |
| ATOM | 1066 | C | CYS | 133 | 29.389 | 2.230 | 93.814 | 1.00 20.00 |
| ATOM | 1067 | O | CYS | 133 | 30.309 | 2.967 | 94.165 | 1.00 20.00 |
| ATOM | 1068 | N | ASN | 134 | 28.102 | 2.508 | 94.085 | 1.00 20.00 |
| ATOM | 1069 | CA | ASN | 134 | 27.765 | 3.698 | 94.803 | 1.00 20.00 |
| ATOM | 1070 | CB | ASN | 134 | 28.367 | 3.735 | 96.219 | 1.00 20.00 |
| ATOM | 1071 | CG | ASN | 134 | 27.653 | 2.690 | 97.066 | 1.00 20.00 |
| ATOM | 1072 | OD1 | ASN | 134 | 26.570 | 2.936 | 97.593 | 1.00 20.00 |
| ATOM | 1073 | ND2 | ASN | 134 | 28.273 | 1.486 | 97.198 | 1.00 20.00 |
| ATOM | 1074 | C | ASN | 134 | 28.325 | 4.848 | 94.026 | 1.00 20.00 |
| ATOM | 1075 | O | ASN | 134 | 28.806 | 5.818 | 94.610 | 1.00 20.00 |
| ATOM | 1076 | N | VAL | 135 | 28.441 | 4.664 | 92.693 | 1.00 20.00 |
| ATOM | 1077 | CA | VAL | 135 | 28.828 | 5.679 | 91.749 | 1.00 20.00 |
| ATOM | 1078 | CB | VAL | 135 | 29.541 | 5.104 | 90.561 | 1.00 20.00 |

Figure 6A-13

| | | | | | | | | |
|---|---|---|---|---|---|---|---|---|
| ATOM | 1079 | CG1 | VAL | 135 | 29.869 | 6.247 | 89.585 | 1.00 20.00 |
| ATOM | 1080 | CG2 | VAL | 135 | 30.775 | 4.333 | 91.058 | 1.00 20.00 |
| ATOM | 1081 | C | VAL | 135 | 27.661 | 6.465 | 91.212 | 1.00 20.00 |
| ATOM | 1082 | O | VAL | 135 | 27.725 | 7.657 | 91.089 | 1.00 20.00 |
| ATOM | 1083 | N | GLU | 136 | 26.569 | 5.752 | 90.849 | 1.00 20.00 |
| ATOM | 1084 | CA | GLU | 136 | 25.403 | 6.303 | 90.197 | 1.00 20.00 |
| ATOM | 1085 | CB | GLU | 136 | 24.397 | 5.239 | 89.724 | 1.00 20.00 |
| ATOM | 1086 | CG | GLU | 136 | 24.872 | 4.364 | 88.564 | 1.00 20.00 |
| ATOM | 1087 | CD | GLU | 136 | 23.716 | 3.438 | 88.207 | 1.00 20.00 |
| ATOM | 1088 | OE1 | GLU | 136 | 22.655 | 3.964 | 87.773 | 1.00 20.00 |
| ATOM | 1089 | OE2 | GLU | 136 | 23.871 | 2.199 | 88.372 | 1.00 20.00 |
| ATOM | 1090 | C | GLU | 136 | 24.646 | 7.159 | 91.148 | 1.00 20.00 |
| ATOM | 1091 | O | GLU | 136 | 23.956 | 8.096 | 90.754 | 1.00 20.00 |
| ATOM | 1092 | N | SER | 137 | 24.750 | 6.798 | 92.430 | 1.00 20.00 |
| ATOM | 1093 | CA | SER | 137 | 24.071 | 7.350 | 93.560 | 1.00 20.00 |
| ATOM | 1094 | CB | SER | 137 | 24.290 | 6.481 | 94.807 | 1.00 20.00 |
| ATOM | 1095 | OG | SER | 137 | 25.680 | 6.249 | 94.980 | 1.00 20.00 |
| ATOM | 1096 | C | SER | 137 | 24.503 | 8.753 | 93.871 | 1.00 20.00 |
| ATOM | 1097 | O | SER | 137 | 23.834 | 9.423 | 94.654 | 1.00 20.00 |
| ATOM | 1098 | N | ILE | 138 | 25.647 | 9.232 | 93.345 | 1.00 20.00 |
| ATOM | 1099 | CA | ILE | 138 | 26.094 | 10.544 | 93.733 | 1.00 20.00 |
| ATOM | 1100 | CB | ILE | 138 | 27.582 | 10.629 | 93.900 | 1.00 20.00 |
| ATOM | 1101 | CG2 | ILE | 138 | 27.945 | 12.095 | 94.188 | 1.00 20.00 |
| ATOM | 1102 | CG1 | ILE | 138 | 28.055 | 9.647 | 94.982 | 1.00 20.00 |
| ATOM | 1103 | CD1 | ILE | 138 | 29.563 | 9.414 | 94.969 | 1.00 20.00 |
| ATOM | 1104 | C | ILE | 138 | 25.724 | 11.578 | 92.710 | 1.00 20.00 |
| ATOM | 1105 | O | ILE | 138 | 25.821 | 11.357 | 91.503 | 1.00 20.00 |
| ATOM | 1106 | N | GLN | 139 | 25.288 | 12.764 | 93.192 | 1.00 20.00 |
| ATOM | 1107 | CA | GLN | 139 | 24.929 | 13.831 | 92.306 | 1.00 20.00 |
| ATOM | 1108 | CB | GLN | 139 | 23.652 | 14.566 | 92.754 | 1.00 20.00 |
| ATOM | 1109 | CG | GLN | 139 | 23.092 | 15.539 | 91.716 | 1.00 20.00 |
| ATOM | 1110 | CD | GLN | 139 | 21.688 | 15.926 | 92.161 | 1.00 20.00 |
| ATOM | 1111 | OE1 | GLN | 139 | 21.024 | 16.749 | 91.532 | 1.00 20.00 |
| ATOM | 1112 | NE2 | GLN | 139 | 21.216 | 15.308 | 93.277 | 1.00 20.00 |
| ATOM | 1113 | C | GLN | 139 | 26.075 | 14.794 | 92.284 | 1.00 20.00 |
| ATOM | 1114 | O | GLN | 139 | 26.160 | 15.724 | 93.085 | 1.00 20.00 |
| ATOM | 1115 | N | TRP | 140 | 26.977 | 14.597 | 91.309 | 1.00 20.00 |
| ATOM | 1116 | CA | TRP | 140 | 28.180 | 15.363 | 91.161 | 1.00 20.00 |
| ATOM | 1117 | CB | TRP | 140 | 29.163 | 14.778 | 90.137 | 1.00 20.00 |
| ATOM | 1118 | CG | TRP | 140 | 29.818 | 13.522 | 90.653 | 1.00 20.00 |
| ATOM | 1119 | CD2 | TRP | 140 | 30.821 | 13.520 | 91.679 | 1.00 20.00 |
| ATOM | 1120 | CD1 | TRP | 140 | 29.592 | 12.217 | 90.330 | 1.00 20.00 |
| ATOM | 1121 | NE1 | TRP | 140 | 30.396 | 11.400 | 91.091 | 1.00 20.00 |
| ATOM | 1122 | CE2 | TRP | 140 | 31.156 | 12.191 | 91.927 | 1.00 20.00 |
| ATOM | 1123 | CE3 | TRP | 140 | 31.410 | 14.545 | 92.364 | 1.00 20.00 |
| ATOM | 1124 | CZ2 | TRP | 140 | 32.090 | 11.863 | 92.869 | 1.00 20.00 |
| ATOM | 1125 | CZ3 | TRP | 140 | 32.355 | 14.211 | 93.308 | 1.00 20.00 |
| ATOM | 1126 | CH2 | TRP | 140 | 32.688 | 12.896 | 93.555 | 1.00 20.00 |
| ATOM | 1127 | C | TRP | 140 | 27.853 | 16.764 | 90.784 | 1.00 20.00 |
| ATOM | 1128 | O | TRP | 140 | 28.699 | 17.646 | 90.889 | 1.00 20.00 |
| ATOM | 1129 | N | ARG | 141 | 26.637 | 17.008 | 90.276 | 1.00 20.00 |
| ATOM | 1130 | CA | ARG | 141 | 26.301 | 18.348 | 89.897 | 1.00 20.00 |
| ATOM | 1131 | CB | ARG | 141 | 24.877 | 18.477 | 89.325 | 1.00 20.00 |
| ATOM | 1132 | CG | ARG | 141 | 24.516 | 19.908 | 88.917 | 1.00 20.00 |
| ATOM | 1133 | CD | ARG | 141 | 23.284 | 20.001 | 88.011 | 1.00 20.00 |
| ATOM | 1134 | NE | ARG | 141 | 22.103 | 19.536 | 88.789 | 1.00 20.00 |
| ATOM | 1135 | CZ | ARG | 141 | 21.404 | 20.418 | 89.561 | 1.00 20.00 |
| ATOM | 1136 | NH1 | ARG | 141 | 21.799 | 21.722 | 89.638 | 1.00 20.00 |
| ATOM | 1137 | NH2 | ARG | 141 | 20.305 | 19.998 | 90.253 | 1.00 20.00 |
| ATOM | 1138 | C | ARG | 141 | 26.410 | 19.219 | 91.109 | 1.00 20.00 |
| ATOM | 1139 | O | ARG | 141 | 26.800 | 20.381 | 91.011 | 1.00 20.00 |
| ATOM | 1140 | N | ASP | 142 | 26.040 | 18.695 | 92.292 | 1.00 20.00 |
| ATOM | 1141 | CA | ASP | 142 | 26.142 | 19.491 | 93.480 | 1.00 20.00 |
| ATOM | 1142 | CB | ASP | 142 | 25.567 | 18.779 | 94.715 | 1.00 20.00 |
| ATOM | 1143 | CG | ASP | 142 | 24.056 | 18.687 | 94.552 | 1.00 20.00 |
| ATOM | 1144 | OD1 | ASP | 142 | 23.505 | 19.441 | 93.706 | 1.00 20.00 |
| ATOM | 1145 | OD2 | ASP | 142 | 23.432 | 17.860 | 95.270 | 1.00 20.00 |
| ATOM | 1146 | C | ASP | 142 | 27.588 | 19.782 | 93.766 | 1.00 20.00 |
| ATOM | 1147 | O | ASP | 142 | 27.964 | 20.923 | 94.034 | 1.00 20.00 |
| ATOM | 1148 | N | ILE | 143 | 28.443 | 18.743 | 93.726 | 1.00 20.00 |
| ATOM | 1149 | CA | ILE | 143 | 29.832 | 18.901 | 94.069 | 1.00 20.00 |
| ATOM | 1150 | CB | ILE | 143 | 30.527 | 17.584 | 94.220 | 1.00 20.00 |
| ATOM | 1151 | CG2 | ILE | 143 | 32.013 | 17.861 | 94.496 | 1.00 20.00 |
| ATOM | 1152 | CG1 | ILE | 143 | 29.841 | 16.766 | 95.327 | 1.00 20.00 |
| ATOM | 1153 | CD1 | ILE | 143 | 30.264 | 15.299 | 95.362 | 1.00 20.00 |
| ATOM | 1154 | C | ILE | 143 | 30.583 | 19.713 | 93.049 | 1.00 20.00 |
| ATOM | 1155 | O | ILE | 143 | 31.338 | 20.615 | 93.409 | 1.00 20.00 |

Figure 6A-14

| | | | | | | | | |
|---|---|---|---|---|---|---|---|---|
| ATOM | 1156 | N | VAL | 144 | 30.393 | 19.425 | 91.746 | 1.00 20.00 |
| ATOM | 1157 | CA | VAL | 144 | 31.124 | -20.114 | 90.716 | 1.00 20.00 |
| ATOM | 1158 | CB | VAL | 144 | 31.795 | 19.194 | 89.741 | 1.00 20.00 |
| ATOM | 1159 | CG1 | VAL | 144 | 32.848 | 18.362 | 90.491 | 1.00 20.00 |
| ATOM | 1160 | CG2 | VAL | 144 | 30.714 | 18.350 | 89.046 | 1.00 20.00 |
| ATOM | 1161 | C | VAL | 144 | 30.141 | 20.931 | 89.943 | 1.00 20.00 |
| ATOM | 1162 | O | VAL | 144 | 28.999 | 20.521 | 89.760 | 1.00 20.00 |
| ATOM | 1163 | N | SER | 145 | 30.563 | 22.110 | 89.449 | 1.00 40.00 |
| ATOM | 1164 | CA | SER | 145 | 29.643 | 22.943 | 88.732 | 1.00 40.00 |
| ATOM | 1165 | CB | SER | 145 | 30.257 | 24.248 | 88.196 | 1.00 40.00 |
| ATOM | 1166 | OG | SER | 145 | 30.673 | 25.071 | 89.276 | 1.00 40.00 |
| ATOM | 1167 | C | SER | 145 | 29.123 | 22.163 | 87.570 | 1.00 40.00 |
| ATOM | 1168 | O | SER | 145 | 29.739 | 21.194 | 87.131 | 1.00 40.00 |
| ATOM | 1169 | N | SER | 146 | 27.951 | 22.580 | 87.055 | 1.00 40.00 |
| ATOM | 1170 | CA | SER | 146 | 27.292 | 21.887 | 85.989 | 1.00 40.00 |
| ATOM | 1171 | CB | SER | 146 | 26.000 | 22.586 | 85.532 | 1.00 40.00 |
| ATOM | 1172 | OG | SER | 146 | 26.304 | 23.856 | 84.973 | 1.00 40.00 |
| ATOM | 1173 | C | SER | 146 | 28.217 | 21.846 | 84.824 | 1.00 40.00 |
| ATOM | 1174 | O | SER | 146 | 28.314 | 20.832 | 84.134 | 1.00 40.00 |
| ATOM | 1175 | N | ASP | 147 | 28.939 | 22.952 | 84.583 | 1.00 40.00 |
| ATOM | 1176 | CA | ASP | 147 | 29.847 | 22.975 | 83.480 | 1.00 40.00 |
| ATOM | 1177 | CB | ASP | 147 | 30.636 | 24.292 | 83.385 | 1.00 40.00 |
| ATOM | 1178 | CG | ASP | 147 | 31.429 | 24.285 | 82.086 | 1.00 40.00 |
| ATOM | 1179 | OD1 | ASP | 147 | 31.400 | 23.245 | 81.376 | 1.00 40.00 |
| ATOM | 1180 | OD2 | ASP | 147 | 32.078 | 25.324 | 81.786 | 1.00 40.00 |
| ATOM | 1181 | C | ASP | 147 | 30.821 | 21.874 | 83.729 | 1.00 40.00 |
| ATOM | 1182 | O | ASP | 147 | 31.224 | 21.159 | 82.815 | 1.00 40.00 |
| ATOM | 1183 | N | PHE | 148 | 31.212 | 21.701 | 85.001 | 1.00 40.00 |
| ATOM | 1184 | CA | PHE | 148 | 32.146 | 20.677 | 85.353 | 1.00 40.00 |
| ATOM | 1185 | CB | PHE | 148 | 32.566 | 20.717 | 86.831 | 1.00 40.00 |
| ATOM | 1186 | CG | PHE | 148 | 33.413 | 21.930 | 87.007 | 1.00 40.00 |
| ATOM | 1187 | CD1 | PHE | 148 | 34.745 | 21.906 | 86.662 | 1.00 40.00 |
| ATOM | 1188 | CD2 | PHE | 148 | 32.881 | 23.090 | 87.517 | 1.00 40.00 |
| ATOM | 1189 | CE1 | PHE | 148 | 35.530 | 23.023 | 86.821 | 1.00 40.00 |
| ATOM | 1190 | CE2 | PHE | 148 | 33.661 | 24.211 | 87.679 | 1.00 40.00 |
| ATOM | 1191 | CZ | PHE | 148 | 34.989 | 24.179 | 87.330 | 1.00 40.00 |
| ATOM | 1192 | C | PHE | 148 | 31.545 | 19.337 | 85.076 | 1.00 40.00 |
| ATOM | 1193 | O | PHE | 148 | 32.255 | 18.412 | 84.685 | 1.00 40.00 |
| ATOM | 1194 | N | LEU | 149 | 30.218 | 19.180 | 85.259 | 1.00 40.00 |
| ATOM | 1195 | CA | LEU | 149 | 29.675 | 17.858 | 85.078 | 1.00 40.00 |
| ATOM | 1196 | CB | LEU | 149 | 28.154 | 17.741 | 85.313 | 1.00 40.00 |
| ATOM | 1197 | CG | LEU | 149 | 27.699 | 17.793 | 86.785 | 1.00 40.00 |
| ATOM | 1198 | CD1 | LEU | 149 | 27.904 | 19.177 | 87.411 | 1.00 40.00 |
| ATOM | 1199 | CD2 | LEU | 149 | 26.256 | 17.287 | 86.934 | 1.00 40.00 |
| ATOM | 1200 | C | LEU | 149 | 29.918 | 17.375 | 83.683 | 1.00 40.00 |
| ATOM | 1201 | O | LEU | 149 | 30.200 | 16.196 | 83.472 | 1.00 40.00 |
| ATOM | 1202 | N | SER | 150 | 29.837 | 18.269 | 82.687 | 1.00 40.00 |
| ATOM | 1203 | CA | SER | 150 | 29.984 | 17.843 | 81.326 | 1.00 40.00 |
| ATOM | 1204 | CB | SER | 150 | 29.921 | 19.017 | 80.335 | 1.00 40.00 |
| ATOM | 1205 | OG | SER | 150 | 30.998 | 19.911 | 80.574 | 1.00 40.00 |
| ATOM | 1206 | C | SER | 150 | 31.315 | 17.175 | 81.149 | 1.00 40.00 |
| ATOM | 1207 | O | SER | 150 | 31.425 | 16.176 | 80.440 | 1.00 40.00 |
| ATOM | 1208 | N | ASN | 151 | 32.360 | 17.717 | 81.799 | 1.00 40.00 |
| ATOM | 1209 | CA | ASN | 151 | 33.712 | 17.251 | 81.665 | 1.00 40.00 |
| ATOM | 1210 | CB | ASN | 151 | 34.724 | 18.153 | 82.390 | 1.00 40.00 |
| ATOM | 1211 | CG | ASN | 151 | 34.738 | 19.512 | 81.705 | 1.00 40.00 |
| ATOM | 1212 | OD1 | ASN | 151 | 34.014 | 19.746 | 80.739 | 1.00 40.00 |
| ATOM | 1213 | ND2 | ASN | 151 | 35.596 | 20.435 | 82.216 | 1.00 40.00 |
| ATOM | 1214 | C | ASN | 151 | 33.889 | 15.871 | 82.230 | 1.00 40.00 |
| ATOM | 1215 | O | ASN | 151 | 34.720 | 15.108 | 81.740 | 1.00 40.00 |
| ATOM | 1216 | N | MET | 152 | 33.128 | 15.513 | 83.283 | 1.00 40.00 |
| ATOM | 1217 | CA | MET | 152 | 33.330 | 14.269 | 83.982 | 1.00 40.00 |
| ATOM | 1218 | CB | MET | 152 | 32.253 | 14.010 | 85.050 | 1.00 40.00 |
| ATOM | 1219 | CG | MET | 152 | 32.593 | 12.883 | 86.026 | 1.00 40.00 |
| ATOM | 1220 | SD | MET | 152 | 31.367 | 12.649 | 87.348 | 1.00 40.00 |
| ATOM | 1221 | CE | MET | 152 | 31.655 | 14.266 | 88.127 | 1.00 40.00 |
| ATOM | 1222 | C | MET | 152 | 33.343 | 13.121 | 83.026 | 1.00 40.00 |
| ATOM | 1223 | O | MET | 152 | 32.474 | 12.997 | 82.165 | 1.00 40.00 |
| ATOM | 1224 | N | SER | 153 | 34.368 | 12.250 | 83.157 | 1.00 40.00 |
| ATOM | 1225 | CA | SER | 153 | 34.471 | 11.123 | 82.280 | 1.00 40.00 |
| ATOM | 1226 | CB | SER | 153 | 35.786 | 11.081 | 81.483 | 1.00 40.00 |
| ATOM | 1227 | OG | SER | 153 | 35.840 | 12.177 | 80.581 | 1.00 40.00 |
| ATOM | 1228 | C | SER | 153 | 34.405 | 9.877 | 83.094 | 1.00 40.00 |
| ATOM | 1229 | O | SER | 153 | 35.285 | 9.594 | 83.907 | 1.00 40.00 |
| ATOM | 1230 | N | MET | 154 | 33.333 | 9.093 | 82.893 | 1.00 40.00 |
| ATOM | 1231 | CA | MET | 154 | 33.238 | 7.859 | 83.601 | 1.00 40.00 |
| ATOM | 1232 | CB | MET | 154 | 31.968 | 7.749 | 84.462 | 1.00 40.00 |

Figure 6A-15

| | | | | | | | | |
|---|---|---|---|---|---|---|---|---|
| ATOM | 1233 | CG | MET | 154 | 31.991 | 8.700 | 85.662 | 1.00 40.00 |
| ATOM | 1234 | SD | MET | 154 | 30.442 | 8.788 | 86.607 | 1.00 40.00 |
| ATOM | 1235 | CE | MET | 154 | 29.667 | 10.012 | 85.513 | 1.00 40.00 |
| ATOM | 1236 | C | MET | 154 | 33.215 | 6.783 | 82.577 | 1.00 40.00 |
| ATOM | 1237 | O | MET | 154 | 32.267 | 6.665 | 81.802 | 1.00 40.00 |
| ATOM | 1238 | N | ASP | 155 | 34.283 | 5.969 | 82.540 | 1.00 40.00 |
| ATOM | 1239 | CA | ASP | 155 | 34.292 | 4.918 | 81.579 | 1.00 40.00 |
| ATOM | 1240 | CB | ASP | 155 | 35.691 | 4.375 | 81.243 | 1.00 40.00 |
| ATOM | 1241 | CG | ASP | 155 | 35.566 | 3.514 | 79.992 | 1.00 40.00 |
| ATOM | 1242 | OD1 | ASP | 155 | 34.446 | 3.465 | 79.417 | 1.00 40.00 |
| ATOM | 1243 | OD2 | ASP | 155 | 36.590 | 2.892 | 79.599 | 1.00 40.00 |
| ATOM | 1244 | C | ASP | 155 | 33.519 | 3.827 | 82.204 | 1.00 40.00 |
| ATOM | 1245 | O | ASP | 155 | 33.637 | 3.600 | 83.411 | 1.00 40.00 |
| ATOM | 1246 | N | PHE | 156 | 32.731 | 3.114 | 81.370 | 1.00 40.00 |
| ATOM | 1247 | CA | PHE | 156 | 31.853 | 2.051 | 81.774 | 1.00 40.00 |
| ATOM | 1248 | CB | PHE | 156 | 31.040 | 1.483 | 80.595 | 1.00 40.00 |
| ATOM | 1249 | CG | PHE | 156 | 30.123 | 2.536 | 80.071 | 1.00 40.00 |
| ATOM | 1250 | CD1 | PHE | 156 | 30.600 | 3.548 | 79.269 | 1.00 40.00 |
| ATOM | 1251 | CD2 | PHE | 156 | 28.779 | 2.498 | 80.364 | 1.00 40.00 |
| ATOM | 1252 | CE1 | PHE | 156 | 29.753 | 4.516 | 78.780 | 1.00 40.00 |
| ATOM | 1253 | CE2 | PHE | 156 | 27.928 | 3.462 | 79.878 | 1.00 40.00 |
| ATOM | 1254 | CZ | PHE | 156 | 28.414 | 4.474 | 79.086 | 1.00 40.00 |
| ATOM | 1255 | C | PHE | 156 | 32.652 | 0.896 | 82.298 | 1.00 40.00 |
| ATOM | 1256 | O | PHE | 156 | 32.133 | -0.214 | 82.406 | 1.00 40.00 |
| ATOM | 1257 | N | GLN | 157 | 33.928 | 1.112 | 82.654 | 1.00 40.00 |
| ATOM | 1258 | CA | GLN | 157 | 34.682 | 0.035 | 83.193 | 1.00 40.00 |
| ATOM | 1259 | CB | GLN | 157 | 36.201 | 0.220 | 83.147 | 1.00 40.00 |
| ATOM | 1260 | CG | GLN | 157 | 36.920 | -1.060 | 83.577 | 1.00 40.00 |
| ATOM | 1261 | CD | GLN | 157 | 36.539 | -2.155 | 82.595 | 1.00 40.00 |
| ATOM | 1262 | OE1 | GLN | 157 | 35.829 | -1.905 | 81.621 | 1.00 40.00 |
| ATOM | 1263 | NE2 | GLN | 157 | 37.018 | -3.400 | 82.859 | 1.00 40.00 |
| ATOM | 1264 | C | GLN | 157 | 34.259 | -0.117 | 84.613 | 1.00 40.00 |
| ATOM | 1265 | O | GLN | 157 | 34.691 | -1.040 | 85.298 | 1.00 40.00 |
| ATOM | 1266 | N | ASN | 158 | 33.416 | 0.812 | 85.106 | 1.00 40.00 |
| ATOM | 1267 | CA | ASN | 158 | 32.945 | 0.694 | 86.456 | 1.00 40.00 |
| ATOM | 1268 | CB | ASN | 158 | 32.249 | 1.957 | 86.991 | 1.00 40.00 |
| ATOM | 1269 | CG | ASN | 158 | 33.321 | 3.010 | 87.232 | 1.00 40.00 |
| ATOM | 1270 | OD1 | ASN | 158 | 34.482 | 2.688 | 87.478 | 1.00 40.00 |
| ATOM | 1271 | ND2 | ASN | 158 | 32.918 | 4.307 | 87.169 | 1.00 40.00 |
| ATOM | 1272 | C | ASN | 158 | 31.962 | -0.434 | 86.502 | 1.00 40.00 |
| ATOM | 1273 | O | ASN | 158 | 31.713 | -1.097 | 85.497 | 1.00 40.00 |
| ATOM | 1274 | N | HIS | 159 | 31.388 | -0.692 | 87.695 | 1.00 40.00 |
| ATOM | 1275 | CA | HIS | 159 | 30.496 | -1.805 | 87.868 | 1.00 40.00 |
| ATOM | 1276 | ND1 | HIS | 159 | 28.560 | -3.969 | 89.655 | 1.00 40.00 |
| ATOM | 1277 | NE2 | HIS | 159 | 29.574 | -5.943 | 89.508 | 1.00 40.00 |
| ATOM | 1278 | CE1 | HIS | 159 | 28.425 | -5.319 | 89.694 | 1.00 40.00 |
| ATOM | 1279 | CD2 | HIS | 159 | 30.498 | -4.927 | 89.342 | 1.00 40.00 |
| ATOM | 1280 | CG | HIS | 159 | 29.893 | -3.710 | 89.428 | 1.00 40.00 |
| ATOM | 1281 | CB | HIS | 159 | 30.482 | -2.337 | 89.311 | 1.00 40.00 |
| ATOM | 1282 | C | HIS | 159 | 29.099 | -1.389 | 87.517 | 1.00 40.00 |
| ATOM | 1283 | O | HIS | 159 | 28.816 | -0.203 | 87.352 | 1.00 40.00 |
| ATOM | 1284 | N | LEU | 160 | 28.187 | -2.379 | 87.382 | 1.00 40.00 |
| ATOM | 1285 | CA | LEU | 160 | 26.814 | -2.106 | 87.060 | 1.00 40.00 |
| ATOM | 1286 | CB | LEU | 160 | 26.107 | -3.247 | 86.307 | 1.00 40.00 |
| ATOM | 1287 | CG | LEU | 160 | 26.696 | -3.508 | 84.908 | 1.00 40.00 |
| ATOM | 1288 | CD1 | LEU | 160 | 28.149 | -4.000 | 84.998 | 1.00 40.00 |
| ATOM | 1289 | CD2 | LEU | 160 | 25.794 | -4.442 | 84.086 | 1.00 40.00 |
| ATOM | 1290 | C | LEU | 160 | 26.070 | -1.873 | 88.341 | 1.00 40.00 |
| ATOM | 1291 | O | LEU | 160 | 26.472 | -2.342 | 89.403 | 1.00 40.00 |
| ATOM | 1292 | N | GLY | 161 | 24.928 | -1.164 | 88.240 | 1.00 40.00 |
| ATOM | 1293 | CA | GLY | 161 | 24.107 | -0.713 | 89.334 | 1.00 40.00 |
| ATOM | 1294 | C | GLY | 161 | 23.611 | -1.851 | 90.176 | 1.00 40.00 |
| ATOM | 1295 | O | GLY | 161 | 22.862 | -1.641 | 91.128 | 1.00 40.00 |
| ATOM | 1296 | N | SER | 162 | 24.007 | -3.088 | 89.846 | 1.00 40.00 |
| ATOM | 1297 | CA | SER | 162 | 23.573 | -4.255 | 90.554 | 1.00 40.00 |
| ATOM | 1298 | CB | SER | 162 | 24.217 | -5.543 | 90.018 | 1.00 40.00 |
| ATOM | 1299 | OG | SER | 162 | 25.617 | -5.519 | 90.253 | 1.00 40.00 |
| ATOM | 1300 | C | SER | 162 | 23.947 | -4.144 | 92.006 | 1.00 40.00 |
| ATOM | 1301 | O | SER | 162 | 23.297 | -4.749 | 92.855 | 1.00 40.00 |
| ATOM | 1302 | N | CYS | 163 | 24.998 | -3.377 | 92.347 | 1.00 20.00 |
| ATOM | 1303 | CA | CYS | 163 | 25.471 | -3.385 | 93.708 | 1.00 20.00 |
| ATOM | 1304 | CB | CYS | 163 | 26.601 | -2.412 | 94.018 | 1.00 20.00 |
| ATOM | 1305 | SG | CYS | 163 | 28.216 | -3.031 | 93.499 | 1.00 20.00 |
| ATOM | 1306 | C | CYS | 163 | 24.431 | -3.146 | 94.769 | 1.00 20.00 |
| ATOM | 1307 | O | CYS | 163 | 24.256 | -4.027 | 95.603 | 1.00 20.00 |
| ATOM | 1308 | N | GLN | 164 | 23.706 | -2.003 | 94.826 | 1.00 40.00 |
| ATOM | 1309 | CA | GLN | 164 | 22.859 | -1.898 | 95.996 | 1.00 40.00 |

Figure 6A-16

| | | | | | | | | |
|---|---|---|---|---|---|---|---|---|
| ATOM | 1310 | CB | GLN | 164 | 23.611 | -1.447 | 97.263 | 1.00 40.00 |
| ATOM | 1311 | CG | GLN | 164 | 24.612 | -2.460 | 97.823 | 1.00 40.00 |
| ATOM | 1312 | CD | GLN | 164 | 25.256 | -1.849 | 99.059 | 1.00 40.00 |
| ATOM | 1313 | OE1 | GLN | 164 | 25.834 | -0.765 | 98.997 | 1.00 40.00 |
| ATOM | 1314 | NE2 | GLN | 164 | 25.155 | -2.558 | 100.216 | 1.00 40.00 |
| ATOM | 1315 | C | GLN | 164 | 21.763 | -0.888 | 95.825 | 1.00 40.00 |
| ATOM | 1316 | O | GLN | 164 | 21.240 | -0.679 | 94.732 | 1.00 40.00 |
| ATOM | 1317 | N | LYS | 165 | 21.374 | -0.272 | 96.971 | 1.00 40.00 |
| ATOM | 1318 | CA | LYS | 165 | 20.320 | 0.702 | 97.072 | 1.00 40.00 |
| ATOM | 1319 | CB | LYS | 165 | 18.957 | 0.054 | 97.384 | 1.00 40.00 |
| ATOM | 1320 | CG | LYS | 165 | 17.794 | 1.038 | 97.503 | 1.00 40.00 |
| ATOM | 1321 | CD | LYS | 165 | 16.420 | 0.361 | 97.435 | 1.00 40.00 |
| ATOM | 1322 | CE | LYS | 165 | 16.216 | -0.741 | 98.479 | 1.00 40.00 |
| ATOM | 1323 | NZ | LYS | 165 | 15.818 | -0.147 | 99.775 | 1.00 40.00 |
| ATOM | 1324 | C | LYS | 165 | 20.660 | 1.625 | 98.213 | 1.00 40.00 |
| ATOM | 1325 | O | LYS | 165 | 21.489 | 1.293 | 99.059 | 1.00 40.00 |
| ATOM | 1326 | N | CYS | 166 | 20.032 | 2.823 | 98.262 | 1.00 20.00 |
| ATOM | 1327 | CA | CYS | 166 | 20.299 | 3.762 | 99.324 | 1.00 20.00 |
| ATOM | 1328 | CB | CYS | 166 | 20.295 | 5.252 | 98.901 | 1.00 20.00 |
| ATOM | 1329 | SG | CYS | 166 | 21.577 | 5.745 | 97.700 | 1.00 20.00 |
| ATOM | 1330 | C | CYS | 166 | 19.219 | 3.620 | 100.350 | 1.00 20.00 |
| ATOM | 1331 | O | CYS | 166 | 18.356 | 2.750 | 100.247 | 1.00 20.00 |
| ATOM | 1332 | N | ASP | 167 | 19.264 | 4.480 | 101.391 | 1.00 20.00 |
| ATOM | 1333 | CA | ASP | 167 | 18.286 | 4.447 | 102.442 | 1.00 20.00 |
| ATOM | 1334 | CB | ASP | 167 | 18.787 | 5.021 | 103.777 | 1.00 20.00 |
| ATOM | 1335 | CG | ASP | 167 | 19.866 | 4.096 | 104.320 | 1.00 20.00 |
| ATOM | 1336 | OD1 | ASP | 167 | 20.212 | 3.110 | 103.616 | 1.00 20.00 |
| ATOM | 1337 | OD2 | ASP | 167 | 20.357 | 4.362 | 105.450 | 1.00 20.00 |
| ATOM | 1338 | C | ASP | 167 | 17.120 | 5.283 | 102.017 | 1.00 20.00 |
| ATOM | 1339 | O | ASP | 167 | 17.221 | 6.116 | 101.119 | 1.00 20.00 |
| ATOM | 1340 | N | PRO | 168 | 15.994 | 5.035 | 102.630 | 1.00 20.00 |
| ATOM | 1341 | CA | PRO | 168 | 14.801 | 5.792 | 102.377 | 1.00 20.00 |
| ATOM | 1342 | CD | PRO | 168 | 15.722 | 3.769 | 103.285 | 1.00 20.00 |
| ATOM | 1343 | CB | PRO | 168 | 13.657 | 5.005 | 103.019 | 1.00 20.00 |
| ATOM | 1344 | CG | PRO | 168 | 14.352 | 3.987 | 103.945 | 1.00 20.00 |
| ATOM | 1345 | C | PRO | 168 | 14.980 | 7.169 | 102.929 | 1.00 20.00 |
| ATOM | 1346 | O | PRO | 168 | 14.295 | 8.089 | 102.485 | 1.00 20.00 |
| ATOM | 1347 | N | SER | 169 | 15.883 | 7.319 | 103.915 | 1.00 20.00 |
| ATOM | 1348 | CA | SER | 169 | 16.143 | 8.581 | 104.541 | 1.00 20.00 |
| ATOM | 1349 | CB | SER | 169 | 17.090 | 8.455 | 105.749 | 1.00 20.00 |
| ATOM | 1350 | OG | SER | 169 | 17.314 | 9.731 | 106.332 | 1.00 20.00 |
| ATOM | 1351 | C | SER | 169 | 16.799 | 9.493 | 103.555 | 1.00 20.00 |
| ATOM | 1352 | O | SER | 169 | 16.481 | 10.679 | 103.488 | 1.00 20.00 |
| ATOM | 1353 | N | CYS | 170 | 17.724 | 8.950 | 102.741 | 1.00 20.00 |
| ATOM | 1354 | CA | CYS | 170 | 18.471 | 9.781 | 101.844 | 1.00 20.00 |
| ATOM | 1355 | CB | CYS | 170 | 19.480 | 9.021 | 100.964 | 1.00 20.00 |
| ATOM | 1356 | SG | CYS | 170 | 20.686 | 8.015 | 101.878 | 1.00 20.00 |
| ATOM | 1357 | C | CYS | 170 | 17.520 | 10.444 | 100.903 | 1.00 20.00 |
| ATOM | 1358 | O | CYS | 170 | 16.343 | 10.101 | 100.801 | 1.00 20.00 |
| ATOM | 1359 | N | PRO | 171 | 18.052 | 11.433 | 100.240 | 1.00 20.00 |
| ATOM | 1360 | CA | PRO | 171 | 17.297 | 12.152 | 99.251 | 1.00 20.00 |
| ATOM | 1361 | CD | PRO | 171 | 19.025 | 12.292 | 100.897 | 1.00 20.00 |
| ATOM | 1362 | CB | PRO | 171 | 18.056 | 13.451 | 99.001 | 1.00 20.00 |
| ATOM | 1363 | CG | PRO | 171 | 18.791 | 13.702 | 100.328 | 1.00 20.00 |
| ATOM | 1364 | C | PRO | 171 | 17.159 | 11.294 | 98.040 | 1.00 20.00 |
| ATOM | 1365 | O | PRO | 171 | 17.841 | 10.274 | 97.962 | 1.00 20.00 |
| ATOM | 1366 | N | ASN | 172 | 16.288 | 11.695 | 97.094 | 1.00 20.00 |
| ATOM | 1367 | CA | ASN | 172 | 15.986 | 10.935 | 95.916 | 1.00 20.00 |
| ATOM | 1368 | CB | ASN | 172 | 15.258 | 11.749 | 94.829 | 1.00 20.00 |
| ATOM | 1369 | CG | ASN | 172 | 13.851 | 12.072 | 95.309 | 1.00 20.00 |
| ATOM | 1370 | OD1 | ASN | 172 | 13.402 | 11.580 | 96.343 | 1.00 20.00 |
| ATOM | 1371 | ND2 | ASN | 172 | 13.128 | 12.919 | 94.529 | 1.00 20.00 |
| ATOM | 1372 | C | ASN | 172 | 17.228 | 10.384 | 95.289 | 1.00 20.00 |
| ATOM | 1373 | O | ASN | 172 | 17.903 | 11.060 | 94.514 | 1.00 20.00 |
| ATOM | 1374 | N | GLY | 173 | 17.558 | 9.125 | 95.632 | 1.00 20.00 |
| ATOM | 1375 | CA | GLY | 173 | 18.622 | 8.401 | 95.000 | 1.00 20.00 |
| ATOM | 1376 | C | GLY | 173 | 19.947 | 9.070 | 95.177 | 1.00 20.00 |
| ATOM | 1377 | O | GLY | 173 | 20.756 | 9.062 | 94.251 | 1.00 20.00 |
| ATOM | 1378 | N | SER | 174 | 20.232 | 9.681 | 96.342 | 1.00 20.00 |
| ATOM | 1379 | CA | SER | 174 | 21.547 | 10.255 | 96.421 | 1.00 20.00 |
| ATOM | 1380 | CB | SER | 174 | 21.547 | 11.791 | 96.495 | 1.00 20.00 |
| ATOM | 1381 | OG | SER | 174 | 20.948 | 12.223 | 97.709 | 1.00 20.00 |
| ATOM | 1382 | C | SER | 174 | 22.229 | 9.761 | 97.659 | 1.00 20.00 |
| ATOM | 1383 | O | SER | 174 | 21.762 | 10.012 | 98.768 | 1.00 20.00 |
| ATOM | 1384 | N | CYS | 175 | 23.350 | 9.024 | 97.506 | 1.00 20.00 |
| ATOM | 1385 | CA | CYS | 175 | 24.068 | 8.612 | 98.680 | 1.00 20.00 |
| ATOM | 1386 | CB | CYS | 175 | 23.349 | 7.514 | 99.504 | 1.00 20.00 |

Figure 6A-17

| ATOM | 1387 | SG | CYS | 175 | 23.313 | 5.847 | 98.761 | 1.00 | 20.00 |
|---|---|---|---|---|---|---|---|---|---|
| ATOM | 1388 | C | CYS | 175 | 25.416 | 8.102 | 98.273 | 1.00 | 20.00 |
| ATOM | 1389 | O | CYS | 175 | 25.587 | 7.585 | 97.173 | 1.00 | 20.00 |
| ATOM | 1390 | N | TRP | 176 | 26.428 | 8.289 | 99.144 | 1.00 | 20.00 |
| ATOM | 1391 | CA | TRP | 176 | 27.758 | 7.808 | 98.885 | 1.00 | 20.00 |
| ATOM | 1392 | CB | TRP | 176 | 28.811 | 8.464 | 99.795 | 1.00 | 20.00 |
| ATOM | 1393 | CG | TRP | 176 | 28.970 | 9.942 | 99.510 | 1.00 | 20.00 |
| ATOM | 1394 | CD2 | TRP | 176 | 29.858 | 10.492 | 98.522 | 1.00 | 20.00 |
| ATOM | 1395 | CD1 | TRP | 176 | 28.324 | 11.001 | 100.077 | 1.00 | 20.00 |
| ATOM | 1396 | NE1 | TRP | 176 | 28.752 | 12.176 | 99.505 | 1.00 | 20.00 |
| ATOM | 1397 | CE2 | TRP | 176 | 29.697 | 11.877 | 98.547 | 1.00 | 20.00 |
| ATOM | 1398 | CE3 | TRP | 176 | 30.737 | 9.892 | 97.666 | 1.00 | 20.00 |
| ATOM | 1399 | CZ2 | TRP | 176 | 30.412 | 12.687 | 97.709 | 1.00 | 20.00 |
| ATOM | 1400 | CZ3 | TRP | 176 | 31.457 | 10.710 | 96.823 | 1.00 | 20.00 |
| ATOM | 1401 | CH2 | TRP | 176 | 31.296 | 12.080 | 96.843 | 1.00 | 20.00 |
| ATOM | 1402 | C | TRP | 176 | 27.786 | 6.323 | 99.068 | 1.00 | 20.00 |
| ATOM | 1403 | O | TRP | 176 | 28.502 | 5.609 | 98.366 | 1.00 | 20.00 |
| ATOM | 1404 | N | GLY | 177 | 27.009 | 5.824 | 100.048 | 1.00 | 20.00 |
| ATOM | 1405 | CA | GLY | 177 | 26.932 | 4.416 | 100.312 | 1.00 | 20.00 |
| ATOM | 1406 | C | GLY | 177 | 25.598 | 4.198 | 100.945 | 1.00 | 20.00 |
| ATOM | 1407 | O | GLY | 177 | 24.833 | 5.142 | 101.132 | 1.00 | 20.00 |
| ATOM | 1408 | N | ALA | 178 | 25.258 | 2.939 | 101.274 | 1.00 | 20.00 |
| ATOM | 1409 | CA | ALA | 178 | 23.995 | 2.740 | 101.918 | 1.00 | 20.00 |
| ATOM | 1410 | CB | ALA | 178 | 23.463 | 1.300 | 101.813 | 1.00 | 20.00 |
| ATOM | 1411 | C | ALA | 178 | 24.195 | 3.049 | 103.365 | 1.00 | 20.00 |
| ATOM | 1412 | O | ALA | 178 | 25.156 | 2.588 | 103.978 | 1.00 | 20.00 |
| ATOM | 1413 | N | GLY | 179 | 23.291 | 3.858 | 103.950 | 1.00 | 20.00 |
| ATOM | 1414 | CA | GLY | 179 | 23.422 | 4.184 | 105.341 | 1.00 | 20.00 |
| ATOM | 1415 | C | GLY | 179 | 22.916 | 5.577 | 105.537 | 1.00 | 20.00 |
| ATOM | 1416 | O | GLY | 179 | 22.867 | 6.374 | 104.602 | 1.00 | 20.00 |
| ATOM | 1417 | N | GLU | 180 | 22.525 | 5.898 | 106.785 | 1.00 | 20.00 |
| ATOM | 1418 | CA | GLU | 180 | 22.012 | 7.195 | 107.111 | 1.00 | 20.00 |
| ATOM | 1419 | CB | GLU | 180 | 21.604 | 7.297 | 108.592 | 1.00 | 20.00 |
| ATOM | 1420 | CG | GLU | 180 | 20.414 | 6.415 | 108.976 | 1.00 | 20.00 |
| ATOM | 1421 | CD | GLU | 180 | 19.136 | 7.190 | 108.693 | 1.00 | 20.00 |
| ATOM | 1422 | OE1 | GLU | 180 | 19.242 | 8.369 | 108.261 | 1.00 | 20.00 |
| ATOM | 1423 | OE2 | GLU | 180 | 18.035 | 6.616 | 108.912 | 1.00 | 20.00 |
| ATOM | 1424 | C | GLU | 180 | 23.103 | 8.195 | 106.903 | 1.00 | 20.00 |
| ATOM | 1425 | O | GLU | 180 | 22.905 | 9.235 | 106.277 | 1.00 | 20.00 |
| ATOM | 1426 | N | GLU | 181 | 24.299 | 7.882 | 107.431 | 1.00 | 20.00 |
| ATOM | 1427 | CA | GLU | 181 | 25.443 | 8.746 | 107.365 | 1.00 | 20.00 |
| ATOM | 1428 | CB | GLU | 181 | 26.633 | 8.195 | 108.170 | 1.00 | 20.00 |
| ATOM | 1429 | CG | GLU | 181 | 27.875 | 9.086 | 108.136 | 1.00 | 20.00 |
| ATOM | 1430 | CD | GLU | 181 | 28.952 | 8.409 | 108.973 | 1.00 | 20.00 |
| ATOM | 1431 | OE1 | GLU | 181 | 28.646 | 7.352 | 109.586 | 1.00 | 20.00 |
| ATOM | 1432 | OE2 | GLU | 181 | 30.095 | 8.939 | 109.009 | 1.00 | 20.00 |
| ATOM | 1433 | C | GLU | 181 | 25.889 | 8.860 | 105.945 | 1.00 | 20.00 |
| ATOM | 1434 | O | GLU | 181 | 26.311 | 9.922 | 105.492 | 1.00 | 20.00 |
| ATOM | 1435 | N | ASN | 182 | 25.780 | 7.746 | 105.206 | 1.00 | 20.00 |
| ATOM | 1436 | CA | ASN | 182 | 26.275 | 7.631 | 103.869 | 1.00 | 20.00 |
| ATOM | 1437 | CB | ASN | 182 | 26.103 | 6.214 | 103.305 | 1.00 | 20.00 |
| ATOM | 1438 | CG | ASN | 182 | 27.010 | 5.283 | 104.099 | 1.00 | 20.00 |
| ATOM | 1439 | OD1 | ASN | 182 | 26.768 | 5.014 | 105.275 | 1.00 | 20.00 |
| ATOM | 1440 | ND2 | ASN | 182 | 28.084 | 4.772 | 103.440 | 1.00 | 20.00 |
| ATOM | 1441 | C | ASN | 182 | 25.580 | 8.593 | 102.956 | 1.00 | 20.00 |
| ATOM | 1442 | O | ASN | 182 | 26.177 | 9.028 | 101.972 | 1.00 | 20.00 |
| ATOM | 1443 | N | CYS | 183 | 24.305 | 8.930 | 103.248 | 1.00 | 20.00 |
| ATOM | 1444 | CA | CYS | 183 | 23.517 | 9.796 | 102.409 | 1.00 | 20.00 |
| ATOM | 1445 | CB | CYS | 183 | 22.234 | 10.333 | 103.070 | 1.00 | 20.00 |
| ATOM | 1446 | SG | CYS | 183 | 21.041 | 9.063 | 103.574 | 1.00 | 20.00 |
| ATOM | 1447 | C | CYS | 183 | 24.299 | 11.001 | 102.038 | 1.00 | 20.00 |
| ATOM | 1448 | O | CYS | 183 | 25.111 | 11.502 | 102.813 | 1.00 | 20.00 |
| ATOM | 1449 | N | GLN | 184 | 24.122 | 11.429 | 100.774 | 1.00 | 40.00 |
| ATOM | 1450 | CA | GLN | 184 | 24.817 | 12.571 | 100.279 | 1.00 | 40.00 |
| ATOM | 1451 | CB | GLN | 184 | 24.808 | 12.622 | 98.740 | 1.00 | 40.00 |
| ATOM | 1452 | CG | GLN | 184 | 25.536 | 13.826 | 98.143 | 1.00 | 40.00 |
| ATOM | 1453 | CD | GLN | 184 | 25.427 | 13.713 | 96.628 | 1.00 | 40.00 |
| ATOM | 1454 | OE1 | GLN | 184 | 24.768 | 12.810 | 96.113 | 1.00 | 40.00 |
| ATOM | 1455 | NE2 | GLN | 184 | 26.092 | 14.644 | 95.894 | 1.00 | 40.00 |
| ATOM | 1456 | C | GLN | 184 | 24.042 | 13.729 | 100.785 | 1.00 | 40.00 |
| ATOM | 1457 | O | GLN | 184 | 23.545 | 14.554 | 100.020 | 1.00 | 40.00 |
| ATOM | 1458 | N | LYS | 185 | 23.937 | 13.801 | 102.122 | 1.00 | 60.00 |
| ATOM | 1459 | CA | LYS | 185 | 23.193 | 14.825 | 102.782 | 1.00 | 60.00 |
| ATOM | 1460 | CB | LYS | 185 | 23.129 | 14.586 | 104.302 | 1.00 | 60.00 |
| ATOM | 1461 | CG | LYS | 185 | 22.030 | 15.362 | 105.034 | 1.00 | 60.00 |
| ATOM | 1462 | CD | LYS | 185 | 21.760 | 14.828 | 106.444 | 1.00 | 60.00 |
| ATOM | 1463 | CE | LYS | 185 | 21.242 | 13.386 | 106.463 | 1.00 | 60.00 |

Figure 6A-18

| | | | | | | | |
|---|---|---|---|---|---|---|---|
| ATOM | 1464 | NZ | LYS | 185 | 21.056 | 12.921 107.859 | 1.00 60.00 |
| ATOM | 1465 | C | LYS | 185 | 23.892 | 16.116 102.525 | 1.00 60.00 |
| ATOM | 1466 | O | LYS | 185 | 23.262 | 17.147 102.293 | 1.00 60.00 |
| ATOM | 1467 | N | LEU | 186 | 25.235 | 16.088 102.550 | 1.00 60.00 |
| ATOM | 1468 | CA | LEU | 186 | 25.946 | 17.314 102.380 | 1.00 60.00 |
| ATOM | 1469 | CB | LEU | 186 | 27.228 | 17.377 103.228 | 1.00 60.00 |
| ATOM | 1470 | CG | LEU | 186 | 26.966 | 17.331 104.746 | 1.00 60.00 |
| ATOM | 1471 | CD1 | LEU | 186 | 26.349 | 15.985 105.164 | 1.00 60.00 |
| ATOM | 1472 | CD2 | LEU | 186 | 28.230 | 17.685 105.546 | 1.00 60.00 |
| ATOM | 1473 | C | LEU | 186 | 26.344 | 17.473 100.947 | 1.00 60.00 |
| ATOM | 1474 | O | LEU | 186 | 27.267 | 16.817 100.466 | 1.00 60.00 |
| ATOM | 1475 | N | THR | 187 | 25.637 | 18.365 100.226 | 1.00 60.00 |
| ATOM | 1476 | CA | THR | 187 | 25.998 | 18.719 98.884 | 1.00 60.00 |
| ATOM | 1477 | CB | THR | 187 | 25.061 | 18.238 97.815 | 1.00 60.00 |
| ATOM | 1478 | OG1 | THR | 187 | 23.785 | 18.834 97.970 | 1.00 60.00 |
| ATOM | 1479 | CG2 | THR | 187 | 24.947 | 16.708 97.901 | 1.00 60.00 |
| ATOM | 1480 | C | THR | 187 | 25.944 | 20.210 98.893 | 1.00 60.00 |
| ATOM | 1481 | O | THR | 187 | 25.146 | 20.793 99.625 | 1.00 60.00 |
| ATOM | 1482 | N | LYS | 188 | 26.808 | 20.883 98.111 | 1.00 60.00 |
| ATOM | 1483 | CA | LYS | 188 | 26.824 | 22.312 98.227 | 1.00 60.00 |
| ATOM | 1484 | CB | LYS | 188 | 27.940 | 22.992 97.410 | 1.00 60.00 |
| ATOM | 1485 | CG | LYS | 188 | 27.754 | 22.935 95.892 | 1.00 60.00 |
| ATOM | 1486 | CD | LYS | 188 | 28.687 | 23.881 95.133 | 1.00 60.00 |
| ATOM | 1487 | CE | LYS | 188 | 28.505 | 23.842 93.615 | 1.00 60.00 |
| ATOM | 1488 | NZ | LYS | 188 | 27.288 | 24.596 93.239 | 1.00 60.00 |
| ATOM | 1489 | C | LYS | 188 | 25.520 | 22.866 97.766 | 1.00 60.00 |
| ATOM | 1490 | O | LYS | 188 | 24.898 | 23.672 98.457 | 1.00 60.00 |
| ATOM | 1491 | N | ILE | 189 | 25.062 | 22.432 96.580 | 1.00 60.00 |
| ATOM | 1492 | CA | ILE | 189 | 23.844 | 22.955 96.045 | 1.00 60.00 |
| ATOM | 1493 | CB | ILE | 189 | 23.578 | 22.493 94.642 | 1.00 60.00 |
| ATOM | 1494 | CG2 | ILE | 189 | 22.174 | 22.972 94.235 | 1.00 60.00 |
| ATOM | 1495 | CG1 | ILE | 189 | 24.696 | 22.988 93.709 | 1.00 60.00 |
| ATOM | 1496 | CD1 | ILE | 189 | 24.675 | 22.336 92.327 | 1.00 60.00 |
| ATOM | 1497 | C | ILE | 189 | 22.706 | 22.515 96.898 | 1.00 60.00 |
| ATOM | 1498 | O | ILE | 189 | 21.809 | 23.302 97.202 | 1.00 60.00 |
| ATOM | 1499 | N | ILE | 190 | 22.712 | 21.239 97.328 | 1.00 60.00 |
| ATOM | 1500 | CA | ILE | 190 | 21.571 | 20.792 98.061 | 1.00 60.00 |
| ATOM | 1501 | CB | ILE | 190 | 21.090 | 19.429 97.664 | 1.00 60.00 |
| ATOM | 1502 | CG2 | ILE | 190 | 19.977 | 19.021 98.641 | 1.00 60.00 |
| ATOM | 1503 | CG1 | ILE | 190 | 20.662 | 19.425 96.187 | 1.00 60.00 |
| ATOM | 1504 | CD1 | ILE | 190 | 19.540 | 20.416 95.881 | 1.00 60.00 |
| ATOM | 1505 | C | ILE | 190 | 21.862 | 20.750 99.521 | 1.00 60.00 |
| ATOM | 1506 | O | ILE | 190 | 22.747 | 20.040 99.995 | 1.00 60.00 |
| ATOM | 1507 | N | CYS | 191 | 21.072 | 21.539 100.263 | 1.00 20.00 |
| ATOM | 1508 | CA | CYS | 191 | 21.065 | 21.609 101.689 | 1.00 20.00 |
| ATOM | 1509 | CB | CYS | 191 | 22.170 | 22.473 102.340 | 1.00 20.00 |
| ATOM | 1510 | SG | CYS | 191 | 22.159 | 22.254 104.150 | 1.00 20.00 |
| ATOM | 1511 | C | CYS | 191 | 19.747 | 22.242 101.948 | 1.00 20.00 |
| ATOM | 1512 | O | CYS | 191 | 18.784 | 21.964 101.234 | 1.00 20.00 |
| ATOM | 1513 | N | ALA | 192 | 19.636 | 23.097 102.974 | 1.00 20.00 |
| ATOM | 1514 | CA | ALA | 192 | 18.346 | 23.705 103.116 | 1.00 20.00 |
| ATOM | 1515 | CB | ALA | 192 | 18.227 | 24.618 104.348 | 1.00 20.00 |
| ATOM | 1516 | C | ALA | 192 | 18.198 | 24.559 101.897 | 1.00 20.00 |
| ATOM | 1517 | O | ALA | 192 | 19.183 | 25.063 101.361 | 1.00 20.00 |
| ATOM | 1518 | N | GLN | 193 | 16.957 | 24.731 101.411 | 1.00 20.00 |
| ATOM | 1519 | CA | GLN | 193 | 16.750 | 25.493 100.215 | 1.00 20.00 |
| ATOM | 1520 | CB | GLN | 193 | 15.265 | 25.621 99.842 | 1.00 20.00 |
| ATOM | 1521 | CG | GLN | 193 | 15.034 | 26.442 98.571 | 1.00 20.00 |
| ATOM | 1522 | CD | GLN | 193 | 13.554 | 26.787 98.487 | 1.00 20.00 |
| ATOM | 1523 | OE1 | GLN | 193 | 12.685 | 25.942 98.699 | 1.00 20.00 |
| ATOM | 1524 | NE2 | GLN | 193 | 13.257 | 28.078 98.180 | 1.00 20.00 |
| ATOM | 1525 | C | GLN | 193 | 17.226 | 26.890 100.449 | 1.00 20.00 |
| ATOM | 1526 | O | GLN | 193 | 17.903 | 27.478 99.607 | 1.00 20.00 |
| ATOM | 1527 | N | GLN | 194 | 16.865 | 27.457 101.611 | 1.00 20.00 |
| ATOM | 1528 | CA | GLN | 194 | 17.176 | 28.820 101.927 | 1.00 20.00 |
| ATOM | 1529 | CB | GLN | 194 | 16.434 | 29.341 103.168 | 1.00 20.00 |
| ATOM | 1530 | CG | GLN | 194 | 14.946 | 29.591 102.911 | 1.00 20.00 |
| ATOM | 1531 | CD | GLN | 194 | 14.829 | 30.818 102.012 | 1.00 20.00 |
| ATOM | 1532 | OE1 | GLN | 194 | 14.266 | 31.837 102.409 | 1.00 20.00 |
| ATOM | 1533 | NE2 | GLN | 194 | 15.375 | 30.727 100.770 | 1.00 20.00 |
| ATOM | 1534 | C | GLN | 194 | 18.636 | 29.041 102.144 | 1.00 20.00 |
| ATOM | 1535 | O | GLN | 194 | 19.155 | 30.084 101.751 | 1.00 20.00 |
| ATOM | 1536 | N | CYS | 195 | 19.338 | 28.079 102.772 | 1.00 20.00 |
| ATOM | 1537 | CA | CYS | 195 | 20.717 | 28.306 103.100 | 1.00 20.00 |
| ATOM | 1538 | CB | CYS | 195 | 21.440 | 27.122 103.762 | 1.00 20.00 |
| ATOM | 1539 | SG | CYS | 195 | 20.920 | 26.836 105.478 | 1.00 20.00 |
| ATOM | 1540 | C | CYS | 195 | 21.489 | 28.676 101.881 | 1.00 20.00 |

Figure 6A-19

| ATOM | 1541 | O | CYS | 195 | 21.258 | 28.163 | 100.786 | 1.00 | 20.00 |
|------|------|-----|-----|-----|--------|--------|---------|------|-------|
| ATOM | 1542 | N | SER | 196 | 22.420 | 29.630 | 102.061 | 1.00 | 20.00 |
| ATOM | 1543 | CA | SER | 196 | 23.256 | 30.069 | 100.992 | 1.00 | 20.00 |
| ATOM | 1544 | CB | SER | 196 | 23.147 | 31.578 | 100.711 | 1.00 | 20.00 |
| ATOM | 1545 | OG | SER | 196 | 24.007 | 31.938 | 99.640 | 1.00 | 20.00 |
| ATOM | 1546 | C | SER | 196 | 24.654 | 29.809 | 101.435 | 1.00 | 20.00 |
| ATOM | 1547 | O | SER | 196 | 24.961 | 29.857 | 102.626 | 1.00 | 20.00 |
| ATOM | 1548 | N | GLY | 197 | 25.546 | 29.508 | 100.478 | 1.00 | 20.00 |
| ATOM | 1549 | CA | GLY | 197 | 26.896 | 29.237 | 100.853 | 1.00 | 20.00 |
| ATOM | 1550 | C | GLY | 197 | 26.969 | 27.802 | 101.256 | 1.00 | 20.00 |
| ATOM | 1551 | O | GLY | 197 | 26.984 | 26.915 | 100.404 | 1.00 | 20.00 |
| ATOM | 1552 | N | ARG | 198 | 27.018 | 27.536 | 102.578 | 1.00 | 20.00 |
| ATOM | 1553 | CA | ARG | 198 | 27.135 | 26.178 | 103.025 | 1.00 | 20.00 |
| ATOM | 1554 | CB | ARG | 198 | 28.563 | 25.809 | 103.458 | 1.00 | 20.00 |
| ATOM | 1555 | CG | ARG | 198 | 29.628 | 26.165 | 102.416 | 1.00 | 20.00 |
| ATOM | 1556 | CD | ARG | 198 | 29.342 | 25.646 | 101.005 | 1.00 | 20.00 |
| ATOM | 1557 | NE | ARG | 198 | 30.472 | 26.087 | 100.137 | 1.00 | 20.00 |
| ATOM | 1558 | CZ | ARG | 198 | 30.458 | 27.330 | 99.573 | 1.00 | 20.00 |
| ATOM | 1559 | NH1 | ARG | 198 | 29.415 | 28.178 | 99.807 | 1.00 | 20.00 |
| ATOM | 1560 | NH2 | ARG | 198 | 31.493 | 27.730 | 98.778 | 1.00 | 20.00 |
| ATOM | 1561 | C | ARG | 198 | 26.263 | 26.027 | 104.229 | 1.00 | 20.00 |
| ATOM | 1562 | O | ARG | 198 | 25.555 | 26.956 | 104.618 | 1.00 | 20.00 |
| ATOM | 1563 | N | CYS | 199 | 26.261 | 24.821 | 104.836 | 1.00 | 20.00 |
| ATOM | 1564 | CA | CYS | 199 | 25.438 | 24.635 | 105.994 | 1.00 | 20.00 |
| ATOM | 1565 | CB | CYS | 199 | 24.029 | 24.136 | 105.630 | 1.00 | 20.00 |
| ATOM | 1566 | SG | CYS | 199 | 24.083 | 22.554 | 104.740 | 1.00 | 20.00 |
| ATOM | 1567 | C | CYS | 199 | 26.071 | 23.617 | 106.894 | 1.00 | 20.00 |
| ATOM | 1568 | O | CYS | 199 | 26.749 | 22.697 | 106.437 | 1.00 | 20.00 |
| ATOM | 1569 | N | ARG | 200 | 25.879 | 23.785 | 108.220 | 1.00 | 20.00 |
| ATOM | 1570 | CA | ARG | 200 | 26.388 | 22.844 | 109.176 | 1.00 | 20.00 |
| ATOM | 1571 | CB | ARG | 200 | 26.172 | 23.288 | 110.631 | 1.00 | 20.00 |
| ATOM | 1572 | CG | ARG | 200 | 26.619 | 22.240 | 111.653 | 1.00 | 20.00 |
| ATOM | 1573 | CD | ARG | 200 | 26.231 | 22.582 | 113.093 | 1.00 | 20.00 |
| ATOM | 1574 | NE | ARG | 200 | 26.636 | 21.432 | 113.950 | 1.00 | 20.00 |
| ATOM | 1575 | CZ | ARG | 200 | 25.759 | 20.411 | 114.180 | 1.00 | 20.00 |
| ATOM | 1576 | NH1 | ARG | 200 | 24.507 | 20.448 | 113.637 | 1.00 | 20.00 |
| ATOM | 1577 | NH2 | ARG | 200 | 26.138 | 19.352 | 114.953 | 1.00 | 20.00 |
| ATOM | 1578 | C | ARG | 200 | 25.634 | 21.571 | 108.991 | 1.00 | 20.00 |
| ATOM | 1579 | O | ARG | 200 | 26.211 | 20.486 | 108.928 | 1.00 | 20.00 |
| ATOM | 1580 | N | GLY | 201 | 24.300 | 21.689 | 108.878 | 1.00 | 20.00 |
| ATOM | 1581 | CA | GLY | 201 | 23.466 | 20.541 | 108.701 | 1.00 | 20.00 |
| ATOM | 1582 | C | GLY | 201 | 22.504 | 20.899 | 107.622 | 1.00 | 20.00 |
| ATOM | 1583 | O | GLY | 201 | 22.487 | 22.032 | 107.146 | 1.00 | 20.00 |
| ATOM | 1584 | N | LYS | 202 | 21.671 | 19.931 | 107.205 | 1.00 | 20.00 |
| ATOM | 1585 | CA | LYS | 202 | 20.746 | 20.212 | 106.151 | 1.00 | 20.00 |
| ATOM | 1586 | CB | LYS | 202 | 19.964 | 18.978 | 105.669 | 1.00 | 20.00 |
| ATOM | 1587 | CG | LYS | 202 | 18.904 | 18.489 | 106.655 | 1.00 | 20.00 |
| ATOM | 1588 | CD | LYS | 202 | 17.921 | 17.492 | 106.037 | 1.00 | 20.00 |
| ATOM | 1589 | CE | LYS | 202 | 16.722 | 17.176 | 106.933 | 1.00 | 20.00 |
| ATOM | 1590 | NZ | LYS | 202 | 17.175 | 16.521 | 108.180 | 1.00 | 20.00 |
| ATOM | 1591 | C | LYS | 202 | 19.757 | 21.209 | 106.664 | 1.00 | 20.00 |
| ATOM | 1592 | O | LYS | 202 | 19.178 | 21.971 | 105.893 | 1.00 | 20.00 |
| ATOM | 1593 | N | SER | 203 | 19.547 | 21.236 | 107.993 | 1.00 | 20.00 |
| ATOM | 1594 | CA | SER | 203 | 18.590 | 22.136 | 108.566 | 1.00 | 20.00 |
| ATOM | 1595 | CB | SER | 203 | 18.554 | 22.101 | 110.103 | 1.00 | 20.00 |
| ATOM | 1596 | OG | SER | 203 | 19.783 | 22.579 | 110.629 | 1.00 | 20.00 |
| ATOM | 1597 | C | SER | 203 | 18.935 | 23.531 | 108.156 | 1.00 | 20.00 |
| ATOM | 1598 | O | SER | 203 | 20.099 | 23.904 | 108.017 | 1.00 | 20.00 |
| ATOM | 1599 | N | PRO | 204 | 17.900 | 24.290 | 107.926 | 1.00 | 20.00 |
| ATOM | 1600 | CA | PRO | 204 | 18.059 | 25.667 | 107.545 | 1.00 | 20.00 |
| ATOM | 1601 | CD | PRO | 204 | 16.689 | 23.710 | 107.368 | 1.00 | 20.00 |
| ATOM | 1602 | CB | PRO | 204 | 16.707 | 26.108 | 106.989 | 1.00 | 20.00 |
| ATOM | 1603 | CG | PRO | 204 | 16.076 | 24.802 | 106.477 | 1.00 | 20.00 |
| ATOM | 1604 | C | PRO | 204 | 18.513 | 26.498 | 108.699 | 1.00 | 20.00 |
| ATOM | 1605 | O | PRO | 204 | 18.963 | 27.622 | 108.484 | 1.00 | 20.00 |
| ATOM | 1606 | N | SER | 205 | 18.384 | 25.979 | 109.931 | 1.00 | 20.00 |
| ATOM | 1607 | CA | SER | 205 | 18.742 | 26.753 | 111.079 | 1.00 | 20.00 |
| ATOM | 1608 | CB | SER | 205 | 18.444 | 26.033 | 112.403 | 1.00 | 20.00 |
| ATOM | 1609 | OG | SER | 205 | 18.825 | 26.855 | 113.496 | 1.00 | 20.00 |
| ATOM | 1610 | C | SER | 205 | 20.208 | 27.037 | 111.052 | 1.00 | 20.00 |
| ATOM | 1611 | O | SER | 205 | 20.633 | 28.159 | 111.324 | 1.00 | 20.00 |
| ATOM | 1612 | N | ASP | 206 | 21.029 | 26.027 | 110.714 | 1.00 | 20.00 |
| ATOM | 1613 | CA | ASP | 206 | 22.436 | 26.268 | 110.780 | 1.00 | 20.00 |
| ATOM | 1614 | CB | ASP | 206 | 23.208 | 25.157 | 111.522 | 1.00 | 20.00 |
| ATOM | 1615 | CG | ASP | 206 | 22.967 | 23.823 | 110.833 | 1.00 | 20.00 |
| ATOM | 1616 | OD1 | ASP | 206 | 22.185 | 23.798 | 109.844 | 1.00 | 20.00 |
| ATOM | 1617 | OD2 | ASP | 206 | 23.553 | 22.807 | 111.293 | 1.00 | 20.00 |

Figure 6A-20

| | | | | | | | | |
|---|---|---|---|---|---|---|---|---|
| ATOM | 1618 | C | ASP | 206 | 23.009 | 26.457 | 109.416 | 1.00 20.00 |
| ATOM | 1619 | O | ASP | 206 | 23.739 | 25.610 | 108.904 | 1.00 20.00 |
| ATOM | 1620 | N | CYS | 207 | 22.698 | 27.600 | 108.781 | 1.00 20.00 |
| ATOM | 1621 | CA | CYS | 207 | 23.320 | 27.850 | 107.520 | 1.00 20.00 |
| ATOM | 1622 | CB | CYS | 207 | 22.685 | 28.994 | 106.712 | 1.00 20.00 |
| ATOM | 1623 | SG | CYS | 207 | 20.941 | 28.696 | 106.295 | 1.00 20.00 |
| ATOM | 1624 | C | CYS | 207 | 24.714 | 28.252 | 107.882 | 1.00 20.00 |
| ATOM | 1625 | O | CYS | 207 | 25.069 | 28.244 | 109.060 | 1.00 20.00 |
| ATOM | 1626 | N | CYS | 208 | 25.558 | 28.599 | 106.891 | 1.00 20.00 |
| ATOM | 1627 | CA | CYS | 208 | 26.904 | 28.962 | 107.237 | 1.00 20.00 |
| ATOM | 1628 | CB | CYS | 208 | 28.002 | 28.034 | 106.664 | 1.00 20.00 |
| ATOM | 1629 | SG | CYS | 208 | 27.933 | 26.299 | 107.211 | 1.00 20.00 |
| ATOM | 1630 | C | CYS | 208 | 27.182 | 30.318 | 106.673 | 1.00 20.00 |
| ATOM | 1631 | O | CYS | 208 | 26.354 | 30.904 | 105.978 | 1.00 20.00 |
| ATOM | 1632 | N | HIS | 209 | 28.378 | 30.856 | 106.983 | 1.00 20.00 |
| ATOM | 1633 | CA | HIS | 209 | 28.761 | 32.157 | 106.516 | 1.00 20.00 |
| ATOM | 1634 | ND1 | HIS | 209 | 31.205 | 34.449 | 105.754 | 1.00 20.00 |
| ATOM | 1635 | NE2 | HIS | 209 | 30.583 | 36.333 | 106.757 | 1.00 20.00 |
| ATOM | 1636 | CE1 | HIS | 209 | 31.279 | 35.802 | 105.767 | 1.00 20.00 |
| ATOM | 1637 | CD2 | HIS | 209 | 30.033 | 35.247 | 107.414 | 1.00 20.00 |
| ATOM | 1638 | CG | HIS | 209 | 30.404 | 34.084 | 106.813 | 1.00 20.00 |
| ATOM | 1639 | CB | HIS | 209 | 30.067 | 32.664 | 107.158 | 1.00 20.00 |
| ATOM | 1640 | C | HIS | 209 | 28.948 | 32.079 | 105.033 | 1.00 20.00 |
| ATOM | 1641 | O | HIS | 209 | 29.128 | 31.004 | 104.466 | 1.00 20.00 |
| ATOM | 1642 | N | ASN | 210 | 28.893 | 33.246 | 104.367 | 1.00 20.00 |
| ATOM | 1643 | CA | ASN | 210 | 29.004 | 33.331 | 102.939 | 1.00 20.00 |
| ATOM | 1644 | CB | ASN | 210 | 28.846 | 34.774 | 102.428 | 1.00 20.00 |
| ATOM | 1645 | CG | ASN | 210 | 28.714 | 34.761 | 100.911 | 1.00 20.00 |
| ATOM | 1646 | OD1 | ASN | 210 | 28.882 | 33.733 | 100.258 | 1.00 20.00 |
| ATOM | 1647 | ND2 | ASN | 210 | 28.416 | 35.952 | 100.326 | 1.00 20.00 |
| ATOM | 1648 | C | ASN | 210 | 30.363 | 32.852 | 102.527 | 1.00 20.00 |
| ATOM | 1649 | O | ASN | 210 | 30.515 | 32.222 | 101.481 | 1.00 20.00 |
| ATOM | 1650 | N | GLN | 211 | 31.390 | 33.178 | 103.333 | 1.00 20.00 |
| ATOM | 1651 | CA | GLN | 211 | 32.767 | 32.859 | 103.063 | 1.00 20.00 |
| ATOM | 1652 | CB | GLN | 211 | 33.737 | 33.596 | 104.003 | 1.00 20.00 |
| ATOM | 1653 | CG | GLN | 211 | 33.714 | 35.117 | 103.836 | 1.00 20.00 |
| ATOM | 1654 | CD | GLN | 211 | 34.323 | 35.463 | 102.485 | 1.00 20.00 |
| ATOM | 1655 | OE1 | GLN | 211 | 34.683 | 34.585 | 101.701 | 1.00 20.00 |
| ATOM | 1656 | NE2 | GLN | 211 | 34.442 | 36.787 | 102.201 | 1.00 20.00 |
| ATOM | 1657 | C | GLN | 211 | 33.052 | 31.398 | 103.194 | 1.00 20.00 |
| ATOM | 1658 | O | GLN | 211 | 33.849 | 30.857 | 102.430 | 1.00 20.00 |
| ATOM | 1659 | N | CYS | 212 | 32.426 | 30.716 | 104.172 | 1.00 20.00 |
| ATOM | 1660 | CA | CYS | 212 | 32.752 | 29.336 | 104.389 | 1.00 20.00 |
| ATOM | 1661 | CB | CYS | 212 | 31.903 | 28.637 | 105.463 | 1.00 20.00 |
| ATOM | 1662 | SG | CYS | 212 | 32.242 | 29.235 | 107.138 | 1.00 20.00 |
| ATOM | 1663 | C | CYS | 212 | 32.532 | 28.570 | 103.132 | 1.00 20.00 |
| ATOM | 1664 | O | CYS | 212 | 31.654 | 28.890 | 102.334 | 1.00 20.00 |
| ATOM | 1665 | N | ALA | 213 | 33.386 | 27.555 | 102.909 | 1.00 20.00 |
| ATOM | 1666 | CA | ALA | 213 | 33.223 | 26.691 | 101.786 | 1.00 20.00 |
| ATOM | 1667 | CB | ALA | 213 | 34.360 | 26.783 | 100.754 | 1.00 20.00 |
| ATOM | 1668 | C | ALA | 213 | 33.221 | 25.317 | 102.367 | 1.00 20.00 |
| ATOM | 1669 | O | ALA | 213 | 33.860 | 25.080 | 103.391 | 1.00 20.00 |
| ATOM | 1670 | N | ALA | 214 | 32.475 | 24.386 | 101.743 | 1.00 20.00 |
| ATOM | 1671 | CA | ALA | 214 | 32.371 | 23.039 | 102.226 | 1.00 20.00 |
| ATOM | 1672 | CB | ALA | 214 | 33.677 | 22.431 | 102.779 | 1.00 20.00 |
| ATOM | 1673 | C | ALA | 214 | 31.318 | 22.983 | 103.291 | 1.00 20.00 |
| ATOM | 1674 | O | ALA | 214 | 30.179 | 22.609 | 103.012 | 1.00 20.00 |
| ATOM | 1675 | N | GLY | 215 | 31.668 | 23.351 | 104.545 | 1.00 20.00 |
| ATOM | 1676 | CA | GLY | 215 | 30.697 | 23.270 | 105.605 | 1.00 20.00 |
| ATOM | 1677 | C | GLY | 215 | 31.138 | 24.140 | 106.743 | 1.00 20.00 |
| ATOM | 1678 | O | GLY | 215 | 31.970 | 25.030 | 106.574 | 1.00 20.00 |
| ATOM | 1679 | N | CYS | 216 | 30.546 | 23.934 | 107.939 | 1.00 20.00 |
| ATOM | 1680 | CA | CYS | 216 | 30.951 | 24.718 | 109.070 | 1.00 20.00 |
| ATOM | 1681 | CB | CYS | 216 | 30.396 | 26.163 | 109.050 | 1.00 20.00 |
| ATOM | 1682 | SG | CYS | 216 | 28.581 | 26.299 | 109.142 | 1.00 20.00 |
| ATOM | 1683 | C | CYS | 216 | 30.505 | 24.038 | 110.327 | 1.00 20.00 |
| ATOM | 1684 | O | CYS | 216 | 29.540 | 23.275 | 110.333 | 1.00 20.00 |
| ATOM | 1685 | N | THR | 217 | 31.244 | 24.267 | 111.432 | 1.00 20.00 |
| ATOM | 1686 | CA | THR | 217 | 30.866 | 23.699 | 112.693 | 1.00 20.00 |
| ATOM | 1687 | CB | THR | 217 | 31.891 | 23.910 | 113.766 | 1.00 20.00 |
| ATOM | 1688 | OG1 | THR | 217 | 32.063 | 25.297 | 114.016 | 1.00 20.00 |
| ATOM | 1689 | CG2 | THR | 217 | 33.215 | 23.275 | 113.306 | 1.00 20.00 |
| ATOM | 1690 | C | THR | 217 | 29.606 | 24.371 | 113.122 | 1.00 20.00 |
| ATOM | 1691 | O | THR | 217 | 28.677 | 23.731 | 113.613 | 1.00 20.00 |
| ATOM | 1692 | N | GLY | 218 | 29.556 | 25.702 | 112.929 | 1.00 20.00 |
| ATOM | 1693 | CA | GLY | 218 | 28.405 | 26.480 | 113.274 | 1.00 20.00 |
| ATOM | 1694 | C | GLY | 218 | 28.579 | 27.771 | 112.553 | 1.00 20.00 |

Figure 6A-21

```
ATOM   1695  O   GLY  218      29.697  28.095 112.124  1.00 20.00
ATOM   1696  N   PRO  219      27.507  28.500 112.390  1.00 20.00
ATOM   1697  CA  PRO  219      27.565  29.741 111.672  1.00 20.00
ATOM   1698  CD  PRO  219      26.411  28.480 113.348  1.00 20.00
ATOM   1699  CB  PRO  219      26.166  30.370 111.845  1.00 20.00
ATOM   1700  CG  PRO  219      25.757  29.869 113.237  1.00 20.00
ATOM   1701  C   PRO  219      28.630  30.604 112.263  1.00 20.00
ATOM   1702  O   PRO  219      28.406  31.211 113.307  1.00 20.00
ATOM   1703  N   ARG  220      29.802  30.688 111.593  1.00 20.00
ATOM   1704  CA  ARG  220      30.887  31.495 112.065  1.00 20.00
ATOM   1705  CB  ARG  220      31.665  30.870 113.235  1.00 20.00
ATOM   1706  CG  ARG  220      30.925  30.632 114.489  1.00 20.00
ATOM   1707  CD  ARG  220      30.773  31.832 115.432  1.00 20.00
ATOM   1708  NE  ARG  220      32.158  32.053 115.935  1.00 20.00
ATOM   1709  CZ  ARG  220      32.453  33.227 116.550  1.00 20.00
ATOM   1710  NH1 ARG  220      31.532  34.190 116.720  1.00 20.00
ATOM   1711  NH2 ARG  220      33.755  33.453 116.990  1.00 20.00
ATOM   1712  C   ARG  220      31.867  31.565 110.941  1.00 20.00
ATOM   1713  O   ARG  220      31.967  30.628 110.154  1.00 20.00
ATOM   1714  N   GLU  221      32.594  32.690 110.835  1.00 20.00
ATOM   1715  CA  GLU  221      33.599  32.850 109.825  1.00 20.00
ATOM   1716  CB  GLU  221      34.140  34.288 109.775  1.00 20.00
ATOM   1717  CG  GLU  221      33.069  35.307 109.379  1.00 20.00
ATOM   1718  CD  GLU  221      33.694  36.692 109.420  1.00 20.00
ATOM   1719  OE1 GLU  221      34.946  36.771 109.530  1.00 20.00
ATOM   1720  OE2 GLU  221      32.928  37.691 109.343  1.00 20.00
ATOM   1721  C   GLU  221      34.739  31.934 110.156  1.00 20.00
ATOM   1722  O   GLU  221      35.399  31.392 109.271  1.00 20.00
ATOM   1723  N   SER  222      35.024  31.785 111.462  1.00 20.00
ATOM   1724  CA  SER  222      36.091  30.965 111.970  1.00 20.00
ATOM   1725  CB  SER  222      36.398  31.242 113.453  1.00 20.00
ATOM   1726  OG  SER  222      35.300  30.848 114.261  1.00 20.00
ATOM   1727  C   SER  222      35.754  29.507 111.851  1.00 20.00
ATOM   1728  O   SER  222      36.642  28.664 111.741  1.00 20.00
ATOM   1729  N   ASP  223      34.451  29.179 111.904  1.00 20.00
ATOM   1730  CA  ASP  223      33.949  27.831 111.941  1.00 20.00
ATOM   1731  CB  ASP  223      32.461  27.745 112.315  1.00 20.00
ATOM   1732  CG  ASP  223      32.362  28.062 113.802  1.00 20.00
ATOM   1733  OD1 ASP  223      33.407  28.447 114.393  1.00 20.00
ATOM   1734  OD2 ASP  223      31.247  27.918 114.371  1.00 20.00
ATOM   1735  C   ASP  223      34.162  27.068 110.665  1.00 20.00
ATOM   1736  O   ASP  223      34.130  25.839 110.685  1.00 20.00
ATOM   1737  N   CYS  224      34.339  27.764 109.527  1.00 20.00
ATOM   1738  CA  CYS  224      34.448  27.151 108.225  1.00 20.00
ATOM   1739  CB  CYS  224      35.043  28.088 107.159  1.00 20.00
ATOM   1740  SG  CYS  224      34.212  29.696 107.044  1.00 20.00
ATOM   1741  C   CYS  224      35.353  25.951 108.244  1.00 20.00
ATOM   1742  O   CYS  224      36.306  25.875 109.018  1.00 20.00
ATOM   1743  N   LEU  225      34.984  24.921 107.449  1.00 20.00
ATOM   1744  CA  LEU  225      35.802  23.766 107.222  1.00 20.00
ATOM   1745  CB  LEU  225      34.996  22.552 106.727  1.00 20.00
ATOM   1746  CG  LEU  225      33.995  22.038 107.776  1.00 20.00
ATOM   1747  CD1 LEU  225      33.262  20.781 107.283  1.00 20.00
ATOM   1748  CD2 LEU  225      34.668  21.843 109.145  1.00 20.00
ATOM   1749  C   LEU  225      36.828  24.117 106.185  1.00 20.00
ATOM   1750  O   LEU  225      37.931  23.578 106.177  1.00 20.00
ATOM   1751  N   VAL  226      36.443  25.009 105.246  1.00 20.00
ATOM   1752  CA  VAL  226      37.293  25.435 104.173  1.00 20.00
ATOM   1753  CB  VAL  226      37.158  24.548 102.967  1.00 20.00
ATOM   1754  CG1 VAL  226      38.085  25.028 101.837  1.00 20.00
ATOM   1755  CG2 VAL  226      37.438  23.100 103.414  1.00 20.00
ATOM   1756  C   VAL  226      36.854  26.821 103.807  1.00 20.00
ATOM   1757  O   VAL  226      35.787  27.264 104.225  1.00 20.00
ATOM   1758  N   CYS  227      37.669  27.551 103.012  1.00 20.00
ATOM   1759  CA  CYS  227      37.333  28.910 102.701  1.00 20.00
ATOM   1760  CB  CYS  227      38.489  29.866 103.045  1.00 20.00
ATOM   1761  SG  CYS  227      38.093  31.630 102.904  1.00 20.00
ATOM   1762  C   CYS  227      37.019  29.003 101.239  1.00 20.00
ATOM   1763  O   CYS  227      37.584  28.279 100.420  1.00 20.00
ATOM   1764  N   ARG  228      36.044  29.869 100.888  1.00 20.00
ATOM   1765  CA  ARG  228      35.667  30.067  99.520  1.00 20.00
ATOM   1766  CB  ARG  228      34.418  30.945  99.346  1.00 20.00
ATOM   1767  CG  ARG  228      34.051  31.131  97.874  1.00 20.00
ATOM   1768  CD  ARG  228      32.728  31.856  97.637  1.00 20.00
ATOM   1769  NE  ARG  228      32.565  31.975  96.161  1.00 20.00
ATOM   1770  CZ  ARG  228      32.078  30.924  95.439  1.00 20.00
ATOM   1771  NH1 ARG  228      31.740  29.762  96.070  1.00 20.00
```

Figure 6A-22

```
ATOM   1772  NH2 ARG   228      31.935  31.036  94.086  1.00 20.00
ATOM   1773  C   ARG   228      36.790  30.753  98.823  1.00 20.00
ATOM   1774  O   ARG   228      37.171  30.389  97.710  1.00 20.00
ATOM   1775  N   LYS   229      37.366  31.763  99.496  1.00 20.00
ATOM   1776  CA  LYS   229      38.413  32.542  98.910  1.00 20.00
ATOM   1777  CB  LYS   229      38.191  34.057  99.044  1.00 20.00
ATOM   1778  CG  LYS   229      37.042  34.561  98.171  1.00 20.00
ATOM   1779  CD  LYS   229      37.253  34.283  96.680  1.00 20.00
ATOM   1780  CE  LYS   229      36.105  34.761  95.790  1.00 20.00
ATOM   1781  NZ  LYS   229      36.184  36.227  95.603  1.00 20.00
ATOM   1782  C   LYS   229      39.687  32.194  99.601  1.00 20.00
ATOM   1783  O   LYS   229      40.193  31.078  99.477  1.00 20.00
ATOM   1784  N   PHE   230      40.258  33.164 100.336  1.00 20.00
ATOM   1785  CA  PHE   230      41.529  32.907 100.942  1.00 20.00
ATOM   1786  CB  PHE   230      42.569  33.977 100.583  1.00 20.00
ATOM   1787  CG  PHE   230      42.657  33.954  99.093  1.00 20.00
ATOM   1788  CD1 PHE   230      43.536  33.115  98.450  1.00 20.00
ATOM   1789  CD2 PHE   230      41.839  34.761  98.336  1.00 20.00
ATOM   1790  CE1 PHE   230      43.610  33.092  97.077  1.00 20.00
ATOM   1791  CE2 PHE   230      41.908  34.743  96.963  1.00 20.00
ATOM   1792  CZ  PHE   230      42.793  33.906  96.330  1.00 20.00
ATOM   1793  C   PHE   230      41.368  32.874 102.427  1.00 20.00
ATOM   1794  O   PHE   230      40.583  33.627 102.998  1.00 20.00
ATOM   1795  N   ARG   231      42.120  31.974 103.091  1.00 20.00
ATOM   1796  CA  ARG   231      42.039  31.849 104.516  1.00 20.00
ATOM   1797  CB  ARG   231      42.237  30.409 105.019  1.00 20.00
ATOM   1798  CG  ARG   231      41.072  29.470 104.701  1.00 20.00
ATOM   1799  CD  ARG   231      40.210  29.136 105.921  1.00 20.00
ATOM   1800  NE  ARG   231      41.072  28.375 106.870  1.00 20.00
ATOM   1801  CZ  ARG   231      40.647  28.124 108.142  1.00 20.00
ATOM   1802  NH1 ARG   231      39.422  28.566 108.553  1.00 20.00
ATOM   1803  NH2 ARG   231      41.447  27.430 109.002  1.00 20.00
ATOM   1804  C   ARG   231      43.141  32.670 105.090  1.00 20.00
ATOM   1805  O   ARG   231      44.256  32.668 104.574  1.00 20.00
ATOM   1806  N   ASP   232      42.846  33.433 106.158  1.00 20.00
ATOM   1807  CA  ASP   232      43.888  34.220 106.741  1.00 20.00
ATOM   1808  CB  ASP   232      43.974  35.641 106.150  1.00 20.00
ATOM   1809  CG  ASP   232      45.245  36.315 106.653  1.00 20.00
ATOM   1810  OD1 ASP   232      45.995  35.669 107.431  1.00 20.00
ATOM   1811  OD2 ASP   232      45.485  37.488 106.260  1.00 20.00
ATOM   1812  C   ASP   232      43.611  34.358 108.202  1.00 20.00
ATOM   1813  O   ASP   232      42.499  34.684 108.606  1.00 20.00
ATOM   1814  N   GLU   233      44.636  34.109 109.036  1.00 20.00
ATOM   1815  CA  GLU   233      44.517  34.286 110.453  1.00 20.00
ATOM   1816  CB  GLU   233      44.360  35.763 110.853  1.00 20.00
ATOM   1817  CG  GLU   233      45.572  36.628 110.505  1.00 20.00
ATOM   1818  CD  GLU   233      45.258  38.056 110.930  1.00 20.00
ATOM   1819  OE1 GLU   233      45.031  38.275 112.150  1.00 20.00
ATOM   1820  OE2 GLU   233      45.235  38.947 110.040  1.00 20.00
ATOM   1821  C   GLU   233      43.320  33.557 110.969  1.00 20.00
ATOM   1822  O   GLU   233      42.500  34.129 111.685  1.00 20.00
ATOM   1823  N   ALA   234      43.190  32.266 110.622  1.00 20.00
ATOM   1824  CA  ALA   234      42.116  31.473 111.146  1.00 20.00
ATOM   1825  CB  ALA   234      42.111  31.424 112.683  1.00 20.00
ATOM   1826  C   ALA   234      40.796  32.011 110.689  1.00 20.00
ATOM   1827  O   ALA   234      39.753  31.543 111.143  1.00 20.00
ATOM   1828  N   THR   235      40.781  32.995 109.769  1.00 20.00
ATOM   1829  CA  THR   235      39.503  33.482 109.337  1.00 20.00
ATOM   1830  CB  THR   235      39.258  34.931 109.648  1.00 20.00
ATOM   1831  OG1 THR   235      40.180  35.753 108.951  1.00 20.00
ATOM   1832  CG2 THR   235      39.406  35.140 111.163  1.00 20.00
ATOM   1833  C   THR   235      39.416  33.319 107.855  1.00 20.00
ATOM   1834  O   THR   235      40.417  33.394 107.146  1.00 20.00
ATOM   1835  N   CYS   236      38.192  33.078 107.349  1.00 20.00
ATOM   1836  CA  CYS   236      38.001  32.892 105.942  1.00 20.00
ATOM   1837  CB  CYS   236      36.800  31.972 105.650  1.00 20.00
ATOM   1838  SG  CYS   236      36.337  31.820 103.901  1.00 20.00
ATOM   1839  C   CYS   236      37.757 -34.243 105.357  1.00 20.00
ATOM   1840  O   CYS   236      36.743  34.876 105.644  1.00 20.00
ATOM   1841  N   LYS   237      38.699  34.721 104.515  1.00 20.00
ATOM   1842  CA  LYS   237      38.564  36.042 103.976  1.00 20.00
ATOM   1843  CB  LYS   237      39.768  36.950 104.271  1.00 20.00
ATOM   1844  CG  LYS   237      39.902  37.225 105.768  1.00 20.00
ATOM   1845  CD  LYS   237      38.629  37.821 106.374  1.00 20.00
ATOM   1846  CE  LYS   237      38.625  37.859 107.902  1.00 20.00
ATOM   1847  NZ  LYS   237      37.326  38.377 108.387  1.00 20.00
ATOM   1848  C   LYS   237      38.355  35.977 102.495  1.00 20.00
```

Figure 6A-23

```
ATOM   1849  C    LYS   237      38.846  35.079 101.814  1.00 20.00
ATOM   1850  N    ASP   238      37.555  36.936 101.986  1.00 20.00
ATOM   1851  CA   ASP   238      37.223  37.080 100.596  1.00 20.00
ATOM   1852  CB   ASP   238      36.171  38.195 100.390  1.00 20.00
ATOM   1853  CG   ASP   238      35.744  38.227  98.928  1.00 20.00
ATOM   1854  OD1  ASP   238      36.331  37.472  98.109  1.00 20.00
ATOM   1855  OD2  ASP   238      34.818  39.023  98.613  1.00 20.00
ATOM   1856  C    ASP   238      38.458  37.477  99.851  1.00 20.00
ATOM   1857  O    ASP   238      38.737  36.982  98.760  1.00 20.00
ATOM   1858  N    THR   239      39.224  38.415 100.431  1.00 20.00
ATOM   1859  CA   THR   239      40.448  38.854  99.832  1.00 20.00
ATOM   1860  CB   THR   239      40.329  40.155  99.097  1.00 20.00
ATOM   1861  OG1  THR   239      39.949  41.189  99.993  1.00 20.00
ATOM   1862  CG2  THR   239      39.277  39.998  97.987  1.00 20.00
ATOM   1863  C    THR   239      41.365  39.080 100.978  1.00 20.00
ATOM   1864  O    THR   239      40.916  39.209 102.116  1.00 20.00
ATOM   1865  N    CYS   240      42.683  39.120 100.733  1.00 20.00
ATOM   1866  CA   CYS   240      43.501  39.293 101.887  1.00 20.00
ATOM   1867  CB   CYS   240      44.812  38.515 101.839  1.00 20.00
ATOM   1868  SG   CYS   240      44.408  36.753 101.902  1.00 20.00
ATOM   1869  C    CYS   240      43.713  40.740 102.138  1.00 20.00
ATOM   1870  O    CYS   240      43.757  41.576 101.237  1.00 20.00
ATOM   1871  N    PRO   241      43.721  41.043 103.407  1.00 60.00
ATOM   1872  CA   PRO   241      44.007  42.383 103.837  1.00 60.00
ATOM   1873  CD   PRO   241      42.818  40.363 104.319  1.00 60.00
ATOM   1874  CB   PRO   241      43.277  42.577 105.167  1.00 60.00
ATOM   1875  CG   PRO   241      42.933  41.151 105.631  1.00 60.00
ATOM   1876  C    PRO   241      45.485  42.554 103.951  1.00 60.00
ATOM   1877  O    PRO   241      46.175  41.569 104.209  1.00 60.00
ATOM   1878  N    PRO   242      45.980  43.743 103.769  1.00 60.00
ATOM   1879  CA   PRO   242      47.389  43.977 103.902  1.00 60.00
ATOM   1880  CD   PRO   242      45.202  44.947 104.007  1.00 60.00
ATOM   1881  CB   PRO   242      47.555  45.487 103.767  1.00 60.00
ATOM   1882  CG   PRO   242      46.240  46.028 104.359  1.00 60.00
ATOM   1883  C    PRO   242      47.770  43.533 105.276  1.00 60.00
ATOM   1884  O    PRO   242      48.885  43.053 105.471  1.00 60.00
ATOM   1885  N    LEU   243      46.850  43.712 106.240  1.00 60.00
ATOM   1886  CA   LEU   243      47.089  43.368 107.608  1.00 60.00
ATOM   1887  CB   LEU   243      47.709  44.505 108.438  1.00 60.00
ATOM   1888  CG   LEU   243      49.158  44.819 108.040  1.00 60.00
ATOM   1889  CD1  LEU   243      49.746  45.960 108.883  1.00 60.00
ATOM   1890  CD2  LEU   243      50.013  43.547 108.079  1.00 60.00
ATOM   1891  C    LEU   243      45.751  43.091 108.189  1.00 60.00
ATOM   1892  O    LEU   243      44.871  42.571 107.504  1.00 60.00
ATOM   1893  N    MET   244      45.582  43.414 109.486  1.00 60.00
ATOM   1894  CA   MET   244      44.310  43.219 110.108  1.00 60.00
ATOM   1895  CB   MET   244      44.244  43.768 111.544  1.00 60.00
ATOM   1896  CG   MET   244      44.404  45.289 111.623  1.00 60.00
ATOM   1897  SD   MET   244      46.031  45.916 111.113  1.00 60.00
ATOM   1898  CE   MET   244      45.606  47.657 111.417  1.00 60.00
ATOM   1899  C    MET   244      43.341  43.983 109.277  1.00 60.00
ATOM   1900  O    MET   244      43.618  45.108 108.861  1.00 60.00
ATOM   1901  N    LEU   245      42.178  43.377 108.983  1.00 60.00
ATOM   1902  CA   LEU   245      41.275  44.062 108.114  1.00 60.00
ATOM   1903  CB   LEU   245      40.482  43.129 107.183  1.00 60.00
ATOM   1904  CG   LEU   245      39.510  43.877 106.252  1.00 60.00
ATOM   1905  CD1  LEU   245      40.262  44.818 105.295  1.00 60.00
ATOM   1906  CD2  LEU   245      38.586  42.898 105.511  1.00 60.00
ATOM   1907  C    LEU   245      40.300  44.820 108.945  1.00 60.00
ATOM   1908  O    LEU   245      39.603  44.260 109.791  1.00 60.00
ATOM   1909  N    TYR   246      40.255  46.143 108.713  1.00 60.00
ATOM   1910  CA   TYR   246      39.355  47.021 109.391  1.00 60.00
ATOM   1911  CB   TYR   246      39.974  47.732 110.606  1.00 60.00
ATOM   1912  CG   TYR   246      40.210  46.669 111.624  1.00 60.00
ATOM   1913  CD1  TYR   246      39.183  46.232 112.429  1.00 60.00
ATOM   1914  CD2  TYR   246      41.454  46.100 111.770  1.00 60.00
ATOM   1915  CE1  TYR   246      39.392  45.248 113.367  1.00 60.00
ATOM   1916  CE2  TYR   246      41.669  45.115 112.706  1.00 60.00
ATOM   1917  CZ   TYR   246      40.638  44.686 113.506  1.00 60.00
ATOM   1918  OH   TYR   246      40.858  43.675 114.466  1.00 60.00
ATOM   1919  C    TYR   246      38.956  48.037 108.378  1.00 60.00
ATOM   1920  O    TYR   246      39.319  47.918 107.209  1.00 60.00
ATOM   1921  N    ASN   247      38.163  49.044 108.784  1.00 60.00
ATOM   1922  CA   ASN   247      37.735  50.024 107.830  1.00 60.00
ATOM   1923  CB   ASN   247      36.289  50.489 108.073  1.00 60.00
ATOM   1924  CG   ASN   247      35.918  51.523 107.024  1.00 60.00
ATOM   1925  OD1  ASN   247      36.117  52.719 107.228  1.00 60.00
```

Figure 6A-24

| | | | | | | | | |
|---|---|---|---|---|---|---|---|---|
| ATOM | 1926 | ND2 | ASN | 247 | 35.367 | 51.057 | 105.871 | 1.00 60.00 |
| ATOM | 1927 | C | ASN | 247 | 38.635 | 51.213 | 107.946 | 1.00 60.00 |
| ATOM | 1928 | O | ASN | 247 | 38.717 | 51.854 | 108.992 | 1.00 60.00 |
| ATOM | 1929 | N | PRO | 248 | 39.339 | 51.502 | 106.887 | 1.00 60.00 |
| ATOM | 1930 | CA | PRO | 248 | 40.192 | 52.656 | 106.911 | 1.00 60.00 |
| ATOM | 1931 | CD | PRO | 248 | 39.911 | 50.433 | 106.084 | 1.00 60.00 |
| ATOM | 1932 | CB | PRO | 248 | 41.218 | 52.451 | 105.801 | 1.00 60.00 |
| ATOM | 1933 | CG | PRO | 248 | 41.306 | 50.922 | 105.667 | 1.00 60.00 |
| ATOM | 1934 | C | PRO | 248 | 39.351 | 53.868 | 106.711 | 1.00 60.00 |
| ATOM | 1935 | O | PRO | 248 | 38.223 | 53.733 | 106.242 | 1.00 60.00 |
| ATOM | 1936 | N | THR | 249 | 39.871 | 55.061 | 107.053 | 1.00 60.00 |
| ATOM | 1937 | CA | THR | 249 | 39.086 | 56.239 | 106.847 | 1.00 60.00 |
| ATOM | 1938 | CB | THR | 249 | 39.776 | 57.502 | 107.296 | 1.00 60.00 |
| ATOM | 1939 | OG1 | THR | 249 | 38.891 | 58.607 | 107.183 | 1.00 60.00 |
| ATOM | 1940 | CG2 | THR | 249 | 41.042 | 57.740 | 106.455 | 1.00 60.00 |
| ATOM | 1941 | C | THR | 249 | 38.823 | 56.315 | 105.381 | 1.00 60.00 |
| ATOM | 1942 | O | THR | 249 | 37.710 | 56.613 | 104.951 | 1.00 60.00 |
| ATOM | 1943 | N | THR | 250 | 39.852 | 56.015 | 104.568 | 1.00 60.00 |
| ATOM | 1944 | CA | THR | 250 | 39.673 | 56.034 | 103.151 | 1.00 60.00 |
| ATOM | 1945 | CB | THR | 250 | 40.961 | 56.078 | 102.379 | 1.00 60.00 |
| ATOM | 1946 | OG1 | THR | 250 | 40.698 | 56.296 | 101.001 | 1.00 60.00 |
| ATOM | 1947 | CG2 | THR | 250 | 41.708 | 54.748 | 102.575 | 1.00 60.00 |
| ATOM | 1948 | C | THR | 250 | 38.962 | 54.774 | 102.789 | 1.00 60.00 |
| ATOM | 1949 | O | THR | 250 | 38.895 | 53.836 | 103.582 | 1.00 60.00 |
| ATOM | 1950 | N | TYR | 251 | 38.386 | 54.732 | 101.575 | 1.00 60.00 |
| ATOM | 1951 | CA | TYR | 251 | 37.687 | 53.553 | 101.168 | 1.00 60.00 |
| ATOM | 1952 | CB | TYR | 251 | 36.806 | 53.729 | 99.916 | 1.00 60.00 |
| ATOM | 1953 | CG | TYR | 251 | 35.559 | 54.427 | 100.344 | 1.00 60.00 |
| ATOM | 1954 | CD1 | TYR | 251 | 35.513 | 55.794 | 100.493 | 1.00 60.00 |
| ATOM | 1955 | CD2 | TYR | 251 | 34.422 | 53.694 | 100.598 | 1.00 60.00 |
| ATOM | 1956 | CE1 | TYR | 251 | 34.351 | 56.416 | 100.892 | 1.00 60.00 |
| ATOM | 1957 | CE2 | TYR | 251 | 33.260 | 54.308 | 100.996 | 1.00 60.00 |
| ATOM | 1958 | CZ | TYR | 251 | 33.222 | 55.673 | 101.145 | 1.00 60.00 |
| ATOM | 1959 | OH | TYR | 251 | 32.028 | 56.303 | 101.556 | 1.00 60.00 |
| ATOM | 1960 | C | TYR | 251 | 38.680 | 52.474 | 100.905 | 1.00 60.00 |
| ATOM | 1961 | O | TYR | 251 | 39.886 | 52.711 | 100.849 | 1.00 60.00 |
| ATOM | 1962 | N | GLN | 252 | 38.166 | 51.240 | 100.763 | 1.00 60.00 |
| ATOM | 1963 | CA | GLN | 252 | 38.975 | 50.082 | 100.535 | 1.00 60.00 |
| ATOM | 1964 | CB | GLN | 252 | 38.148 | 48.790 | 100.443 | 1.00 60.00 |
| ATOM | 1965 | CG | GLN | 252 | 37.505 | 48.392 | 101.772 | 1.00 60.00 |
| ATOM | 1966 | CD | GLN | 252 | 36.708 | 47.119 | 101.544 | 1.00 60.00 |
| ATOM | 1967 | OE1 | GLN | 252 | 37.174 | 46.185 | 100.893 | 1.00 60.00 |
| ATOM | 1968 | NE2 | GLN | 252 | 35.460 | 47.086 | 102.084 | 1.00 60.00 |
| ATOM | 1969 | C | GLN | 252 | 39.689 | 50.261 | 99.240 | 1.00 60.00 |
| ATOM | 1970 | O | GLN | 252 | 40.852 | 49.882 | 99.115 | 1.00 60.00 |
| ATOM | 1971 | N | MET | 253 | 39.012 | 50.852 | 98.238 | 1.00 60.00 |
| ATOM | 1972 | CA | MET | 253 | 39.666 | 51.035 | 96.978 | 1.00 60.00 |
| ATOM | 1973 | CB | MET | 253 | 38.803 | 51.762 | 95.932 | 1.00 60.00 |
| ATOM | 1974 | CG | MET | 253 | 37.538 | 50.994 | 95.541 | 1.00 60.00 |
| ATOM | 1975 | SD | MET | 253 | 36.238 | 50.995 | 96.811 | 1.00 60.00 |
| ATOM | 1976 | CE | MET | 253 | 35.821 | 52.749 | 96.594 | 1.00 60.00 |
| ATOM | 1977 | C | MET | 253 | 40.861 | 51.886 | 97.245 | 1.00 60.00 |
| ATOM | 1978 | O | MET | 253 | 40.743 | 53.069 | 97.561 | 1.00 60.00 |
| ATOM | 1979 | N | ASP | 254 | 42.057 | 51.277 | 97.145 | 1.00 60.00 |
| ATOM | 1980 | CA | ASP | 254 | 43.266 | 51.991 | 97.418 | 1.00 60.00 |
| ATOM | 1981 | CB | ASP | 254 | 44.085 | 51.384 | 98.570 | 1.00 60.00 |
| ATOM | 1982 | CG | ASP | 254 | 43.316 | 51.602 | 99.864 | 1.00 60.00 |
| ATOM | 1983 | OD1 | ASP | 254 | 42.585 | 52.625 | 99.951 | 1.00 60.00 |
| ATOM | 1984 | OD2 | ASP | 254 | 43.444 | 50.747 | 100.780 | 1.00 60.00 |
| ATOM | 1985 | C | ASP | 254 | 44.116 | 51.908 | 96.197 | 1.00 60.00 |
| ATOM | 1986 | O | ASP | 254 | 43.918 | 51.045 | 95.343 | 1.00 60.00 |
| ATOM | 1987 | N | VAL | 255 | 45.089 | 52.829 | 96.084 | 1.00 60.00 |
| ATOM | 1988 | CA | VAL | 255 | 45.953 | 52.809 | 94.946 | 1.00 60.00 |
| ATOM | 1989 | CB | VAL | 255 | 46.998 | 53.885 | 94.986 | 1.00 60.00 |
| ATOM | 1990 | CG1 | VAL | 255 | 47.930 | 53.705 | 93.775 | 1.00 60.00 |
| ATOM | 1991 | CG2 | VAL | 255 | 46.297 | 55.252 | 95.031 | 1.00 60.00 |
| ATOM | 1992 | C | VAL | 255 | 46.667 | 51.504 | 94.987 | 1.00 60.00 |
| ATOM | 1993 | O | VAL | 255 | 46.804 | 50.822 | 93.972 | 1.00 60.00 |
| ATOM | 1994 | N | ASN | 256 | 47.126 | 51.119 | 96.191 | 1.00 60.00 |
| ATOM | 1995 | CA | ASN | 256 | 47.840 | 49.891 | 96.350 | 1.00 60.00 |
| ATOM | 1996 | CB | ASN | 256 | 48.691 | 49.839 | 97.632 | 1.00 60.00 |
| ATOM | 1997 | CG | ASN | 256 | 47.769 | 50.002 | 98.834 | 1.00 60.00 |
| ATOM | 1998 | OD1 | ASN | 256 | 47.369 | 49.025 | 99.464 | 1.00 60.00 |
| ATOM | 1999 | ND2 | ASN | 256 | 47.426 | 51.276 | 99.168 | 1.00 60.00 |
| ATOM | 2000 | C | ASN | 256 | 46.861 | 48.765 | 96.388 | 1.00 60.00 |
| ATOM | 2001 | O | ASN | 256 | 45.669 | 48.921 | 96.648 | 1.00 60.00 |
| ATOM | 2002 | N | PRO | 257 | 47.406 | 47.623 | 96.086 | 1.00 60.00 |

Figure 6A-25

| | | | | | | | | |
|---|---|---|---|---|---|---|---|---|
| ATOM | 2003 | CA | PRO | 257 | 46.650 | 46.404 | 96.101 | 1.00 60.00 |
| ATOM | 2004 | CD | PRO | 257 | 48.448 | 47.591 | 95.072 | 1.00 60.00 |
| ATOM | 2005 | CB | PRO | 257 | 47.457 | 45.393 | 95.293 | 1.00 60.00 |
| ATOM | 2006 | CG | PRO | 257 | 48.253 | 46.269 | 94.314 | 1.00 60.00 |
| ATOM | 2007 | C | PRO | 257 | 46.453 | 46.004 | 97.521 | 1.00 60.00 |
| ATOM | 2008 | O | PRO | 257 | 46.812 | 46.779 | 98.406 | 1.00 60.00 |
| ATOM | 2009 | N | GLU | 258 | 45.895 | 44.800 | 97.748 | 1.00 60.00 |
| ATOM | 2010 | CA | GLU | 258 | 45.609 | 44.329 | 99.069 | 1.00 60.00 |
| ATOM | 2011 | CB | GLU | 258 | 45.214 | 42.842 | 99.071 | 1.00 60.00 |
| ATOM | 2012 | CG | GLU | 258 | 43.949 | 42.540 | 98.261 | 1.00 60.00 |
| ATOM | 2013 | CD | GLU | 258 | 42.761 | 43.181 | 99.963 | 1.00 60.00 |
| ATOM | 2014 | OE1 | GLU | 258 | 42.962 | 43.742 | 100.073 | 1.00 60.00 |
| ATOM | 2015 | OE2 | GLU | 258 | 41.637 | 43.117 | 98.398 | 1.00 60.00 |
| ATOM | 2016 | C | GLU | 258 | 46.878 | 44.453 | 99.847 | 1.00 60.00 |
| ATOM | 2017 | O | GLU | 258 | 46.881 | 44.955 | 100.970 | 1.00 60.00 |
| ATOM | 2018 | N | GLY | 259 | 48.003 | 44.023 | 99.253 | 1.00 60.00 |
| ATOM | 2019 | CA | GLY | 259 | 49.261 | 44.185 | 99.918 | 1.00 60.00 |
| ATOM | 2020 | C | GLY | 259 | 49.596 | 42.908 | 100.603 | 1.00 60.00 |
| ATOM | 2021 | O | GLY | 259 | 50.761 | 42.640 | 100.895 | 1.00 60.00 |
| ATOM | 2022 | N | LYS | 260 | 48.582 | 42.071 | 100.880 | 1.00 60.00 |
| ATOM | 2023 | CA | LYS | 260 | 48.905 | 40.825 | 101.498 | 1.00 60.00 |
| ATOM | 2024 | CB | LYS | 260 | 47.732 | 40.172 | 102.250 | 1.00 60.00 |
| ATOM | 2025 | CG | LYS | 260 | 48.120 | 38.889 | 102.989 | 1.00 60.00 |
| ATOM | 2026 | CD | LYS | 260 | 49.128 | 39.111 | 104.121 | 1.00 60.00 |
| ATOM | 2027 | CE | LYS | 260 | 48.621 | 40.026 | 105.238 | 1.00 60.00 |
| ATOM | 2028 | NZ | LYS | 260 | 47.632 | 39.310 | 106.074 | 1.00 60.00 |
| ATOM | 2029 | C | LYS | 260 | 49.315 | 39.934 | 100.381 | 1.00 60.00 |
| ATOM | 2030 | O | LYS | 260 | 49.010 | 40.209 | 99.221 | 1.00 60.00 |
| ATOM | 2031 | N | TYR | 261 | 50.046 | 38.847 | 100.684 | 1.00 20.00 |
| ATOM | 2032 | CA | TYR | 261 | 50.449 | 38.037 | 99.581 | 1.00 20.00 |
| ATOM | 2033 | CB | TYR | 261 | 51.947 | 37.694 | 99.596 | 1.00 20.00 |
| ATOM | 2034 | CG | TYR | 261 | 52.632 | 39.011 | 99.718 | 1.00 20.00 |
| ATOM | 2035 | CD1 | TYR | 261 | 52.617 | 39.914 | 98.681 | 1.00 20.00 |
| ATOM | 2036 | CD2 | TYR | 261 | 53.241 | 39.371 | 100.898 | 1.00 20.00 |
| ATOM | 2037 | CE1 | TYR | 261 | 53.234 | 41.137 | 98.810 | 1.00 20.00 |
| ATOM | 2038 | CE2 | TYR | 261 | 53.861 | 40.591 | 101.025 | 1.00 20.00 |
| ATOM | 2039 | CZ | TYR | 261 | 53.863 | 41.478 | 99.981 | 1.00 20.00 |
| ATOM | 2040 | OH | TYR | 261 | 54.500 | 42.729 | 100.118 | 1.00 20.00 |
| ATOM | 2041 | C | TYR | 261 | 49.663 | 36.775 | 99.661 | 1.00 20.00 |
| ATOM | 2042 | O | TYR | 261 | 49.593 | 36.140 | 100.712 | 1.00 20.00 |
| ATOM | 2043 | N | SER | 262 | 49.030 | 36.386 | 98.540 | 1.00 20.00 |
| ATOM | 2044 | CA | SER | 262 | 48.241 | 35.193 | 98.557 | 1.00 20.00 |
| ATOM | 2045 | CB | SER | 262 | 47.000 | 35.258 | 97.653 | 1.00 20.00 |
| ATOM | 2046 | OG | SER | 262 | 47.396 | 35.388 | 96.296 | 1.00 20.00 |
| ATOM | 2047 | C | SER | 262 | 49.101 | 34.091 | 98.047 | 1.00 20.00 |
| ATOM | 2048 | O | SER | 262 | 49.756 | 34.222 | 97.014 | 1.00 20.00 |
| ATOM | 2049 | N | PHE | 263 | 49.141 | 32.972 | 98.791 | 1.00 20.00 |
| ATOM | 2050 | CA | PHE | 263 | 49.945 | 31.874 | 98.362 | 1.00 20.00 |
| ATOM | 2051 | CB | PHE | 263 | 51.182 | 31.651 | 99.250 | 1.00 20.00 |
| ATOM | 2052 | CG | PHE | 263 | 51.934 | 30.486 | 98.706 | 1.00 20.00 |
| ATOM | 2053 | CD1 | PHE | 263 | 52.842 | 30.657 | 97.686 | 1.00 20.00 |
| ATOM | 2054 | CD2 | PHE | 263 | 51.733 | 29.224 | 99.214 | 1.00 20.00 |
| ATOM | 2055 | CE1 | PHE | 263 | 53.539 | 29.584 | 97.182 | 1.00 20.00 |
| ATOM | 2056 | CE2 | PHE | 263 | 52.427 | 28.148 | 98.713 | 1.00 20.00 |
| ATOM | 2057 | CZ | PHE | 263 | 53.333 | 28.327 | 97.695 | 1.00 20.00 |
| ATOM | 2058 | C | PHE | 263 | 49.066 | 30.674 | 98.520 | 1.00 20.00 |
| ATOM | 2059 | O | PHE | 263 | 48.600 | 30.378 | 99.618 | 1.00 20.00 |
| ATOM | 2060 | N | GLY | 264 | 48.807 | 29.940 | 97.425 | 1.00 20.00 |
| ATOM | 2061 | CA | GLY | 264 | 47.937 | 28.810 | 97.570 | 1.00 20.00 |
| ATOM | 2062 | C | GLY | 264 | 46.566 | 29.344 | 97.894 | 1.00 20.00 |
| ATOM | 2063 | O | GLY | 264 | 46.089 | 30.251 | 97.221 | 1.00 20.00 |
| ATOM | 2064 | N | ALA | 265 | 45.864 | 28.715 | 98.867 | 1.00 20.00 |
| ATOM | 2065 | CA | ALA | 265 | 44.568 | 29.095 | 99.377 | 1.00 20.00 |
| ATOM | 2066 | CB | ALA | 265 | 43.845 | 27.934 | 100.080 | 1.00 20.00 |
| ATOM | 2067 | C | ALA | 265 | 44.664 | 30.215 | 100.375 | 1.00 20.00 |
| ATOM | 2068 | O | ALA | 265 | 43.738 | 31.012 | 100.506 | 1.00 20.00 |
| ATOM | 2069 | N | THR | 266 | 45.779 | 30.280 | 101.130 | 1.00 20.00 |
| ATOM | 2070 | CA | THR | 266 | 45.922 | 31.197 | 102.231 | 1.00 20.00 |
| ATOM | 2071 | CB | THR | 266 | 46.519 | 30.528 | 103.439 | 1.00 20.00 |
| ATOM | 2072 | OG1 | THR | 266 | 46.489 | 31.387 | 104.569 | 1.00 20.00 |
| ATOM | 2073 | CG2 | THR | 266 | 47.970 | 30.135 | 103.111 | 1.00 20.00 |
| ATOM | 2074 | C | THR | 266 | 46.836 | 32.317 | 101.850 | 1.00 20.00 |
| ATOM | 2075 | O | THR | 266 | 47.360 | 32.360 | 100.738 | 1.00 20.00 |
| ATOM | 2076 | N | CYS | 267 | 47.017 | 33.281 | 102.777 | 1.00 20.00 |
| ATOM | 2077 | CA | CYS | 267 | 47.856 | 34.409 | 102.505 | 1.00 20.00 |
| ATOM | 2078 | CB | CYS | 267 | 47.107 | 35.736 | 102.555 | 1.00 20.00 |
| ATOM | 2079 | SG | CYS | 267 | 46.042 | 35.896 | 101.105 | 1.00 20.00 |

Figure 6A-26

| | | | | | | | |
|---|---|---|---|---|---|---|---|
| ATOM | 2080 | C | CYS | 267 | 49.973 | 34.484 | 103.496 | 1.00 20.00 |
| ATOM | 2081 | O | CYS | 267 | 48.868 | 33.985 | 104.616 | 1.00 20.00 |
| ATOM | 2082 | N | VAL | 268 | 50.090 | 35.112 | 103.072 | 1.00 20.00 |
| ATOM | 2083 | CA | VAL | 268 | 51.246 | 35.256 | 103.914 | 1.00 20.00 |
| ATOM | 2084 | CB | VAL | 268 | 52.450 | 34.530 | 103.389 | 1.00 20.00 |
| ATOM | 2085 | CG1 | VAL | 268 | 53.613 | 34.767 | 104.364 | 1.00 20.00 |
| ATOM | 2086 | CG2 | VAL | 268 | 52.092 | 33.048 | 103.198 | 1.00 20.00 |
| ATOM | 2087 | C | VAL | 268 | 51.585 | 36.715 | 103.960 | 1.00 20.00 |
| ATOM | 2088 | O | VAL | 268 | 51.367 | 37.444 | 102.991 | 1.00 20.00 |
| ATOM | 2089 | N | LYS | 269 | 52.113 | 37.182 | 105.112 | 1.00 20.00 |
| ATOM | 2090 | CA | LYS | 269 | 52.451 | 38.568 | 105.266 | 1.00 20.00 |
| ATOM | 2091 | CB | LYS | 269 | 52.897 | 38.932 | 106.691 | 1.00 20.00 |
| ATOM | 2092 | CG | LYS | 269 | 53.252 | 40.415 | 106.830 | 1.00 20.00 |
| ATOM | 2093 | CD | LYS | 269 | 52.054 | 41.348 | 106.639 | 1.00 20.00 |
| ATOM | 2094 | CE | LYS | 269 | 52.436 | 42.829 | 106.565 | 1.00 20.00 |
| ATOM | 2095 | NZ | LYS | 269 | 52.973 | 43.147 | 105.223 | 1.00 20.00 |
| ATOM | 2096 | C | LYS | 269 | 53.570 | 38.919 | 104.343 | 1.00 20.00 |
| ATOM | 2097 | O | LYS | 269 | 53.514 | 39.939 | 103.656 | 1.00 20.00 |
| ATOM | 2098 | N | LYS | 270 | 54.617 | 38.072 | 104.293 | 1.00 20.00 |
| ATOM | 2099 | CA | LYS | 270 | 55.742 | 38.377 | 103.458 | 1.00 20.00 |
| ATOM | 2100 | CB | LYS | 270 | 57.039 | 38.620 | 104.246 | 1.00 20.00 |
| ATOM | 2101 | CG | LYS | 270 | 56.941 | 39.777 | 105.244 | 1.00 20.00 |
| ATOM | 2102 | CD | LYS | 270 | 56.596 | 41.126 | 104.611 | 1.00 20.00 |
| ATOM | 2103 | CE | LYS | 270 | 56.481 | 42.265 | 105.627 | 1.00 20.00 |
| ATOM | 2104 | NZ | LYS | 270 | 56.117 | 43.527 | 104.941 | 1.00 20.00 |
| ATOM | 2105 | C | LYS | 270 | 55.968 | 37.190 | 102.584 | 1.00 20.00 |
| ATOM | 2106 | O | LYS | 270 | 55.479 | 36.096 | 102.855 | 1.00 20.00 |
| ATOM | 2107 | N | CYS | 271 | 56.716 | 37.390 | 101.486 | 1.00 20.00 |
| ATOM | 2108 | CA | CYS | 271 | 56.954 | 36.331 | 100.554 | 1.00 20.00 |
| ATOM | 2109 | CB | CYS | 271 | 57.364 | 36.914 | 99.188 | 1.00 20.00 |
| ATOM | 2110 | SG | CYS | 271 | 57.362 | 35.766 | 97.784 | 1.00 20.00 |
| ATOM | 2111 | C | CYS | 271 | 58.038 | 35.470 | 101.128 | 1.00 20.00 |
| ATOM | 2112 | O | CYS | 271 | 59.021 | 35.964 | 101.675 | 1.00 20.00 |
| ATOM | 2113 | N | PRO | 272 | 57.859 | 34.179 | 101.035 | 1.00 20.00 |
| ATOM | 2114 | CA | PRO | 272 | 58.826 | 33.259 | 101.566 | 1.00 20.00 |
| ATOM | 2115 | CD | PRO | 272 | 56.523 | 33.611 | 101.055 | 1.00 20.00 |
| ATOM | 2116 | CB | PRO | 272 | 58.117 | 31.907 | 101.681 | 1.00 20.00 |
| ATOM | 2117 | CG | PRO | 272 | 56.772 | 32.101 | 100.956 | 1.00 20.00 |
| ATOM | 2118 | C | PRO | 272 | 60.056 | 33.247 | 100.722 | 1.00 20.00 |
| ATOM | 2119 | O | PRO | 272 | 60.007 | 33.707 | 99.583 | 1.00 20.00 |
| ATOM | 2120 | N | ARG | 273 | 61.171 | 32.732 | 101.270 | 1.00 20.00 |
| ATOM | 2121 | CA | ARG | 273 | 62.413 | 32.734 | 100.559 | 1.00 20.00 |
| ATOM | 2122 | CB | ARG | 273 | 63.550 | 32.037 | 101.326 | 1.00 20.00 |
| ATOM | 2123 | CG | ARG | 273 | 64.913 | 32.136 | 100.638 | 1.00 20.00 |
| ATOM | 2124 | CD | ARG | 273 | 66.068 | 31.639 | 101.511 | 1.00 20.00 |
| ATOM | 2125 | NE | ARG | 273 | 65.997 | 30.152 | 101.561 | 1.00 20.00 |
| ATOM | 2126 | CZ | ARG | 273 | 66.655 | 29.407 | 100.625 | 1.00 20.00 |
| ATOM | 2127 | NH1 | ARG | 273 | 67.376 | 30.026 | 99.645 | 1.00 20.00 |
| ATOM | 2128 | NH2 | ARG | 273 | 66.595 | 28.044 | 100.672 | 1.00 20.00 |
| ATOM | 2129 | C | ARG | 273 | 62.202 | 32.027 | 99.262 | 1.00 20.00 |
| ATOM | 2130 | O | ARG | 273 | 61.289 | 31.216 | 99.133 | 1.00 20.00 |
| ATOM | 2131 | N | ASN | 274 | 63.045 | 32.370 | 98.265 | 1.00 20.00 |
| ATOM | 2132 | CA | ASN | 274 | 63.051 | 31.844 | 96.926 | 1.00 20.00 |
| ATOM | 2133 | CB | ASN | 274 | 63.505 | 30.369 | 96.793 | 1.00 20.00 |
| ATOM | 2134 | CG | ASN | 274 | 62.563 | 29.415 | 97.519 | 1.00 20.00 |
| ATOM | 2135 | OD1 | ASN | 274 | 62.809 | 29.031 | 98.661 | 1.00 20.00 |
| ATOM | 2136 | ND2 | ASN | 274 | 61.448 | 29.024 | 96.845 | 1.00 20.00 |
| ATOM | 2137 | C | ASN | 274 | 61.712 | 32.030 | 96.278 | 1.00 20.00 |
| ATOM | 2138 | O | ASN | 274 | 61.322 | 31.258 | 95.402 | 1.00 20.00 |
| ATOM | 2139 | N | TYR | 275 | 60.979 | 33.086 | 96.685 | 1.00 20.00 |
| ATOM | 2140 | CA | TYR | 275 | 59.712 | 33.421 | 96.095 | 1.00 20.00 |
| ATOM | 2141 | CB | TYR | 275 | 58.493 | 33.076 | 96.975 | 1.00 20.00 |
| ATOM | 2142 | CG | TYR | 275 | 58.268 | 31.602 | 96.996 | 1.00 20.00 |
| ATOM | 2143 | CD1 | TYR | 275 | 57.473 | 31.010 | 96.042 | 1.00 20.00 |
| ATOM | 2144 | CD2 | TYR | 275 | 58.838 | 30.812 | 97.965 | 1.00 20.00 |
| ATOM | 2145 | CE1 | TYR | 275 | 57.252 | 29.653 | 96.049 | 1.00 20.00 |
| ATOM | 2146 | CE2 | TYR | 275 | 58.623 | 29.454 | 97.980 | 1.00 20.00 |
| ATOM | 2147 | CZ | TYR | 275 | 57.830 | 28.872 | 97.020 | 1.00 20.00 |
| ATOM | 2148 | OH | TYR | 275 | 57.608 | 27.477 | 97.034 | 1.00 20.00 |
| ATOM | 2149 | C | TYR | 275 | 59.716 | 34.909 | 95.932 | 1.00 20.00 |
| ATOM | 2150 | O | TYR | 275 | 60.361 | 35.621 | 96.698 | 1.00 20.00 |
| ATOM | 2151 | N | VAL | 276 | 58.988 | 35.421 | 94.920 | 1.00 20.00 |
| ATOM | 2152 | CA | VAL | 276 | 58.972 | 36.835 | 94.683 | 1.00 20.00 |
| ATOM | 2153 | CB | VAL | 276 | 59.460 | 37.200 | 93.315 | 1.00 20.00 |
| ATOM | 2154 | CG1 | VAL | 276 | 60.930 | 36.768 | 93.186 | 1.00 20.00 |
| ATOM | 2155 | CG2 | VAL | 276 | 58.525 | 36.544 | 92.285 | 1.00 20.00 |
| ATOM | 2156 | C | VAL | 276 | 57.553 | 37.302 | 94.770 | 1.00 20.00 |

Figure 6A-27

| ATOM | 2157 | C | VAL | 276 | 56.618 | 36.514 | 94.641 | 1.00 | 20.00 |
| --- | --- | --- | --- | --- | --- | --- | --- | --- | --- |
| ATOM | 2158 | N | VAL | 277 | 57.362 | 38.614 | 95.011 | 1.00 | 20.00 |
| ATOM | 2159 | CA | VAL | 277 | 56.037 | 39.152 | 95.109 | 1.00 | 20.00 |
| ATOM | 2160 | CB | VAL | 277 | 55.890 | 40.173 | 96.197 | 1.00 | 20.00 |
| ATOM | 2161 | CG1 | VAL | 277 | 54.450 | 40.714 | 96.171 | 1.00 | 20.00 |
| ATOM | 2162 | CG2 | VAL | 277 | 56.288 | 39.520 | 97.530 | 1.00 | 20.00 |
| ATOM | 2163 | C | VAL | 277 | 55.745 | 39.832 | 93.815 | 1.00 | 20.00 |
| ATOM | 2164 | O | VAL | 277 | 56.453 | 40.754 | 93.421 | 1.00 | 20.00 |
| ATOM | 2165 | N | THR | 278 | 54.679 | 39.389 | 93.114 | 1.00 | 20.00 |
| ATOM | 2166 | CA | THR | 278 | 54.407 | 39.977 | 91.852 | 1.00 | 20.00 |
| ATOM | 2167 | CB | THR | 278 | 54.585 | 39.022 | 90.709 | 1.00 | 20.00 |
| ATOM | 2168 | OG1 | THR | 278 | 55.915 | 38.522 | 90.691 | 1.00 | 20.00 |
| ATOM | 2169 | CG2 | THR | 278 | 54.287 | 39.766 | 89.399 | 1.00 | 20.00 |
| ATOM | 2170 | C | THR | 278 | 52.998 | 40.458 | 91.817 | 1.00 | 20.00 |
| ATOM | 2171 | O | THR | 278 | 52.111 | 39.887 | 92.450 | 1.00 | 20.00 |
| ATOM | 2172 | N | ASP | 279 | 52.777 | 41.551 | 91.063 | 1.00 | 20.00 |
| ATOM | 2173 | CA | ASP | 279 | 51.474 | 42.111 | 90.851 | 1.00 | 20.00 |
| ATOM | 2174 | CB | ASP | 279 | 50.531 | 41.179 | 90.103 | 1.00 | 20.00 |
| ATOM | 2175 | CG | ASP | 279 | 51.055 | 41.088 | 88.679 | 1.00 | 20.00 |
| ATOM | 2176 | OD1 | ASP | 279 | 51.507 | 42.139 | 88.152 | 1.00 | 20.00 |
| ATOM | 2177 | OD2 | ASP | 279 | 51.023 | 39.967 | 88.104 | 1.00 | 20.00 |
| ATOM | 2178 | C | ASP | 279 | 50.875 | 42.370 | 92.215 | 1.00 | 20.00 |
| ATOM | 2179 | O | ASP | 279 | 49.674 | 42.165 | 92.391 | 1.00 | 20.00 |
| ATOM | 2180 | N | HIS | 280 | 51.717 | 42.851 | 93.156 | 1.00 | 20.00 |
| ATOM | 2181 | CA | HIS | 280 | 51.368 | 43.212 | 94.502 | 1.00 | 20.00 |
| ATOM | 2182 | ND1 | HIS | 280 | 52.070 | 46.097 | 92.922 | 1.00 | 20.00 |
| ATOM | 2183 | NE2 | HIS | 280 | 53.524 | 47.211 | 94.183 | 1.00 | 20.00 |
| ATOM | 2184 | CE1 | HIS | 280 | 53.071 | 47.013 | 92.959 | 1.00 | 20.00 |
| ATOM | 2185 | CD2 | HIS | 280 | 52.764 | 46.369 | 94.976 | 1.00 | 20.00 |
| ATOM | 2186 | CG | HIS | 280 | 51.869 | 45.679 | 94.219 | 1.00 | 20.00 |
| ATOM | 2187 | CB | HIS | 280 | 50.849 | 44.657 | 94.624 | 1.00 | 20.00 |
| ATOM | 2188 | C | HIS | 280 | 50.317 | 42.294 | 95.034 | 1.00 | 20.00 |
| ATOM | 2189 | O | HIS | 280 | 49.125 | 42.521 | 94.835 | 1.00 | 20.00 |
| ATOM | 2190 | N | GLY | 281 | 50.720 | 41.240 | 95.766 | 1.00 | 20.00 |
| ATOM | 2191 | CA | GLY | 281 | 49.688 | 40.384 | 96.265 | 1.00 | 20.00 |
| ATOM | 2192 | C | GLY | 281 | 49.950 | 38.953 | 95.920 | 1.00 | 20.00 |
| ATOM | 2193 | O | GLY | 281 | 49.344 | 38.064 | 96.512 | 1.00 | 20.00 |
| ATOM | 2194 | N | SER | 282 | 50.823 | 38.648 | 94.949 | 1.00 | 20.00 |
| ATOM | 2195 | CA | SER | 282 | 51.016 | 37.241 | 94.763 | 1.00 | 20.00 |
| ATOM | 2196 | CB | SER | 282 | 50.689 | 36.754 | 93.340 | 1.00 | 20.00 |
| ATOM | 2197 | OG | SER | 282 | 50.912 | 35.356 | 93.243 | 1.00 | 20.00 |
| ATOM | 2198 | C | SER | 282 | 52.458 | 36.940 | 95.009 | 1.00 | 20.00 |
| ATOM | 2199 | O | SER | 282 | 53.346 | 37.526 | 94.393 | 1.00 | 20.00 |
| ATOM | 2200 | N | CYS | 283 | 52.727 | 36.015 | 95.947 | 1.00 | 20.00 |
| ATOM | 2201 | CA | CYS | 283 | 54.070 | 35.598 | 96.216 | 1.00 | 20.00 |
| ATOM | 2202 | CB | CYS | 283 | 54.318 | 35.411 | 97.723 | 1.00 | 20.00 |
| ATOM | 2203 | SG | CYS | 283 | 55.825 | 34.499 | 98.162 | 1.00 | 20.00 |
| ATOM | 2204 | C | CYS | 283 | 54.204 | 34.280 | 95.544 | 1.00 | 20.00 |
| ATOM | 2205 | O | CYS | 283 | 53.664 | 33.273 | 95.999 | 1.00 | 20.00 |
| ATOM | 2206 | N | VAL | 284 | 54.924 | 34.272 | 94.411 | 1.00 | 20.00 |
| ATOM | 2207 | CA | VAL | 284 | 55.105 | 33.072 | 93.660 | 1.00 | 20.00 |
| ATOM | 2208 | CB | VAL | 284 | 54.524 | 33.155 | 92.280 | 1.00 | 20.00 |
| ATOM | 2209 | CG1 | VAL | 284 | 55.139 | 34.372 | 91.571 | 1.00 | 20.00 |
| ATOM | 2210 | CG2 | VAL | 284 | 54.771 | 31.820 | 91.556 | 1.00 | 20.00 |
| ATOM | 2211 | C | VAL | 284 | 56.574 | 32.850 | 93.542 | 1.00 | 20.00 |
| ATOM | 2212 | O | VAL | 284 | 57.366 | 33.781 | 93.672 | 1.00 | 20.00 |
| ATOM | 2213 | N | ARG | 285 | 56.977 | 31.587 | 93.311 | 1.00 | 20.00 |
| ATOM | 2214 | CA | ARG | 285 | 58.372 | 31.270 | 93.249 | 1.00 | 20.00 |
| ATOM | 2215 | CB | ARG | 285 | 58.665 | 29.774 | 93.046 | 1.00 | 20.00 |
| ATOM | 2216 | CG | ARG | 285 | 60.167 | 29.484 | 92.987 | 1.00 | 20.00 |
| ATOM | 2217 | CD | ARG | 285 | 60.519 | 28.046 | 92.605 | 1.00 | 20.00 |
| ATOM | 2218 | NE | ARG | 285 | 60.007 | 27.152 | 93.680 | 1.00 | 20.00 |
| ATOM | 2219 | CZ | ARG | 285 | 60.487 | 25.879 | 93.789 | 1.00 | 20.00 |
| ATOM | 2220 | NH1 | ARG | 285 | 61.467 | 25.446 | 92.942 | 1.00 | 20.00 |
| ATOM | 2221 | NH2 | ARG | 285 | 59.989 | 25.040 | 94.743 | 1.00 | 20.00 |
| ATOM | 2222 | C | ARG | 285 | 58.996 | 31.986 | 92.101 | 1.00 | 20.00 |
| ATOM | 2223 | O | ARG | 285 | 60.115 | 32.481 | 92.219 | 1.00 | 20.00 |
| ATOM | 2224 | N | ALA | 286 | 58.299 | 32.062 | 90.951 | 1.00 | 20.00 |
| ATOM | 2225 | CA | ALA | 286 | 58.919 | 32.693 | 89.823 | 1.00 | 20.00 |
| ATOM | 2226 | CB | ALA | 286 | 59.147 | 31.737 | 88.641 | 1.00 | 20.00 |
| ATOM | 2227 | C | ALA | 286 | 58.041 | 33.793 | 89.334 | 1.00 | 20.00 |
| ATOM | 2228 | O | ALA | 286 | 56.823 | 33.767 | 89.497 | 1.00 | 20.00 |
| ATOM | 2229 | N | CYS | 287 | 58.663 | 34.801 | 88.698 | 1.00 | 20.00 |
| ATOM | 2230 | CA | CYS | 287 | 57.932 | 35.932 | 88.223 | 1.00 | 20.00 |
| ATOM | 2231 | CB | CYS | 287 | 58.821 | 37.148 | 88.001 | 1.00 | 20.00 |
| ATOM | 2232 | SG | CYS | 287 | 59.371 | 37.729 | 89.624 | 1.00 | 20.00 |
| ATOM | 2233 | C | CYS | 287 | 57.220 | 35.562 | 86.973 | 1.00 | 20.00 |

Figure 6A-28

| | | | | | | | | |
|---|---|---|---|---|---|---|---|---|
| ATOM | 2234 | O | CYS | 287 | 57.434 | 34.486 | 86.416 | 1.00 20.00 |
| ATOM | 2235 | N | GLY | 288 | 56.313 | 36.450 | 86.526 | 1.00 20.00 |
| ATOM | 2236 | CA | GLY | 288 | 55.567 | 36.180 | 85.339 | 1.00 20.00 |
| ATOM | 2237 | C | GLY | 288 | 56.571 | 36.093 | 84.235 | 1.00 20.00 |
| ATOM | 2238 | O | GLY | 288 | 57.707 | 36.543 | 84.371 | 1.00 20.00 |
| ATOM | 2239 | N | ALA | 289 | 56.147 | 35.526 | 83.091 | 1.00 20.00 |
| ATOM | 2240 | CA | ALA | 289 | 57.019 | 35.255 | 81.986 | 1.00 20.00 |
| ATOM | 2241 | CB | ALA | 289 | 56.254 | 34.835 | 80.719 | 1.00 20.00 |
| ATOM | 2242 | C | ALA | 289 | 57.856 | 36.445 | 81.630 | 1.00 20.00 |
| ATOM | 2243 | O | ALA | 289 | 59.054 | 36.465 | 81.896 | 1.00 20.00 |
| ATOM | 2244 | N | ASP | 290 | 57.232 | 37.480 | 81.038 | 1.00 20.00 |
| ATOM | 2245 | CA | ASP | 290 | 57.915 | 38.634 | 80.522 | 1.00 20.00 |
| ATOM | 2246 | CB | ASP | 290 | 56.966 | 39.629 | 79.835 | 1.00 20.00 |
| ATOM | 2247 | CG | ASP | 290 | 56.517 | 39.010 | 78.519 | 1.00 20.00 |
| ATOM | 2248 | OD1 | ASP | 290 | 57.304 | 38.210 | 77.945 | 1.00 20.00 |
| ATOM | 2249 | OD2 | ASP | 290 | 55.383 | 39.325 | 78.071 | 1.00 20.00 |
| ATOM | 2250 | C | ASP | 290 | 58.629 | 39.368 | 81.613 | 1.00 20.00 |
| ATOM | 2251 | O | ASP | 290 | 59.445 | 40.242 | 81.327 | 1.00 20.00 |
| ATOM | 2252 | N | SER | 291 | 58.343 | 39.063 | 82.892 | 1.00 20.00 |
| ATOM | 2253 | CA | SER | 291 | 58.974 | 39.823 | 83.937 | 1.00 20.00 |
| ATOM | 2254 | CB | SER | 291 | 58.083 | 39.996 | 85.177 | 1.00 20.00 |
| ATOM | 2255 | OG | SER | 291 | 57.857 | 38.735 | 85.790 | 1.00 20.00 |
| ATOM | 2256 | C | SER | 291 | 60.230 | 39.147 | 84.393 | 1.00 20.00 |
| ATOM | 2257 | O | SER | 291 | 60.313 | 37.920 | 84.434 | 1.00 20.00 |
| ATOM | 2258 | N | TYR | 292 | 61.260 | 39.953 | 84.740 | 1.00 20.00 |
| ATOM | 2259 | CA | TYR | 292 | 62.483 | 39.388 | 85.236 | 1.00 20.00 |
| ATOM | 2260 | CB | TYR | 292 | 63.702 | 39.590 | 84.319 | 1.00 20.00 |
| ATOM | 2261 | CG | TYR | 292 | 64.847 | 38.888 | 84.968 | 1.00 20.00 |
| ATOM | 2262 | CD1 | TYR | 292 | 64.939 | 37.514 | 84.919 | 1.00 20.00 |
| ATOM | 2263 | CD2 | TYR | 292 | 65.832 | 39.596 | 85.616 | 1.00 20.00 |
| ATOM | 2264 | CE1 | TYR | 292 | 65.991 | 36.857 | 85.512 | 1.00 20.00 |
| ATOM | 2265 | CE2 | TYR | 292 | 66.887 | 38.945 | 86.210 | 1.00 20.00 |
| ATOM | 2266 | CZ | TYR | 292 | 66.966 | 37.574 | 86.160 | 1.00 20.00 |
| ATOM | 2267 | OH | TYR | 292 | 68.047 | 36.903 | 86.772 | 1.00 20.00 |
| ATOM | 2268 | C | TYR | 292 | 62.771 | 40.031 | 86.558 | 1.00 20.00 |
| ATOM | 2269 | O | TYR | 292 | 62.343 | 41.153 | 86.827 | 1.00 20.00 |
| ATOM | 2270 | N | GLU | 293 | 63.506 | 39.310 | 87.424 | 1.00 20.00 |
| ATOM | 2271 | CA | GLU | 293 | 63.817 | 39.765 | 88.747 | 1.00 20.00 |
| ATOM | 2272 | CB | GLU | 293 | 64.760 | 38.802 | 89.492 | 1.00 20.00 |
| ATOM | 2273 | CG | GLU | 293 | 64.180 | 37.407 | 89.727 | 1.00 20.00 |
| ATOM | 2274 | CD | GLU | 293 | 65.318 | 36.507 | 90.193 | 1.00 20.00 |
| ATOM | 2275 | OE1 | GLU | 293 | 66.481 | 36.755 | 89.775 | 1.00 20.00 |
| ATOM | 2276 | OE2 | GLU | 293 | 65.040 | 35.559 | 90.975 | 1.00 20.00 |
| ATOM | 2277 | C | GLU | 293 | 64.542 | 41.062 | 88.625 | 1.00 20.00 |
| ATOM | 2278 | O | GLU | 293 | 65.427 | 41.219 | 87.788 | 1.00 20.00 |
| ATOM | 2279 | N | MET | 294 | 64.173 | 42.042 | 89.468 | 1.00 20.00 |
| ATOM | 2280 | CA | MET | 294 | 64.826 | 43.315 | 89.429 | 1.00 20.00 |
| ATOM | 2281 | CB | MET | 294 | 64.217 | 44.319 | 90.420 | 1.00 20.00 |
| ATOM | 2282 | CG | MET | 294 | 64.869 | 45.702 | 90.379 | 1.00 20.00 |
| ATOM | 2283 | SD | MET | 294 | 64.156 | 46.897 | 91.550 | 1.00 20.00 |
| ATOM | 2284 | CE | MET | 294 | 65.245 | 48.265 | 91.060 | 1.00 20.00 |
| ATOM | 2285 | C | MET | 294 | 66.251 | 43.095 | 89.822 | 1.00 20.00 |
| ATOM | 2286 | O | MET | 294 | 67.168 | 43.650 | 89.218 | 1.00 20.00 |
| ATOM | 2287 | N | GLU | 295 | 66.474 | 42.249 | 90.844 | 1.00 40.00 |
| ATOM | 2288 | CA | GLU | 295 | 67.805 | 42.008 | 91.314 | 1.00 40.00 |
| ATOM | 2289 | CB | GLU | 295 | 68.039 | 42.506 | 92.750 | 1.00 40.00 |
| ATOM | 2290 | CG | GLU | 295 | 67.891 | 44.022 | 92.895 | 1.00 40.00 |
| ATOM | 2291 | CD | GLU | 295 | 69.035 | 44.691 | 92.148 | 1.00 40.00 |
| ATOM | 2292 | OE1 | GLU | 295 | 70.192 | 44.615 | 92.642 | 1.00 40.00 |
| ATOM | 2293 | OE2 | GLU | 295 | 68.767 | 45.289 | 91.072 | 1.00 40.00 |
| ATOM | 2294 | C | GLU | 295 | 67.994 | 40.529 | 91.327 | 1.00 40.00 |
| ATOM | 2295 | O | GLU | 295 | 67.235 | 39.788 | 90.707 | 1.00 40.00 |
| ATOM | 2296 | N | GLU | 296 | 69.037 | 40.054 | 92.037 | 1.00 40.00 |
| ATOM | 2297 | CA | GLU | 296 | 69.282 | 38.644 | 92.111 | 1.00 40.00 |
| ATOM | 2298 | CB | GLU | 296 | 70.540 | 38.261 | 92.910 | 1.00 40.00 |
| ATOM | 2299 | CG | GLU | 296 | 71.859 | 38.629 | 92.226 | 1.00 40.00 |
| ATOM | 2300 | CD | GLU | 296 | 72.137 | 40.107 | 92.460 | 1.00 40.00 |
| ATOM | 2301 | OE1 | GLU | 296 | 71.486 | 40.950 | 91.786 | 1.00 40.00 |
| ATOM | 2302 | OE2 | GLU | 296 | 73.008 | 40.413 | 93.317 | 1.00 40.00 |
| ATOM | 2303 | C | GLU | 296 | 68.118 | 38.016 | 92.802 | 1.00 40.00 |
| ATOM | 2304 | O | GLU | 296 | 67.159 | 38.693 | 93.168 | 1.00 40.00 |
| ATOM | 2305 | N | ASP | 297 | 68.183 | 36.684 | 92.990 | 1.00 40.00 |
| ATOM | 2306 | CA | ASP | 297 | 67.104 | 35.969 | 93.604 | 1.00 40.00 |
| ATOM | 2307 | CB | ASP | 297 | 67.407 | 34.485 | 93.883 | 1.00 40.00 |
| ATOM | 2308 | CG | ASP | 297 | 68.533 | 34.410 | 94.905 | 1.00 40.00 |
| ATOM | 2309 | OD1 | ASP | 297 | 69.311 | 35.396 | 95.007 | 1.00 40.00 |
| ATOM | 2310 | OD2 | ASP | 297 | 68.625 | 33.365 | 95.604 | 1.00 40.00 |

Figure 6A-29

| | | | | | | | | |
|---|---|---|---|---|---|---|---|---|
| ATOM | 2311 | C | ASP | 297 | 66.807 | 36.618 | 94.909 | 1.00 40.00 |
| ATOM | 2312 | O | ASP | 297 | 67.661 | 37.271 | 95.505 | 1.00 40.00 |
| ATOM | 2313 | N | GLY | 298 | 65.555 | 36.477 | 95.372 | 1.00 40.00 |
| ATOM | 2314 | CA | GLY | 298 | 65.194 | 37.090 | 96.609 | 1.00 40.00 |
| ATOM | 2315 | C | GLY | 298 | 64.645 | 38.434 | 96.276 | 1.00 40.00 |
| ATOM | 2316 | O | GLY | 298 | 63.967 | 39.056 | 97.091 | 1.00 40.00 |
| ATOM | 2317 | N | VAL | 299 | 64.926 | 38.924 | 95.052 | 1.00 40.00 |
| ATOM | 2318 | CA | VAL | 299 | 64.379 | 40.198 | 94.705 | 1.00 40.00 |
| ATOM | 2319 | CB | VAL | 299 | 64.782 | 40.690 | 93.341 | 1.00 40.00 |
| ATOM | 2320 | CG1 | VAL | 299 | 64.331 | 39.676 | 92.277 | 1.00 40.00 |
| ATOM | 2321 | CG2 | VAL | 299 | 64.195 | 42.098 | 93.142 | 1.00 40.00 |
| ATOM | 2322 | C | VAL | 299 | 62.898 | 40.028 | 94.753 | 1.00 40.00 |
| ATOM | 2323 | O | VAL | 299 | 62.330 | 39.173 | 94.078 | 1.00 40.00 |
| ATOM | 2324 | N | ARG | 300 | 62.237 | 40.824 | 95.608 | 1.00 40.00 |
| ATOM | 2325 | CA | ARG | 300 | 60.821 | 40.703 | 95.771 | 1.00 40.00 |
| ATOM | 2326 | CB | ARG | 300 | 60.278 | 41.579 | 96.912 | 1.00 40.00 |
| ATOM | 2327 | CG | ARG | 300 | 60.740 | 41.130 | 98.298 | 1.00 40.00 |
| ATOM | 2328 | CD | ARG | 300 | 60.201 | 41.999 | 99.436 | 1.00 40.00 |
| ATOM | 2329 | NE | ARG | 300 | 60.665 | 41.392 | 100.714 | 1.00 40.00 |
| ATOM | 2330 | CZ | ARG | 300 | 59.910 | 40.425 | 101.313 | 1.00 40.00 |
| ATOM | 2331 | NH1 | ARG | 300 | 58.740 | 40.020 | 100.739 | 1.00 40.00 |
| ATOM | 2332 | NH2 | ARG | 300 | 60.323 | 39.863 | 102.486 | 1.00 40.00 |
| ATOM | 2333 | C | ARG | 300 | 60.124 | 41.135 | 94.527 | 1.00 40.00 |
| ATOM | 2334 | O | ARG | 300 | 59.193 | 40.474 | 94.069 | 1.00 40.00 |
| ATOM | 2335 | N | LYS | 301 | 60.575 | 42.252 | 93.927 | 1.00 20.00 |
| ATOM | 2336 | CA | LYS | 301 | 59.834 | 42.778 | 92.822 | 1.00 20.00 |
| ATOM | 2337 | CB | LYS | 301 | 59.763 | 44.316 | 92.798 | 1.00 20.00 |
| ATOM | 2338 | CG | LYS | 301 | 58.943 | 44.919 | 93.941 | 1.00 20.00 |
| ATOM | 2339 | CD | LYS | 301 | 59.127 | 46.431 | 94.097 | 1.00 20.00 |
| ATOM | 2340 | CE | LYS | 301 | 58.320 | 47.032 | 95.251 | 1.00 20.00 |
| ATOM | 2341 | NZ | LYS | 301 | 58.597 | 48.482 | 95.362 | 1.00 20.00 |
| ATOM | 2342 | C | LYS | 301 | 60.455 | 42.360 | 91.538 | 1.00 20.00 |
| ATOM | 2343 | O | LYS | 301 | 61.671 | 42.221 | 91.417 | 1.00 20.00 |
| ATOM | 2344 | N | CYS | 302 | 59.590 | 42.113 | 90.540 | 1.00 20.00 |
| ATOM | 2345 | CA | CYS | 302 | 60.075 | 41.810 | 89.236 | 1.00 20.00 |
| ATOM | 2346 | CB | CYS | 302 | 59.598 | 40.492 | 88.645 | 1.00 20.00 |
| ATOM | 2347 | SG | CYS | 302 | 60.700 | 39.150 | 89.141 | 1.00 20.00 |
| ATOM | 2348 | C | CYS | 302 | 59.652 | 42.915 | 88.338 | 1.00 20.00 |
| ATOM | 2349 | O | CYS | 302 | 58.613 | 43.540 | 88.545 | 1.00 20.00 |
| ATOM | 2350 | N | LYS | 303 | 60.484 | 43.194 | 87.320 | 1.00 20.00 |
| ATOM | 2351 | CA | LYS | 303 | 60.197 | 44.268 | 86.423 | 1.00 20.00 |
| ATOM | 2352 | CB | LYS | 303 | 61.373 | 45.234 | 86.218 | 1.00 20.00 |
| ATOM | 2353 | CG | LYS | 303 | 62.526 | 44.582 | 85.452 | 1.00 20.00 |
| ATOM | 2354 | CD | LYS | 303 | 63.533 | 45.572 | 84.864 | 1.00 20.00 |
| ATOM | 2355 | CE | LYS | 303 | 64.622 | 44.898 | 84.026 | 1.00 20.00 |
| ATOM | 2356 | NZ | LYS | 303 | 65.408 | 45.921 | 83.300 | 1.00 20.00 |
| ATOM | 2357 | C | LYS | 303 | 59.942 | 43.671 | 85.081 | 1.00 20.00 |
| ATOM | 2358 | O | LYS | 303 | 60.253 | 42.506 | 84.837 | 1.00 20.00 |
| ATOM | 2359 | N | LYS | 304 | 59.351 | 44.469 | 84.170 | 1.00 20.00 |
| ATOM | 2360 | CA | LYS | 304 | 59.076 | 43.966 | 82.860 | 1.00 20.00 |
| ATOM | 2361 | CB | LYS | 304 | 57.951 | 44.714 | 82.124 | 1.00 20.00 |
| ATOM | 2362 | CG | LYS | 304 | 57.501 | 44.010 | 80.842 | 1.00 20.00 |
| ATOM | 2363 | CD | LYS | 304 | 56.098 | 44.414 | 80.381 | 1.00 20.00 |
| ATOM | 2364 | CE | LYS | 304 | 55.802 | 45.906 | 80.526 | 1.00 20.00 |
| ATOM | 2365 | NZ | LYS | 304 | 56.339 | 46.645 | 79.364 | 1.00 20.00 |
| ATOM | 2366 | C | LYS | 304 | 60.333 | 44.013 | 82.062 | 1.00 20.00 |
| ATOM | 2367 | O | LYS | 304 | 61.229 | 44.813 | 82.327 | 1.00 20.00 |
| ATOM | 2368 | N | CYS | 305 | 60.426 | 43.120 | 81.060 | 1.00 20.00 |
| ATOM | 2369 | CA | CYS | 305 | 61.605 | 43.022 | 80.255 | 1.00 20.00 |
| ATOM | 2370 | CB | CYS | 305 | 61.923 | 41.576 | 79.836 | 1.00 20.00 |
| ATOM | 2371 | SG | CYS | 305 | 62.261 | 40.466 | 81.234 | 1.00 20.00 |
| ATOM | 2372 | C | CYS | 305 | 61.348 | 43.763 | 78.990 | 1.00 20.00 |
| ATOM | 2373 | O | CYS | 305 | 60.357 | 43.515 | 78.304 | 1.00 20.00 |
| ATOM | 2374 | N | GLU | 306 | 62.237 | 44.713 | 78.647 | 1.00 20.00 |
| ATOM | 2375 | CA | GLU | 306 | 62.038 | 45.388 | 77.405 | 1.00 20.00 |
| ATOM | 2376 | CB | GLU | 306 | 63.069 | 46.499 | 77.143 | 1.00 20.00 |
| ATOM | 2377 | CG | GLU | 306 | 62.966 | 47.682 | 78.108 | 1.00 20.00 |
| ATOM | 2378 | CD | GLU | 306 | 64.070 | 48.668 | 77.755 | 1.00 20.00 |
| ATOM | 2379 | OE1 | GLU | 306 | 65.025 | 48.253 | 77.046 | 1.00 20.00 |
| ATOM | 2380 | OE2 | GLU | 306 | 63.975 | 49.847 | 78.191 | 1.00 20.00 |
| ATOM | 2381 | C | GLU | 306 | 62.236 | 44.343 | 76.362 | 1.00 20.00 |
| ATOM | 2382 | O | GLU | 306 | 63.354 | 43.882 | 76.138 | 1.00 20.00 |
| ATOM | 2383 | N | GLY | 307 | 61.141 | 43.941 | 75.690 | 1.00 20.00 |
| ATOM | 2384 | CA | GLY | 307 | 61.249 | 42.931 | 74.680 | 1.00 20.00 |
| ATOM | 2385 | C | GLY | 307 | 61.336 | 41.605 | 75.359 | 1.00 20.00 |
| ATOM | 2386 | O | GLY | 307 | 60.880 | 41.425 | 76.487 | 1.00 20.00 |
| ATOM | 2387 | N | PRO | 308 | 61.915 | 40.663 | 74.674 | 1.00 20.00 |

Figure 6A-30

| | | | | | | | | |
|---|---|---|---|---|---|---|---|---|
| ATOM | 2388 | CA | PRO | 308 | 62.045 | 39.363 | 75.260 | 1.00 20.00 |
| ATOM | 2389 | CD | PRO | 308 | 61.778 | 40.595 | 73.229 | 1.00 20.00 |
| ATOM | 2390 | CB | PRO | 308 | 62.453 | 38.433 | 74.123 | 1.00 20.00 |
| ATOM | 2391 | CG | PRO | 308 | 61.825 | 39.097 | 72.882 | 1.00 20.00 |
| ATOM | 2392 | C | PRO | 308 | 63.009 | 39.444 | 76.395 | 1.00 20.00 |
| ATOM | 2393 | O | PRO | 308 | 63.960 | 40.219 | 76.315 | 1.00 20.00 |
| ATOM | 2394 | N | CYS | 309 | 62.782 | 38.656 | 77.461 | 1.00 20.00 |
| ATOM | 2395 | CA | CYS | 309 | 63.646 | 38.731 | 78.600 | 1.00 20.00 |
| ATOM | 2396 | CB | CYS | 309 | 63.155 | 37.947 | 79.827 | 1.00 20.00 |
| ATOM | 2397 | SG | CYS | 309 | 61.647 | 38.660 | 80.535 | 1.00 20.00 |
| ATOM | 2398 | C | CYS | 309 | 64.968 | 38.170 | 78.213 | 1.00 20.00 |
| ATOM | 2399 | O | CYS | 309 | 65.075 | 37.383 | 77.274 | 1.00 20.00 |
| ATOM | 2400 | N | ARG | 310 | 66.021 | 38.587 | 78.939 | 1.00 20.00 |
| ATOM | 2401 | CA | ARG | 310 | 67.329 | 38.103 | 78.638 | 1.00 20.00 |
| ATOM | 2402 | CB | ARG | 310 | 68.455 | 38.788 | 79.429 | 1.00 20.00 |
| ATOM | 2403 | CG | ARG | 310 | 68.714 | 40.248 | 79.060 | 1.00 20.00 |
| ATOM | 2404 | CD | ARG | 310 | 69.852 | 40.857 | 79.880 | 1.00 20.00 |
| ATOM | 2405 | NE | ARG | 310 | 70.033 | 42.269 | 79.445 | 1.00 20.00 |
| ATOM | 2406 | CZ | ARG | 310 | 70.714 | 43.137 | 80.248 | 1.00 20.00 |
| ATOM | 2407 | NH1 | ARG | 310 | 71.199 | 42.711 | 81.451 | 1.00 20.00 |
| ATOM | 2408 | NH2 | ARG | 310 | 70.907 | 44.428 | 79.851 | 1.00 20.00 |
| ATOM | 2409 | C | ARG | 310 | 67.381 | 36.665 | 79.018 | 1.00 20.00 |
| ATOM | 2410 | O | ARG | 310 | 66.769 | 36.240 | 79.998 | 1.00 20.00 |
| ATOM | 2411 | N | LYS | 311 | 68.105 | 35.874 | 78.210 | 1.00 20.00 |
| ATOM | 2412 | CA | LYS | 311 | 68.309 | 34.493 | 78.507 | 1.00 20.00 |
| ATOM | 2413 | CB | LYS | 311 | 67.442 | 33.546 | 77.659 | 1.00 20.00 |
| ATOM | 2414 | CG | LYS | 311 | 67.695 | 33.660 | 76.155 | 1.00 20.00 |
| ATOM | 2415 | CD | LYS | 311 | 67.052 | 32.535 | 75.341 | 1.00 20.00 |
| ATOM | 2416 | CE | LYS | 311 | 65.524 | 32.593 | 75.322 | 1.00 20.00 |
| ATOM | 2417 | NZ | LYS | 311 | 64.982 | 31.475 | 74.516 | 1.00 20.00 |
| ATOM | 2418 | C | LYS | 311 | 69.739 | 34.229 | 78.170 | 1.00 20.00 |
| ATOM | 2419 | O | LYS | 311 | 70.274 | 34.799 | 77.221 | 1.00 20.00 |
| ATOM | 2420 | N | VAL | 312 | 70.408 | 33.369 | 78.957 | 1.00 20.00 |
| ATOM | 2421 | CA | VAL | 312 | 71.785 | 33.090 | 78.680 | 1.00 20.00 |
| ATOM | 2422 | CB | VAL | 312 | 72.524 | 32.534 | 79.860 | 1.00 20.00 |
| ATOM | 2423 | CG1 | VAL | 312 | 72.548 | 33.595 | 80.972 | 1.00 20.00 |
| ATOM | 2424 | CG2 | VAL | 312 | 71.850 | 31.214 | 80.272 | 1.00 20.00 |
| ATOM | 2425 | C | VAL | 312 | 71.810 | 32.027 | 77.590 | 1.00 20.00 |
| ATOM | 2426 | O | VAL | 312 | 70.709 | 31.582 | 77.169 | 1.00 20.00 |
| ATOM | 2427 | OXT | VAL | 312 | 72.933 | 31.643 | 77.168 | 1.00 20.00 |
| TER | | | | | | | | |
| ATOM | 1 | N | CYS | 313 | 73.141 | 29.695 | 76.381 | 1.00 40.00 |
| ATOM | 2 | CA | CYS | 313 | 73.419 | 28.319 | 75.901 | 1.00 40.00 |
| ATOM | 3 | C | CYS | 313 | 74.891 | 28.025 | 76.031 | 1.00 40.00 |
| ATOM | 4 | O | CYS | 313 | 75.701 | 28.940 | 75.935 | 1.00 40.00 |
| ATOM | 5 | CB | CYS | 313 | 72.951 | 28.209 | 74.438 | 1.00 40.00 |
| ATOM | 6 | SG | CYS | 313 | 71.140 | 28.384 | 74.330 | 1.00 40.00 |
| ATOM | 7 | N | ASN | 314 | 75.288 | 26.752 | 76.281 | 1.00 40.00 |
| ATOM | 8 | CA | ASN | 314 | 76.686 | 26.424 | 76.461 | 1.00 40.00 |
| ATOM | 9 | C | ASN | 314 | 77.304 | 26.180 | 75.118 | 1.00 40.00 |
| ATOM | 10 | O | ASN | 314 | 76.621 | 26.277 | 74.100 | 1.00 40.00 |
| ATOM | 11 | CB | ASN | 314 | 76.926 | 25.170 | 77.321 | 1.00 40.00 |
| ATOM | 12 | CG | ASN | 314 | 76.570 | 25.510 | 78.763 | 1.00 40.00 |
| ATOM | 13 | OD1 | ASN | 314 | 76.310 | 26.665 | 79.098 | 1.00 40.00 |
| ATOM | 14 | ND2 | ASN | 314 | 76.568 | 24.476 | 79.646 | 1.00 40.00 |
| ATOM | 15 | N | GLY | 315 | 78.627 | 25.876 | 75.097 | 1.00 40.00 |
| ATOM | 16 | CA | GLY | 315 | 79.353 | 25.621 | 73.879 | 1.00 40.00 |
| ATOM | 17 | C | GLY | 315 | 78.558 | 24.618 | 73.123 | 1.00 40.00 |
| ATOM | 18 | O | GLY | 315 | 78.278 | 23.531 | 73.622 | 1.00 40.00 |
| ATOM | 19 | N | ILE | 316 | 78.173 | 24.968 | 71.884 | 1.00 40.00 |
| ATOM | 20 | CA | ILE | 316 | 77.311 | 24.088 | 71.163 | 1.00 40.00 |
| ATOM | 21 | C | ILE | 316 | 78.041 | 23.538 | 69.985 | 1.00 40.00 |
| ATOM | 22 | O | ILE | 316 | 78.765 | 24.250 | 69.291 | 1.00 40.00 |
| ATOM | 23 | CB | ILE | 316 | 76.080 | 24.780 | 70.659 | 1.00 40.00 |
| ATOM | 24 | CG1 | ILE | 316 | 75.285 | 25.360 | 71.842 | 1.00 40.00 |
| ATOM | 25 | CG2 | ILE | 316 | 75.280 | 23.781 | 69.805 | 1.00 40.00 |
| ATOM | 26 | CD1 | ILE | 316 | 74.190 | 26.340 | 71.429 | 1.00 40.00 |
| ATOM | 27 | N | GLY | 317 | 77.876 | 22.223 | 69.747 | 1.00 40.00 |
| ATOM | 28 | CA | GLY | 317 | 78.486 | 21.627 | 68.598 | 1.00 40.00 |
| ATOM | 29 | C | GLY | 317 | 77.374 | 21.042 | 67.793 | 1.00 40.00 |
| ATOM | 30 | O | GLY | 317 | 76.969 | 19.900 | 68.006 | 1.00 40.00 |
| ATOM | 31 | N | ILE | 318 | 76.870 | 21.823 | 66.820 | 1.00 40.00 |
| ATOM | 32 | CA | ILE | 318 | 75.788 | 21.390 | 65.989 | 1.00 40.00 |
| ATOM | 33 | C | ILE | 318 | 76.396 | 20.564 | 64.903 | 1.00 40.00 |
| ATOM | 34 | O | ILE | 318 | 77.604 | 20.613 | 64.678 | 1.00 40.00 |
| ATOM | 35 | CB | ILE | 318 | 75.047 | 22.550 | 65.370 | 1.00 40.00 |
| ATOM | 36 | CG1 | ILE | 318 | 74.531 | 23.485 | 66.475 | 1.00 40.00 |

Figure 6A-31

| | | | | | | | | |
|---|---|---|---|---|---|---|---|---|
| ATOM | 37 | CG2 | ILE | 318 | 73.909 | 22.013 | 64.486 | 1.00 40.00 |
| ATOM | 38 | CD1 | ILE | 318 | 73.552 | 22.811 | 67.434 | 1.00 40.00 |
| ATOM | 39 | N | GLY | 319 | 75.571 | 19.755 | 64.212 | 1.00 40.00 |
| ATOM | 40 | CA | GLY | 319 | 76.088 | 18.939 | 63.155 | 1.00 40.00 |
| ATOM | 41 | C | GLY | 319 | 76.427 | 17.606 | 63.734 | 1.00 40.00 |
| ATOM | 42 | O | GLY | 319 | 76.272 | 17.374 | 64.932 | 1.00 40.00 |
| ATOM | 43 | N | GLU | 320 | 76.901 | 16.690 | 62.869 | 1.00 40.00 |
| ATOM | 44 | CA | GLU | 320 | 77.247 | 15.367 | 63.294 | 1.00 40.00 |
| ATOM | 45 | C | GLU | 320 | 78.718 | 15.216 | 63.107 | 1.00 40.00 |
| ATOM | 46 | O | GLU | 320 | 79.383 | 16.103 | 62.573 | 1.00 40.00 |
| ATOM | 47 | CB | GLU | 320 | 76.570 | 14.257 | 62.473 | 1.00 40.00 |
| ATOM | 48 | CG | GLU | 320 | 75.058 | 14.187 | 62.694 | 1.00 40.00 |
| ATOM | 49 | CD | GLU | 320 | 74.817 | 13.615 | 64.083 | 1.00 40.00 |
| ATOM | 50 | OE1 | GLU | 320 | 75.209 | 12.439 | 64.312 | 1.00 40.00 |
| ATOM | 51 | OE2 | GLU | 320 | 74.242 | 14.343 | 64.934 | 1.00 40.00 |
| ATOM | 52 | N | PHE | 321 | 79.270 | 14.081 | 63.574 | 1.00 60.00 |
| ATOM | 53 | CA | PHE | 321 | 80.678 | 13.870 | 63.447 | 1.00 60.00 |
| ATOM | 54 | C | PHE | 321 | 81.006 | 13.918 | 61.993 | 1.00 60.00 |
| ATOM | 55 | O | PHE | 321 | 80.186 | 13.574 | 61.144 | 1.00 60.00 |
| ATOM | 56 | CB | PHE | 321 | 81.158 | 12.514 | 63.994 | 1.00 60.00 |
| ATOM | 57 | CG | PHE | 321 | 80.977 | 12.521 | 65.474 | 1.00 60.00 |
| ATOM | 58 | CD1 | PHE | 321 | 79.764 | 12.188 | 66.031 | 1.00 60.00 |
| ATOM | 59 | CD2 | PHE | 321 | 82.020 | 12.858 | 66.305 | 1.00 60.00 |
| ATOM | 60 | CE1 | PHE | 321 | 79.595 | 12.192 | 67.397 | 1.00 60.00 |
| ATOM | 61 | CE2 | PHE | 321 | 81.859 | 12.864 | 67.670 | 1.00 60.00 |
| ATOM | 62 | CZ | PHE | 321 | 80.642 | 12.531 | 68.219 | 1.00 60.00 |
| ATOM | 63 | N | LYS | 322 | 82.230 | 14.378 | 61.679 | 1.00 60.00 |
| ATOM | 64 | CA | LYS | 322 | 82.658 | 14.500 | 60.319 | 1.00 60.00 |
| ATOM | 65 | C | LYS | 322 | 82.709 | 13.137 | 59.717 | 1.00 60.00 |
| ATOM | 66 | O | LYS | 322 | 82.299 | 12.937 | 58.575 | 1.00 60.00 |
| ATOM | 67 | CB | LYS | 322 | 84.067 | 15.103 | 60.187 | 1.00 60.00 |
| ATOM | 68 | CG | LYS | 322 | 85.161 | 14.223 | 60.795 | 1.00 60.00 |
| ATOM | 69 | CD | LYS | 322 | 86.576 | 14.625 | 60.377 | 1.00 60.00 |
| ATOM | 70 | CE | LYS | 322 | 87.666 | 13.743 | 60.989 | 1.00 60.00 |
| ATOM | 71 | NZ | LYS | 322 | 89.000 | 14.195 | 60.533 | 1.00 60.00 |
| ATOM | 72 | N | ASP | 323 | 83.210 | 12.152 | 60.484 | 1.00 60.00 |
| ATOM | 73 | CA | ASP | 323 | 83.348 | 10.833 | 59.946 | 1.00 60.00 |
| ATOM | 74 | C | ASP | 323 | 81.994 | 10.353 | 59.549 | 1.00 60.00 |
| ATOM | 75 | O | ASP | 323 | 81.817 | 9.818 | 58.455 | 1.00 60.00 |
| ATOM | 76 | CB | ASP | 323 | 83.924 | 9.827 | 60.961 | 1.00 60.00 |
| ATOM | 77 | CG | ASP | 323 | 84.217 | 8.514 | 60.245 | 1.00 60.00 |
| ATOM | 78 | OD1 | ASP | 323 | 83.830 | 8.377 | 59.054 | 1.00 60.00 |
| ATOM | 79 | OD2 | ASP | 323 | 84.835 | 7.624 | 60.888 | 1.00 60.00 |
| ATOM | 80 | N | SER | 324 | 80.988 | 10.546 | 60.419 | 1.00 60.00 |
| ATOM | 81 | CA | SER | 324 | 79.691 | 10.070 | 60.054 | 1.00 60.00 |
| ATOM | 82 | C | SER | 324 | 79.241 | 10.862 | 58.874 | 1.00 60.00 |
| ATOM | 83 | O | SER | 324 | 79.250 | 12.091 | 58.894 | 1.00 60.00 |
| ATOM | 84 | CB | SER | 324 | 78.635 | 10.219 | 61.163 | 1.00 60.00 |
| ATOM | 85 | OG | SER | 324 | 78.416 | 11.592 | 61.453 | 1.00 60.00 |
| ATOM | 86 | N | LEU | 325 | 78.851 | 10.156 | 57.796 | 1.00 60.00 |
| ATOM | 87 | CA | LEU | 325 | 78.392 | 10.817 | 56.614 | 1.00 60.00 |
| ATOM | 88 | C | LEU | 325 | 77.121 | 11.514 | 56.961 | 1.00 60.00 |
| ATOM | 89 | O | LEU | 325 | 76.893 | 12.652 | 56.555 | 1.00 60.00 |
| ATOM | 90 | CB | LEU | 325 | 78.086 | 9.846 | 55.458 | 1.00 60.00 |
| ATOM | 91 | CG | LEU | 325 | 79.330 | 9.127 | 54.907 | 1.00 60.00 |
| ATOM | 92 | CD1 | LEU | 325 | 80.303 | 10.118 | 54.249 | 1.00 60.00 |
| ATOM | 93 | CD2 | LEU | 325 | 79.998 | 8.257 | 55.983 | 1.00 60.00 |
| ATOM | 94 | N | SER | 326 | 76.262 | 10.841 | 57.746 | 1.00 60.00 |
| ATOM | 95 | CA | SER | 326 | 75.004 | 11.425 | 58.094 | 1.00 60.00 |
| ATOM | 96 | C | SER | 326 | 75.270 | 12.652 | 58.895 | 1.00 60.00 |
| ATOM | 97 | O | SER | 326 | 76.143 | 12.672 | 59.762 | 1.00 60.00 |
| ATOM | 98 | CB | SER | 326 | 74.111 | 10.504 | 58.942 | 1.00 60.00 |
| ATOM | 99 | OG | SER | 326 | 74.705 | 10.289 | 60.215 | 1.00 60.00 |
| ATOM | 100 | N | ILE | 327 | 74.516 | 13.727 | 58.600 | 1.00 60.00 |
| ATOM | 101 | CA | ILE | 327 | 74.664 | 14.952 | 59.323 | 1.00 60.00 |
| ATOM | 102 | C | ILE | 327 | 73.323 | 15.261 | 59.890 | 1.00 60.00 |
| ATOM | 103 | O | ILE | 327 | 72.301 | 14.971 | 59.270 | 1.00 60.00 |
| ATOM | 104 | CB | ILE | 327 | 75.059 | 16.121 | 58.465 | 1.00 60.00 |
| ATOM | 105 | CG1 | ILE | 327 | 73.974 | 16.438 | 57.418 | 1.00 60.00 |
| ATOM | 106 | CG2 | ILE | 327 | 76.433 | 15.806 | 57.851 | 1.00 60.00 |
| ATOM | 107 | CD1 | ILE | 327 | 73.735 | 15.320 | 56.404 | 1.00 60.00 |
| ATOM | 108 | N | ASN | 328 | 73.283 | 15.840 | 61.105 | 1.00 40.00 |
| ATOM | 109 | CA | ASN | 328 | 72.004 | 16.147 | 61.667 | 1.00 40.00 |
| ATOM | 110 | C | ASN | 328 | 71.761 | 17.606 | 61.479 | 1.00 40.00 |
| ATOM | 111 | O | ASN | 328 | 72.239 | 18.439 | 62.248 | 1.00 40.00 |
| ATOM | 112 | CB | ASN | 328 | 71.899 | 15.849 | 63.172 | 1.00 40.00 |
| ATOM | 113 | CG | ASN | 328 | 71.874 | 14.337 | 63.352 | 1.00 40.00 |

Figure 6A-32

| | | | | | | | | |
|---|---|---|---|---|---|---|---|---|
| ATOM | 114 | CD1 | ASN | 328 | 71.796 | 13.832 | 64.471 | 1.00 40.00 |
| ATOM | 115 | ND2 | ASN | 328 | 71.943 | 13.591 | 62.217 | 1.00 40.00 |
| ATOM | 116 | N | ALA | 329 | 71.003 | 17.944 | 60.421 | 1.00 40.00 |
| ATOM | 117 | CA | ALA | 329 | 70.649 | 19.301 | 60.133 | 1.00 40.00 |
| ATOM | 118 | C | ALA | 329 | 69.694 | 19.720 | 61.196 | 1.00 40.00 |
| ATOM | 119 | O | ALA | 329 | 69.693 | 20.870 | 61.633 | 1.00 40.00 |
| ATOM | 120 | CB | ALA | 329 | 69.934 | 19.457 | 58.780 | 1.00 40.00 |
| ATOM | 121 | N | THR | 330 | 68.891 | 18.753 | 61.672 | 1.00 40.00 |
| ATOM | 122 | CA | THR | 330 | 67.833 | 19.948 | 62.619 | 1.00 40.00 |
| ATOM | 123 | C | THR | 330 | 68.393 | 19.563 | 63.859 | 1.00 40.00 |
| ATOM | 124 | O | THR | 330 | 67.671 | 20.212 | 64.612 | 1.00 40.00 |
| ATOM | 125 | CB | THR | 330 | 67.171 | 17.662 | 63.016 | 1.00 40.00 |
| ATOM | 126 | OG1 | THR | 330 | 66.028 | 17.923 | 63.816 | 1.00 40.00 |
| ATOM | 127 | CG2 | THR | 330 | 68.183 | 16.804 | 63.794 | 1.00 40.00 |
| ATOM | 128 | N | ASN | 331 | 69.699 | 19.365 | 64.098 | 1.00 40.00 |
| ATOM | 129 | CA | ASN | 331 | 70.371 | 19.838 | 65.274 | 1.00 40.00 |
| ATOM | 130 | C | ASN | 331 | 70.292 | 21.336 | 65.372 | 1.00 40.00 |
| ATOM | 131 | O | ASN | 331 | 70.402 | 21.883 | 66.467 | 1.00 40.00 |
| ATOM | 132 | CB | ASN | 331 | 71.860 | 19.449 | 65.312 | 1.00 40.00 |
| ATOM | 133 | CG | ASN | 331 | 71.946 | 17.950 | 65.562 | 1.00 40.00 |
| ATOM | 134 | OD1 | ASN | 331 | 70.960 | 17.310 | 65.920 | 1.00 40.00 |
| ATOM | 135 | ND2 | ASN | 331 | 73.165 | 17.374 | 65.382 | 1.00 40.00 |
| ATOM | 136 | N | ILE | 332 | 70.092 | 22.042 | 64.242 | 1.00 40.00 |
| ATOM | 137 | CA | ILE | 332 | 70.108 | 23.485 | 64.191 | 1.00 40.00 |
| ATOM | 138 | C | ILE | 332 | 69.051 | 24.037 | 65.100 | 1.00 40.00 |
| ATOM | 139 | O | ILE | 332 | 69.149 | 25.179 | 65.541 | 1.00 40.00 |
| ATOM | 140 | CB | ILE | 332 | 69.769 | 24.053 | 62.844 | 1.00 40.00 |
| ATOM | 141 | CG1 | ILE | 332 | 68.266 | 23.885 | 62.540 | 1.00 40.00 |
| ATOM | 142 | CG2 | ILE | 332 | 70.704 | 23.413 | 61.806 | 1.00 40.00 |
| ATOM | 143 | CD1 | ILE | 332 | 67.726 | 22.463 | 62.660 | 1.00 40.00 |
| ATOM | 144 | N | LYS | 333 | 67.992 | 23.251 | 65.363 | 1.00 40.00 |
| ATOM | 145 | CA | LYS | 333 | 66.837 | 23.647 | 66.124 | 1.00 40.00 |
| ATOM | 146 | C | LYS | 333 | 67.199 | 24.000 | 67.537 | 1.00 40.00 |
| ATOM | 147 | O | LYS | 333 | 66.528 | 24.820 | 68.160 | 1.00 40.00 |
| ATOM | 148 | CB | LYS | 333 | 65.769 | 22.542 | 66.172 | 1.00 40.00 |
| ATOM | 149 | CG | LYS | 333 | 65.218 | 22.199 | 64.787 | 1.00 40.00 |
| ATOM | 150 | CD | LYS | 333 | 64.406 | 20.905 | 64.744 | 1.00 40.00 |
| ATOM | 151 | CE | LYS | 333 | 63.906 | 20.545 | 63.344 | 1.00 40.00 |
| ATOM | 152 | NZ | LYS | 333 | 63.016 | 21.610 | 62.832 | 1.00 40.00 |
| ATOM | 153 | N | HIS | 334 | 68.273 | 23.406 | 68.084 | 1.00 40.00 |
| ATOM | 154 | CA | HIS | 334 | 68.644 | 23.624 | 69.456 | 1.00 40.00 |
| ATOM | 155 | C | HIS | 334 | 68.796 | 25.099 | 69.680 | 1.00 40.00 |
| ATOM | 156 | O | HIS | 334 | 68.549 | 25.598 | 70.776 | 1.00 40.00 |
| ATOM | 157 | CB | HIS | 334 | 69.985 | 22.955 | 69.807 | 1.00 40.00 |
| ATOM | 158 | CG | HIS | 334 | 70.406 | 23.151 | 71.234 | 1.00 40.00 |
| ATOM | 159 | ND1 | HIS | 334 | 69.981 | 22.368 | 72.281 | 1.00 40.00 |
| ATOM | 160 | CD2 | HIS | 334 | 71.250 | 24.073 | 71.777 | 1.00 40.00 |
| ATOM | 161 | CE1 | HIS | 334 | 70.583 | 22.848 | 73.400 | 1.00 40.00 |
| ATOM | 162 | NE2 | HIS | 334 | 71.363 | 23.882 | 73.142 | 1.00 40.00 |
| ATOM | 163 | N | PHE | 335 | 69.224 | 25.820 | 68.629 | 1.00 40.00 |
| ATOM | 164 | CA | PHE | 335 | 69.474 | 27.234 | 68.584 | 1.00 40.00 |
| ATOM | 165 | C | PHE | 335 | 68.254 | 28.089 | 68.681 | 1.00 40.00 |
| ATOM | 166 | O | PHE | 335 | 68.374 | 29.298 | 68.858 | 1.00 40.00 |
| ATOM | 167 | CB | PHE | 335 | 70.297 | 27.691 | 67.370 | 1.00 40.00 |
| ATOM | 168 | CG | PHE | 335 | 71.706 | 27.589 | 67.820 | 1.00 40.00 |
| ATOM | 169 | CD1 | PHE | 335 | 72.240 | 28.629 | 68.545 | 1.00 40.00 |
| ATOM | 170 | CD2 | PHE | 335 | 72.483 | 26.488 | 67.544 | 1.00 40.00 |
| ATOM | 171 | CE1 | PHE | 335 | 73.535 | 28.586 | 68.995 | 1.00 40.00 |
| ATOM | 172 | CE2 | PHE | 335 | 73.781 | 26.440 | 67.991 | 1.00 40.00 |
| ATOM | 173 | CZ | PHE | 335 | 74.304 | 27.487 | 68.715 | 1.00 40.00 |
| ATOM | 174 | N | LYS | 336 | 67.051 | 27.522 | 68.531 | 1.00 40.00 |
| ATOM | 175 | CA | LYS | 336 | 65.866 | 28.333 | 68.487 | 1.00 40.00 |
| ATOM | 176 | C | LYS | 336 | 65.759 | 29.252 | 69.680 | 1.00 40.00 |
| ATOM | 177 | O | LYS | 336 | 65.379 | 30.408 | 69.520 | 1.00 40.00 |
| ATOM | 178 | CB | LYS | 336 | 64.598 | 27.464 | 68.435 | 1.00 40.00 |
| ATOM | 179 | CG | LYS | 336 | 64.487 | 26.491 | 69.611 | 1.00 40.00 |
| ATOM | 180 | CD | LYS | 336 | 63.202 | 25.662 | 69.617 | 1.00 40.00 |
| ATOM | 181 | CE | LYS | 336 | 61.952 | 26.448 | 70.013 | 1.00 40.00 |
| ATOM | 182 | NZ | LYS | 336 | 60.772 | 25.556 | 69.986 | 1.00 40.00 |
| ATOM | 183 | N | ASN | 337 | 66.049 | 28.781 | 70.909 | 1.00 40.00 |
| ATOM | 184 | CA | ASN | 337 | 65.885 | 29.587 | 72.098 | 1.00 40.00 |
| ATOM | 185 | C | ASN | 337 | 66.954 | 30.630 | 72.351 | 1.00 40.00 |
| ATOM | 186 | O | ASN | 337 | 66.645 | 31.726 | 72.818 | 1.00 40.00 |
| ATOM | 187 | CB | ASN | 337 | 65.786 | 28.723 | 73.367 | 1.00 40.00 |
| ATOM | 188 | CG | ASN | 337 | 64.491 | 27.932 | 73.266 | 1.00 40.00 |
| ATOM | 189 | OD1 | ASN | 337 | 63.580 | 28.306 | 72.528 | 1.00 40.00 |
| ATOM | 190 | ND2 | ASN | 337 | 64.399 | 26.811 | 74.031 | 1.00 40.00 |

Figure 6A-33

| | | | | | | | | |
|---|---|---|---|---|---|---|---|---|
| ATOM | 191 | N | CYS | 338 | 68.234 | 30.326 | 72.051 | 1.00 20.00 |
| ATOM | 192 | CA | CYS | 338 | 69.379 | 31.096 | 72.480 | 1.00 20.00 |
| ATOM | 193 | C | CYS | 338 | 69.420 | 32.509 | 71.971 | 1.00 20.00 |
| ATOM | 194 | O | CYS | 338 | 69.349 | 32.762 | 70.769 | 1.00 20.00 |
| ATOM | 195 | CB | CYS | 338 | 70.719 | 30.436 | 72.074 | 1.00 20.00 |
| ATOM | 196 | SG | CYS | 338 | 70.739 | 28.635 | 72.353 | 1.00 20.00 |
| ATOM | 197 | N | THR | 339 | 69.443 | 33.478 | 72.915 | 1.00 20.00 |
| ATOM | 198 | CA | THR | 339 | 69.719 | 34.859 | 72.633 | 1.00 20.00 |
| ATOM | 199 | C | THR | 339 | 71.203 | 35.045 | 72.625 | 1.00 20.00 |
| ATOM | 200 | O | THR | 339 | 71.760 | 35.738 | 71.778 | 1.00 20.00 |
| ATOM | 201 | CB | THR | 339 | 69.148 | 35.778 | 73.671 | 1.00 20.00 |
| ATOM | 202 | OG1 | THR | 339 | 69.710 | 35.492 | 74.943 | 1.00 20.00 |
| ATOM | 203 | CG2 | THR | 339 | 67.622 | 35.583 | 73.710 | 1.00 20.00 |
| ATOM | 204 | N | SER | 340 | 71.899 | 34.433 | 73.604 | 1.00 20.00 |
| ATOM | 205 | CA | SER | 340 | 73.322 | 34.600 | 73.667 | 1.00 20.00 |
| ATOM | 206 | C | SER | 340 | 73.943 | 33.319 | 74.101 | 1.00 20.00 |
| ATOM | 207 | O | SER | 340 | 73.883 | 32.957 | 75.275 | 1.00 20.00 |
| ATOM | 208 | CB | SER | 340 | 73.760 | 35.676 | 74.671 | 1.00 20.00 |
| ATOM | 209 | OG | SER | 340 | 75.174 | 35.789 | 74.682 | 1.00 20.00 |
| ATOM | 210 | N | ILE | 341 | 74.599 | 32.602 | 73.174 | 1.00 20.00 |
| ATOM | 211 | CA | ILE | 341 | 75.211 | 31.387 | 73.606 | 1.00 20.00 |
| ATOM | 212 | C | ILE | 341 | 76.462 | 31.743 | 74.326 | 1.00 20.00 |
| ATOM | 213 | O | ILE | 341 | 77.368 | 32.347 | 73.758 | 1.00 20.00 |
| ATOM | 214 | CB | ILE | 341 | 75.562 | 30.414 | 72.516 | 1.00 20.00 |
| ATOM | 215 | CG1 | ILE | 341 | 76.509 | 31.042 | 71.490 | 1.00 20.00 |
| ATOM | 216 | CG2 | ILE | 341 | 74.273 | 29.845 | 71.926 | 1.00 20.00 |
| ATOM | 217 | CD1 | ILE | 341 | 77.062 | 30.019 | 70.499 | 1.00 20.00 |
| ATOM | 218 | N | SER | 342 | 76.524 | 31.398 | 75.626 | 1.00 20.00 |
| ATOM | 219 | CA | SER | 342 | 77.714 | 31.658 | 76.372 | 1.00 20.00 |
| ATOM | 220 | C | SER | 342 | 78.615 | 30.489 | 76.153 | 1.00 20.00 |
| ATOM | 221 | O | SER | 342 | 78.595 | 29.507 | 76.896 | 1.00 20.00 |
| ATOM | 222 | CB | SER | 342 | 77.474 | 31.836 | 77.885 | 1.00 20.00 |
| ATOM | 223 | OG | SER | 342 | 76.898 | 30.667 | 78.447 | 1.00 20.00 |
| ATOM | 224 | N | GLY | 343 | 79.443 | 30.578 | 75.098 | 1.00 20.00 |
| ATOM | 225 | CA | GLY | 343 | 80.341 | 29.520 | 74.757 | 1.00 20.00 |
| ATOM | 226 | C | GLY | 343 | 80.654 | 29.709 | 73.312 | 1.00 20.00 |
| ATOM | 227 | O | GLY | 343 | 80.673 | 30.832 | 72.814 | 1.00 20.00 |
| ATOM | 228 | N | ASP | 344 | 80.915 | 28.606 | 72.589 | 1.00 20.00 |
| ATOM | 229 | CA | ASP | 344 | 81.237 | 28.744 | 71.201 | 1.00 20.00 |
| ATOM | 230 | C | ASP | 344 | 80.220 | 27.989 | 70.417 | 1.00 20.00 |
| ATOM | 231 | O | ASP | 344 | 79.543 | 27.108 | 70.942 | 1.00 20.00 |
| ATOM | 232 | CB | ASP | 344 | 82.618 | 28.172 | 70.836 | 1.00 20.00 |
| ATOM | 233 | CG | ASP | 344 | 83.680 | 29.048 | 71.486 | 1.00 20.00 |
| ATOM | 234 | OD1 | ASP | 344 | 83.453 | 30.284 | 71.582 | 1.00 20.00 |
| ATOM | 235 | OD2 | ASP | 344 | 84.728 | 28.491 | 71.907 | 1.00 20.00 |
| ATOM | 236 | N | LEU | 345 | 80.060 | 28.353 | 69.130 | 1.00 20.00 |
| ATOM | 237 | CA | LEU | 345 | 79.138 | 27.650 | 68.291 | 1.00 20.00 |
| ATOM | 238 | C | LEU | 345 | 79.914 | 27.012 | 67.189 | 1.00 20.00 |
| ATOM | 239 | O | LEU | 345 | 80.743 | 27.652 | 66.545 | 1.00 20.00 |
| ATOM | 240 | CB | LEU | 345 | 78.064 | 28.545 | 67.655 | 1.00 20.00 |
| ATOM | 241 | CG | LEU | 345 | 77.216 | 27.798 | 66.613 | 1.00 20.00 |
| ATOM | 242 | CD1 | LEU | 345 | 76.625 | 26.510 | 67.202 | 1.00 20.00 |
| ATOM | 243 | CD2 | LEU | 345 | 76.147 | 28.719 | 66.005 | 1.00 20.00 |
| ATOM | 244 | N | HIS | 346 | 79.679 | 25.705 | 66.964 | 1.00 20.00 |
| ATOM | 245 | CA | HIS | 346 | 80.368 | 25.032 | 65.906 | 1.00 20.00 |
| ATOM | 246 | C | HIS | 346 | 79.332 | 24.417 | 65.028 | 1.00 20.00 |
| ATOM | 247 | O | HIS | 346 | 78.422 | 23.742 | 65.505 | 1.00 20.00 |
| ATOM | 248 | CB | HIS | 346 | 81.271 | 23.880 | 66.379 | 1.00 20.00 |
| ATOM | 249 | CG | HIS | 346 | 82.367 | 24.324 | 67.299 | 1.00 20.00 |
| ATOM | 250 | ND1 | HIS | 346 | 82.427 | 24.010 | 68.639 | 1.00 20.00 |
| ATOM | 251 | CD2 | HIS | 346 | 83.468 | 25.083 | 67.046 | 1.00 20.00 |
| ATOM | 252 | CE1 | HIS | 346 | 83.553 | 24.588 | 69.126 | 1.00 20.00 |
| ATOM | 253 | NE2 | HIS | 346 | 84.218 | 25.249 | 68.197 | 1.00 20.00 |
| ATOM | 254 | N | ILE | 347 | 79.422 | 24.663 | 63.709 | 1.00 20.00 |
| ATOM | 255 | CA | ILE | 347 | 78.486 | 24.019 | 62.842 | 1.00 20.00 |
| ATOM | 256 | C | ILE | 347 | 79.288 | 23.208 | 61.878 | 1.00 20.00 |
| ATOM | 257 | O | ILE | 347 | 79.766 | 23.709 | 60.861 | 1.00 20.00 |
| ATOM | 258 | CB | ILE | 347 | 77.616 | 24.986 | 62.092 | 1.00 20.00 |
| ATOM | 259 | CG1 | ILE | 347 | 76.777 | 25.795 | 63.099 | 1.00 20.00 |
| ATOM | 260 | CG2 | ILE | 347 | 76.768 | 24.202 | 61.078 | 1.00 20.00 |
| ATOM | 261 | CD1 | ILE | 347 | 76.006 | 26.959 | 62.479 | 1.00 20.00 |
| ATOM | 262 | N | LEU | 348 | 79.435 | 21.906 | 62.181 | 1.00 20.00 |
| ATOM | 263 | CA | LEU | 348 | 80.215 | 21.016 | 61.373 | 1.00 20.00 |
| ATOM | 264 | C | LEU | 348 | 79.431 | 20.711 | 60.144 | 1.00 20.00 |
| ATOM | 265 | O | LEU | 348 | 78.298 | 21.163 | 59.978 | 1.00 20.00 |
| ATOM | 266 | CB | LEU | 348 | 80.538 | 19.677 | 62.066 | 1.00 20.00 |
| ATOM | 267 | CG | LEU | 348 | 81.462 | 19.807 | 63.290 | 1.00 20.00 |

Figure 6A-34

| | | | | | | | | |
|---|---|---|---|---|---|---|---|---|
| ATOM | 268 | CD1 | LEU | 348 | 80.781 | 20.573 | 64.436 | 1.00 20.00 |
| ATOM | 269 | CD2 | LEU | 348 | 81.998 | 18.435 | 63.728 | 1.00 20.00 |
| ATOM | 270 | N | PRO | 349 | 80.010 | 19.931 | 59.276 | 1.00 20.00 |
| ATOM | 271 | CA | PRO | 349 | 79.366 | 19.644 | 58.037 | 1.00 20.00 |
| ATOM | 272 | C | PRO | 349 | 78.014 | 19.067 | 58.219 | 1.00 20.00 |
| ATOM | 273 | O | PRO | 349 | 77.885 | 17.991 | 58.798 | 1.00 20.00 |
| ATOM | 274 | CB | PRO | 349 | 80.352 | 18.799 | 57.240 | 1.00 20.00 |
| ATOM | 275 | CG | PRO | 349 | 81.723 | 19.295 | 57.748 | 1.00 20.00 |
| ATOM | 276 | CD | PRO | 349 | 81.455 | 19.787 | 59.184 | 1.00 20.00 |
| ATOM | 277 | N | VAL | 350 | 76.993 | 19.788 | 57.726 | 1.00 40.00 |
| ATOM | 278 | CA | VAL | 350 | 75.647 | 19.318 | 57.787 | 1.00 40.00 |
| ATOM | 279 | C | VAL | 350 | 75.029 | 19.699 | 56.487 | 1.00 40.00 |
| ATOM | 280 | O | VAL | 350 | 75.424 | 20.690 | 55.873 | 1.00 40.00 |
| ATOM | 281 | CB | VAL | 350 | 74.835 | 19.957 | 58.874 | 1.00 40.00 |
| ATOM | 282 | CG1 | VAL | 350 | 73.395 | 19.422 | 58.788 | 1.00 40.00 |
| ATOM | 283 | CG2 | VAL | 350 | 75.520 | 19.681 | 60.223 | 1.00 40.00 |
| ATOM | 284 | N | ALA | 351 | 74.046 | 18.887 | 56.054 | 1.00 40.00 |
| ATOM | 285 | CA | ALA | 351 | 73.308 | 19.114 | 54.850 | 1.00 40.00 |
| ATOM | 286 | C | ALA | 351 | 71.882 | 18.863 | 55.211 | 1.00 40.00 |
| ATOM | 287 | O | ALA | 351 | 71.592 | 18.324 | 56.278 | 1.00 40.00 |
| ATOM | 288 | CB | ALA | 351 | 73.670 | 18.147 | 53.711 | 1.00 40.00 |
| ATOM | 289 | N | PHE | 352 | 70.942 | 19.266 | 54.337 | 1.00 60.00 |
| ATOM | 290 | CA | PHE | 352 | 69.562 | 19.052 | 54.655 | 1.00 60.00 |
| ATOM | 291 | C | PHE | 352 | 69.115 | 17.830 | 53.923 | 1.00 60.00 |
| ATOM | 292 | O | PHE | 352 | 69.436 | 17.639 | 52.752 | 1.00 60.00 |
| ATOM | 293 | CB | PHE | 352 | 68.644 | 20.213 | 54.235 | 1.00 60.00 |
| ATOM | 294 | CG | PHE | 352 | 68.734 | 20.336 | 52.754 | 1.00 60.00 |
| ATOM | 295 | CD1 | PHE | 352 | 69.765 | 21.037 | 52.174 | 1.00 60.00 |
| ATOM | 296 | CD2 | PHE | 352 | 67.787 | 19.750 | 51.945 | 1.00 60.00 |
| ATOM | 297 | CE1 | PHE | 352 | 69.852 | 21.153 | 50.807 | 1.00 60.00 |
| ATOM | 298 | CE2 | PHE | 352 | 67.869 | 19.863 | 50.578 | 1.00 60.00 |
| ATOM | 299 | CZ | PHE | 352 | 68.903 | 20.566 | 50.006 | 1.00 60.00 |
| ATOM | 300 | N | ARG | 353 | 68.370 | 16.954 | 54.623 | 1.00 60.00 |
| ATOM | 301 | CA | ARG | 353 | 67.910 | 15.741 | 54.018 | 1.00 60.00 |
| ATOM | 302 | C | ARG | 353 | 66.481 | 15.567 | 54.413 | 1.00 60.00 |
| ATOM | 303 | O | ARG | 353 | 65.982 | 16.254 | 55.303 | 1.00 60.00 |
| ATOM | 304 | CB | ARG | 353 | 68.631 | 14.488 | 54.539 | 1.00 60.00 |
| ATOM | 305 | CG | ARG | 353 | 68.391 | 14.268 | 56.034 | 1.00 60.00 |
| ATOM | 306 | CD | ARG | 353 | 69.082 | 13.034 | 56.616 | 1.00 60.00 |
| ATOM | 307 | NE | ARG | 353 | 68.733 | 12.984 | 58.065 | 1.00 60.00 |
| ATOM | 308 | CZ | ARG | 353 | 69.009 | 11.868 | 58.801 | 1.00 60.00 |
| ATOM | 309 | NH1 | ARG | 353 | 69.624 | 10.799 | 58.217 | 1.00 60.00 |
| ATOM | 310 | NH2 | ARG | 353 | 68.671 | 11.823 | 60.123 | 1.00 60.00 |
| ATOM | 311 | N | GLY | 354 | 65.781 | 14.634 | 53.741 | 1.00 60.00 |
| ATOM | 312 | CA | GLY | 354 | 64.425 | 14.346 | 54.097 | 1.00 60.00 |
| ATOM | 313 | C | GLY | 354 | 63.538 | 15.391 | 53.511 | 1.00 60.00 |
| ATOM | 314 | O | GLY | 354 | 62.364 | 15.484 | 53.867 | 1.00 60.00 |
| ATOM | 315 | N | ASP | 355 | 64.073 | 16.214 | 52.592 | 1.00 60.00 |
| ATOM | 316 | CA | ASP | 355 | 63.241 | 17.225 | 52.017 | 1.00 60.00 |
| ATOM | 317 | C | ASP | 355 | 62.771 | 16.715 | 50.698 | 1.00 60.00 |
| ATOM | 318 | O | ASP | 355 | 63.557 | 16.218 | 49.893 | 1.00 60.00 |
| ATOM | 319 | CB | ASP | 355 | 63.970 | 18.556 | 51.761 | 1.00 60.00 |
| ATOM | 320 | CG | ASP | 355 | 64.250 | 19.201 | 53.110 | 1.00 60.00 |
| ATOM | 321 | OD1 | ASP | 355 | 63.577 | 18.815 | 54.103 | 1.00 60.00 |
| ATOM | 322 | OD2 | ASP | 355 | 65.141 | 20.089 | 53.166 | 1.00 60.00 |
| ATOM | 323 | N | SER | 356 | 61.451 | 16.815 | 50.456 | 1.00 60.00 |
| ATOM | 324 | CA | SER | 356 | 60.917 | 16.363 | 49.208 | 1.00 60.00 |
| ATOM | 325 | C | SER | 356 | 61.282 | 17.388 | 48.192 | 1.00 60.00 |
| ATOM | 326 | O | SER | 356 | 61.483 | 18.558 | 48.518 | 1.00 60.00 |
| ATOM | 327 | CB | SER | 356 | 59.387 | 16.213 | 49.205 | 1.00 60.00 |
| ATOM | 328 | OG | SER | 356 | 58.771 | 17.476 | 49.400 | 1.00 60.00 |
| ATOM | 329 | N | PHE | 357 | 61.399 | 16.964 | 46.921 | 1.00 60.00 |
| ATOM | 330 | CA | PHE | 357 | 61.770 | 17.890 | 45.898 | 1.00 60.00 |
| ATOM | 331 | C | PHE | 357 | 60.708 | 18.934 | 45.814 | 1.00 60.00 |
| ATOM | 332 | O | PHE | 357 | 61.003 | 20.127 | 45.781 | 1.00 60.00 |
| ATOM | 333 | CB | PHE | 357 | 61.884 | 17.240 | 44.509 | 1.00 60.00 |
| ATOM | 334 | CG | PHE | 357 | 63.068 | 16.333 | 44.530 | 1.00 60.00 |
| ATOM | 335 | CD1 | PHE | 357 | 64.329 | 16.834 | 44.306 | 1.00 60.00 |
| ATOM | 336 | CD2 | PHE | 357 | 62.917 | 14.987 | 44.771 | 1.00 60.00 |
| ATOM | 337 | CE1 | PHE | 357 | 65.426 | 16.005 | 44.322 | 1.00 60.00 |
| ATOM | 338 | CE2 | PHE | 357 | 64.010 | 14.154 | 44.789 | 1.00 60.00 |
| ATOM | 339 | CZ | PHE | 357 | 65.267 | 14.662 | 44.564 | 1.00 60.00 |
| ATOM | 340 | N | THR | 358 | 59.431 | 18.510 | 45.796 | 1.00 60.00 |
| ATOM | 341 | CA | THR | 358 | 58.392 | 19.485 | 45.675 | 1.00 60.00 |
| ATOM | 342 | C | THR | 358 | 57.591 | 19.500 | 46.933 | 1.00 60.00 |
| ATOM | 343 | O | THR | 358 | 57.220 | 18.457 | 47.469 | 1.00 60.00 |
| ATOM | 344 | CB | THR | 358 | 57.446 | 19.217 | 44.540 | 1.00 60.00 |

Figure 6A-35

| | | | | | | | | |
|---|---|---|---|---|---|---|---|---|
| ATOM | 345 | OG1 | THR | 358 | 56.552 | 23.308 | 44.379 | 1.00 60.00 |
| ATOM | 346 | CG2 | THR | 358 | 56.666 | 17.923 | 44.833 | 1.00 60.00 |
| ATOM | 347 | N | HIS | 359 | 57.329 | 20.716 | 47.445 | 1.00 60.00 |
| ATOM | 348 | CA | HIS | 359 | 56.531 | 20.894 | 48.621 | 1.00 60.00 |
| ATOM | 349 | C | HIS | 359 | 56.047 | 22.293 | 48.561 | 1.00 60.00 |
| ATOM | 350 | O | HIS | 359 | 56.372 | 23.022 | 47.623 | 1.00 60.00 |
| ATOM | 351 | CB | HIS | 359 | 57.315 | 20.697 | 49.933 | 1.00 60.00 |
| ATOM | 352 | CG | HIS | 359 | 56.429 | 20.549 | 51.136 | 1.00 60.00 |
| ATOM | 353 | ND1 | HIS | 359 | 55.994 | 21.596 | 51.926 | 1.00 60.00 |
| ATOM | 354 | CD2 | HIS | 359 | 55.890 | 19.423 | 51.680 | 1.00 60.00 |
| ATOM | 355 | CE1 | HIS | 359 | 55.222 | 21.046 | 52.899 | 1.00 60.00 |
| ATOM | 356 | NE2 | HIS | 359 | 55.129 | 19.734 | 52.791 | 1.00 60.00 |
| ATOM | 357 | N | THR | 360 | 55.238 | 22.726 | 49.547 | 1.00 60.00 |
| ATOM | 358 | CA | THR | 360 | 54.780 | 24.083 | 49.509 | 1.00 60.00 |
| ATOM | 359 | C | THR | 360 | 55.676 | 24.869 | 50.406 | 1.00 60.00 |
| ATOM | 360 | O | THR | 360 | 55.799 | 24.583 | 51.597 | 1.00 60.00 |
| ATOM | 361 | CB | THR | 360 | 53.376 | 24.261 | 50.010 | 1.00 60.00 |
| ATOM | 362 | OG1 | THR | 360 | 52.473 | 23.498 | 49.224 | 1.00 60.00 |
| ATOM | 363 | CG2 | THR | 360 | 53.014 | 25.754 | 49.934 | 1.00 60.00 |
| ATOM | 364 | N | PRO | 361 | 56.334 | 25.840 | 49.840 | 1.00 60.00 |
| ATOM | 365 | CA | PRO | 361 | 57.221 | 26.630 | 50.645 | 1.00 60.00 |
| ATOM | 366 | C | PRO | 361 | 56.479 | 27.590 | 51.514 | 1.00 60.00 |
| ATOM | 367 | O | PRO | 361 | 55.427 | 28.084 | 51.114 | 1.00 60.00 |
| ATOM | 368 | CB | PRO | 361 | 58.181 | 27.312 | 49.673 | 1.00 60.00 |
| ATOM | 369 | CG | PRO | 361 | 58.220 | 26.351 | 48.472 | 1.00 60.00 |
| ATOM | 370 | CD | PRO | 361 | 56.840 | 25.673 | 48.486 | 1.00 60.00 |
| ATOM | 371 | N | PRO | 362 | 56.999 | 27.822 | 52.683 | 1.00 60.00 |
| ATOM | 372 | CA | PRO | 362 | 56.413 | 28.808 | 53.549 | 1.00 60.00 |
| ATOM | 373 | C | PRO | 362 | 56.920 | 30.135 | 53.099 | 1.00 60.00 |
| ATOM | 374 | O | PRO | 362 | 57.846 | 30.166 | 52.290 | 1.00 60.00 |
| ATOM | 375 | CB | PRO | 362 | 56.860 | 28.452 | 54.965 | 1.00 60.00 |
| ATOM | 376 | CG | PRO | 362 | 57.141 | 26.943 | 54.894 | 1.00 60.00 |
| ATOM | 377 | CD | PRO | 362 | 57.562 | 26.711 | 53.436 | 1.00 60.00 |
| ATOM | 378 | N | LEU | 363 | 56.338 | 31.243 | 53.595 | 1.00 60.00 |
| ATOM | 379 | CA | LEU | 363 | 56.852 | 32.514 | 53.187 | 1.00 60.00 |
| ATOM | 380 | C | LEU | 363 | 58.279 | 32.531 | 53.615 | 1.00 60.00 |
| ATOM | 381 | O | LEU | 363 | 59.170 | 32.867 | 52.835 | 1.00 60.00 |
| ATOM | 382 | CB | LEU | 363 | 56.147 | 33.699 | 53.871 | 1.00 60.00 |
| ATOM | 383 | CG | LEU | 363 | 54.671 | 33.865 | 53.464 | 1.00 60.00 |
| ATOM | 384 | CD1 | LEU | 363 | 54.541 | 34.253 | 51.983 | 1.00 60.00 |
| ATOM | 385 | CD2 | LEU | 363 | 53.845 | 32.621 | 53.830 | 1.00 60.00 |
| ATOM | 386 | N | ASP | 364 | 58.535 | 32.141 | 54.878 | 1.00 60.00 |
| ATOM | 387 | CA | ASP | 364 | 59.884 | 32.075 | 55.347 | 1.00 60.00 |
| ATOM | 388 | C | ASP | 364 | 60.034 | 30.739 | 55.998 | 1.00 60.00 |
| ATOM | 389 | O | ASP | 364 | 59.242 | 30.367 | 56.862 | 1.00 60.00 |
| ATOM | 390 | CB | ASP | 364 | 60.220 | 33.144 | 56.398 | 1.00 60.00 |
| ATOM | 391 | CG | ASP | 364 | 61.724 | 33.115 | 56.629 | 1.00 60.00 |
| ATOM | 392 | OD1 | ASP | 364 | 62.382 | 32.172 | 56.114 | 1.00 60.00 |
| ATOM | 393 | OD2 | ASP | 364 | 62.234 | 34.038 | 57.317 | 1.00 60.00 |
| ATOM | 394 | N | PRO | 365 | 61.018 | 29.993 | 55.587 | 1.00 60.00 |
| ATOM | 395 | CA | PRO | 365 | 61.183 | 28.703 | 56.196 | 1.00 60.00 |
| ATOM | 396 | C | PRO | 365 | 61.803 | 28.818 | 57.548 | 1.00 60.00 |
| ATOM | 397 | O | PRO | 365 | 62.597 | 29.730 | 57.772 | 1.00 60.00 |
| ATOM | 398 | CB | PRO | 365 | 61.980 | 27.861 | 55.207 | 1.00 60.00 |
| ATOM | 399 | CG | PRO | 365 | 61.649 | 28.494 | 53.844 | 1.00 60.00 |
| ATOM | 400 | CD | PRO | 365 | 61.360 | 29.968 | 54.173 | 1.00 60.00 |
| ATOM | 401 | N | GLN | 366 | 61.429 | 27.908 | 58.467 | 1.00 60.00 |
| ATOM | 402 | CA | GLN | 366 | 61.933 | 27.893 | 59.809 | 1.00 60.00 |
| ATOM | 403 | C | GLN | 366 | 63.377 | 27.500 | 59.802 | 1.00 60.00 |
| ATOM | 404 | O | GLN | 366 | 64.192 | 28.068 | 60.527 | 1.00 60.00 |
| ATOM | 405 | CB | GLN | 366 | 61.201 | 26.866 | 60.691 | 1.00 60.00 |
| ATOM | 406 | CG | GLN | 366 | 59.715 | 27.169 | 60.889 | 1.00 60.00 |
| ATOM | 407 | CD | GLN | 366 | 59.598 | 28.345 | 61.848 | 1.00 60.00 |
| ATOM | 408 | OE1 | GLN | 366 | 60.192 | 29.401 | 61.635 | 1.00 60.00 |
| ATOM | 409 | NE2 | GLN | 366 | 58.814 | 28.154 | 62.942 | 1.00 60.00 |
| ATOM | 410 | N | GLU | 367 | 63.724 | 26.506 | 58.965 | 1.00 60.00 |
| ATOM | 411 | CA | GLU | 367 | 65.044 | 25.946 | 58.944 | 1.00 60.00 |
| ATOM | 412 | C | GLU | 367 | 66.047 | 26.988 | 58.576 | 1.00 60.00 |
| ATOM | 413 | O | GLU | 367 | 67.143 | 27.027 | 59.132 | 1.00 60.00 |
| ATOM | 414 | CB | GLU | 367 | 65.193 | 24.808 | 57.921 | 1.00 60.00 |
| ATOM | 415 | CG | GLU | 367 | 66.599 | 24.204 | 57.891 | 1.00 60.00 |
| ATOM | 416 | CD | GLU | 367 | 66.623 | 23.098 | 56.846 | 1.00 60.00 |
| ATOM | 417 | OE1 | GLU | 367 | 65.554 | 22.842 | 56.230 | 1.00 60.00 |
| ATOM | 418 | OE2 | GLU | 367 | 67.711 | 22.497 | 56.648 | 1.00 60.00 |
| ATOM | 419 | N | LEU | 368 | 65.692 | 27.870 | 57.631 | 1.00 40.00 |
| ATOM | 420 | CA | LEU | 368 | 66.639 | 28.826 | 57.149 | 1.00 40.00 |
| ATOM | 421 | C | LEU | 368 | 67.144 | 29.693 | 58.252 | 1.00 40.00 |

Figure 6A-36

| | | | | | | | | |
|---|---|---|---|---|---|---|---|---|
| ATOM | 422 | O | LEU | 368 | 69.335 | 29.999 | 58.289 | 1.00 40.00 |
| ATOM | 423 | CB | LEU | 368 | 66.064 | 29.752 | 56.062 | 1.00 40.00 |
| ATOM | 424 | CG | LEU | 368 | 65.883 | 29.062 | 54.699 | 1.00 40.00 |
| ATOM | 425 | CD1 | LEU | 368 | 64.978 | 27.828 | 54.805 | 1.00 40.00 |
| ATOM | 426 | CD2 | LEU | 368 | 65.403 | 30.061 | 53.635 | 1.00 40.00 |
| ATOM | 427 | N | ASP | 369 | 66.285 | 30.128 | 59.191 | 1.00 40.00 |
| ATOM | 428 | CA | ASP | 369 | 66.841 | 31.074 | 60.102 | 1.00 40.00 |
| ATOM | 429 | C | ASP | 369 | 66.613 | 30.516 | 61.452 | 1.00 40.00 |
| ATOM | 430 | O | ASP | 369 | 65.469 | 30.262 | 61.829 | 1.00 40.00 |
| ATOM | 431 | CB | ASP | 369 | 66.170 | 32.458 | 60.047 | 1.00 40.00 |
| ATOM | 432 | CG | ASP | 369 | 66.548 | 33.104 | 58.722 | 1.00 40.00 |
| ATOM | 433 | OD1 | ASP | 369 | 67.460 | 32.565 | 58.041 | 1.00 40.00 |
| ATOM | 434 | OD2 | ASP | 369 | 65.930 | 34.146 | 58.375 | 1.00 40.00 |
| ATOM | 435 | N | ILE | 370 | 67.712 | 30.280 | 62.196 | 1.00 40.00 |
| ATOM | 436 | CA | ILE | 370 | 67.553 | 29.772 | 63.520 | 1.00 40.00 |
| ATOM | 437 | C | ILE | 370 | 66.701 | 30.773 | 64.204 | 1.00 40.00 |
| ATOM | 438 | O | ILE | 370 | 65.566 | 30.470 | 64.562 | 1.00 40.00 |
| ATOM | 439 | CB | ILE | 370 | 68.847 | 29.669 | 64.271 | 1.00 40.00 |
| ATOM | 440 | CG1 | ILE | 370 | 69.762 | 28.617 | 63.621 | 1.00 40.00 |
| ATOM | 441 | CG2 | ILE | 370 | 68.511 | 29.380 | 65.741 | 1.00 40.00 |
| ATOM | 442 | CD1 | ILE | 370 | 70.227 | 28.988 | 62.213 | 1.00 40.00 |
| ATOM | 443 | N | LEU | 371 | 67.219 | 32.008 | 64.350 | 1.00 40.00 |
| ATOM | 444 | CA | LEU | 371 | 66.429 | 33.061 | 64.908 | 1.00 40.00 |
| ATOM | 445 | C | LEU | 371 | 67.159 | 34.349 | 64.879 | 1.00 40.00 |
| ATOM | 446 | O | LEU | 371 | 68.388 | 34.417 | 64.889 | 1.00 40.00 |
| ATOM | 447 | CB | LEU | 371 | 65.945 | 32.913 | 66.367 | 1.00 40.00 |
| ATOM | 448 | CG | LEU | 371 | 64.669 | 32.077 | 66.572 | 1.00 40.00 |
| ATOM | 449 | CD1 | LEU | 371 | 64.092 | 32.270 | 67.981 | 1.00 40.00 |
| ATOM | 450 | CD2 | LEU | 371 | 63.638 | 32.356 | 65.466 | 1.00 40.00 |
| ATOM | 451 | N | LYS | 372 | 66.340 | 35.410 | 64.862 | 1.00 40.00 |
| ATOM | 452 | CA | LYS | 372 | 66.715 | 36.782 | 64.924 | 1.00 40.00 |
| ATOM | 453 | C | LYS | 372 | 67.209 | 36.968 | 66.320 | 1.00 40.00 |
| ATOM | 454 | O | LYS | 372 | 67.897 | 37.934 | 66.640 | 1.00 40.00 |
| ATOM | 455 | CB | LYS | 372 | 65.504 | 37.709 | 64.728 | 1.00 40.00 |
| ATOM | 456 | CG | LYS | 372 | 64.697 | 37.378 | 63.470 | 1.00 40.00 |
| ATOM | 457 | CD | LYS | 372 | 65.522 | 37.345 | 62.182 | 1.00 40.00 |
| ATOM | 458 | CE | LYS | 372 | 64.722 | 36.862 | 60.970 | 1.00 40.00 |
| ATOM | 459 | NZ | LYS | 372 | 65.633 | 36.538 | 59.850 | 1.00 40.00 |
| ATOM | 460 | N | THR | 373 | 66.817 | 36.028 | 67.196 | 1.00 20.00 |
| ATOM | 461 | CA | THR | 373 | 67.096 | 36.060 | 68.601 | 1.00 20.00 |
| ATOM | 462 | C | THR | 373 | 68.570 | 36.057 | 68.880 | 1.00 20.00 |
| ATOM | 463 | O | THR | 373 | 68.998 | 36.664 | 69.859 | 1.00 20.00 |
| ATOM | 464 | CB | THR | 373 | 66.506 | 34.891 | 69.335 | 1.00 20.00 |
| ATOM | 465 | OG1 | THR | 373 | 66.624 | 35.085 | 70.737 | 1.00 20.00 |
| ATOM | 466 | CG2 | THR | 373 | 67.254 | 33.616 | 68.912 | 1.00 20.00 |
| ATOM | 467 | N | VAL | 374 | 69.395 | 35.381 | 68.054 | 1.00 20.00 |
| ATOM | 468 | CA | VAL | 374 | 70.787 | 35.278 | 68.409 | 1.00 20.00 |
| ATOM | 469 | C | VAL | 374 | 71.534 | 36.552 | 68.122 | 1.00 20.00 |
| ATOM | 470 | O | VAL | 374 | 71.901 | 36.845 | 66.984 | 1.00 20.00 |
| ATOM | 471 | CB | VAL | 374 | 71.482 | 34.137 | 67.722 | 1.00 20.00 |
| ATOM | 472 | CG1 | VAL | 374 | 70.891 | 32.822 | 68.257 | 1.00 20.00 |
| ATOM | 473 | CG2 | VAL | 374 | 71.308 | 34.292 | 66.201 | 1.00 20.00 |
| ATOM | 474 | N | LYS | 375 | 71.703 | 37.377 | 69.179 | 1.00 20.00 |
| ATOM | 475 | CA | LYS | 375 | 72.455 | 38.601 | 69.171 | 1.00 20.00 |
| ATOM | 476 | C | LYS | 375 | 73.934 | 38.356 | 69.276 | 1.00 20.00 |
| ATOM | 477 | O | LYS | 375 | 74.724 | 38.952 | 68.548 | 1.00 20.00 |
| ATOM | 478 | CB | LYS | 375 | 72.104 | 39.515 | 70.357 | 1.00 20.00 |
| ATOM | 479 | CG | LYS | 375 | 70.652 | 39.992 | 70.380 | 1.00 20.00 |
| ATOM | 480 | CD | LYS | 375 | 70.253 | 40.621 | 71.716 | 1.00 20.00 |
| ATOM | 481 | CE | LYS | 375 | 70.283 | 39.635 | 72.886 | 1.00 20.00 |
| ATOM | 482 | NZ | LYS | 375 | 70.032 | 40.347 | 74.158 | 1.00 20.00 |
| ATOM | 483 | N | GLU | 376 | 74.370 | 37.463 | 70.191 | 1.00 20.00 |
| ATOM | 484 | CA | GLU | 376 | 75.790 | 37.398 | 70.390 | 1.00 20.00 |
| ATOM | 485 | C | GLU | 376 | 76.248 | 36.006 | 70.665 | 1.00 20.00 |
| ATOM | 486 | O | GLU | 376 | 75.456 | 35.084 | 70.842 | 1.00 20.00 |
| ATOM | 487 | CB | GLU | 376 | 76.269 | 38.271 | 71.562 | 1.00 20.00 |
| ATOM | 488 | CG | GLU | 376 | 75.648 | 37.879 | 72.903 | 1.00 20.00 |
| ATOM | 489 | CD | GLU | 376 | 76.201 | 38.809 | 73.974 | 1.00 20.00 |
| ATOM | 490 | OE1 | GLU | 376 | 77.445 | 39.001 | 74.011 | 1.00 20.00 |
| ATOM | 491 | OE2 | GLU | 376 | 75.380 | 39.346 | 74.768 | 1.00 20.00 |
| ATOM | 492 | N | ILE | 377 | 77.586 | 35.845 | 70.643 | 1.00 20.00 |
| ATOM | 493 | CA | ILE | 377 | 78.258 | 34.625 | 70.961 | 1.00 20.00 |
| ATOM | 494 | C | ILE | 377 | 79.458 | 35.085 | 71.726 | 1.00 20.00 |
| ATOM | 495 | O | ILE | 377 | 80.208 | 35.939 | 71.258 | 1.00 20.00 |
| ATOM | 496 | CB | ILE | 377 | 78.729 | 33.891 | 69.741 | 1.00 20.00 |
| ATOM | 497 | CG1 | ILE | 377 | 77.532 | 33.564 | 68.831 | 1.00 20.00 |
| ATOM | 498 | CG2 | ILE | 377 | 79.513 | 32.649 | 70.196 | 1.00 20.00 |

Figure 6A-37

| | | | | | | | | |
|---|---|---|---|---|---|---|---|---|
| ATOM | 499 | CD1 | ILE | 377 | 77.935 | 33.095 | 67.437 | 1.00 20.00 |
| ATOM | 500 | N | THR | 378 | 79.661 | 34.537 | 72.932 | 1.00 20.00 |
| ATOM | 501 | CA | THR | 378 | 80.705 | 34.958 | 73.820 | 1.00 20.00 |
| ATOM | 502 | C | THR | 378 | 82.055 | 34.508 | 73.356 | 1.00 20.00 |
| ATOM | 503 | O | THR | 378 | 83.055 | 34.926 | 73.931 | 1.00 20.00 |
| ATOM | 504 | CB | THR | 378 | 80.542 | 34.462 | 75.221 | 1.00 20.00 |
| ATOM | 505 | OG1 | THR | 378 | 81.409 | 35.173 | 76.091 | 1.00 20.00 |
| ATOM | 506 | CG2 | THR | 378 | 80.913 | 32.976 | 75.242 | 1.00 20.00 |
| ATOM | 507 | N | GLY | 379 | 82.134 | 33.568 | 72.394 | 1.00 20.00 |
| ATOM | 508 | CA | GLY | 379 | 83.421 | 33.057 | 72.000 | 1.00 20.00 |
| ATOM | 509 | C | GLY | 379 | 83.656 | 33.297 | 70.540 | 1.00 20.00 |
| ATOM | 510 | O | GLY | 379 | 83.799 | 34.434 | 70.097 | 1.00 20.00 |
| ATOM | 511 | N | PHE | 380 | 83.754 | 32.204 | 69.755 | 1.00 20.00 |
| ATOM | 512 | CA | PHE | 380 | 83.990 | 32.339 | 68.346 | 1.00 20.00 |
| ATOM | 513 | C | PHE | 380 | 82.939 | 31.569 | 67.615 | 1.00 20.00 |
| ATOM | 514 | O | PHE | 380 | 82.209 | 30.782 | 68.214 | 1.00 20.00 |
| ATOM | 515 | CB | PHE | 380 | 85.380 | 31.855 | 67.885 | 1.00 20.00 |
| ATOM | 516 | CG | PHE | 380 | 85.531 | 30.395 | 68.158 | 1.00 20.00 |
| ATOM | 517 | CD1 | PHE | 380 | 85.154 | 29.462 | 67.218 | 1.00 20.00 |
| ATOM | 518 | CD2 | PHE | 380 | 86.057 | 29.961 | 69.352 | 1.00 20.00 |
| ATOM | 519 | CE1 | PHE | 380 | 85.298 | 28.117 | 67.467 | 1.00 20.00 |
| ATOM | 520 | CE2 | PHE | 380 | 86.203 | 28.617 | 69.604 | 1.00 20.00 |
| ATOM | 521 | CZ | PHE | 380 | 85.823 | 27.693 | 68.663 | 1.00 20.00 |
| ATOM | 522 | N | LEU | 381 | 82.806 | 31.821 | 66.294 | 1.00 20.00 |
| ATOM | 523 | CA | LEU | 381 | 81.819 | 31.147 | 65.497 | 1.00 20.00 |
| ATOM | 524 | C | LEU | 381 | 82.535 | 30.365 | 64.432 | 1.00 20.00 |
| ATOM | 525 | O | LEU | 381 | 83.324 | 30.913 | 63.665 | 1.00 20.00 |
| ATOM | 526 | CB | LEU | 381 | 80.845 | 32.133 | 64.819 | 1.00 20.00 |
| ATOM | 527 | CG | LEU | 381 | 79.760 | 31.487 | 63.942 | 1.00 20.00 |
| ATOM | 528 | CD1 | LEU | 381 | 78.861 | 30.553 | 64.762 | 1.00 20.00 |
| ATOM | 529 | CD2 | LEU | 381 | 78.952 | 32.558 | 63.189 | 1.00 20.00 |
| ATOM | 530 | N | LEU | 382 | 82.277 | 29.040 | 64.360 | 1.00 20.00 |
| ATOM | 531 | CA | LEU | 382 | 82.974 | 28.221 | 63.407 | 1.00 20.00 |
| ATOM | 532 | C | LEU | 382 | 81.989 | 27.496 | 62.539 | 1.00 20.00 |
| ATOM | 533 | O | LEU | 382 | 81.199 | 26.684 | 63.018 | 1.00 20.00 |
| ATOM | 534 | CB | LEU | 382 | 83.864 | 27.171 | 64.102 | 1.00 20.00 |
| ATOM | 535 | CG | LEU | 382 | 84.655 | 26.245 | 63.164 | 1.00 20.00 |
| ATOM | 536 | CD1 | LEU | 382 | 85.636 | 27.027 | 62.283 | 1.00 20.00 |
| ATOM | 537 | CD2 | LEU | 382 | 85.343 | 25.128 | 63.965 | 1.00 20.00 |
| ATOM | 538 | N | ILE | 383 | 82.013 | 27.781 | 61.220 | 1.00 20.00 |
| ATOM | 539 | CA | ILE | 383 | 81.137 | 27.094 | 60.316 | 1.00 20.00 |
| ATOM | 540 | C | ILE | 383 | 82.015 | 26.374 | 59.348 | 1.00 20.00 |
| ATOM | 541 | O | ILE | 383 | 82.648 | 26.989 | 58.493 | 1.00 20.00 |
| ATOM | 542 | CB | ILE | 383 | 80.282 | 28.016 | 59.500 | 1.00 20.00 |
| ATOM | 543 | CG1 | ILE | 383 | 79.404 | 28.888 | 60.409 | 1.00 20.00 |
| ATOM | 544 | CG2 | ILE | 383 | 79.482 | 27.156 | 58.505 | 1.00 20.00 |
| ATOM | 545 | CD1 | ILE | 383 | 78.460 | 28.082 | 61.296 | 1.00 20.00 |
| ATOM | 546 | N | GLN | 384 | 82.074 | 25.038 | 59.443 | 1.00 20.00 |
| ATOM | 547 | CA | GLN | 384 | 82.915 | 24.339 | 58.526 | 1.00 20.00 |
| ATOM | 548 | C | GLN | 384 | 82.054 | 23.458 | 57.685 | 1.00 20.00 |
| ATOM | 549 | O | GLN | 384 | 81.117 | 22.832 | 58.177 | 1.00 20.00 |
| ATOM | 550 | CB | GLN | 384 | 83.961 | 23.439 | 59.207 | 1.00 20.00 |
| ATOM | 551 | CG | GLN | 384 | 84.855 | 22.697 | 58.213 | 1.00 20.00 |
| ATOM | 552 | CD | GLN | 384 | 85.837 | 21.843 | 59.002 | 1.00 20.00 |
| ATOM | 553 | OE1 | GLN | 384 | 86.450 | 22.308 | 59.961 | 1.00 20.00 |
| ATOM | 554 | NE2 | GLN | 384 | 85.991 | 20.556 | 58.592 | 1.00 20.00 |
| ATOM | 555 | N | ALA | 385 | 82.371 | 23.410 | 56.375 | 1.00 20.00 |
| ATOM | 556 | CA | ALA | 385 | 81.706 | 22.591 | 55.398 | 1.00 20.00 |
| ATOM | 557 | C | ALA | 385 | 80.224 | 22.590 | 55.601 | 1.00 20.00 |
| ATOM | 558 | O | ALA | 385 | 79.661 | 21.620 | 56.106 | 1.00 20.00 |
| ATOM | 559 | CB | ALA | 385 | 82.195 | 21.134 | 55.384 | 1.00 20.00 |
| ATOM | 560 | N | TRP | 386 | 79.551 | 23.693 | 55.231 | 1.00 40.00 |
| ATOM | 561 | CA | TRP | 386 | 78.121 | 23.719 | 55.326 | 1.00 40.00 |
| ATOM | 562 | C | TRP | 386 | 77.603 | 23.977 | 53.951 | 1.00 40.00 |
| ATOM | 563 | O | TRP | 386 | 77.704 | 25.086 | 53.430 | 1.00 40.00 |
| ATOM | 564 | CB | TRP | 386 | 77.603 | 24.843 | 56.245 | 1.00 40.00 |
| ATOM | 565 | CG | TRP | 386 | 76.100 | 25.012 | 56.311 | 1.00 40.00 |
| ATOM | 566 | CD1 | TRP | 386 | 75.148 | 24.767 | 55.365 | 1.00 40.00 |
| ATOM | 567 | CD2 | TRP | 386 | 75.403 | 25.494 | 57.469 | 1.00 40.00 |
| ATOM | 568 | NE1 | TRP | 386 | 73.904 | 25.079 | 55.856 | 1.00 40.00 |
| ATOM | 569 | CE2 | TRP | 386 | 74.046 | 25.525 | 57.152 | 1.00 40.00 |
| ATOM | 570 | CE3 | TRP | 386 | 75.857 | 25.881 | 58.698 | 1.00 40.00 |
| ATOM | 571 | CZ2 | TRP | 386 | 73.118 | 25.943 | 58.063 | 1.00 40.00 |
| ATOM | 572 | CZ3 | TRP | 386 | 74.919 | 26.302 | 59.614 | 1.00 40.00 |
| ATOM | 573 | CH2 | TRP | 386 | 73.575 | 26.332 | 59.302 | 1.00 40.00 |
| ATOM | 574 | N | PRO | 387 | 77.111 | 22.950 | 53.320 | 1.00 40.00 |
| ATOM | 575 | CA | PRO | 387 | 76.494 | 23.181 | 52.046 | 1.00 40.00 |

Figure 6A-38

| | | | | | | | | |
|---|---|---|---|---|---|---|---|---|
| ATOM | 576 | C | PRO | 387 | 75.195 | 23.656 | 52.308 | 1.00 40.00 |
| ATOM | 577 | O | PRO | 387 | 74.483 | 23.158 | 53.248 | 1.00 40.00 |
| ATOM | 578 | CB | PRO | 387 | 76.548 | 21.853 | 51.296 | 1.00 40.00 |
| ATOM | 579 | CG | PRO | 387 | 77.766 | 21.143 | 51.909 | 1.00 40.00 |
| ATOM | 580 | CD | PRO | 387 | 77.837 | 21.690 | 53.344 | 1.00 40.00 |
| ATOM | 581 | N | GLU | 388 | 74.578 | 24.599 | 51.507 | 1.00 60.00 |
| ATOM | 582 | CA | GLU | 388 | 73.232 | 25.004 | 51.769 | 1.00 60.00 |
| ATOM | 583 | C | GLU | 388 | 72.859 | 26.053 | 50.778 | 1.00 60.00 |
| ATOM | 584 | O | GLU | 388 | 73.128 | 27.236 | 50.973 | 1.00 60.00 |
| ATOM | 585 | CB | GLU | 388 | 73.036 | 25.606 | 53.170 | 1.00 60.00 |
| ATOM | 586 | CG | GLU | 388 | 71.562 | 25.867 | 53.513 | 1.00 60.00 |
| ATOM | 587 | CD | GLU | 388 | 70.889 | 24.525 | 53.757 | 1.00 60.00 |
| ATOM | 588 | OE1 | GLU | 388 | 71.564 | 23.618 | 54.314 | 1.00 60.00 |
| ATOM | 589 | OE2 | GLU | 388 | 69.693 | 24.388 | 53.386 | 1.00 60.00 |
| ATOM | 590 | N | ASN | 389 | 72.238 | 25.631 | 49.664 | 1.00 60.00 |
| ATOM | 591 | CA | ASN | 389 | 71.795 | 26.572 | 48.685 | 1.00 60.00 |
| ATOM | 592 | C | ASN | 389 | 70.669 | 27.338 | 49.296 | 1.00 60.00 |
| ATOM | 593 | O | ASN | 389 | 70.529 | 28.543 | 49.090 | 1.00 60.00 |
| ATOM | 594 | CB | ASN | 389 | 71.262 | 25.904 | 47.407 | 1.00 60.00 |
| ATOM | 595 | CG | ASN | 389 | 72.438 | 25.279 | 46.670 | 1.00 60.00 |
| ATOM | 596 | OD1 | ASN | 389 | 73.467 | 25.921 | 46.464 | 1.00 60.00 |
| ATOM | 597 | ND2 | ASN | 389 | 72.287 | 23.990 | 46.266 | 1.00 60.00 |
| ATOM | 598 | N | ARG | 390 | 69.832 | 26.632 | 50.079 | 1.00 60.00 |
| ATOM | 599 | CA | ARG | 390 | 68.661 | 27.215 | 50.663 | 1.00 60.00 |
| ATOM | 600 | C | ARG | 390 | 69.044 | 28.334 | 51.576 | 1.00 60.00 |
| ATOM | 601 | O | ARG | 390 | 68.487 | 29.427 | 51.481 | 1.00 60.00 |
| ATOM | 602 | CB | ARG | 390 | 67.859 | 26.203 | 51.500 | 1.00 60.00 |
| ATOM | 603 | CG | ARG | 390 | 67.276 | 25.053 | 50.678 | 1.00 60.00 |
| ATOM | 604 | CD | ARG | 390 | 66.479 | 24.044 | 51.508 | 1.00 60.00 |
| ATOM | 605 | NE | ARG | 390 | 65.180 | 24.678 | 51.872 | 1.00 60.00 |
| ATOM | 606 | CZ | ARG | 390 | 64.189 | 23.927 | 52.437 | 1.00 60.00 |
| ATOM | 607 | NH1 | ARG | 390 | 64.394 | 22.599 | 52.678 | 1.00 60.00 |
| ATOM | 608 | NH2 | ARG | 390 | 62.995 | 24.504 | 52.761 | 1.00 60.00 |
| ATOM | 609 | N | THR | 391 | 70.013 | 28.112 | 52.482 | 1.00 60.00 |
| ATOM | 610 | CA | THR | 391 | 70.321 | 29.182 | 53.385 | 1.00 60.00 |
| ATOM | 611 | C | THR | 391 | 71.800 | 29.287 | 53.543 | 1.00 60.00 |
| ATOM | 612 | O | THR | 391 | 72.554 | 28.398 | 53.154 | 1.00 60.00 |
| ATOM | 613 | CB | THR | 391 | 69.738 | 29.001 | 54.755 | 1.00 60.00 |
| ATOM | 614 | OG1 | THR | 391 | 69.919 | 30.181 | 55.524 | 1.00 60.00 |
| ATOM | 615 | CG2 | THR | 391 | 70.431 | 27.808 | 55.437 | 1.00 60.00 |
| ATOM | 616 | N | ASP | 392 | 72.250 | 30.418 | 54.118 | 1.00 60.00 |
| ATOM | 617 | CA | ASP | 392 | 73.648 | 30.631 | 54.330 | 1.00 60.00 |
| ATOM | 618 | C | ASP | 392 | 73.787 | 31.156 | 55.719 | 1.00 60.00 |
| ATOM | 619 | O | ASP | 392 | 73.183 | 30.646 | 56.662 | 1.00 60.00 |
| ATOM | 620 | CB | ASP | 392 | 74.243 | 31.706 | 53.404 | 1.00 60.00 |
| ATOM | 621 | CG | ASP | 392 | 74.233 | 31.177 | 51.977 | 1.00 60.00 |
| ATOM | 622 | OD1 | ASP | 392 | 74.199 | 29.930 | 51.808 | 1.00 60.00 |
| ATOM | 623 | OD2 | ASP | 392 | 74.257 | 32.017 | 51.038 | 1.00 60.00 |
| ATOM | 624 | N | LEU | 393 | 74.608 | 32.211 | 55.857 | 1.00 40.00 |
| ATOM | 625 | CA | LEU | 393 | 74.836 | 32.877 | 57.102 | 1.00 40.00 |
| ATOM | 626 | C | LEU | 393 | 73.560 | 33.562 | 57.449 | 1.00 40.00 |
| ATOM | 627 | O | LEU | 393 | 73.360 | 33.992 | 58.584 | 1.00 40.00 |
| ATOM | 628 | CB | LEU | 393 | 75.983 | 33.887 | 57.086 | 1.00 40.00 |
| ATOM | 629 | CG | LEU | 393 | 77.357 | 33.257 | 56.797 | 1.00 40.00 |
| ATOM | 630 | CD1 | LEU | 393 | 77.402 | 32.639 | 55.390 | 1.00 40.00 |
| ATOM | 631 | CD2 | LEU | 393 | 78.494 | 34.263 | 57.041 | 1.00 40.00 |
| ATOM | 632 | N | HIS | 394 | 72.640 | 33.649 | 56.465 | 1.00 40.00 |
| ATOM | 633 | CA | HIS | 394 | 71.336 | 34.221 | 56.682 | 1.00 40.00 |
| ATOM | 634 | C | HIS | 394 | 70.664 | 33.594 | 57.865 | 1.00 40.00 |
| ATOM | 635 | O | HIS | 394 | 69.672 | 34.124 | 58.366 | 1.00 40.00 |
| ATOM | 636 | CB | HIS | 394 | 70.393 | 34.073 | 55.475 | 1.00 40.00 |
| ATOM | 637 | CG | HIS | 394 | 70.691 | 35.047 | 54.373 | 1.00 40.00 |
| ATOM | 638 | ND1 | HIS | 394 | 70.133 | 36.304 | 54.295 | 1.00 40.00 |
| ATOM | 639 | CD2 | HIS | 394 | 71.506 | 34.935 | 53.289 | 1.00 40.00 |
| ATOM | 640 | CE1 | HIS | 394 | 70.635 | 36.887 | 53.177 | 1.00 40.00 |
| ATOM | 641 | NE2 | HIS | 394 | 71.473 | 36.094 | 52.534 | 1.00 40.00 |
| ATOM | 642 | N | ALA | 395 | 71.155 | 32.439 | 58.340 | 1.00 20.00 |
| ATOM | 643 | CA | ALA | 395 | 70.542 | 31.844 | 59.484 | 1.00 20.00 |
| ATOM | 644 | C | ALA | 395 | 70.580 | 32.834 | 60.613 | 1.00 20.00 |
| ATOM | 645 | O | ALA | 395 | 69.605 | 32.955 | 61.356 | 1.00 20.00 |
| ATOM | 646 | CB | ALA | 395 | 71.272 | 30.573 | 59.954 | 1.00 20.00 |
| ATOM | 647 | N | PHE | 396 | 71.698 | 33.575 | 60.788 | 1.00 20.00 |
| ATOM | 648 | CA | PHE | 396 | 71.740 | 34.491 | 61.898 | 1.00 20.00 |
| ATOM | 649 | C | PHE | 396 | 71.749 | 35.899 | 61.382 | 1.00 20.00 |
| ATOM | 650 | O | PHE | 396 | 72.802 | 36.531 | 61.312 | 1.00 20.00 |
| ATOM | 651 | CB | PHE | 396 | 73.029 | 34.358 | 62.727 | 1.00 20.00 |
| ATOM | 652 | CG | PHE | 396 | 73.183 | 32.935 | 63.142 | 1.00 20.00 |

Figure 6A-39

| | | | | | | | | |
|---|---|---|---|---|---|---|---|---|
| ATOM | 653 | CD1 | PHE | 396 | 72.612 | 32.450 | 64.300 | 1.00 20.00 |
| ATOM | 654 | CD2 | PHE | 396 | 73.905 | 32.065 | 62.358 | 1.00 20.00 |
| ATOM | 655 | CE1 | PHE | 396 | 72.762 | 31.145 | 64.670 | 1.00 20.00 |
| ATOM | 656 | CE2 | PHE | 396 | 74.060 | 30.747 | 62.720 | 1.00 20.00 |
| ATOM | 657 | CZ | PHE | 396 | 73.487 | 30.285 | 63.881 | 1.00 20.00 |
| ATOM | 658 | N | GLU | 397 | 70.573 | 36.462 | 61.049 | 1.00 20.00 |
| ATOM | 659 | CA | GLU | 397 | 70.594 | 37.795 | 60.516 | 1.00 20.00 |
| ATOM | 660 | C | GLU | 397 | 70.975 | 38.794 | 61.582 | 1.00 20.00 |
| ATOM | 661 | O | GLU | 397 | 71.603 | 39.794 | 61.287 | 1.00 20.00 |
| ATOM | 662 | CB | GLU | 397 | 69.278 | 38.264 | 59.887 | 1.00 20.00 |
| ATOM | 663 | CG | GLU | 397 | 68.147 | 38.537 | 60.877 | 1.00 20.00 |
| ATOM | 664 | CD | GLU | 397 | 67.181 | 39.513 | 60.218 | 1.00 20.00 |
| ATOM | 665 | OE1 | GLU | 397 | 66.395 | 39.079 | 59.337 | 1.00 20.00 |
| ATOM | 666 | OE2 | GLU | 397 | 67.230 | 40.716 | 60.587 | 1.00 20.00 |
| ATOM | 667 | N | ASN | 398 | 70.554 | 38.545 | 62.837 | 1.00 20.00 |
| ATOM | 668 | CA | ASN | 398 | 70.744 | 39.439 | 63.953 | 1.00 20.00 |
| ATOM | 669 | C | ASN | 398 | 72.098 | 39.433 | 64.607 | 1.00 20.00 |
| ATOM | 670 | O | ASN | 398 | 72.390 | 40.373 | 65.344 | 1.00 20.00 |
| ATOM | 671 | CB | ASN | 398 | 69.706 | 39.249 | 65.061 | 1.00 20.00 |
| ATOM | 672 | CG | ASN | 398 | 68.421 | 39.874 | 64.550 | 1.00 20.00 |
| ATOM | 673 | OD1 | ASN | 398 | 68.058 | 40.988 | 64.927 | 1.00 20.00 |
| ATOM | 674 | ND2 | ASN | 398 | 67.725 | 39.151 | 63.637 | 1.00 20.00 |
| ATOM | 675 | N | LEU | 399 | 72.927 | 38.382 | 64.425 | 1.00 20.00 |
| ATOM | 676 | CA | LEU | 399 | 74.176 | 38.231 | 65.142 | 1.00 20.00 |
| ATOM | 677 | C | LEU | 399 | 74.964 | 39.516 | 65.126 | 1.00 20.00 |
| ATOM | 678 | O | LEU | 399 | 75.513 | 39.904 | 64.095 | 1.00 20.00 |
| ATOM | 679 | CB | LEU | 399 | 75.056 | 37.121 | 64.540 | 1.00 20.00 |
| ATOM | 680 | CG | LEU | 399 | 76.401 | 36.912 | 65.257 | 1.00 20.00 |
| ATOM | 681 | CD1 | LEU | 399 | 76.193 | 36.416 | 66.702 | 1.00 20.00 |
| ATOM | 682 | CD2 | LEU | 399 | 77.320 | 35.989 | 64.438 | 1.00 20.00 |
| ATOM | 683 | N | GLU | 400 | 74.935 | 40.242 | 66.273 | 1.00 20.00 |
| ATOM | 684 | CA | GLU | 400 | 75.597 | 41.501 | 66.503 | 1.00 20.00 |
| ATOM | 685 | C | GLU | 400 | 77.060 | 41.434 | 66.883 | 1.00 20.00 |
| ATOM | 686 | O | GLU | 400 | 77.869 | 42.168 | 66.319 | 1.00 20.00 |
| ATOM | 687 | CB | GLU | 400 | 74.861 | 42.348 | 67.559 | 1.00 20.00 |
| ATOM | 688 | CG | GLU | 400 | 74.722 | 41.671 | 68.923 | 1.00 20.00 |
| ATOM | 689 | CD | GLU | 400 | 73.765 | 42.509 | 69.759 | 1.00 20.00 |
| ATOM | 690 | OE1 | GLU | 400 | 72.878 | 43.169 | 69.156 | 1.00 20.00 |
| ATOM | 691 | OE2 | GLU | 400 | 73.906 | 42.499 | 71.011 | 1.00 20.00 |
| ATOM | 692 | N | ILE | 401 | 77.466 | 40.569 | 67.842 | 1.00 20.00 |
| ATOM | 693 | CA | ILE | 401 | 78.841 | 40.653 | 68.276 | 1.00 20.00 |
| ATOM | 694 | C | ILE | 401 | 79.358 | 39.294 | 68.644 | 1.00 20.00 |
| ATOM | 695 | O | ILE | 401 | 78.609 | 38.434 | 69.104 | 1.00 20.00 |
| ATOM | 696 | CB | ILE | 401 | 79.008 | 41.515 | 69.498 | 1.00 20.00 |
| ATOM | 697 | CG1 | ILE | 401 | 78.513 | 42.946 | 69.227 | 1.00 20.00 |
| ATOM | 698 | CG2 | ILE | 401 | 80.479 | 41.456 | 69.940 | 1.00 20.00 |
| ATOM | 699 | CD1 | ILE | 401 | 78.378 | 43.788 | 70.495 | 1.00 20.00 |
| ATOM | 700 | N | ILE | 402 | 80.677 | 39.078 | 68.431 | 1.00 20.00 |
| ATOM | 701 | CA | ILE | 402 | 81.346 | 37.859 | 68.793 | 1.00 20.00 |
| ATOM | 702 | C | ILE | 402 | 82.483 | 38.282 | 69.677 | 1.00 20.00 |
| ATOM | 703 | O | ILE | 402 | 83.526 | 38.710 | 69.195 | 1.00 20.00 |
| ATOM | 704 | CB | ILE | 402 | 81.934 | 37.164 | 67.596 | 1.00 20.00 |
| ATOM | 705 | CG1 | ILE | 402 | 80.828 | 36.793 | 66.594 | 1.00 20.00 |
| ATOM | 706 | CG2 | ILE | 402 | 82.752 | 35.959 | 68.080 | 1.00 20.00 |
| ATOM | 707 | CD1 | ILE | 402 | 81.361 | 36.374 | 65.225 | 1.00 20.00 |
| ATOM | 708 | N | ARG | 403 | 82.340 | 38.091 | 71.000 | 1.00 20.00 |
| ATOM | 709 | CA | ARG | 403 | 83.248 | 38.630 | 71.978 | 1.00 20.00 |
| ATOM | 710 | C | ARG | 403 | 84.656 | 38.156 | 71.775 | 1.00 20.00 |
| ATOM | 711 | O | ARG | 403 | 85.595 | 38.916 | 72.000 | 1.00 20.00 |
| ATOM | 712 | CB | ARG | 403 | 82.835 | 38.270 | 73.414 | 1.00 20.00 |
| ATOM | 713 | CG | ARG | 403 | 81.404 | 38.709 | 73.735 | 1.00 20.00 |
| ATOM | 714 | CD | ARG | 403 | 81.024 | 38.588 | 75.212 | 1.00 20.00 |
| ATOM | 715 | NE | ARG | 403 | 80.986 | 39.968 | 75.776 | 1.00 20.00 |
| ATOM | 716 | CZ | ARG | 403 | 82.100 | 40.523 | 76.334 | 1.00 20.00 |
| ATOM | 717 | NH1 | ARG | 403 | 83.264 | 39.812 | 76.393 | 1.00 20.00 |
| ATOM | 718 | NH2 | ARG | 403 | 82.049 | 41.791 | 76.836 | 1.00 20.00 |
| ATOM | 719 | N | GLY | 404 | 84.866 | 36.889 | 71.383 | 1.00 20.00 |
| ATOM | 720 | CA | GLY | 404 | 86.209 | 36.427 | 71.177 | 1.00 20.00 |
| ATOM | 721 | C | GLY | 404 | 86.879 | 36.183 | 72.495 | 1.00 20.00 |
| ATOM | 722 | O | GLY | 404 | 88.106 | 36.208 | 72.584 | 1.00 20.00 |
| ATOM | 723 | N | ARG | 405 | 86.099 | 35.916 | 73.559 | 1.00 20.00 |
| ATOM | 724 | CA | ARG | 405 | 86.700 | 35.672 | 74.839 | 1.00 20.00 |
| ATOM | 725 | C | ARG | 405 | 87.611 | 34.502 | 74.670 | 1.00 20.00 |
| ATOM | 726 | O | ARG | 405 | 88.728 | 34.489 | 75.184 | 1.00 20.00 |
| ATOM | 727 | CB | ARG | 405 | 85.674 | 35.303 | 75.925 | 1.00 20.00 |
| ATOM | 728 | CG | ARG | 405 | 84.794 | 36.474 | 76.364 | 1.00 20.00 |
| ATOM | 729 | CD | ARG | 405 | 85.274 | 37.144 | 77.654 | 1.00 20.00 |

Figure 6A-40

| | | | | | | | | |
|---|---|---|---|---|---|---|---|---|
| ATOM | 730 | HE | ARG | 405 | 86.553 | 37.843 | 77.350 | 1.00 20.00 |
| ATOM | 731 | CZ | ARG | 405 | 87.191 | 38.551 | 78.326 | 1.00 20.00 |
| ATOM | 732 | NH1 | ARG | 405 | 86.659 | 38.613 | 79.582 | 1.00 20.00 |
| ATOM | 733 | NH2 | ARG | 405 | 88.362 | 39.196 | 78.049 | 1.00 20.00 |
| ATOM | 734 | N | THR | 406 | 87.144 | 33.483 | 73.930 | 1.00 20.00 |
| ATOM | 735 | CA | THR | 406 | 87.965 | 32.345 | 73.649 | 1.00 20.00 |
| ATOM | 736 | C | THR | 406 | 88.001 | 32.248 | 72.162 | 1.00 20.00 |
| ATOM | 737 | O | THR | 406 | 86.972 | 32.378 | 71.504 | 1.00 20.00 |
| ATOM | 738 | CB | THR | 406 | 87.399 | 31.054 | 74.160 | 1.00 20.00 |
| ATOM | 739 | OG1 | THR | 406 | 87.233 | 31.114 | 75.569 | 1.00 20.00 |
| ATOM | 740 | CG2 | THR | 406 | 88.359 | 29.913 | 73.786 | 1.00 20.00 |
| ATOM | 741 | N | LYS | 407 | 89.193 | 32.019 | 71.586 | 1.00 20.00 |
| ATOM | 742 | CA | LYS | 407 | 89.261 | 31.979 | 70.157 | 1.00 20.00 |
| ATOM | 743 | C | LYS | 407 | 89.797 | 30.645 | 69.747 | 1.00 20.00 |
| ATOM | 744 | O | LYS | 407 | 90.399 | 29.926 | 70.543 | 1.00 20.00 |
| ATOM | 745 | CB | LYS | 407 | 90.238 | 33.037 | 69.581 | 1.00 20.00 |
| ATOM | 746 | CG | LYS | 407 | 91.679 | 32.884 | 70.077 | 1.00 20.00 |
| ATOM | 747 | CD | LYS | 407 | 91.825 | 33.046 | 71.593 | 1.00 20.00 |
| ATOM | 748 | CE | LYS | 407 | 93.248 | 32.835 | 72.110 | 1.00 20.00 |
| ATOM | 749 | NZ | LYS | 407 | 93.280 | 33.013 | 73.580 | 1.00 20.00 |
| ATOM | 750 | N | GLN | 408 | 89.538 | 30.258 | 68.481 | 1.00 20.00 |
| ATOM | 751 | CA | GLN | 408 | 90.096 | 29.017 | 68.051 | 1.00 20.00 |
| ATOM | 752 | C | GLN | 408 | 91.483 | 29.349 | 67.630 | 1.00 20.00 |
| ATOM | 753 | O | GLN | 408 | 91.763 | 30.501 | 67.296 | 1.00 20.00 |
| ATOM | 754 | CB | GLN | 408 | 89.396 | 28.341 | 66.863 | 1.00 20.00 |
| ATOM | 755 | CG | GLN | 408 | 89.499 | 29.103 | 65.547 | 1.00 20.00 |
| ATOM | 756 | CD | GLN | 408 | 89.073 | 28.124 | 64.465 | 1.00 20.00 |
| ATOM | 757 | OE1 | GLN | 408 | 88.607 | 28.513 | 63.398 | 1.00 20.00 |
| ATOM | 758 | NE2 | GLN | 408 | 89.245 | 26.805 | 64.747 | 1.00 20.00 |
| ATOM | 759 | N | HIS | 409 | 92.375 | 28.340 | 67.629 | 1.00 20.00 |
| ATOM | 760 | CA | HIS | 409 | 93.764 | 28.549 | 67.341 | 1.00 20.00 |
| ATOM | 761 | C | HIS | 409 | 93.872 | 29.295 | 66.062 | 1.00 20.00 |
| ATOM | 762 | O | HIS | 409 | 93.018 | 29.181 | 65.186 | 1.00 20.00 |
| ATOM | 763 | CB | HIS | 409 | 94.579 | 27.249 | 67.237 | 1.00 20.00 |
| ATOM | 764 | CG | HIS | 409 | 94.658 | 26.518 | 68.547 | 1.00 20.00 |
| ATOM | 765 | ND1 | HIS | 409 | 93.716 | 25.615 | 68.986 | 1.00 20.00 |
| ATOM | 766 | CD2 | HIS | 409 | 95.598 | 26.582 | 69.531 | 1.00 20.00 |
| ATOM | 767 | CE1 | HIS | 409 | 94.127 | 25.180 | 70.204 | 1.00 20.00 |
| ATOM | 768 | NE2 | HIS | 409 | 95.263 | 25.739 | 70.577 | 1.00 20.00 |
| ATOM | 769 | N | GLY | 410 | 94.929 | 30.113 | 65.945 | 1.00 20.00 |
| ATOM | 770 | CA | GLY | 410 | 95.035 | 30.978 | 64.815 | 1.00 20.00 |
| ATOM | 771 | C | GLY | 410 | 94.356 | 32.221 | 65.273 | 1.00 20.00 |
| ATOM | 772 | O | GLY | 410 | 94.314 | 33.233 | 64.575 | 1.00 20.00 |
| ATOM | 773 | N | GLN | 411 | 93.822 | 32.149 | 66.508 | 1.00 20.00 |
| ATOM | 774 | CA | GLN | 411 | 93.134 | 33.238 | 67.131 | 1.00 20.00 |
| ATOM | 775 | C | GLN | 411 | 92.065 | 33.728 | 66.212 | 1.00 20.00 |
| ATOM | 776 | O | GLN | 411 | 92.036 | 34.909 | 65.870 | 1.00 20.00 |
| ATOM | 777 | CB | GLN | 411 | 94.060 | 34.416 | 67.478 | 1.00 20.00 |
| ATOM | 778 | CG | GLN | 411 | 95.138 | 34.061 | 68.503 | 1.00 20.00 |
| ATOM | 779 | CD | GLN | 411 | 95.978 | 35.307 | 68.753 | 1.00 20.00 |
| ATOM | 780 | OE1 | GLN | 411 | 96.291 | 35.640 | 69.895 | 1.00 20.00 |
| ATOM | 781 | NE2 | GLN | 411 | 96.362 | 36.010 | 67.656 | 1.00 20.00 |
| ATOM | 782 | N | PHE | 412 | 91.150 | 32.832 | 65.791 | 1.00 20.00 |
| ATOM | 783 | CA | PHE | 412 | 90.107 | 33.253 | 64.904 | 1.00 20.00 |
| ATOM | 784 | C | PHE | 412 | 88.828 | 33.358 | 65.669 | 1.00 20.00 |
| ATOM | 785 | O | PHE | 412 | 88.440 | 32.453 | 66.404 | 1.00 20.00 |
| ATOM | 786 | CB | PHE | 412 | 89.843 | 32.287 | 63.737 | 1.00 20.00 |
| ATOM | 787 | CG | PHE | 412 | 91.064 | 32.280 | 62.885 | 1.00 20.00 |
| ATOM | 788 | CD1 | PHE | 412 | 91.356 | 33.347 | 62.070 | 1.00 20.00 |
| ATOM | 789 | CD2 | PHE | 412 | 91.911 | 31.197 | 62.892 | 1.00 20.00 |
| ATOM | 790 | CE1 | PHE | 412 | 92.482 | 33.338 | 61.279 | 1.00 20.00 |
| ATOM | 791 | CE2 | PHE | 412 | 93.037 | 31.184 | 62.103 | 1.00 20.00 |
| ATOM | 792 | CZ | PHE | 412 | 93.326 | 32.256 | 61.296 | 1.00 20.00 |
| ATOM | 793 | N | SER | 413 | 88.193 | 34.538 | 65.568 | 1.00 20.00 |
| ATOM | 794 | CA | SER | 413 | 86.914 | 34.839 | 66.139 | 1.00 20.00 |
| ATOM | 795 | C | SER | 413 | 85.866 | 34.220 | 65.282 | 1.00 20.00 |
| ATOM | 796 | O | SER | 413 | 84.871 | 33.694 | 65.779 | 1.00 20.00 |
| ATOM | 797 | CB | SER | 413 | 86.618 | 36.342 | 66.092 | 1.00 20.00 |
| ATOM | 798 | OG | SER | 413 | 87.743 | 37.068 | 66.556 | 1.00 20.00 |
| ATOM | 799 | N | LEU | 414 | 86.058 | 34.318 | 63.953 | 1.00 20.00 |
| ATOM | 800 | CA | LEU | 414 | 85.098 | 33.828 | 63.009 | 1.00 20.00 |
| ATOM | 801 | C | LEU | 414 | 85.822 | 33.010 | 61.998 | 1.00 20.00 |
| ATOM | 802 | O | LEU | 414 | 86.615 | 33.527 | 61.212 | 1.00 20.00 |
| ATOM | 803 | CB | LEU | 414 | 84.395 | 34.969 | 62.249 | 1.00 20.00 |
| ATOM | 804 | CG | LEU | 414 | 83.351 | 34.505 | 61.219 | 1.00 20.00 |
| ATOM | 805 | CD1 | LEU | 414 | 82.172 | 33.785 | 61.890 | 1.00 20.00 |
| ATOM | 806 | CD2 | LEU | 414 | 82.913 | 35.673 | 60.318 | 1.00 20.00 |

Figure 6A-41

| ATOM | 807 | N | ALA | 415 | 85.568 | 31.694 | 61.983 | 1.00 | 20.00 |
|------|-----|-----|-----|-----|--------|--------|--------|------|-------|
| ATOM | 808 | CA | ALA | 415 | 86.220 | 30.917 | 60.979 | 1.00 | 20.00 |
| ATOM | 809 | C | ALA | 415 | 85.159 | 30.337 | 60.115 | 1.00 | 20.00 |
| ATOM | 810 | O | ALA | 415 | 84.230 | 29.704 | 60.610 | 1.00 | 20.00 |
| ATOM | 811 | CB | ALA | 415 | 87.039 | 29.744 | 61.526 | 1.00 | 20.00 |
| ATOM | 812 | N | VAL | 416 | 85.251 | 30.584 | 58.794 | 1.00 | 20.00 |
| ATOM | 813 | CA | VAL | 416 | 84.332 | 29.982 | 57.878 | 1.00 | 20.00 |
| ATOM | 814 | C | VAL | 416 | 85.159 | 29.237 | 56.878 | 1.00 | 20.00 |
| ATOM | 815 | O | VAL | 416 | 85.846 | 29.824 | 56.045 | 1.00 | 20.00 |
| ATOM | 816 | CB | VAL | 416 | 83.440 | 30.973 | 57.174 | 1.00 | 20.00 |
| ATOM | 817 | CG1 | VAL | 416 | 82.494 | 31.577 | 58.227 | 1.00 | 20.00 |
| ATOM | 818 | CG2 | VAL | 416 | 84.296 | 32.038 | 56.465 | 1.00 | 20.00 |
| ATOM | 819 | N | VAL | 417 | 85.121 | 27.894 | 56.935 | 1.00 | 20.00 |
| ATOM | 820 | CA | VAL | 417 | 85.951 | 27.162 | 56.027 | 1.00 | 20.00 |
| ATOM | 821 | C | VAL | 417 | 85.085 | 26.285 | 55.183 | 1.00 | 20.00 |
| ATOM | 822 | O | VAL | 417 | 84.125 | 25.692 | 55.673 | 1.00 | 20.00 |
| ATOM | 823 | CB | VAL | 417 | 86.949 | 26.276 | 56.717 | 1.00 | 20.00 |
| ATOM | 824 | CG1 | VAL | 417 | 87.911 | 27.163 | 57.525 | 1.00 | 20.00 |
| ATOM | 825 | CG2 | VAL | 417 | 86.189 | 25.247 | 57.571 | 1.00 | 20.00 |
| ATOM | 826 | N | SER | 418 | 85.433 | 26.185 | 53.881 | 1.00 | 20.00 |
| ATOM | 827 | CA | SER | 418 | 84.746 | 25.369 | 52.915 | 1.00 | 20.00 |
| ATOM | 828 | C | SER | 418 | 83.262 | 25.480 | 53.085 | 1.00 | 20.00 |
| ATOM | 829 | O | SER | 418 | 82.659 | 24.722 | 53.844 | 1.00 | 20.00 |
| ATOM | 830 | CB | SER | 418 | 85.129 | 23.878 | 52.994 | 1.00 | 20.00 |
| ATOM | 831 | OG | SER | 418 | 86.506 | 23.711 | 52.690 | 1.00 | 20.00 |
| ATOM | 832 | N | LEU | 419 | 82.626 | 26.440 | 52.377 | 1.00 | 40.00 |
| ATOM | 833 | CA | LEU | 419 | 81.198 | 26.607 | 52.499 | 1.00 | 40.00 |
| ATOM | 834 | C | LEU | 419 | 80.599 | 26.821 | 51.129 | 1.00 | 40.00 |
| ATOM | 835 | O | LEU | 419 | 81.324 | 26.980 | 50.149 | 1.00 | 40.00 |
| ATOM | 836 | CB | LEU | 419 | 80.813 | 27.822 | 53.355 | 1.00 | 40.00 |
| ATOM | 837 | CG | LEU | 419 | 81.278 | 27.699 | 54.818 | 1.00 | 40.00 |
| ATOM | 838 | CD1 | LEU | 419 | 80.866 | 28.927 | 55.644 | 1.00 | 40.00 |
| ATOM | 839 | CD2 | LEU | 419 | 80.810 | 26.376 | 55.444 | 1.00 | 40.00 |
| ATOM | 840 | N | ASN | 420 | 79.246 | 26.799 | 51.015 | 1.00 | 40.00 |
| ATOM | 841 | CA | ASN | 420 | 78.582 | 27.032 | 49.755 | 1.00 | 40.00 |
| ATOM | 842 | C | ASN | 420 | 77.866 | 28.337 | 49.879 | 1.00 | 40.00 |
| ATOM | 843 | O | ASN | 420 | 76.665 | 28.429 | 49.637 | 1.00 | 40.00 |
| ATOM | 844 | CB | ASN | 420 | 77.537 | 25.962 | 49.404 | 1.00 | 40.00 |
| ATOM | 845 | CG | ASN | 420 | 78.284 | 24.676 | 49.081 | 1.00 | 40.00 |
| ATOM | 846 | OD1 | ASN | 420 | 77.826 | 23.580 | 49.398 | 1.00 | 40.00 |
| ATOM | 847 | ND2 | ASN | 420 | 79.471 | 24.810 | 48.432 | 1.00 | 40.00 |
| ATOM | 848 | N | ILE | 421 | 78.599 | 29.408 | 50.228 | 1.00 | 40.00 |
| ATOM | 849 | CA | ILE | 421 | 77.930 | 30.654 | 50.448 | 1.00 | 40.00 |
| ATOM | 850 | C | ILE | 421 | 78.329 | 31.647 | 49.411 | 1.00 | 40.00 |
| ATOM | 851 | O | ILE | 421 | 79.478 | 31.695 | 48.975 | 1.00 | 40.00 |
| ATOM | 852 | CB | ILE | 421 | 78.234 | 31.277 | 51.781 | 1.00 | 40.00 |
| ATOM | 853 | CG1 | ILE | 421 | 79.727 | 31.638 | 51.901 | 1.00 | 40.00 |
| ATOM | 854 | CG2 | ILE | 421 | 77.741 | 30.314 | 52.872 | 1.00 | 40.00 |
| ATOM | 855 | CD1 | ILE | 421 | 80.670 | 30.435 | 51.849 | 1.00 | 40.00 |
| ATOM | 856 | N | THR | 422 | 77.330 | 32.426 | 48.948 | 1.00 | 20.00 |
| ATOM | 857 | CA | THR | 422 | 77.505 | 33.504 | 48.023 | 1.00 | 20.00 |
| ATOM | 858 | C | THR | 422 | 78.110 | 34.676 | 48.736 | 1.00 | 20.00 |
| ATOM | 859 | O | THR | 422 | 78.923 | 35.399 | 48.167 | 1.00 | 20.00 |
| ATOM | 860 | CB | THR | 422 | 76.212 | 33.956 | 47.406 | 1.00 | 20.00 |
| ATOM | 861 | OG1 | THR | 422 | 76.466 | 34.883 | 46.361 | 1.00 | 20.00 |
| ATOM | 862 | CG2 | THR | 422 | 75.333 | 34.600 | 48.491 | 1.00 | 20.00 |
| ATOM | 863 | N | SER | 423 | 77.702 | 34.922 | 49.999 | 1.00 | 20.00 |
| ATOM | 864 | CA | SER | 423 | 78.239 | 36.037 | 50.731 | 1.00 | 20.00 |
| ATOM | 865 | C | SER | 423 | 78.036 | 35.761 | 52.185 | 1.00 | 20.00 |
| ATOM | 866 | O | SER | 423 | 77.447 | 34.742 | 52.540 | 1.00 | 20.00 |
| ATOM | 867 | CB | SER | 423 | 77.550 | 37.380 | 50.422 | 1.00 | 20.00 |
| ATOM | 868 | OG | SER | 423 | 77.807 | 37.759 | 49.078 | 1.00 | 20.00 |
| ATOM | 869 | N | LEU | 424 | 78.604 | 36.620 | 53.062 | 1.00 | 20.00 |
| ATOM | 870 | CA | LEU | 424 | 78.421 | 36.471 | 54.481 | 1.00 | 20.00 |
| ATOM | 871 | C | LEU | 424 | 77.017 | 36.847 | 54.874 | 1.00 | 20.00 |
| ATOM | 872 | O | LEU | 424 | 76.307 | 36.058 | 55.489 | 1.00 | 20.00 |
| ATOM | 873 | CB | LEU | 424 | 79.396 | 37.332 | 55.300 | 1.00 | 20.00 |
| ATOM | 874 | CG | LEU | 424 | 80.867 | 36.906 | 55.136 | 1.00 | 20.00 |
| ATOM | 875 | CD1 | LEU | 424 | 81.356 | 37.119 | 53.693 | 1.00 | 20.00 |
| ATOM | 876 | CD2 | LEU | 424 | 81.768 | 37.587 | 56.179 | 1.00 | 20.00 |
| ATOM | 877 | N | GLY | 425 | 76.546 | 38.060 | 54.523 | 1.00 | 20.00 |
| ATOM | 878 | CA | GLY | 425 | 75.185 | 38.410 | 54.857 | 1.00 | 20.00 |
| ATOM | 879 | C | GLY | 425 | 75.018 | 38.638 | 56.342 | 1.00 | 20.00 |
| ATOM | 880 | O | GLY | 425 | 73.901 | 38.723 | 56.847 | 1.00 | 20.00 |
| ATOM | 881 | N | LEU | 426 | 76.139 | 38.782 | 57.065 | 1.00 | 20.00 |
| ATOM | 882 | CA | LEU | 426 | 76.274 | 38.987 | 58.487 | 1.00 | 20.00 |
| ATOM | 883 | C | LEU | 426 | 75.966 | 40.403 | 58.841 | 1.00 | 20.00 |

Figure 6A-42

| ATOM | 884 | C   | LEU | 426 | 76.454 | 40.879 | 59.856 | 1.00 | 20.00 |
| ATOM | 885 | O   | LEU | 426 | 77.665 | 38.670 | 59.065 | 1.00 | 20.00 |
| ATOM | 886 | CB  | LEU | 426 | 77.984 | 37.166 | 59.134 | 1.00 | 20.00 |
| ATOM | 887 | CD1 | LEU | 426 | 79.351 | 36.919 | 59.793 | 1.00 | 20.00 |
| ATOM | 888 | CD2 | LEU | 426 | 76.845 | 36.388 | 59.817 | 1.00 | 20.00 |
| ATOM | 889 | N   | ARG | 427 | 75.213 | 41.139 | 58.004 | 1.00 | 20.00 |
| ATOM | 890 | CA  | ARG | 427 | 75.050 | 42.570 | 58.084 | 1.00 | 20.00 |
| ATOM | 891 | C   | ARG | 427 | 74.921 | 43.120 | 59.484 | 1.00 | 20.00 |
| ATOM | 892 | O   | ARG | 427 | 75.357 | 44.244 | 59.721 | 1.00 | 20.00 |
| ATOM | 893 | CB  | ARG | 427 | 73.819 | 43.068 | 57.306 | 1.00 | 20.00 |
| ATOM | 894 | CG  | ARG | 427 | 72.502 | 42.478 | 57.815 | 1.00 | 20.00 |
| ATOM | 895 | CD  | ARG | 427 | 71.259 | 43.106 | 57.181 | 1.00 | 20.00 |
| ATOM | 896 | NE  | ARG | 427 | 71.144 | 44.495 | 57.707 | 1.00 | 20.00 |
| ATOM | 897 | CZ  | ARG | 427 | 70.482 | 44.719 | 58.880 | 1.00 | 20.00 |
| ATOM | 898 | NH1 | ARG | 427 | 69.939 | 43.671 | 59.566 | 1.00 | 20.00 |
| ATOM | 899 | NH2 | ARG | 427 | 70.362 | 45.988 | 59.367 | 1.00 | 20.00 |
| ATOM | 900 | N   | SER | 428 | 74.298 | 42.406 | 60.435 | 1.00 | 20.00 |
| ATOM | 901 | CA  | SER | 428 | 74.149 | 42.909 | 61.783 | 1.00 | 20.00 |
| ATOM | 902 | C   | SER | 428 | 75.460 | 42.961 | 62.532 | 1.00 | 20.00 |
| ATOM | 903 | O   | SER | 428 | 75.575 | 43.673 | 63.528 | 1.00 | 20.00 |
| ATOM | 904 | CB  | SER | 428 | 73.175 | 42.073 | 62.631 | 1.00 | 20.00 |
| ATOM | 905 | OG  | SER | 428 | 71.852 | 42.215 | 62.138 | 1.00 | 20.00 |
| ATOM | 906 | N   | LEU | 429 | 76.467 | 42.179 | 62.104 | 1.00 | 20.00 |
| ATOM | 907 | CA  | LEU | 429 | 77.715 | 42.012 | 62.799 | 1.00 | 20.00 |
| ATOM | 908 | C   | LEU | 429 | 78.461 | 43.309 | 62.909 | 1.00 | 20.00 |
| ATOM | 909 | O   | LEU | 429 | 79.082 | 43.771 | 61.954 | 1.00 | 20.00 |
| ATOM | 910 | CB  | LEU | 429 | 78.615 | 40.974 | 62.104 | 1.00 | 20.00 |
| ATOM | 911 | CG  | LEU | 429 | 79.973 | 40.719 | 62.780 | 1.00 | 20.00 |
| ATOM | 912 | CD1 | LEU | 429 | 79.789 | 40.131 | 64.184 | 1.00 | 20.00 |
| ATOM | 913 | CD2 | LEU | 429 | 80.876 | 39.845 | 61.889 | 1.00 | 20.00 |
| ATOM | 914 | N   | LYS | 430 | 78.337 | 43.962 | 64.085 | 1.00 | 20.00 |
| ATOM | 915 | CA  | LYS | 430 | 78.999 | 45.194 | 64.413 | 1.00 | 20.00 |
| ATOM | 916 | C   | LYS | 430 | 80.437 | 45.016 | 64.804 | 1.00 | 20.00 |
| ATOM | 917 | O   | LYS | 430 | 81.300 | 45.741 | 64.316 | 1.00 | 20.00 |
| ATOM | 918 | CB  | LYS | 430 | 78.307 | 45.927 | 65.569 | 1.00 | 20.00 |
| ATOM | 919 | CG  | LYS | 430 | 76.905 | 46.414 | 65.208 | 1.00 | 20.00 |
| ATOM | 920 | CD  | LYS | 430 | 76.894 | 47.386 | 64.028 | 1.00 | 20.00 |
| ATOM | 921 | CE  | LYS | 430 | 75.571 | 48.138 | 63.871 | 1.00 | 20.00 |
| ATOM | 922 | NZ  | LYS | 430 | 74.464 | 47.180 | 63.655 | 1.00 | 20.00 |
| ATOM | 923 | N   | GLU | 431 | 80.758 | 44.056 | 65.702 | 1.00 | 20.00 |
| ATOM | 924 | CA  | GLU | 431 | 82.132 | 44.025 | 66.118 | 1.00 | 20.00 |
| ATOM | 925 | C   | GLU | 431 | 82.509 | 42.685 | 66.660 | 1.00 | 20.00 |
| ATOM | 926 | O   | GLU | 431 | 81.699 | 41.977 | 67.258 | 1.00 | 20.00 |
| ATOM | 927 | CB  | GLU | 431 | 82.446 | 45.028 | 67.241 | 1.00 | 20.00 |
| ATOM | 928 | CG  | GLU | 431 | 81.668 | 44.740 | 68.528 | 1.00 | 20.00 |
| ATOM | 929 | CD  | GLU | 431 | 82.096 | 45.745 | 69.589 | 1.00 | 20.00 |
| ATOM | 930 | OE1 | GLU | 431 | 82.225 | 46.950 | 69.246 | 1.00 | 20.00 |
| ATOM | 931 | OE2 | GLU | 431 | 82.303 | 45.317 | 70.756 | 1.00 | 20.00 |
| ATOM | 932 | N   | ILE | 432 | 83.788 | 42.315 | 66.444 | 1.00 | 20.00 |
| ATOM | 933 | CA  | ILE | 432 | 84.335 | 41.119 | 67.001 | 1.00 | 20.00 |
| ATOM | 934 | C   | ILE | 432 | 85.346 | 41.587 | 67.993 | 1.00 | 20.00 |
| ATOM | 935 | O   | ILE | 432 | 86.499 | 41.848 | 67.665 | 1.00 | 20.00 |
| ATOM | 936 | CB  | ILE | 432 | 84.984 | 40.225 | 65.983 | 1.00 | 20.00 |
| ATOM | 937 | CG1 | ILE | 432 | 83.908 | 39.705 | 65.013 | 1.00 | 20.00 |
| ATOM | 938 | CG2 | ILE | 432 | 85.746 | 39.111 | 66.717 | 1.00 | 20.00 |
| ATOM | 939 | CD1 | ILE | 432 | 84.454 | 38.933 | 63.813 | 1.00 | 20.00 |
| ATOM | 940 | N   | SER | 433 | 84.939 | 41.581 | 69.269 | 1.00 | 20.00 |
| ATOM | 941 | CA  | SER | 433 | 85.652 | 42.184 | 70.355 | 1.00 | 20.00 |
| ATOM | 942 | C   | SER | 433 | 87.089 | 41.763 | 70.341 | 1.00 | 20.00 |
| ATOM | 943 | O   | SER | 433 | 87.962 | 42.579 | 70.631 | 1.00 | 20.00 |
| ATOM | 944 | CB  | SER | 433 | 85.041 | 41.785 | 71.709 | 1.00 | 20.00 |
| ATOM | 945 | OG  | SER | 433 | 85.756 | 42.390 | 72.772 | 1.00 | 20.00 |
| ATOM | 946 | N   | ASP | 434 | 87.398 | 40.491 | 70.036 | 1.00 | 20.00 |
| ATOM | 947 | CA  | ASP | 434 | 88.792 | 40.137 | 70.012 | 1.00 | 20.00 |
| ATOM | 948 | C   | ASP | 434 | 88.986 | 39.013 | 69.053 | 1.00 | 20.00 |
| ATOM | 949 | O   | ASP | 434 | 88.073 | 38.225 | 68.822 | 1.00 | 20.00 |
| ATOM | 950 | CB  | ASP | 434 | 89.345 | 39.663 | 71.368 | 1.00 | 20.00 |
| ATOM | 951 | CG  | ASP | 434 | 89.544 | 40.873 | 72.272 | 1.00 | 20.00 |
| ATOM | 952 | OD1 | ASP | 434 | 90.112 | 41.887 | 71.787 | 1.00 | 20.00 |
| ATOM | 953 | OD2 | ASP | 434 | 89.131 | 40.797 | 73.459 | 1.00 | 20.00 |
| ATOM | 954 | N   | GLY | 435 | 90.201 | 38.911 | 68.476 | 1.00 | 20.00 |
| ATOM | 955 | CA  | GLY | 435 | 90.509 | 37.847 | 67.569 | 1.00 | 20.00 |
| ATOM | 956 | C   | GLY | 435 | 90.299 | 38.335 | 66.175 | 1.00 | 20.00 |
| ATOM | 957 | O   | GLY | 435 | 89.702 | 39.386 | 65.949 | 1.00 | 20.00 |
| ATOM | 958 | N   | ASP | 436 | 90.797 | 37.547 | 65.201 | 1.00 | 20.00 |
| ATOM | 959 | CA  | ASP | 436 | 90.748 | 37.886 | 63.811 | 1.00 | 20.00 |
| ATOM | 960 | C   | ASP | 436 | 89.743 | 36.994 | 63.146 | 1.00 | 20.00 |

Figure 6A-43

| | | | | | | | | |
|---|---|---|---|---|---|---|---|---|
| ATOM | 961 | O | ASP | 436 | 88.975 | 36.311 | 63.820 | 1.00 20.00 |
| ATOM | 962 | CB | ASP | 436 | 92.099 | 37.626 | 63.148 | 1.00 20.00 |
| ATOM | 963 | CG | ASP | 436 | 93.063 | 38.494 | 63.935 | 1.00 20.00 |
| ATOM | 964 | OD1 | ASP | 436 | 92.854 | 39.736 | 63.973 | 1.00 20.00 |
| ATOM | 965 | OD2 | ASP | 436 | 94.027 | 37.924 | 64.513 | 1.00 20.00 |
| ATOM | 966 | N | VAL | 437 | 89.705 | 36.998 | 61.799 | 1.00 20.00 |
| ATOM | 967 | CA | VAL | 437 | 88.778 | 36.153 | 61.094 | 1.00 20.00 |
| ATOM | 968 | C | VAL | 437 | 89.533 | 35.336 | 60.083 | 1.00 20.00 |
| ATOM | 969 | O | VAL | 437 | 90.631 | 35.701 | 59.673 | 1.00 20.00 |
| ATOM | 970 | CB | VAL | 437 | 87.706 | 36.907 | 60.361 | 1.00 20.00 |
| ATOM | 971 | CG1 | VAL | 437 | 88.358 | 37.745 | 59.251 | 1.00 20.00 |
| ATOM | 972 | CG2 | VAL | 437 | 86.664 | 35.904 | 59.841 | 1.00 20.00 |
| ATOM | 973 | N | ILE | 438 | 88.977 | 34.168 | 59.687 | 1.00 20.00 |
| ATOM | 974 | CA | ILE | 438 | 89.627 | 33.355 | 58.695 | 1.00 20.00 |
| ATOM | 975 | C | ILE | 438 | 88.610 | 32.924 | 57.684 | 1.00 20.00 |
| ATOM | 976 | O | ILE | 438 | 87.763 | 32.072 | 57.947 | 1.00 20.00 |
| ATOM | 977 | CB | ILE | 438 | 90.289 | 32.125 | 59.272 | 1.00 20.00 |
| ATOM | 978 | CG1 | ILE | 438 | 90.967 | 31.298 | 58.166 | 1.00 20.00 |
| ATOM | 979 | CG2 | ILE | 438 | 89.263 | 31.352 | 60.116 | 1.00 20.00 |
| ATOM | 980 | CD1 | ILE | 438 | 92.186 | 31.974 | 57.542 | 1.00 20.00 |
| ATOM | 981 | N | ILE | 439 | 88.661 | 33.500 | 56.470 | 1.00 20.00 |
| ATOM | 982 | CA | ILE | 439 | 87.704 | 33.084 | 55.485 | 1.00 20.00 |
| ATOM | 983 | C | ILE | 439 | 88.464 | 32.338 | 54.433 | 1.00 20.00 |
| ATOM | 984 | O | ILE | 439 | 89.074 | 32.941 | 53.551 | 1.00 20.00 |
| ATOM | 985 | CB | ILE | 439 | 87.012 | 34.237 | 54.821 | 1.00 20.00 |
| ATOM | 986 | CG1 | ILE | 439 | 86.286 | 35.093 | 55.872 | 1.00 20.00 |
| ATOM | 987 | CG2 | ILE | 439 | 86.072 | 33.677 | 53.742 | 1.00 20.00 |
| ATOM | 988 | CD1 | ILE | 439 | 85.804 | 36.437 | 55.330 | 1.00 20.00 |
| ATOM | 989 | N | SER | 440 | 88.423 | 30.992 | 54.478 | 1.00 20.00 |
| ATOM | 990 | CA | SER | 440 | 89.229 | 30.270 | 53.536 | 1.00 20.00 |
| ATOM | 991 | C | SER | 440 | 88.437 | 29.227 | 52.811 | 1.00 20.00 |
| ATOM | 992 | O | SER | 440 | 87.424 | 28.723 | 53.291 | 1.00 20.00 |
| ATOM | 993 | CB | SER | 440 | 90.421 | 29.548 | 54.186 | 1.00 20.00 |
| ATOM | 994 | OG | SER | 440 | 89.955 | 28.529 | 55.058 | 1.00 20.00 |
| ATOM | 995 | N | GLY | 441 | 88.909 | 28.903 | 51.590 | 1.00 20.00 |
| ATOM | 996 | CA | GLY | 441 | 88.382 | 27.844 | 50.778 | 1.00 20.00 |
| ATOM | 997 | C | GLY | 441 | 86.915 | 28.009 | 50.546 | 1.00 20.00 |
| ATOM | 998 | O | GLY | 441 | 86.135 | 27.138 | 50.929 | 1.00 20.00 |
| ATOM | 999 | N | ASN | 442 | 86.488 | 29.137 | 49.944 | 1.00 20.00 |
| ATOM | 1000 | CA | ASN | 442 | 85.093 | 29.274 | 49.632 | 1.00 20.00 |
| ATOM | 1001 | C | ASN | 442 | 85.005 | 29.741 | 48.213 | 1.00 20.00 |
| ATOM | 1002 | O | ASN | 442 | 84.894 | 30.937 | 47.952 | 1.00 20.00 |
| ATOM | 1003 | CB | ASN | 442 | 84.401 | 30.319 | 50.520 | 1.00 20.00 |
| ATOM | 1004 | CG | ASN | 442 | 84.451 | 29.776 | 51.941 | 1.00 20.00 |
| ATOM | 1005 | OD1 | ASN | 442 | 83.812 | 28.776 | 52.260 | 1.00 20.00 |
| ATOM | 1006 | ND2 | ASN | 442 | 85.252 | 30.441 | 52.817 | 1.00 20.00 |
| ATOM | 1007 | N | LYS | 443 | 84.937 | 28.795 | 47.258 | 1.00 20.00 |
| ATOM | 1008 | CA | LYS | 443 | 85.043 | 29.139 | 45.867 | 1.00 20.00 |
| ATOM | 1009 | C | LYS | 443 | 84.022 | 30.166 | 45.477 | 1.00 20.00 |
| ATOM | 1010 | O | LYS | 443 | 84.353 | 31.140 | 44.806 | 1.00 20.00 |
| ATOM | 1011 | CB | LYS | 443 | 84.851 | 27.932 | 44.933 | 1.00 20.00 |
| ATOM | 1012 | CG | LYS | 443 | 84.961 | 28.283 | 43.446 | 1.00 20.00 |
| ATOM | 1013 | CD | LYS | 443 | 86.362 | 28.724 | 43.015 | 1.00 20.00 |
| ATOM | 1014 | CE | LYS | 443 | 86.715 | 30.148 | 43.450 | 1.00 20.00 |
| ATOM | 1015 | NZ | LYS | 443 | 88.081 | 30.495 | 42.995 | 1.00 20.00 |
| ATOM | 1016 | N | ASN | 444 | 82.761 | 29.968 | 45.891 | 1.00 20.00 |
| ATOM | 1017 | CA | ASN | 444 | 81.633 | 30.792 | 45.550 | 1.00 20.00 |
| ATOM | 1018 | C | ASN | 444 | 81.579 | 32.096 | 46.295 | 1.00 20.00 |
| ATOM | 1019 | O | ASN | 444 | 80.856 | 32.998 | 45.877 | 1.00 20.00 |
| ATOM | 1020 | CB | ASN | 444 | 80.292 | 30.080 | 45.800 | 1.00 20.00 |
| ATOM | 1021 | CG | ASN | 444 | 80.205 | 28.911 | 44.830 | 1.00 20.00 |
| ATOM | 1022 | OD1 | ASN | 444 | 80.454 | 29.057 | 43.635 | 1.00 20.00 |
| ATOM | 1023 | ND2 | ASN | 444 | 79.848 | 27.710 | 45.358 | 1.00 20.00 |
| ATOM | 1024 | N | LEU | 445 | 82.270 | 32.229 | 47.442 | 1.00 20.00 |
| ATOM | 1025 | CA | LEU | 445 | 82.091 | 33.401 | 48.260 | 1.00 20.00 |
| ATOM | 1026 | C | LEU | 445 | 82.414 | 34.664 | 47.523 | 1.00 20.00 |
| ATOM | 1027 | O | LEU | 445 | 83.490 | 34.830 | 46.952 | 1.00 20.00 |
| ATOM | 1028 | CB | LEU | 445 | 82.912 | 33.364 | 49.560 | 1.00 20.00 |
| ATOM | 1029 | CG | LEU | 445 | 82.731 | 34.599 | 50.458 | 1.00 20.00 |
| ATOM | 1030 | CD1 | LEU | 445 | 81.271 | 34.737 | 50.921 | 1.00 20.00 |
| ATOM | 1031 | CD2 | LEU | 445 | 83.718 | 34.585 | 51.634 | 1.00 20.00 |
| ATOM | 1032 | N | CYS | 446 | 81.451 | 35.606 | 47.569 | 1.00 20.00 |
| ATOM | 1033 | CA | CYS | 446 | 81.490 | 36.899 | 46.945 | 1.00 20.00 |
| ATOM | 1034 | C | CYS | 446 | 81.246 | 37.908 | 48.018 | 1.00 20.00 |
| ATOM | 1035 | O | CYS | 446 | 81.101 | 37.568 | 49.188 | 1.00 20.00 |
| ATOM | 1036 | CB | CYS | 446 | 80.329 | 37.132 | 45.973 | 1.00 20.00 |
| ATOM | 1037 | SG | CYS | 446 | 80.593 | 36.580 | 44.273 | 1.00 20.00 |

Figure 6A-44

```
ATOM   1038  N    TYR  447      81.208  39.193  47.621  1.00 20.00
ATOM   1039  CA   TYR  447      80.942  40.283  48.514  1.00 20.00
ATOM   1040  C    TYR  447      81.790  40.152  49.734  1.00 20.00
ATOM   1041  O    TYR  447      81.303  40.330  50.848  1.00 20.00
ATOM   1042  CB   TYR  447      79.468  40.423  48.929  1.00 20.00
ATOM   1043  CG   TYR  447      78.752  40.916  47.703  1.00 20.00
ATOM   1044  CD1  TYR  447      78.867  42.231  47.339  1.00 20.00
ATOM   1045  CD2  TYR  447      77.964  40.074  46.980  1.00 20.00
ATOM   1046  CE1  TYR  447      78.211  42.699  46.224  1.00 20.00
ATOM   1047  CE2  TYR  447      77.306  40.535  45.866  1.00 20.00
ATOM   1048  CZ   TYR  447      77.428  41.847  45.484  1.00 20.00
ATOM   1049  OH   TYR  447      76.749  42.311  44.338  1.00 20.00
ATOM   1050  N    ALA  448      83.035  39.671  49.544  1.00 20.00
ATOM   1051  CA   ALA  448      84.047  39.625  50.560  1.00 20.00
ATOM   1052  C    ALA  448      84.817  40.914  50.607  1.00 20.00
ATOM   1053  O    ALA  448      85.147  41.427  51.675  1.00 20.00
ATOM   1054  CB   ALA  448      85.067  38.499  50.319  1.00 20.00
ATOM   1055  N    ASN  449      85.149  41.438  49.409  1.00 20.00
ATOM   1056  CA   ASN  449      85.956  42.611  49.186  1.00 20.00
ATOM   1057  C    ASN  449      85.186  43.841  49.539  1.00 20.00
ATOM   1058  O    ASN  449      85.757  44.898  49.794  1.00 20.00
ATOM   1059  CB   ASN  449      86.414  42.724  47.726  1.00 20.00
ATOM   1060  CG   ASN  449      87.368  41.562  47.496  1.00 20.00
ATOM   1061  OD1  ASN  449      86.976  40.516  46.981  1.00 20.00
ATOM   1062  ND2  ASN  449      88.653  41.744  47.901  1.00 20.00
ATOM   1063  N    THR  450      83.855  43.710  49.505  1.00 20.00
ATOM   1064  CA   THR  450      82.848  44.704  49.737  1.00 20.00
ATOM   1065  C    THR  450      82.824  45.181  51.165  1.00 20.00
ATOM   1066  O    THR  450      82.274  46.249  51.425  1.00 20.00
ATOM   1067  CB   THR  450      81.487  44.148  49.424  1.00 20.00
ATOM   1068  OG1  THR  450      81.272  42.971  50.188  1.00 20.00
ATOM   1069  CG2  THR  450      81.405  43.804  47.930  1.00 20.00
ATOM   1070  N    ILE  451      83.354  44.407  52.139  1.00 20.00
ATOM   1071  CA   ILE  451      83.195  44.795  53.519  1.00 20.00
ATOM   1072  C    ILE  451      84.451  45.383  54.096  1.00 20.00
ATOM   1073  O    ILE  451      85.564  44.986  53.756  1.00 20.00
ATOM   1074  CB   ILE  451      82.814  43.642  54.403  1.00 20.00
ATOM   1075  CG1  ILE  451      81.477  43.039  53.944  1.00 20.00
ATOM   1076  CG2  ILE  451      82.796  44.140  55.858  1.00 20.00
ATOM   1077  CD1  ILE  451      80.310  44.022  54.008  1.00 20.00
ATOM   1078  N    ASN  452      84.287  46.381  54.997  1.00 20.00
ATOM   1079  CA   ASN  452      85.430  46.946  55.651  1.00 20.00
ATOM   1080  C    ASN  452      85.537  46.312  57.010  1.00 20.00
ATOM   1081  O    ASN  452      84.909  46.715  57.988  1.00 20.00
ATOM   1082  CB   ASN  452      85.415  48.488  55.772  1.00 20.00
ATOM   1083  CG   ASN  452      84.231  48.971  56.598  1.00 20.00
ATOM   1084  OD1  ASN  452      83.264  48.244  56.818  1.00 20.00
ATOM   1085  ND2  ASN  452      84.303  50.246  57.063  1.00 20.00
ATOM   1086  N    TRP  453      86.388  45.281  57.094  1.00 20.00
ATOM   1087  CA   TRP  453      86.577  44.505  58.283  1.00 20.00
ATOM   1088  C    TRP  453      87.207  45.377  59.309 -1.00 20.00
ATOM   1089  O    TRP  453      87.187  45.058  60.494  1.00 20.00
ATOM   1090  CB   TRP  453      87.466  43.272  58.049  1.00 20.00
ATOM   1091  CG   TRP  453      86.841  42.273  57.099  1.00 20.00
ATOM   1092  CD1  TRP  453      87.149  42.011  55.795  1.00 20.00
ATOM   1093  CD2  TRP  453      85.737  41.418  57.433  1.00 20.00
ATOM   1094  NE1  TRP  453      86.309  41.042  55.299  1.00 20.00
ATOM   1095  CE2  TRP  453      85.434  40.669  56.296  1.00 20.00
ATOM   1096  CE3  TRP  453      85.027  41.273  58.590  1.00 20.00
ATOM   1097  CZ2  TRP  453      84.414  39.760  56.303  1.00 20.00
ATOM   1098  CZ3  TRP  453      84.004  40.350  58.596  1.00 20.00
ATOM   1099  CH2  TRP  453      83.704  39.608  57.474  1.00 20.00
ATOM   1100  N    LYS  454      87.824  46.487  58.878  1.00 20.00
ATOM   1101  CA   LYS  454      88.483  47.362  59.799  1.00 20.00
ATOM   1102  C    LYS  454      87.483  47.842  60.798  1.00 20.00
ATOM   1103  O    LYS  454      87.787  47.939  61.986  1.00 20.00
ATOM   1104  CB   LYS  454      89.063  48.610  59.116  1.00 20.00
ATOM   1105  CG   LYS  454      90.195  48.302  58.136  1.00 20.00
ATOM   1106  CD   LYS  454      90.542  49.475  57.217  1.00 20.00
ATOM   1107  CE   LYS  454      91.674  49.169  56.236  1.00 20.00
ATOM   1108  NZ   LYS  454      91.903  50.330  55.347  1.00 20.00
ATOM   1109  N    LYS  455      86.261  48.173  60.343  1.00 20.00
ATOM   1110  CA   LYS  455      85.279  48.670  61.258  1.00 20.00
ATOM   1111  C    LYS  455      84.933  47.599  62.247  1.00 20.00
ATOM   1112  O    LYS  455      84.895  47.843  63.452  1.00 20.00
ATOM   1113  CB   LYS  455      83.975  49.093  60.560  1.00 20.00
ATOM   1114  CG   LYS  455      83.005  49.844  61.476  1.00 20.00
```

Figure 6A-45

| | | | | | | | | |
|---|---|---|---|---|---|---|---|---|
| ATOM | 1115 | CD | LYS | 455 | 81.875 | 50.551 | 60.724 | 1.00 20.00 |
| ATOM | 1116 | CE | LYS | 455 | 80.957 | 51.378 | 61.626 | 1.00 20.00 |
| ATOM | 1117 | NZ | LYS | 455 | 80.201 | 50.493 | 62.555 | 1.00 20.00 |
| ATOM | 1118 | N | LEU | 456 | 84.673 | 46.372 | 61.758 | 1.00 20.00 |
| ATOM | 1119 | CA | LEU | 456 | 84.270 | 45.300 | 62.627 | 1.00 20.00 |
| ATOM | 1120 | C | LEU | 456 | 85.381 | 44.885 | 63.545 | 1.00 20.00 |
| ATOM | 1121 | O | LEU | 456 | 85.180 | 44.757 | 64.752 | 1.00 20.00 |
| ATOM | 1122 | CB | LEU | 456 | 83.834 | 44.040 | 61.859 | 1.00 20.00 |
| ATOM | 1123 | CG | LEU | 456 | 82.556 | 44.232 | 61.021 | 1.00 20.00 |
| ATOM | 1124 | CD1 | LEU | 456 | 82.773 | 45.256 | 59.896 | 1.00 20.00 |
| ATOM | 1125 | CD2 | LEU | 456 | 82.015 | 42.887 | 60.510 | 1.00 20.00 |
| ATOM | 1126 | N | PHE | 457 | 86.594 | 44.675 | 62.996 | 1.00 20.00 |
| ATOM | 1127 | CA | PHE | 457 | 87.692 | 44.185 | 63.780 | 1.00 20.00 |
| ATOM | 1128 | C | PHE | 457 | 88.572 | 45.337 | 64.119 | 1.00 20.00 |
| ATOM | 1129 | O | PHE | 457 | 89.281 | 45.859 | 63.260 | 1.00 20.00 |
| ATOM | 1130 | CB | PHE | 457 | 88.622 | 43.229 | 63.012 | 1.00 20.00 |
| ATOM | 1131 | CG | PHE | 457 | 87.894 | 41.992 | 62.626 | 1.00 20.00 |
| ATOM | 1132 | CD1 | PHE | 457 | 87.862 | 40.906 | 63.468 | 1.00 20.00 |
| ATOM | 1133 | CD2 | PHE | 457 | 87.249 | 41.919 | 61.414 | 1.00 20.00 |
| ATOM | 1134 | CE1 | PHE | 457 | 87.195 | 39.761 | 63.103 | 1.00 20.00 |
| ATOM | 1135 | CE2 | PHE | 457 | 86.580 | 40.777 | 61.046 | 1.00 20.00 |
| ATOM | 1136 | CZ | PHE | 457 | 86.552 | 39.695 | 61.891 | 1.00 20.00 |
| ATOM | 1137 | N | GLY | 458 | 88.516 | 45.793 | 65.378 | 1.00 40.00 |
| ATOM | 1138 | CA | GLY | 458 | 89.413 | 46.825 | 65.797 | 1.00 40.00 |
| ATOM | 1139 | C | GLY | 458 | 90.750 | 46.212 | 66.045 | 1.00 40.00 |
| ATOM | 1140 | O | GLY | 458 | 91.788 | 46.777 | 65.701 | 1.00 40.00 |
| ATOM | 1141 | N | THR | 459 | 90.738 | 44.999 | 66.632 | 1.00 40.00 |
| ATOM | 1142 | CA | THR | 459 | 91.936 | 44.364 | 67.094 | 1.00 40.00 |
| ATOM | 1143 | C | THR | 459 | 92.968 | 44.320 | 66.017 | 1.00 40.00 |
| ATOM | 1144 | O | THR | 459 | 94.062 | 44.855 | 66.195 | 1.00 40.00 |
| ATOM | 1145 | CB | THR | 459 | 91.699 | 42.973 | 67.625 | 1.00 40.00 |
| ATOM | 1146 | OG1 | THR | 459 | 92.918 | 42.422 | 68.100 | 1.00 40.00 |
| ATOM | 1147 | CG2 | THR | 459 | 91.087 | 42.085 | 66.529 | 1.00 40.00 |
| ATOM | 1148 | N | SER | 460 | 92.668 | 43.707 | 64.857 | 1.00 40.00 |
| ATOM | 1149 | CA | SER | 460 | 93.716 | 43.681 | 63.885 | 1.00 40.00 |
| ATOM | 1150 | C | SER | 460 | 93.211 | 43.055 | 62.631 | 1.00 40.00 |
| ATOM | 1151 | O | SER | 460 | 93.008 | 41.845 | 62.562 | 1.00 40.00 |
| ATOM | 1152 | CB | SER | 460 | 94.946 | 42.869 | 64.325 | 1.00 40.00 |
| ATOM | 1153 | OG | SER | 460 | 95.932 | 42.890 | 63.306 | 1.00 40.00 |
| ATOM | 1154 | N | GLY | 461 | 92.988 | 43.894 | 61.606 | 1.00 20.00 |
| ATOM | 1155 | CA | GLY | 461 | 92.549 | 43.439 | 60.323 | 1.00 20.00 |
| ATOM | 1156 | C | GLY | 461 | 93.676 | 42.723 | 59.644 | 1.00 20.00 |
| ATOM | 1157 | O | GLY | 461 | 93.459 | 41.809 | 58.850 | 1.00 20.00 |
| ATOM | 1158 | N | GLN | 462 | 94.924 | 43.132 | 59.934 | 1.00 20.00 |
| ATOM | 1159 | CA | GLN | 462 | 96.068 | 42.589 | 59.258 | 1.00 20.00 |
| ATOM | 1160 | C | GLN | 462 | 96.146 | 41.114 | 59.504 | 1.00 20.00 |
| ATOM | 1161 | O | GLN | 462 | 96.552 | 40.356 | 58.625 | 1.00 20.00 |
| ATOM | 1162 | CB | GLN | 462 | 97.398 | 43.204 | 59.729 | 1.00 20.00 |
| ATOM | 1163 | CG | GLN | 462 | 98.619 | 42.625 | 59.012 | 1.00 20.00 |
| ATOM | 1164 | CD | GLN | 462 | 99.864 | 43.306 | 59.562 | 1.00 20.00 |
| ATOM | 1165 | OE1 | GLN | 462 | 100.784 | 42.650 | 60.044 | 1.00 20.00 |
| ATOM | 1166 | NE2 | GLN | 462 | 99.901 | 44.663 | 59.474 | 1.00 20.00 |
| ATOM | 1167 | N | LYS | 463 | 95.759 | 40.681 | 60.713 | 1.00 20.00 |
| ATOM | 1168 | CA | LYS | 463 | 95.867 | 39.310 | 61.128 | 1.00 20.00 |
| ATOM | 1169 | C | LYS | 463 | 94.938 | 38.418 | 60.357 | 1.00 20.00 |
| ATOM | 1170 | O | LYS | 463 | 95.195 | 37.220 | 60.242 | 1.00 20.00 |
| ATOM | 1171 | CB | LYS | 463 | 95.609 | 39.129 | 62.625 | 1.00 20.00 |
| ATOM | 1172 | CG | LYS | 463 | 96.582 | 39.909 | 63.511 | 1.00 20.00 |
| ATOM | 1173 | CD | LYS | 463 | 98.052 | 39.562 | 63.269 | 1.00 20.00 |
| ATOM | 1174 | CE | LYS | 463 | 98.679 | 40.355 | 62.120 | 1.00 20.00 |
| ATOM | 1175 | NZ | LYS | 463 | 98.788 | 41.784 | 62.493 | 1.00 20.00 |
| ATOM | 1176 | N | THR | 464 | 93.814 | 38.949 | 59.837 | 1.00 20.00 |
| ATOM | 1177 | CA | THR | 464 | 92.864 | 38.124 | 59.134 | 1.00 20.00 |
| ATOM | 1178 | C | THR | 464 | 93.550 | 37.341 | 58.060 | 1.00 20.00 |
| ATOM | 1179 | O | THR | 464 | 94.479 | 37.825 | 57.415 | 1.00 20.00 |
| ATOM | 1180 | CB | THR | 464 | 91.764 | 38.900 | 58.472 | 1.00 20.00 |
| ATOM | 1181 | OG1 | THR | 464 | 91.012 | 39.617 | 59.441 | 1.00 20.00 |
| ATOM | 1182 | CG2 | THR | 464 | 90.863 | 37.917 | 57.709 | 1.00 20.00 |
| ATOM | 1183 | N | LYS | 465 | 93.109 | 36.080 | 57.863 | 1.00 20.00 |
| ATOM | 1184 | CA | LYS | 465 | 93.702 | 35.266 | 56.843 | 1.00 20.00 |
| ATOM | 1185 | C | LYS | 465 | 92.636 | 34.900 | 55.865 | 1.00 20.00 |
| ATOM | 1186 | O | LYS | 465 | 91.615 | 34.310 | 56.218 | 1.00 20.00 |
| ATOM | 1187 | CB | LYS | 465 | 94.341 | 33.974 | 57.380 | 1.00 20.00 |
| ATOM | 1188 | CG | LYS | 465 | 95.607 | 34.234 | 58.201 | 1.00 20.00 |
| ATOM | 1189 | CD | LYS | 465 | 96.091 | 33.027 | 59.008 | 1.00 20.00 |
| ATOM | 1190 | CE | LYS | 465 | 97.369 | 33.295 | 59.806 | 1.00 20.00 |
| ATOM | 1191 | NZ | LYS | 465 | 97.091 | 34.252 | 60.898 | 1.00 20.00 |

Figure 6A-46

| | | | | | | | |
|---|---|---|---|---|---|---|---|
| ATOM | 1192 | N | ILE | 466 | 92.846 | 35.262 | 54.586 | 1.00 20.00 |
| ATOM | 1193 | CA | ILE | 466 | 91.848 | 34.946 | 53.614 | 1.00 20.00 |
| ATOM | 1194 | C | ILE | 466 | 92.517 | 34.355 | 52.417 | 1.00 20.00 |
| ATOM | 1195 | O | ILE | 466 | 93.466 | 34.923 | 51.861 | 1.00 20.00 |
| ATOM | 1196 | CB | ILE | 466 | 91.074 | 36.151 | 53.170 | 1.00 20.00 |
| ATOM | 1197 | CG1 | ILE | 466 | 90.333 | 36.766 | 54.365 | 1.00 20.00 |
| ATOM | 1198 | CG2 | ILE | 466 | 90.152 | 35.737 | 52.013 | 1.00 20.00 |
| ATOM | 1199 | CD1 | ILE | 466 | 89.731 | 38.139 | 54.076 | 1.00 20.00 |
| ATOM | 1200 | N | ILE | 467 | 92.035 | 33.172 | 51.984 | 1.00 20.00 |
| ATOM | 1201 | CA | ILE | 467 | 92.573 | 32.536 | 50.817 | 1.00 20.00 |
| ATOM | 1202 | C | ILE | 467 | 91.536 | 31.584 | 50.304 | 1.00 20.00 |
| ATOM | 1203 | O | ILE | 467 | 90.683 | 31.122 | 51.058 | 1.00 20.00 |
| ATOM | 1204 | CB | ILE | 467 | 93.788 | 31.696 | 51.094 | 1.00 20.00 |
| ATOM | 1205 | CG1 | ILE | 467 | 93.422 | 30.542 | 52.043 | 1.00 20.00 |
| ATOM | 1206 | CG2 | ILE | 467 | 94.909 | 32.604 | 51.623 | 1.00 20.00 |
| ATOM | 1207 | CD1 | ILE | 467 | 94.498 | 29.462 | 52.139 | 1.00 20.00 |
| ATOM | 1208 | N | SER | 468 | 91.619 | 31.255 | 48.995 | 1.00 20.00 |
| ATOM | 1209 | CA | SER | 468 | 90.783 | 30.284 | 48.343 | 1.00 20.00 |
| ATOM | 1210 | C | SER | 468 | 89.360 | 30.746 | 48.165 | 1.00 20.00 |
| ATOM | 1211 | O | SER | 468 | 88.467 | 29.925 | 47.970 | 1.00 20.00 |
| ATOM | 1212 | CB | SER | 468 | 90.779 | 28.934 | 49.089 | 1.00 20.00 |
| ATOM | 1213 | OG | SER | 468 | 90.070 | 27.948 | 48.353 | 1.00 20.00 |
| ATOM | 1214 | N | ASN | 469 | 89.097 | 32.068 | 48.185 | 1.00 20.00 |
| ATOM | 1215 | CA | ASN | 469 | 87.747 | 32.520 | 47.969 | 1.00 20.00 |
| ATOM | 1216 | C | ASN | 469 | 87.572 | 32.802 | 46.507 | 1.00 20.00 |
| ATOM | 1217 | O | ASN | 469 | 88.441 | 32.493 | 45.695 | 1.00 20.00 |
| ATOM | 1218 | CB | ASN | 469 | 87.384 | 33.794 | 48.749 | 1.00 20.00 |
| ATOM | 1219 | CG | ASN | 469 | 87.287 | 33.412 | 50.217 | 1.00 20.00 |
| ATOM | 1220 | OD1 | ASN | 469 | 86.717 | 32.378 | 50.565 | 1.00 20.00 |
| ATOM | 1221 | ND2 | ASN | 469 | 87.864 | 34.263 | 51.106 | 1.00 20.00 |
| ATOM | 1222 | N | ARG | 470 | 86.410 | 33.377 | 46.130 | 1.00 20.00 |
| ATOM | 1223 | CA | ARG | 470 | 86.132 | 33.660 | 44.748 | 1.00 20.00 |
| ATOM | 1224 | C | ARG | 470 | 86.921 | 34.869 | 44.341 | 1.00 20.00 |
| ATOM | 1225 | O | ARG | 470 | 87.221 | 35.734 | 45.161 | 1.00 20.00 |
| ATOM | 1226 | CB | ARG | 470 | 84.637 | 33.931 | 44.482 | 1.00 20.00 |
| ATOM | 1227 | CG | ARG | 470 | 84.275 | 34.019 | 42.999 | 1.00 20.00 |
| ATOM | 1228 | CD | ARG | 470 | 82.772 | 34.139 | 42.737 | 1.00 20.00 |
| ATOM | 1229 | NE | ARG | 470 | 82.588 | 34.216 | 41.260 | 1.00 20.00 |
| ATOM | 1230 | CZ | ARG | 470 | 81.339 | 34.380 | 40.735 | 1.00 20.00 |
| ATOM | 1231 | NH1 | ARG | 470 | 80.257 | 34.478 | 41.562 | 1.00 20.00 |
| ATOM | 1232 | NH2 | ARG | 470 | 81.173 | 34.450 | 39.381 | 1.00 20.00 |
| ATOM | 1233 | N | GLY | 471 | 87.287 | 34.952 | 43.042 | 1.00 40.00 |
| ATOM | 1234 | CA | GLY | 471 | 88.067 | 36.057 | 42.562 | 1.00 40.00 |
| ATOM | 1235 | C | GLY | 471 | 87.152 | 37.224 | 42.377 | 1.00 40.00 |
| ATOM | 1236 | O | GLY | 471 | 86.076 | 37.104 | 41.795 | 1.00 40.00 |
| ATOM | 1237 | N | GLU | 472 | 87.613 | 38.410 | 42.811 | 1.00 40.00 |
| ATOM | 1238 | CA | GLU | 472 | 86.824 | 39.608 | 42.795 | 1.00 40.00 |
| ATOM | 1239 | C | GLU | 472 | 86.359 | 39.843 | 41.394 | 1.00 40.00 |
| ATOM | 1240 | O | GLU | 472 | 85.213 | 40.227 | 41.168 | 1.00 40.00 |
| ATOM | 1241 | CB | GLU | 472 | 87.656 | 40.849 | 43.158 | 1.00 40.00 |
| ATOM | 1242 | CG | GLU | 472 | 88.242 | 40.851 | 44.569 | 1.00 40.00 |
| ATOM | 1243 | CD | GLU | 472 | 89.222 | 42.008 | 44.650 | 1.00 40.00 |
| ATOM | 1244 | OE1 | GLU | 472 | 90.181 | 42.018 | 43.832 | 1.00 40.00 |
| ATOM | 1245 | OE2 | GLU | 472 | 89.027 | 42.895 | 45.523 | 1.00 40.00 |
| ATOM | 1246 | N | ASN | 473 | 87.251 | 39.624 | 40.412 | 1.00 40.00 |
| ATOM | 1247 | CA | ASN | 473 | 86.911 | 39.872 | 39.041 | 1.00 40.00 |
| ATOM | 1248 | C | ASN | 473 | 85.811 | 38.947 | 38.630 | 1.00 40.00 |
| ATOM | 1249 | O | ASN | 473 | 84.872 | 39.352 | 37.944 | 1.00 40.00 |
| ATOM | 1250 | CB | ASN | 473 | 88.101 | 39.653 | 38.087 | 1.00 40.00 |
| ATOM | 1251 | CG | ASN | 473 | 88.545 | 38.201 | 38.192 | 1.00 40.00 |
| ATOM | 1252 | OD1 | ASN | 473 | 88.650 | 37.650 | 39.286 | 1.00 40.00 |
| ATOM | 1253 | ND2 | ASN | 473 | 88.816 | 37.562 | 37.022 | 1.00 40.00 |
| ATOM | 1254 | N | SER | 474 | 85.903 | 37.672 | 39.044 | 1.00 20.00 |
| ATOM | 1255 | CA | SER | 474 | 84.930 | 36.687 | 38.670 | 1.00 20.00 |
| ATOM | 1256 | C | SER | 474 | 83.616 | 37.035 | 39.267 | 1.00 20.00 |
| ATOM | 1257 | O | SER | 474 | 82.566 | 36.879 | 38.667 | 1.00 20.00 |
| ATOM | 1258 | CB | SER | 474 | 85.310 | 35.274 | 39.145 | 1.00 20.00 |
| ATOM | 1259 | OG | SER | 474 | 84.316 | 34.339 | 38.752 | 1.00 20.00 |
| ATOM | 1260 | N | CYS | 475 | 83.632 | 37.527 | 40.538 | 1.00 20.00 |
| ATOM | 1261 | CA | CYS | 475 | 82.399 | 37.791 | 41.211 | 1.00 20.00 |
| ATOM | 1262 | C | CYS | 475 | 81.660 | 38.870 | 40.491 | 1.00 20.00 |
| ATOM | 1263 | O | CYS | 475 | 80.436 | 38.823 | 40.377 | 1.00 20.00 |
| ATOM | 1264 | CB | CYS | 475 | 82.545 | 38.242 | 42.667 | 1.00 20.00 |
| ATOM | 1265 | SG | CYS | 475 | 80.882 | 38.368 | 43.362 | 1.00 20.00 |
| ATOM | 1266 | N | LYS | 476 | 82.387 | 39.878 | 39.979 | 1.00 60.00 |
| ATOM | 1267 | CA | LYS | 476 | 81.730 | 40.949 | 39.291 | 1.00 60.00 |
| ATOM | 1268 | C | LYS | 476 | 80.842 | 41.650 | 40.265 | 1.00 60.00 |

Figure 6A-47

| | | | | | | | | |
|---|---|---|---|---|---|---|---|---|
| ATOM | 1269 | C | LYS | 476 | 79.807 | 40.206 | 39.902 | 1.00 60.00 |
| ATOM | 1270 | CB | LYS | 476 | 80.873 | 40.477 | 38.102 | 1.00 60.00 |
| ATOM | 1271 | CG | LYS | 476 | 81.696 | 39.957 | 36.918 | 1.00 60.00 |
| ATOM | 1272 | CD | LYS | 476 | 80.866 | 39.204 | 35.876 | 1.00 60.00 |
| ATOM | 1273 | CE | LYS | 476 | 81.658 | 38.912 | 34.626 | 1.00 60.00 |
| ATOM | 1274 | NZ | LYS | 476 | 81.946 | 40.016 | 33.814 | 1.00 60.00 |
| ATOM | 1275 | N | ALA | 477 | 81.240 | 41.631 | 41.547 | 1.00 60.00 |
| ATOM | 1276 | CA | ALA | 477 | 80.531 | 42.330 | 42.571 | 1.00 60.00 |
| ATOM | 1277 | C | ALA | 477 | 81.458 | 43.425 | 42.964 | 1.00 60.00 |
| ATOM | 1278 | O | ALA | 477 | 82.140 | 43.988 | 42.107 | 1.00 60.00 |
| ATOM | 1279 | CB | ALA | 477 | 80.270 | 41.476 | 43.822 | 1.00 60.00 |
| ATOM | 1280 | N | THR | 478 | 81.434 | 43.762 | 44.271 | 1.00 60.00 |
| ATOM | 1281 | CA | THR | 478 | 82.280 | 44.706 | 44.946 | 1.00 60.00 |
| ATOM | 1282 | C | THR | 478 | 81.379 | 45.659 | 45.645 | 1.00 60.00 |
| ATOM | 1283 | O | THR | 478 | 80.158 | 45.535 | 45.621 | 1.00 60.00 |
| ATOM | 1284 | CB | THR | 478 | 83.241 | 45.491 | 44.091 | 1.00 60.00 |
| ATOM | 1285 | OG1 | THR | 478 | 84.170 | 46.190 | 44.905 | 1.00 60.00 |
| ATOM | 1286 | CG2 | THR | 478 | 82.449 | 46.475 | 43.218 | 1.00 60.00 |
| ATOM | 1287 | N | GLY | 479 | 81.961 | 46.668 | 46.311 | 1.00 60.00 |
| ATOM | 1288 | CA | GLY | 479 | 81.135 | 47.620 | 46.982 | 1.00 60.00 |
| ATOM | 1289 | C | GLY | 479 | 80.339 | 48.282 | 45.917 | 1.00 60.00 |
| ATOM | 1290 | O | GLY | 479 | 79.229 | 48.758 | 46.150 | 1.00 60.00 |
| ATOM | 1291 | N | GLN | 480 | 80.915 | 48.323 | 44.705 | 1.00 60.00 |
| ATOM | 1292 | CA | GLN | 480 | 80.274 | 48.950 | 43.593 | 1.00 60.00 |
| ATOM | 1293 | C | GLN | 480 | 79.022 | 48.293 | 43.269 | 1.00 60.00 |
| ATOM | 1294 | O | GLN | 480 | 77.964 | 48.807 | 43.111 | 1.00 60.00 |
| ATOM | 1295 | CB | GLN | 480 | 81.150 | 48.968 | 42.329 | 1.00 60.00 |
| ATOM | 1296 | CG | GLN | 480 | 80.508 | 49.691 | 41.145 | 1.00 60.00 |
| ATOM | 1297 | CD | GLN | 480 | 80.495 | 51.178 | 41.465 | 1.00 60.00 |
| ATOM | 1298 | OE1 | GLN | 480 | 79.907 | 51.606 | 42.458 | 1.00 60.00 |
| ATOM | 1299 | NE2 | GLN | 480 | 81.164 | 51.991 | 40.604 | 1.00 60.00 |
| ATOM | 1300 | N | VAL | 481 | 79.086 | 46.857 | 43.177 | 1.00 60.00 |
| ATOM | 1301 | CA | VAL | 481 | 77.874 | 46.197 | 42.794 | 1.00 60.00 |
| ATOM | 1302 | C | VAL | 481 | 77.040 | 46.010 | 44.018 | 1.00 60.00 |
| ATOM | 1303 | O | VAL | 481 | 76.809 | 44.890 | 44.459 | 1.00 60.00 |
| ATOM | 1304 | CB | VAL | 481 | 78.100 | 44.852 | 42.165 | 1.00 60.00 |
| ATOM | 1305 | CG1 | VAL | 481 | 76.738 | 44.232 | 41.800 | 1.00 60.00 |
| ATOM | 1306 | CG2 | VAL | 481 | 79.045 | 45.029 | 40.961 | 1.00 60.00 |
| ATOM | 1307 | N | CYS | 482 | 76.550 | 47.117 | 44.594 | 1.00 20.00 |
| ATOM | 1308 | CA | CYS | 482 | 75.700 | 46.981 | 45.737 | 1.00 20.00 |
| ATOM | 1309 | C | CYS | 482 | 74.501 | 47.830 | 45.449 | 1.00 20.00 |
| ATOM | 1310 | O | CYS | 482 | 74.309 | 48.262 | 44.314 | 1.00 20.00 |
| ATOM | 1311 | CB | CYS | 482 | 76.306 | 47.484 | 47.059 | 1.00 20.00 |
| ATOM | 1312 | SG | CYS | 482 | 75.422 | 46.745 | 48.459 | 1.00 20.00 |
| ATOM | 1313 | N | HIS | 483 | 73.647 | 48.093 | 46.459 | 1.00 20.00 |
| ATOM | 1314 | CA | HIS | 483 | 72.490 | 48.892 | 46.177 | 1.00 20.00 |
| ATOM | 1315 | C | HIS | 483 | 72.962 | 50.278 | 45.890 | 1.00 20.00 |
| ATOM | 1316 | O | HIS | 483 | 74.064 | 50.667 | 46.277 | 1.00 20.00 |
| ATOM | 1317 | CB | HIS | 483 | 71.455 | 48.954 | 47.314 | 1.00 20.00 |
| ATOM | 1318 | CG | HIS | 483 | 70.136 | 49.489 | 46.841 | 1.00 20.00 |
| ATOM | 1319 | ND1 | HIS | 483 | 69.832 | 50.827 | 46.731 | 1.00 20.00 |
| ATOM | 1320 | CD2 | HIS | 483 | 69.027 | 48.820 | 46.420 | 1.00 20.00 |
| ATOM | 1321 | CE1 | HIS | 483 | 68.565 | 50.902 | 46.253 | 1.00 20.00 |
| ATOM | 1322 | NE2 | HIS | 483 | 68.035 | 49.709 | 46.048 | 1.00 20.00 |
| ATOM | 1323 | N | ALA | 484 | 72.129 | 51.056 | 45.177 | 1.00 20.00 |
| ATOM | 1324 | CA | ALA | 484 | 72.479 | 52.397 | 44.810 | 1.00 20.00 |
| ATOM | 1325 | C | ALA | 484 | 72.633 | 53.183 | 46.070 | 1.00 20.00 |
| ATOM | 1326 | O | ALA | 484 | 73.512 | 54.036 | 46.182 | 1.00 20.00 |
| ATOM | 1327 | CB | ALA | 484 | 71.397 | 53.086 | 43.963 | 1.00 20.00 |
| ATOM | 1328 | N | LEU | 485 | 71.761 | 52.894 | 47.053 | 1.00 20.00 |
| ATOM | 1329 | CA | LEU | 485 | 71.700 | 53.607 | 48.296 | 1.00 20.00 |
| ATOM | 1330 | C | LEU | 485 | 72.942 | 53.404 | 49.104 | 1.00 20.00 |
| ATOM | 1331 | O | LEU | 485 | 73.430 | 54.351 | 49.719 | 1.00 20.00 |
| ATOM | 1332 | CB | LEU | 485 | 70.524 | 53.126 | 49.167 | 1.00 20.00 |
| ATOM | 1333 | CG | LEU | 485 | 69.159 | 53.245 | 48.467 | 1.00 20.00 |
| ATOM | 1334 | CD1 | LEU | 485 | 68.011 | 52.771 | 49.377 | 1.00 20.00 |
| ATOM | 1335 | CD2 | LEU | 485 | 68.937 | 54.658 | 47.908 | 1.00 20.00 |
| ATOM | 1336 | N | CYS | 486 | 73.484 | 52.168 | 49.133 | 1.00 20.00 |
| ATOM | 1337 | CA | CYS | 486 | 74.625 | 51.904 | 49.965 | 1.00 20.00 |
| ATOM | 1338 | C | CYS | 486 | 75.706 | 52.850 | 49.592 | 1.00 20.00 |
| ATOM | 1339 | O | CYS | 486 | 75.889 | 53.172 | 48.420 | 1.00 20.00 |
| ATOM | 1340 | CB | CYS | 486 | 75.216 | 50.493 | 49.810 | 1.00 20.00 |
| ATOM | 1341 | SG | CYS | 486 | 74.121 | 49.204 | 50.457 | 1.00 20.00 |
| ATOM | 1342 | N | SER | 487 | 76.435 | 53.359 | 50.600 | 1.00 20.00 |
| ATOM | 1343 | CA | SER | 487 | 77.514 | 54.217 | 50.245 | 1.00 20.00 |
| ATOM | 1344 | C | SER | 487 | 78.465 | 53.328 | 49.553 | 1.00 20.00 |
| ATOM | 1345 | O | SER | 487 | 78.379 | 52.106 | 49.660 | 1.00 20.00 |

Figure 6A-48

```
ATOM   1346  CB   SER  487      78.291  54.827  51.430  1.00 20.00
ATOM   1347  OG   SER  487      77.478  55.768  52.122  1.00 20.00
ATOM   1348  N    PRO  488      79.382  53.939  48.865  1.00 20.00
ATOM   1349  CA   PRO  488      80.388  53.191  48.173  1.00 20.00
ATOM   1350  C    PRO  488      81.308  52.611  49.194  1.00 20.00
ATOM   1351  O    PRO  488      82.218  51.872  48.822  1.00 20.00
ATOM   1352  CB   PRO  488      81.050  54.175  47.213  1.00 20.00
ATOM   1353  CG   PRO  488      79.936  55.196  46.918  1.00 20.00
ATOM   1354  CD   PRO  488      79.074  55.190  48.190  1.00 20.00
ATOM   1355  N    GLU  489      81.082  52.939  50.480  1.00 20.00
ATOM   1356  CA   GLU  489      81.867  52.429  51.541  1.00 20.00
ATOM   1357  C    GLU  489      81.934  50.937  51.382  1.00 20.00
ATOM   1358  O    GLU  489      83.018  50.363  51.263  1.00 20.00
ATOM   1359  CB   GLU  489      81.309  52.775  52.922  1.00 20.00
ATOM   1360  CG   GLU  489      81.341  54.263  53.271  1.00 20.00
ATOM   1361  CD   GLU  489      82.584  54.519  54.109  1.00 20.00
ATOM   1362  OE1  GLU  489      83.273  53.525  54.462  1.00 20.00
ATOM   1363  OE2  GLU  489      82.857  55.710  54.413  1.00 20.00
ATOM   1364  N    GLY  490      80.767  50.256  51.324  1.00 20.00
ATOM   1365  CA   GLY  490      80.835  48.832  51.130  1.00 20.00
ATOM   1366  C    GLY  490      79.555  48.203  51.585  1.00 20.00
ATOM   1367  O    GLY  490      78.679  48.877  52.122  1.00 20.00
ATOM   1368  N    CYS  491      79.399  46.879  51.350  1.00 20.00
ATOM   1369  CA   CYS  491      78.209  46.235  51.827  1.00 20.00
ATOM   1370  C    CYS  491      78.399  44.758  51.876  1.00 20.00
ATOM   1371  O    CYS  491      79.286  44.211  51.229  1.00 20.00
ATOM   1372  CB   CYS  491      76.949  46.530  50.999  1.00 20.00
ATOM   1373  SG   CYS  491      76.845  45.656  49.412  1.00 20.00
ATOM   1374  N    TRP  492      77.572  44.077  52.696  1.00 20.00
ATOM   1375  CA   TRP  492      77.645  42.652  52.854  1.00 20.00
ATOM   1376  C    TRP  492      77.156  41.956  51.623  1.00 20.00
ATOM   1377  O    TRP  492      77.706  40.931  51.222  1.00 20.00
ATOM   1378  CB   TRP  492      76.839  42.138  54.059  1.00 20.00
ATOM   1379  CG   TRP  492      77.411  42.582  55.386  1.00 20.00
ATOM   1380  CD1  TRP  492      77.066  43.652  56.161  1.00 20.00
ATOM   1381  CD2  TRP  492      78.486  41.917  56.070  1.00 20.00
ATOM   1382  NE1  TRP  492      77.856  43.693  57.285  1.00 20.00
ATOM   1383  CE2  TRP  492      78.736  42.632  57.241  1.00 20.00
ATOM   1384  CE3  TRP  492      79.206  40.803  55.747  1.00 20.00
ATOM   1385  CZ2  TRP  492      79.715  42.241  58.110  1.00 20.00
ATOM   1386  CZ3  TRP  492      80.192  40.412  56.627  1.00 20.00
ATOM   1387  CH2  TRP  492      80.441  41.116  57.786  1.00 20.00
ATOM   1388  N    GLY  493      76.091  42.480  50.992  1.00 20.00
ATOM   1389  CA   GLY  493      75.577  41.839  49.816  1.00 20.00
ATOM   1390  C    GLY  493      74.674  42.826  49.170  1.00 20.00
ATOM   1391  O    GLY  493      74.517  43.940  49.662  1.00 20.00
ATOM   1392  N    PRO  494      74.085  42.478  48.066  1.00 20.00
ATOM   1393  CA   PRO  494      73.181  43.411  47.475  1.00 20.00
ATOM   1394  C    PRO  494      71.957  43.495  48.320  1.00 20.00
ATOM   1395  O    PRO  494      71.244  42.499  48.441  1.00 20.00
ATOM   1396  CB   PRO  494      72.967  42.955  46.028  1.00 20.00
ATOM   1397  CG   PRO  494      73.674  41.587  45.944  1.00 20.00
ATOM   1398  CD   PRO  494      74.719  41.636  47.071  1.00 20.00
ATOM   1399  N    GLU  495      71.693  44.674  48.908  1.00 20.00
ATOM   1400  CA   GLU  495      70.524  44.863  49.712  1.00 20.00
ATOM   1401  C    GLU  495      70.697  46.191  50.372  1.00 20.00
ATOM   1402  O    GLU  495      71.821  46.621  50.624  1.00 20.00
ATOM   1403  CB   GLU  495      70.360  43.811  50.823  1.00 20.00
ATOM   1404  CG   GLU  495      69.053  43.951  51.605  1.00 20.00
ATOM   1405  CD   GLU  495      67.919  43.469  50.712  1.00 20.00
ATOM   1406  OE1  GLU  495      68.141  42.490  49.951  1.00 20.00
ATOM   1407  OE2  GLU  495      66.816  44.076  50.776  1.00 20.00
ATOM   1408  N    PRO  496      69.617  46.867  50.634  1.00 20.00
ATOM   1409  CA   PRO  496      69.728  48.144  51.288  1.00 20.00
ATOM   1410  C    PRO  496      70.094  48.034  52.738  1.00 20.00
ATOM   1411  O    PRO  496      70.527  49.029  53.317  1.00 20.00
ATOM   1412  CB   PRO  496      68.397  48.852  51.047  1.00 20.00
ATOM   1413  CG   PRO  496      67.898  48.245  49.724  1.00 20.00
ATOM   1414  CD   PRO  496      68.500  46.831  49.702  1.00 20.00
ATOM   1415  N    ARG  497      69.850  46.863  53.358  1.00 20.00
ATOM   1416  CA   ARG  497      70.163  46.614  54.740  1.00 20.00
ATOM   1417  C    ARG  497      71.634  46.371  54.907  1.00 20.00
ATOM   1418  O    ARG  497      72.213  46.670  55.950  1.00 20.00
ATOM   1419  CB   ARG  497      69.455  45.366  55.292  1.00 20.00
ATOM   1420  CG   ARG  497      67.933  45.495  55.370  1.00 20.00
ATOM   1421  CD   ARG  497      67.248  44.244  55.923  1.00 20.00
ATOM   1422  NE   ARG  497      65.783  44.507  55.944  1.00 20.00
```

Figure 6A-49

| ATOM | 1423 | CZ | ARG | 497 | 64.913 | 43.539 | 55.532 | 1.00 | 20.00 |
|------|------|-----|-----|-----|--------|--------|--------|------|-------|
| ATOM | 1424 | NH1 | ARG | 497 | 65.388 | 42.340 | 55.084 | 1.00 | 20.00 |
| ATOM | 1425 | NH2 | ARG | 497 | 63.569 | 43.771 | 55.562 | 1.00 | 20.00 |
| ATOM | 1426 | N | ASP | 498 | 72.258 | 45.786 | 53.971 | 1.00 | 20.00 |
| ATOM | 1427 | CA | ASP | 498 | 73.619 | 45.318 | 53.850 | 1.00 | 20.00 |
| ATOM | 1428 | C | ASP | 498 | 74.635 | 46.415 | 53.995 | 1.00 | 20.00 |
| ATOM | 1429 | O | ASP | 498 | 75.734 | 46.167 | 54.491 | 1.00 | 20.00 |
| ATOM | 1430 | CB | ASP | 498 | 73.972 | 44.490 | 52.632 | 1.00 | 20.00 |
| ATOM | 1431 | CG | ASP | 498 | 73.265 | 43.137 | 52.762 | 1.00 | 20.00 |
| ATOM | 1432 | OD1 | ASP | 498 | 72.794 | 42.828 | 53.880 | 1.00 | 20.00 |
| ATOM | 1433 | OD2 | ASP | 498 | 73.244 | 42.394 | 51.745 | 1.00 | 20.00 |
| ATOM | 1434 | N | CYS | 499 | 74.309 | 47.632 | 53.523 | 1.00 | 20.00 |
| ATOM | 1435 | CA | CYS | 499 | 75.217 | 48.746 | 53.443 | 1.00 | 20.00 |
| ATOM | 1436 | C | CYS | 499 | 76.076 | 48.873 | 54.667 | 1.00 | 20.00 |
| ATOM | 1437 | O | CYS | 499 | 75.673 | 48.537 | 55.778 | 1.00 | 20.00 |
| ATOM | 1438 | CB | CYS | 499 | 74.499 | 50.098 | 53.319 | 1.00 | 20.00 |
| ATOM | 1439 | SG | CYS | 499 | 73.235 | 50.193 | 52.019 | 1.00 | 20.00 |
| ATOM | 1440 | N | VAL | 500 | 77.353 | 49.258 | 54.458 | 1.00 | 20.00 |
| ATOM | 1441 | CA | VAL | 500 | 78.214 | 49.603 | 55.551 | 1.00 | 20.00 |
| ATOM | 1442 | C | VAL | 500 | 77.873 | 51.010 | 55.951 | 1.00 | 20.00 |
| ATOM | 1443 | O | VAL | 500 | 77.909 | 51.356 | 57.131 | 1.00 | 20.00 |
| ATOM | 1444 | CB | VAL | 500 | 79.667 | 49.524 | 55.206 | 1.00 | 20.00 |
| ATOM | 1445 | CG1 | VAL | 500 | 80.029 | 48.057 | 54.924 | 1.00 | 20.00 |
| ATOM | 1446 | CG2 | VAL | 500 | 79.904 | 50.443 | 54.009 | 1.00 | 20.00 |
| ATOM | 1447 | N | SER | 501 | 77.545 | 51.866 | 54.952 | 1.00 | 20.00 |
| ATOM | 1448 | CA | SER | 501 | 77.198 | 53.242 | 55.189 | 1.00 | 20.00 |
| ATOM | 1449 | C | SER | 501 | 76.137 | 53.625 | 54.200 | 1.00 | 20.00 |
| ATOM | 1450 | O | SER | 501 | 75.859 | 52.874 | 53.268 | 1.00 | 20.00 |
| ATOM | 1451 | CB | SER | 501 | 78.376 | 54.213 | 54.995 | 1.00 | 20.00 |
| ATOM | 1452 | OG | SER | 501 | 77.960 | 55.546 | 55.248 | 1.00 | 20.00 |
| ATOM | 1453 | N | CYS | 502 | 75.517 | 54.815 | 54.380 | 1.00 | 20.00 |
| ATOM | 1454 | CA | CYS | 502 | 74.431 | 55.218 | 53.523 | 1.00 | 20.00 |
| ATOM | 1455 | C | CYS | 502 | 74.844 | 56.410 | 52.722 | 1.00 | 20.00 |
| ATOM | 1456 | O | CYS | 502 | 75.623 | 57.247 | 53.175 | 1.00 | 20.00 |
| ATOM | 1457 | CB | CYS | 502 | 73.156 | 55.608 | 54.284 | 1.00 | 20.00 |
| ATOM | 1458 | SG | CYS | 502 | 72.458 | 54.244 | 55.262 | 1.00 | 20.00 |
| ATOM | 1459 | N | ARG | 503 | 74.362 | 56.473 | 51.463 | 1.00 | 20.00 |
| ATOM | 1460 | CA | ARG | 503 | 74.650 | 57.568 | 50.582 | 1.00 | 20.00 |
| ATOM | 1461 | C | ARG | 503 | 73.932 | 58.782 | 51.070 | 1.00 | 20.00 |
| ATOM | 1462 | O | ARG | 503 | 74.479 | 59.884 | 51.077 | 1.00 | 20.00 |
| ATOM | 1463 | CB | ARG | 503 | 74.209 | 57.298 | 49.134 | 1.00 | 20.00 |
| ATOM | 1464 | CG | ARG | 503 | 74.559 | 58.432 | 48.168 | 1.00 | 20.00 |
| ATOM | 1465 | CD | ARG | 503 | 74.378 | 58.051 | 46.698 | 1.00 | 20.00 |
| ATOM | 1466 | NE | ARG | 503 | 75.343 | 56.950 | 46.414 | 1.00 | 20.00 |
| ATOM | 1467 | CZ | ARG | 503 | 75.391 | 56.381 | 45.175 | 1.00 | 20.00 |
| ATOM | 1468 | NH1 | ARG | 503 | 74.567 | 56.830 | 44.183 | 1.00 | 20.00 |
| ATOM | 1469 | NH2 | ARG | 503 | 76.264 | 55.361 | 44.929 | 1.00 | 20.00 |
| ATOM | 1470 | N | ASN | 504 | 72.675 | 58.592 | 51.510 | 1.00 | 20.00 |
| ATOM | 1471 | CA | ASN | 504 | 71.854 | 59.676 | 51.964 | 1.00 | 20.00 |
| ATOM | 1472 | C | ASN | 504 | 71.698 | 59.517 | 53.442 | 1.00 | 20.00 |
| ATOM | 1473 | O | ASN | 504 | 72.674 | 59.580 | 54.188 | 1.00 | 20.00 |
| ATOM | 1474 | CB | ASN | 504 | 70.443 | 59.663 | 51.353 | 1.00 | 20.00 |
| ATOM | 1475 | CG | ASN | 504 | 70.559 | 60.054 | 49.887 | 1.00 | 20.00 |
| ATOM | 1476 | OD1 | ASN | 504 | 70.337 | 61.208 | 49.524 | 1.00 | 20.00 |
| ATOM | 1477 | ND2 | ASN | 504 | 70.931 | 59.074 | 49.021 | 1.00 | 20.00 |
| ATOM | 1478 | N | VAL | 505 | 70.445 | 59.326 | 53.902 | 1.00 | 20.00 |
| ATOM | 1479 | CA | VAL | 505 | 70.183 | 59.225 | 55.308 | 1.00 | 20.00 |
| ATOM | 1480 | C | VAL | 505 | 69.850 | 57.813 | 55.663 | 1.00 | 20.00 |
| ATOM | 1481 | O | VAL | 505 | 69.209 | 57.094 | 54.899 | 1.00 | 20.00 |
| ATOM | 1482 | CB | VAL | 505 | 69.023 | 60.068 | 55.753 | 1.00 | 20.00 |
| ATOM | 1483 | CG1 | VAL | 505 | 69.370 | 61.547 | 55.508 | 1.00 | 20.00 |
| ATOM | 1484 | CG2 | VAL | 505 | 67.760 | 59.592 | 55.015 | 1.00 | 20.00 |
| ATOM | 1485 | N | SER | 506 | 70.288 | 57.376 | 56.861 | 1.00 | 20.00 |
| ATOM | 1486 | CA | SER | 506 | 70.013 | 56.032 | 57.274 | 1.00 | 20.00 |
| ATOM | 1487 | C | SER | 506 | 68.874 | 56.071 | 58.232 | 1.00 | 20.00 |
| ATOM | 1488 | O | SER | 506 | 68.829 | 56.923 | 59.116 | 1.00 | 20.00 |
| ATOM | 1489 | CB | SER | 506 | 71.196 | 55.346 | 57.979 | 1.00 | 20.00 |
| ATOM | 1490 | OG | SER | 506 | 71.513 | 56.029 | 59.184 | 1.00 | 20.00 |
| ATOM | 1491 | N | ARG | 507 | 67.889 | 55.167 | 58.054 | 1.00 | 20.00 |
| ATOM | 1492 | CA | ARG | 507 | 66.805 | 55.162 | 58.986 | 1.00 | 20.00 |
| ATOM | 1493 | C | ARG | 507 | 66.316 | 53.760 | 59.162 | 1.00 | 20.00 |
| ATOM | 1494 | O | ARG | 507 | 66.135 | 53.024 | 58.195 | 1.00 | 20.00 |
| ATOM | 1495 | CB | ARG | 507 | 65.582 | 55.976 | 58.540 | 1.00 | 20.00 |
| ATOM | 1496 | CG | ARG | 507 | 64.569 | 56.137 | 59.674 | 1.00 | 20.00 |
| ATOM | 1497 | CD | ARG | 507 | 63.128 | 56.325 | 59.207 | 1.00 | 20.00 |
| ATOM | 1498 | NE | ARG | 507 | 62.640 | 54.978 | 58.799 | 1.00 | 20.00 |
| ATOM | 1499 | CZ | ARG | 507 | 62.196 | 54.103 | 59.749 | 1.00 | 20.00 |

Figure 6A-50

| | | | | | | | | |
|---|---|---|---|---|---|---|---|---|
| ATOM | 1500 | NH1 | ARG | 507 | 62.193 | 54.466 | 61.063 | 1.00 20.00 |
| ATOM | 1501 | NH2 | ARG | 507 | 61.767 | 52.860 | 59.384 | 1.00 20.00 |
| ATOM | 1502 | N | GLY | 508 | 66.092 | 53.353 | 60.427 | 1.00 20.00 |
| ATOM | 1503 | CA | GLY | 508 | 65.512 | 52.070 | 60.708 | 1.00 20.00 |
| ATOM | 1504 | C | GLY | 508 | 66.299 | 50.986 | 60.045 | 1.00 20.00 |
| ATOM | 1505 | O | GLY | 508 | 65.732 | 50.122 | 59.379 | 1.00 20.00 |
| ATOM | 1506 | N | ARG | 509 | 67.634 | 51.005 | 60.199 | 1.00 20.00 |
| ATOM | 1507 | CA | ARG | 509 | 68.449 | 49.952 | 59.663 | 1.00 20.00 |
| ATOM | 1508 | C | ARG | 509 | 68.364 | 49.934 | 58.167 | 1.00 20.00 |
| ATOM | 1509 | O | ARG | 509 | 68.854 | 48.999 | 57.537 | 1.00 20.00 |
| ATOM | 1510 | CB | ARG | 509 | 68.033 | 48.563 | 60.175 | 1.00 20.00 |
| ATOM | 1511 | CG | ARG | 509 | 68.312 | 48.359 | 61.665 | 1.00 20.00 |
| ATOM | 1512 | CD | ARG | 509 | 67.553 | 49.333 | 62.566 | 1.00 20.00 |
| ATOM | 1513 | NE | ARG | 509 | 67.924 | 49.017 | 63.973 | 1.00 20.00 |
| ATOM | 1514 | CZ | ARG | 509 | 68.352 | 50.012 | 64.803 | 1.00 20.00 |
| ATOM | 1515 | NH1 | ARG | 509 | 68.460 | 51.291 | 64.334 | 1.00 20.00 |
| ATOM | 1516 | NH2 | ARG | 509 | 68.695 | 49.728 | 66.097 | 1.00 20.00 |
| ATOM | 1517 | N | GLU | 510 | 67.772 | 50.970 | 57.542 | 1.00 20.00 |
| ATOM | 1518 | CA | GLU | 510 | 67.718 | 50.937 | 56.106 | 1.00 20.00 |
| ATOM | 1519 | C | GLU | 510 | 68.333 | 52.195 | 55.588 | 1.00 20.00 |
| ATOM | 1520 | O | GLU | 510 | 68.194 | 53.259 | 56.189 | 1.00 20.00 |
| ATOM | 1521 | CB | GLU | 510 | 66.288 | 50.867 | 55.545 | 1.00 20.00 |
| ATOM | 1522 | CG | GLU | 510 | 65.582 | 49.546 | 55.849 | 1.00 20.00 |
| ATOM | 1523 | CD | GLU | 510 | 64.187 | 49.607 | 55.244 | 1.00 20.00 |
| ATOM | 1524 | OE1 | GLU | 510 | 63.465 | 50.600 | 55.520 | 1.00 20.00 |
| ATOM | 1525 | OE2 | GLU | 510 | 63.828 | 48.660 | 54.492 | 1.00 20.00 |
| ATOM | 1526 | N | CYS | 511 | 69.047 | 52.103 | 54.447 | 1.00 20.00 |
| ATOM | 1527 | CA | CYS | 511 | 69.634 | 53.289 | 53.898 | 1.00 20.00 |
| ATOM | 1528 | C | CYS | 511 | 68.588 | 53.932 | 53.058 | 1.00 20.00 |
| ATOM | 1529 | O | CYS | 511 | 68.168 | 53.366 | 52.050 | 1.00 20.00 |
| ATOM | 1530 | CB | CYS | 511 | 70.861 | 53.056 | 53.004 | 1.00 20.00 |
| ATOM | 1531 | SG | CYS | 511 | 72.367 | 52.696 | 53.951 | 1.00 20.00 |
| ATOM | 1532 | N | VAL | 512 | 68.147 | 55.145 | 53.455 | 1.00 20.00 |
| ATOM | 1533 | CA | VAL | 512 | 67.083 | 55.770 | 52.731 | 1.00 20.00 |
| ATOM | 1534 | C | VAL | 512 | 67.616 | 56.996 | 52.045 | 1.00 20.00 |
| ATOM | 1535 | O | VAL | 512 | 68.571 | 57.622 | 52.500 | 1.00 20.00 |
| ATOM | 1536 | CB | VAL | 512 | 65.925 | 56.163 | 53.592 | 1.00 20.00 |
| ATOM | 1537 | CG1 | VAL | 512 | 64.874 | 56.802 | 52.679 | 1.00 20.00 |
| ATOM | 1538 | CG2 | VAL | 512 | 65.431 | 54.930 | 54.370 | 1.00 20.00 |
| ATOM | 1539 | N | ASP | 513 | 67.031 | 57.324 | 50.876 | 1.00 20.00 |
| ATOM | 1540 | CA | ASP | 513 | 67.399 | 58.471 | 50.092 | 1.00 20.00 |
| ATOM | 1541 | C | ASP | 513 | 66.971 | 59.731 | 50.782 | 1.00 20.00 |
| ATOM | 1542 | O | ASP | 513 | 67.655 | 60.752 | 50.705 | 1.00 20.00 |
| ATOM | 1543 | CB | ASP | 513 | 66.741 | 58.477 | 48.701 | 1.00 20.00 |
| ATOM | 1544 | CG | ASP | 513 | 67.445 | 57.430 | 47.852 | 1.00 20.00 |
| ATOM | 1545 | OD1 | ASP | 513 | 68.703 | 57.390 | 47.899 | 1.00 20.00 |
| ATOM | 1546 | OD2 | ASP | 513 | 66.739 | 56.654 | 47.153 | 1.00 20.00 |
| ATOM | 1547 | N | LYS | 514 | 65.792 | 59.711 | 51.433 | 1.00 20.00 |
| ATOM | 1548 | CA | LYS | 514 | 65.328 | 60.890 | 52.111 | 1.00 20.00 |
| ATOM | 1549 | C | LYS | 514 | 64.543 | 60.445 | 53.303 | 1.00 20.00 |
| ATOM | 1550 | O | LYS | 514 | 64.072 | 59.314 | 53.363 | 1.00 20.00 |
| ATOM | 1551 | CB | LYS | 514 | 64.418 | 61.783 | 51.250 | 1.00 20.00 |
| ATOM | 1552 | CG | LYS | 514 | 65.171 | 62.493 | 50.121 | 1.00 20.00 |
| ATOM | 1553 | CD | LYS | 514 | 64.262 | 63.132 | 49.070 | 1.00 20.00 |
| ATOM | 1554 | CE | LYS | 514 | 65.032 | 63.843 | 47.956 | 1.00 20.00 |
| ATOM | 1555 | NZ | LYS | 514 | 64.091 | 64.362 | 46.939 | 1.00 20.00 |
| ATOM | 1556 | N | CYS | 515 | 64.364 | 61.331 | 54.298 | 1.00 20.00 |
| ATOM | 1557 | CA | CYS | 515 | 63.702 | 60.901 | 55.494 | 1.00 20.00 |
| ATOM | 1558 | C | CYS | 515 | 62.260 | 60.630 | 55.213 | 1.00 20.00 |
| ATOM | 1559 | O | CYS | 515 | 61.617 | 61.322 | 54.424 | 1.00 20.00 |
| ATOM | 1560 | CB | CYS | 515 | 63.779 | 61.925 | 56.639 | 1.00 20.00 |
| ATOM | 1561 | SG | CYS | 515 | 65.495 | 62.245 | 57.135 | 1.00 20.00 |
| ATOM | 1562 | N | LYS | 516 | 61.715 | 59.587 | 55.874 | 1.00 20.00 |
| ATOM | 1563 | CA | LYS | 516 | 60.338 | 59.248 | 55.681 | 1.00 20.00 |
| ATOM | 1564 | C | LYS | 516 | 59.508 | 60.268 | 56.388 | 1.00 20.00 |
| ATOM | 1565 | O | LYS | 516 | 60.028 | 61.176 | 57.034 | 1.00 20.00 |
| ATOM | 1566 | CB | LYS | 516 | 59.937 | 57.853 | 56.196 | 1.00 20.00 |
| ATOM | 1567 | CG | LYS | 516 | 60.407 | 56.721 | 55.281 | 1.00 20.00 |
| ATOM | 1568 | CD | LYS | 516 | 60.131 | 55.319 | 55.828 | 1.00 20.00 |
| ATOM | 1569 | CE | LYS | 516 | 60.375 | 54.214 | 54.799 | 1.00 20.00 |
| ATOM | 1570 | NZ | LYS | 516 | 59.995 | 52.899 | 55.363 | 1.00 20.00 |
| ATOM | 1571 | N | LEU | 517 | 58.173 | 60.138 | 56.266 | 1.00 20.00 |
| ATOM | 1572 | CA | LEU | 517 | 57.262 | 61.090 | 56.830 | 1.00 20.00 |
| ATOM | 1573 | C | LEU | 517 | 57.420 | 61.100 | 58.318 | 1.00 20.00 |
| ATOM | 1574 | O | LEU | 517 | 57.760 | 60.087 | 58.929 | 1.00 20.00 |
| ATOM | 1575 | CB | LEU | 517 | 55.786 | 60.760 | 56.550 | 1.00 20.00 |
| ATOM | 1576 | CG | LEU | 517 | 55.421 | 60.732 | 55.055 | 1.00 20.00 |

Figure 6A-51

| ATOM | 1577 | CD1 | LEU | 517 | 53.936 | 60.393 | 54.851 | 1.00 | 20.00 |
|------|------|-----|-----|-----|--------|--------|--------|------|-------|
| ATOM | 1578 | CD2 | LEU | 517 | 55.842 | 62.028 | 54.350 | 1.00 | 20.00 |
| ATOM | 1579 | N   | LEU | 518 | 57.184 | 62.275 | 58.926 | 1.00 | 20.00 |
| ATOM | 1580 | CA  | LEU | 518 | 57.206 | 62.441 | 60.351 | 1.00 | 20.00 |
| ATOM | 1581 | C   | LEU | 518 | 58.616 | 62.527 | 60.845 | 1.00 | 20.00 |
| ATOM | 1582 | O   | LEU | 518 | 58.919 | 63.349 | 61.710 | 1.00 | 20.00 |
| ATOM | 1583 | CB  | LEU | 518 | 56.481 | 61.310 | 61.099 | 1.00 | 20.00 |
| ATOM | 1584 | CG  | LEU | 518 | 54.964 | 61.303 | 60.837 | 1.00 | 20.00 |
| ATOM | 1585 | CD1 | LEU | 518 | 54.269 | 60.161 | 61.599 | 1.00 | 20.00 |
| ATOM | 1586 | CD2 | LEU | 518 | 54.345 | 62.679 | 61.130 | 1.00 | 20.00 |
| ATOM | 1587 | N   | GLU | 519 | 59.531 | 61.699 | 60.306 | 1.00 | 20.00 |
| ATOM | 1588 | CA  | GLU | 519 | 60.877 | 61.766 | 60.797 | 1.00 | 20.00 |
| ATOM | 1589 | C   | GLU | 519 | 61.592 | 62.839 | 60.047 | 1.00 | 20.00 |
| ATOM | 1590 | O   | GLU | 519 | 61.258 | 63.149 | 58.904 | 1.00 | 20.00 |
| ATOM | 1591 | CB  | GLU | 519 | 61.672 | 60.458 | 60.641 | 1.00 | 20.00 |
| ATOM | 1592 | CG  | GLU | 519 | 61.238 | 59.365 | 61.624 | 1.00 | 20.00 |
| ATOM | 1593 | CD  | GLU | 519 | 59.893 | 58.814 | 61.175 | 1.00 | 20.00 |
| ATOM | 1594 | OE1 | GLU | 519 | 59.860 | 58.108 | 60.134 | 1.00 | 20.00 |
| ATOM | 1595 | OE2 | GLU | 519 | 58.880 | 59.092 | 61.872 | 1.00 | 20.00 |
| ATOM | 1596 | N   | GLY | 520 | 62.600 | 63.450 | 60.700 | 1.00 | 20.00 |
| ATOM | 1597 | CA  | GLY | 520 | 63.343 | 64.505 | 60.084 | 1.00 | 20.00 |
| ATOM | 1598 | C   | GLY | 520 | 64.786 | 64.197 | 60.269 | 1.00 | 20.00 |
| ATOM | 1599 | O   | GLY | 520 | 65.170 | 63.520 | 61.219 | 1.00 | 20.00 |
| ATOM | 1600 | N   | GLU | 521 | 65.634 | 64.696 | 59.351 | 1.00 | 20.00 |
| ATOM | 1601 | CA  | GLU | 521 | 67.033 | 64.438 | 59.482 | 1.00 | 20.00 |
| ATOM | 1602 | C   | GLU | 521 | 67.477 | 65.134 | 60.722 | 1.00 | 20.00 |
| ATOM | 1603 | O   | GLU | 521 | 67.161 | 66.299 | 60.953 | 1.00 | 20.00 |
| ATOM | 1604 | CB  | GLU | 521 | 67.854 | 64.944 | 58.281 | 1.00 | 20.00 |
| ATOM | 1605 | CG  | GLU | 521 | 67.662 | 66.433 | 57.990 | 1.00 | 20.00 |
| ATOM | 1606 | CD  | GLU | 521 | 68.339 | 66.736 | 56.660 | 1.00 | 20.00 |
| ATOM | 1607 | OE1 | GLU | 521 | 68.965 | 65.804 | 56.089 | 1.00 | 20.00 |
| ATOM | 1608 | OE2 | GLU | 521 | 68.232 | 67.902 | 56.194 | 1.00 | 20.00 |
| ATOM | 1609 | N   | PRO | 522 | 68.191 | 64.445 | 61.571 | 1.00 | 40.00 |
| ATOM | 1610 | CA  | PRO | 522 | 68.590 | 65.051 | 62.816 | 1.00 | 40.00 |
| ATOM | 1611 | C   | PRO | 522 | 69.641 | 66.105 | 62.691 | 1.00 | 40.00 |
| ATOM | 1612 | O   | PRO | 522 | 70.631 | 65.866 | 61.995 | 1.00 | 40.00 |
| ATOM | 1613 | CB  | PRO | 522 | 68.963 | 63.902 | 63.758 | 1.00 | 40.00 |
| ATOM | 1614 | CG  | PRO | 522 | 68.931 | 62.640 | 62.873 | 1.00 | 40.00 |
| ATOM | 1615 | CD  | PRO | 522 | 67.980 | 63.018 | 61.729 | 1.00 | 40.00 |
| ATOM | 1616 | N   | ARG | 523 | 69.439 | 67.259 | 63.361 | 1.00 | 60.00 |
| ATOM | 1617 | CA  | ARG | 523 | 70.404 | 68.317 | 63.323 | 1.00 | 60.00 |
| ATOM | 1618 | C   | ARG | 523 | 71.615 | 67.918 | 64.106 | 1.00 | 60.00 |
| ATOM | 1619 | O   | ARG | 523 | 72.742 | 68.050 | 63.632 | 1.00 | 60.00 |
| ATOM | 1620 | CB  | ARG | 523 | 69.898 | 69.639 | 63.931 | 1.00 | 60.00 |
| ATOM | 1621 | CG  | ARG | 523 | 70.919 | 70.776 | 63.818 | 1.00 | 60.00 |
| ATOM | 1622 | CD  | ARG | 523 | 70.536 | 72.058 | 64.564 | 1.00 | 60.00 |
| ATOM | 1623 | NE  | ARG | 523 | 71.636 | 73.041 | 64.343 | 1.00 | 60.00 |
| ATOM | 1624 | CZ  | ARG | 523 | 71.887 | 74.014 | 65.267 | 1.00 | 60.00 |
| ATOM | 1625 | NH1 | ARG | 523 | 71.129 | 74.090 | 66.400 | 1.00 | 60.00 |
| ATOM | 1626 | NH2 | ARG | 523 | 72.906 | 74.901 | 65.068 | 1.00 | 60.00 |
| ATOM | 1627 | N   | GLU | 524 | 71.410 | 67.395 | 65.334 | 1.00 | 60.00 |
| ATOM | 1628 | CA  | GLU | 524 | 72.537 | 67.073 | 66.160 | 1.00 | 60.00 |
| ATOM | 1629 | C   | GLU | 524 | 73.343 | 66.039 | 65.461 | 1.00 | 60.00 |
| ATOM | 1630 | O   | GLU | 524 | 74.560 | 66.165 | 65.332 | 1.00 | 60.00 |
| ATOM | 1631 | CB  | GLU | 524 | 72.162 | 66.483 | 67.533 | 1.00 | 60.00 |
| ATOM | 1632 | CG  | GLU | 524 | 71.570 | 67.491 | 68.523 | 1.00 | 60.00 |
| ATOM | 1633 | CD  | GLU | 524 | 70.085 | 67.643 | 68.235 | 1.00 | 60.00 |
| ATOM | 1634 | OE1 | GLU | 524 | 69.607 | 67.051 | 67.231 | 1.00 | 60.00 |
| ATOM | 1635 | OE2 | GLU | 524 | 69.406 | 68.354 | 69.023 | 1.00 | 60.00 |
| ATOM | 1636 | N   | PHE | 525 | 72.674 | 64.984 | 64.971 | 1.00 | 60.00 |
| ATOM | 1637 | CA  | PHE | 525 | 73.415 | 63.963 | 64.305 | 1.00 | 60.00 |
| ATOM | 1638 | C   | PHE | 525 | 73.617 | 64.492 | 62.925 | 1.00 | 60.00 |
| ATOM | 1639 | O   | PHE | 525 | 73.082 | 65.545 | 62.585 | 1.00 | 60.00 |
| ATOM | 1640 | CB  | PHE | 525 | 72.657 | 62.627 | 64.219 | 1.00 | 60.00 |
| ATOM | 1641 | CG  | PHE | 525 | 73.668 | 61.556 | 64.006 | 1.00 | 60.00 |
| ATOM | 1642 | CD1 | PHE | 525 | 74.325 | 61.016 | 65.090 | 1.00 | 60.00 |
| ATOM | 1643 | CD2 | PHE | 525 | 73.963 | 61.087 | 62.748 | 1.00 | 60.00 |
| ATOM | 1644 | CE1 | PHE | 525 | 75.264 | 60.028 | 64.924 | 1.00 | 60.00 |
| ATOM | 1645 | CE2 | PHE | 525 | 74.903 | 60.099 | 62.579 | 1.00 | 60.00 |
| ATOM | 1646 | CZ  | PHE | 525 | 75.555 | 59.567 | 63.664 | 1.00 | 60.00 |
| ATOM | 1647 | N   | VAL | 526 | 74.415 | 63.797 | 62.095 | 1.00 | 60.00 |
| ATOM | 1648 | CA  | VAL | 526 | 74.595 | 64.304 | 60.771 | 1.00 | 60.00 |
| ATOM | 1649 | C   | VAL | 526 | 73.243 | 64.306 | 60.144 | 1.00 | 60.00 |
| ATOM | 1650 | O   | VAL | 526 | 72.482 | 63.349 | 60.278 | 1.00 | 60.00 |
| ATOM | 1651 | CB  | VAL | 526 | 75.510 | 63.469 | 59.921 | 1.00 | 60.00 |
| ATOM | 1652 | CG1 | VAL | 526 | 75.562 | 64.081 | 58.511 | 1.00 | 60.00 |
| ATOM | 1653 | CG2 | VAL | 526 | 76.883 | 63.396 | 60.612 | 1.00 | 60.00 |

Figure 6A-52

| | | | | | | | | |
|---|---|---|---|---|---|---|---|---|
| ATOM | 1654 | N | GLU | 527 | 72.897 | 65.409 | 59.458 | 1.00 60.00 |
| ATOM | 1655 | CA | GLU | 527 | 71.597 | 65.488 | 58.869 | 1.00 60.00 |
| ATOM | 1656 | C | GLU | 527 | 71.514 | 64.370 | 57.891 | 1.00 60.00 |
| ATOM | 1657 | O | GLU | 527 | 70.545 | 63.613 | 57.861 | 1.00 60.00 |
| ATOM | 1658 | CB | GLU | 527 | 71.392 | 66.768 | 58.072 | 1.00 60.00 |
| ATOM | 1659 | CG | GLU | 527 | 71.414 | 68.055 | 58.928 | 1.00 60.00 |
| ATOM | 1660 | CD | GLU | 527 | 71.252 | 69.250 | 57.999 | 1.00 60.00 |
| ATOM | 1661 | OE1 | GLU | 527 | 71.035 | 69.028 | 56.770 | 1.00 60.00 |
| ATOM | 1662 | OE2 | GLU | 527 | 71.293 | 70.403 | 58.506 | 1.00 60.00 |
| ATOM | 1663 | N | ASN | 528 | 72.567 | 64.244 | 57.068 | 1.00 60.00 |
| ATOM | 1664 | CA | ASN | 528 | 72.618 | 63.234 | 56.060 | 1.00 60.00 |
| ATOM | 1665 | C | ASN | 528 | 72.710 | 61.890 | 56.701 | 1.00 60.00 |
| ATOM | 1666 | O | ASN | 528 | 72.087 | 60.941 | 56.241 | 1.00 60.00 |
| ATOM | 1667 | CB | ASN | 528 | 73.838 | 63.379 | 55.135 | 1.00 60.00 |
| ATOM | 1668 | CG | ASN | 528 | 73.641 | 64.626 | 54.287 | 1.00 60.00 |
| ATOM | 1669 | OD1 | ASN | 528 | 74.432 | 65.565 | 54.344 | 1.00 60.00 |
| ATOM | 1670 | ND2 | ASN | 528 | 72.552 | 64.636 | 53.473 | 1.00 60.00 |
| ATOM | 1671 | N | SER | 529 | 73.478 | 61.760 | 57.793 | 1.00 60.00 |
| ATOM | 1672 | CA | SER | 529 | 73.716 | 60.445 | 58.313 | 1.00 60.00 |
| ATOM | 1673 | C | SER | 529 | 72.448 | 59.746 | 58.702 | 1.00 60.00 |
| ATOM | 1674 | O | SER | 529 | 72.248 | 58.593 | 58.323 | 1.00 60.00 |
| ATOM | 1675 | CB | SER | 529 | 74.643 | 60.435 | 59.538 | 1.00 60.00 |
| ATOM | 1676 | OG | SER | 529 | 74.829 | 59.100 | 59.984 | 1.00 60.00 |
| ATOM | 1677 | N | GLU | 530 | 71.541 | 60.397 | 59.456 | 1.00 40.00 |
| ATOM | 1678 | CA | GLU | 530 | 70.397 | 59.636 | 59.881 | 1.00 40.00 |
| ATOM | 1679 | C | GLU | 530 | 69.179 | 60.502 | 59.862 | 1.00 40.00 |
| ATOM | 1680 | O | GLU | 530 | 69.253 | 61.698 | 59.585 | 1.00 40.00 |
| ATOM | 1681 | CB | GLU | 530 | 70.544 | 59.105 | 61.320 | 1.00 40.00 |
| ATOM | 1682 | CG | GLU | 530 | 69.478 | 58.092 | 61.745 | 1.00 40.00 |
| ATOM | 1683 | CD | GLU | 530 | 69.711 | 57.758 | 63.212 | 1.00 40.00 |
| ATOM | 1684 | OE1 | GLU | 530 | 70.606 | 58.395 | 63.829 | 1.00 40.00 |
| ATOM | 1685 | OE2 | GLU | 530 | 68.993 | 56.865 | 63.737 | 1.00 40.00 |
| ATOM | 1686 | N | CYS | 531 | 68.010 | 59.880 | 60.133 | 1.00 20.00 |
| ATOM | 1687 | CA | CYS | 531 | 66.759 | 60.567 | 60.248 | 1.00 20.00 |
| ATOM | 1688 | C | CYS | 531 | 66.246 | 60.216 | 61.610 | 1.00 20.00 |
| ATOM | 1689 | O | CYS | 531 | 66.410 | 59.086 | 62.065 | 1.00 20.00 |
| ATOM | 1690 | CB | CYS | 531 | 65.703 | 60.088 | 59.241 | 1.00 20.00 |
| ATOM | 1691 | SG | CYS | 531 | 66.199 | 60.382 | 57.521 | 1.00 20.00 |
| ATOM | 1692 | N | ILE | 532 | 65.626 | 61.184 | 62.311 | 1.00 20.00 |
| ATOM | 1693 | CA | ILE | 532 | 65.117 | 60.898 | 63.621 | 1.00 20.00 |
| ATOM | 1694 | C | ILE | 532 | 63.678 | 61.295 | 63.671 | 1.00 20.00 |
| ATOM | 1695 | O | ILE | 532 | 63.192 | 62.029 | 62.815 | 1.00 20.00 |
| ATOM | 1696 | CB | ILE | 532 | 65.823 | 61.617 | 64.733 | 1.00 20.00 |
| ATOM | 1697 | CG1 | ILE | 532 | 65.724 | 63.139 | 64.540 | 1.00 20.00 |
| ATOM | 1698 | CG2 | ILE | 532 | 67.251 | 61.058 | 64.841 | 1.00 20.00 |
| ATOM | 1699 | CD1 | ILE | 532 | 66.167 | 63.939 | 65.763 | 1.00 20.00 |
| ATOM | 1700 | N | GLN | 533 | 62.951 | 60.788 | 64.686 | 1.00 20.00 |
| ATOM | 1701 | CA | GLN | 533 | 61.553 | 61.067 | 64.813 | 1.00 20.00 |
| ATOM | 1702 | C | GLN | 533 | 61.371 | 62.413 | 65.417 | 1.00 20.00 |
| ATOM | 1703 | O | GLN | 533 | 62.119 | 62.823 | 66.302 | 1.00 20.00 |
| ATOM | 1704 | CB | GLN | 533 | 60.804 | 60.057 | 65.701 | 1.00 20.00 |
| ATOM | 1705 | CG | GLN | 533 | 60.794 | 58.634 | 65.136 | 1.00 20.00 |
| ATOM | 1706 | CD | GLN | 533 | 60.032 | 57.743 | 66.106 | 1.00 20.00 |
| ATOM | 1707 | OE1 | GLN | 533 | 60.333 | 57.691 | 67.296 | 1.00 20.00 |
| ATOM | 1708 | NE2 | GLN | 533 | 59.003 | 57.022 | 65.581 | 1.00 20.00 |
| ATOM | 1709 | N | CYS | 534 | 60.367 | 63.148 | 64.910 | 1.00 20.00 |
| ATOM | 1710 | CA | CYS | 534 | 60.022 | 64.403 | 65.495 | 1.00 20.00 |
| ATOM | 1711 | C | CYS | 534 | 58.574 | 64.280 | 65.865 | 1.00 20.00 |
| ATOM | 1712 | O | CYS | 534 | 57.948 | 63.256 | 65.598 | 1.00 20.00 |
| ATOM | 1713 | CB | CYS | 534 | 60.157 | 65.644 | 64.582 | 1.00 20.00 |
| ATOM | 1714 | SG | CYS | 534 | 61.866 | 66.147 | 64.183 | 1.00 20.00 |
| ATOM | 1715 | N | HIS | 535 | 58.003 | 65.315 | 66.513 | 1.00 20.00 |
| ATOM | 1716 | CA | HIS | 535 | 56.617 | 65.244 | 66.889 | 1.00 20.00 |
| ATOM | 1717 | C | HIS | 535 | 55.831 | 65.268 | 65.620 | 1.00 20.00 |
| ATOM | 1718 | O | HIS | 535 | 56.310 | 65.745 | 64.593 | 1.00 20.00 |
| ATOM | 1719 | CB | HIS | 535 | 56.161 | 66.422 | 67.770 | 1.00 20.00 |
| ATOM | 1720 | CG | HIS | 535 | 54.770 | 66.262 | 68.309 | 1.00 20.00 |
| ATOM | 1721 | ND1 | HIS | 535 | 53.636 | 66.718 | 67.675 | 1.00 20.00 |
| ATOM | 1722 | CD2 | HIS | 535 | 54.340 | 65.670 | 69.457 | 1.00 20.00 |
| ATOM | 1723 | CE1 | HIS | 535 | 52.584 | 66.382 | 68.464 | 1.00 20.00 |
| ATOM | 1724 | NE2 | HIS | 535 | 52.961 | 65.742 | 69.556 | 1.00 20.00 |
| ATOM | 1725 | N | PRO | 536 | 54.644 | 64.732 | 65.647 | 1.00 20.00 |
| ATOM | 1726 | CA | PRO | 536 | 53.823 | 64.689 | 64.473 | 1.00 20.00 |
| ATOM | 1727 | C | PRO | 536 | 53.461 | 66.068 | 64.022 | 1.00 20.00 |
| ATOM | 1728 | O | PRO | 536 | 53.280 | 66.271 | 62.822 | 1.00 20.00 |
| ATOM | 1729 | CB | PRO | 536 | 52.638 | 63.781 | 64.819 | 1.00 20.00 |
| ATOM | 1730 | CG | PRO | 536 | 52.756 | 63.534 | 66.338 | 1.00 20.00 |

Figure 6A-53

| | | | | | | | |
|---|---|---|---|---|---|---|---|
| ATOM | 1731 | CD | PRO | 536 | 54.250 | 63.742 | 66.631 | 1.00 20.00 |
| ATOM | 1732 | N | GLU | 537 | 53.317 | 67.015 | 64.965 | 1.00 20.00 |
| ATOM | 1733 | CA | GLU | 537 | 52.970 | 68.366 | 64.641 | 1.00 20.00 |
| ATOM | 1734 | C | GLU | 537 | 54.125 | 69.112 | 64.053 | 1.00 20.00 |
| ATOM | 1735 | O | GLU | 537 | 53.932 | 69.949 | 63.171 | 1.00 20.00 |
| ATOM | 1736 | CB | GLU | 537 | 52.434 | 69.166 | 65.841 | 1.00 20.00 |
| ATOM | 1737 | CG | GLU | 537 | 51.026 | 68.734 | 66.257 | 1.00 20.00 |
| ATOM | 1738 | CD | GLU | 537 | 50.080 | 69.061 | 65.105 | 1.00 20.00 |
| ATOM | 1739 | OE1 | GLU | 537 | 50.515 | 69.775 | 64.162 | 1.00 20.00 |
| ATOM | 1740 | OE2 | GLU | 537 | 48.909 | 68.599 | 65.152 | 1.00 20.00 |
| ATOM | 1741 | N | CYS | 538 | 55.359 | 68.847 | 64.529 | 1.00 20.00 |
| ATOM | 1742 | CA | CYS | 538 | 56.479 | 69.589 | 64.027 | 1.00 20.00 |
| ATOM | 1743 | C | CYS | 538 | 56.535 | 69.399 | 62.554 | 1.00 20.00 |
| ATOM | 1744 | O | CYS | 538 | 56.200 | 68.338 | 62.039 | 1.00 20.00 |
| ATOM | 1745 | CB | CYS | 538 | 57.849 | 69.144 | 64.565 | 1.00 20.00 |
| ATOM | 1746 | SG | CYS | 538 | 58.114 | 69.567 | 66.305 | 1.00 20.00 |
| ATOM | 1747 | N | LEU | 539 | 56.913 | 70.467 | 61.832 | 1.00 40.00 |
| ATOM | 1748 | CA | LEU | 539 | 57.049 | 70.324 | 60.421 | 1.00 40.00 |
| ATOM | 1749 | C | LEU | 539 | 58.462 | 70.668 | 60.113 | 1.00 40.00 |
| ATOM | 1750 | O | LEU | 539 | 58.920 | 71.783 | 60.360 | 1.00 40.00 |
| ATOM | 1751 | CB | LEU | 539 | 56.156 | 71.279 | 59.613 | 1.00 40.00 |
| ATOM | 1752 | CG | LEU | 539 | 56.308 | 71.113 | 58.090 | 1.00 40.00 |
| ATOM | 1753 | CD1 | LEU | 539 | 55.841 | 69.723 | 57.627 | 1.00 40.00 |
| ATOM | 1754 | CD2 | LEU | 539 | 55.618 | 72.257 | 57.330 | 1.00 40.00 |
| ATOM | 1755 | N | PRO | 540 | 59.166 | 69.715 | 59.576 | 1.00 60.00 |
| ATOM | 1756 | CA | PRO | 540 | 60.536 | 69.937 | 59.213 | 1.00 60.00 |
| ATOM | 1757 | C | PRO | 540 | 60.630 | 70.650 | 57.905 | 1.00 60.00 |
| ATOM | 1758 | O | PRO | 540 | 59.692 | 70.573 | 57.113 | 1.00 60.00 |
| ATOM | 1759 | CB | PRO | 540 | 61.209 | 68.561 | 59.211 | 1.00 60.00 |
| ATOM | 1760 | CG | PRO | 540 | 60.042 | 67.557 | 59.204 | 1.00 60.00 |
| ATOM | 1761 | CD | PRO | 540 | 58.906 | 68.323 | 59.898 | 1.00 60.00 |
| ATOM | 1762 | N | GLN | 541 | 61.752 | 71.357 | 57.667 | 1.00 60.00 |
| ATOM | 1763 | CA | GLN | 541 | 61.955 | 72.030 | 56.420 | 1.00 60.00 |
| ATOM | 1764 | C | GLN | 541 | 63.198 | 71.447 | 55.840 | 1.00 60.00 |
| ATOM | 1765 | O | GLN | 541 | 64.142 | 71.139 | 56.564 | 1.00 60.00 |
| ATOM | 1766 | CB | GLN | 541 | 62.188 | 73.543 | 56.560 | 1.00 60.00 |
| ATOM | 1767 | CG | GLN | 541 | 60.949 | 74.310 | 57.026 | 1.00 60.00 |
| ATOM | 1768 | CD | GLN | 541 | 59.944 | 74.291 | 55.883 | 1.00 60.00 |
| ATOM | 1769 | OE1 | GLN | 541 | 59.626 | 73.234 | 55.340 | 1.00 60.00 |
| ATOM | 1770 | NE2 | GLN | 541 | 59.436 | 75.492 | 55.500 | 1.00 60.00 |
| ATOM | 1771 | N | ALA | 542 | 63.223 | 71.245 | 54.511 | 1.00 60.00 |
| ATOM | 1772 | CA | ALA | 542 | 64.400 | 70.665 | 53.941 | 1.00 60.00 |
| ATOM | 1773 | C | ALA | 542 | 65.538 | 71.612 | 54.146 | 1.00 60.00 |
| ATOM | 1774 | O | ALA | 542 | 66.570 | 71.247 | 54.706 | 1.00 60.00 |
| ATOM | 1775 | CB | ALA | 542 | 64.271 | 70.421 | 52.428 | 1.00 60.00 |
| ATOM | 1776 | N | MET | 543 | 65.368 | 72.872 | 53.701 | 1.00 60.00 |
| ATOM | 1777 | CA | MET | 543 | 66.419 | 73.835 | 53.841 | 1.00 60.00 |
| ATOM | 1778 | C | MET | 543 | 66.577 | 74.177 | 55.283 | 1.00 60.00 |
| ATOM | 1779 | O | MET | 543 | 67.692 | 74.256 | 55.799 | 1.00 60.00 |
| ATOM | 1780 | CB | MET | 543 | 66.151 | 75.148 | 53.086 | 1.00 60.00 |
| ATOM | 1781 | CG | MET | 543 | 67.326 | 76.128 | 53.160 | 1.00 60.00 |
| ATOM | 1782 | SD | MET | 543 | 67.069 | 77.701 | 52.287 | 1.00 60.00 |
| ATOM | 1783 | CE | MET | 543 | 68.699 | 78.380 | 52.710 | 1.00 60.00 |
| ATOM | 1784 | N | ASN | 544 | 65.443 | 74.378 | 55.976 | 1.00 60.00 |
| ATOM | 1785 | CA | ASN | 544 | 65.489 | 74.780 | 57.349 | 1.00 60.00 |
| ATOM | 1786 | C | ASN | 544 | 65.876 | 73.603 | 58.174 | 1.00 60.00 |
| ATOM | 1787 | O | ASN | 544 | 65.982 | 72.482 | 57.681 | 1.00 60.00 |
| ATOM | 1788 | CB | ASN | 544 | 64.147 | 75.310 | 57.883 | 1.00 60.00 |
| ATOM | 1789 | CG | ASN | 544 | 63.857 | 76.629 | 57.180 | 1.00 60.00 |
| ATOM | 1790 | OD1 | ASN | 544 | 63.812 | 76.694 | 55.952 | 1.00 60.00 |
| ATOM | 1791 | ND2 | ASN | 544 | 63.657 | 77.711 | 57.977 | 1.00 60.00 |
| ATOM | 1792 | N | ILE | 545 | 66.130 | 73.853 | 59.470 | 1.00 60.00 |
| ATOM | 1793 | CA | ILE | 545 | 66.510 | 72.802 | 60.358 | 1.00 60.00 |
| ATOM | 1794 | C | ILE | 545 | 65.274 | 72.045 | 60.699 | 1.00 60.00 |
| ATOM | 1795 | O | ILE | 545 | 64.176 | 72.384 | 60.262 | 1.00 60.00 |
| ATOM | 1796 | CB | ILE | 545 | 67.099 | 73.290 | 61.649 | 1.00 60.00 |
| ATOM | 1797 | CG1 | ILE | 545 | 66.061 | 74.113 | 62.430 | 1.00 60.00 |
| ATOM | 1798 | CG2 | ILE | 545 | 68.389 | 74.064 | 61.325 | 1.00 60.00 |
| ATOM | 1799 | CD1 | ILE | 545 | 66.466 | 74.394 | 63.876 | 1.00 60.00 |
| ATOM | 1800 | N | THR | 546 | 65.441 | 70.974 | 61.493 | 1.00 40.00 |
| ATOM | 1801 | CA | THR | 546 | 64.335 | 70.165 | 61.904 | 1.00 40.00 |
| ATOM | 1802 | C | THR | 546 | 64.243 | 70.322 | 63.381 | 1.00 40.00 |
| ATOM | 1803 | O | THR | 546 | 64.991 | 71.105 | 63.966 | 1.00 40.00 |
| ATOM | 1804 | CB | THR | 546 | 64.522 | 68.703 | 61.620 | 1.00 40.00 |
| ATOM | 1805 | OG1 | THR | 546 | 63.322 | 67.992 | 61.887 | 1.00 40.00 |
| ATOM | 1806 | CG2 | THR | 546 | 65.667 | 68.171 | 62.499 | 1.00 40.00 |
| ATOM | 1807 | N | CYS | 547 | 63.289 | 69.606 | 64.012 | 1.00 20.00 |

Figure 6A-54

| ATOM | 1808 | CA | CYS | 547 | 63.128 | 69.673 | 65.427 | 1.00 | 20.00 |
| ATOM | 1809 | C | CYS | 547 | 64.449 | 69.456 | 66.074 | 1.00 | 20.00 |
| ATOM | 1810 | O | CYS | 547 | 65.209 | 68.567 | 65.694 | 1.00 | 20.00 |
| ATOM | 1811 | CB | CYS | 547 | 62.115 | 68.643 | 65.958 | 1.00 | 20.00 |
| ATOM | 1812 | SG | CYS | 547 | 62.634 | 66.895 | 65.919 | 1.00 | 20.00 |
| ATOM | 1813 | N | THR | 548 | 64.765 | 70.309 | 67.067 | 1.00 | 20.00 |
| ATOM | 1814 | CA | THR | 548 | 66.007 | 70.178 | 67.764 | 1.00 | 20.00 |
| ATOM | 1815 | C | THR | 548 | 65.964 | 68.871 | 68.481 | 1.00 | 20.00 |
| ATOM | 1816 | O | THR | 548 | 66.935 | 68.114 | 68.464 | 1.00 | 20.00 |
| ATOM | 1817 | CB | THR | 548 | 66.227 | 71.258 | 68.783 | 1.00 | 20.00 |
| ATOM | 1818 | OG1 | THR | 548 | 66.223 | 72.530 | 68.153 | 1.00 | 20.00 |
| ATOM | 1819 | CG2 | THR | 548 | 67.582 | 71.015 | 69.470 | 1.00 | 20.00 |
| ATOM | 1820 | N | GLY | 549 | 64.808 | 68.565 | 69.096 | 1.00 | 20.00 |
| ATOM | 1821 | CA | GLY | 549 | 64.662 | 67.326 | 69.797 | 1.00 | 20.00 |
| ATOM | 1822 | C | GLY | 549 | 63.215 | 66.988 | 69.737 | 1.00 | 20.00 |
| ATOM | 1823 | O | GLY | 549 | 62.392 | 67.828 | 69.376 | 1.00 | 20.00 |
| ATOM | 1824 | N | ARG | 550 | 62.850 | 65.740 | 70.091 | 1.00 | 20.00 |
| ATOM | 1825 | CA | ARG | 550 | 61.455 | 65.449 | 70.004 | 1.00 | 20.00 |
| ATOM | 1826 | C | ARG | 550 | 60.772 | 66.258 | 71.052 | 1.00 | 20.00 |
| ATOM | 1827 | O | ARG | 550 | 61.294 | 66.467 | 72.146 | 1.00 | 20.00 |
| ATOM | 1828 | CB | ARG | 550 | 61.080 | 63.967 | 70.173 | 1.00 | 20.00 |
| ATOM | 1829 | CG | ARG | 550 | 61.455 | 63.132 | 68.947 | 1.00 | 20.00 |
| ATOM | 1830 | CD | ARG | 550 | 60.714 | 61.798 | 68.835 | 1.00 | 20.00 |
| ATOM | 1831 | NE | ARG | 550 | 61.225 | 60.868 | 69.897 | 1.00 | 20.00 |
| ATOM | 1832 | CZ | ARG | 550 | 60.590 | 59.702 | 70.129 | 1.00 | 20.00 |
| ATOM | 1833 | NH1 | ARG | 550 | 59.473 | 59.377 | 69.414 | 1.00 | 20.00 |
| ATOM | 1834 | NH2 | ARG | 550 | 61.072 | 58.842 | 71.073 | 1.00 | 20.00 |
| ATOM | 1835 | N | GLY | 551 | 59.575 | 66.762 | 70.706 | 1.00 | 20.00 |
| ATOM | 1836 | CA | GLY | 551 | 58.803 | 67.591 | 71.578 | 1.00 | 20.00 |
| ATOM | 1837 | C | GLY | 551 | 58.177 | 68.610 | 70.684 | 1.00 | 20.00 |
| ATOM | 1838 | O | GLY | 551 | 58.788 | 69.056 | 69.715 | 1.00 | 20.00 |
| ATOM | 1839 | N | PRO | 552 | 56.968 | 68.981 | 70.986 | 1.00 | 20.00 |
| ATOM | 1840 | CA | PRO | 552 | 56.283 | 69.935 | 70.152 | 1.00 | 20.00 |
| ATOM | 1841 | C | PRO | 552 | 56.820 | 71.333 | 70.250 | 1.00 | 20.00 |
| ATOM | 1842 | O | PRO | 552 | 56.470 | 72.163 | 69.411 | 1.00 | 20.00 |
| ATOM | 1843 | CB | PRO | 552 | 54.804 | 69.819 | 70.517 | 1.00 | 20.00 |
| ATOM | 1844 | CG | PRO | 552 | 54.662 | 68.367 | 71.004 | 1.00 | 20.00 |
| ATOM | 1845 | CD | PRO | 552 | 56.047 | 68.021 | 71.575 | 1.00 | 20.00 |
| ATOM | 1846 | N | ASP | 553 | 57.596 | 71.636 | 71.304 | 1.00 | 20.00 |
| ATOM | 1847 | CA | ASP | 553 | 58.187 | 72.933 | 71.507 | 1.00 | 20.00 |
| ATOM | 1848 | C | ASP | 553 | 59.368 | 73.115 | 70.593 | 1.00 | 20.00 |
| ATOM | 1849 | O | ASP | 553 | 59.695 | 74.227 | 70.184 | 1.00 | 20.00 |
| ATOM | 1850 | CB | ASP | 553 | 58.699 | 73.113 | 72.947 | 1.00 | 20.00 |
| ATOM | 1851 | CG | ASP | 553 | 59.092 | 74.568 | 73.163 | 1.00 | 20.00 |
| ATOM | 1852 | OD1 | ASP | 553 | 58.823 | 75.401 | 72.258 | 1.00 | 20.00 |
| ATOM | 1853 | OD2 | ASP | 553 | 59.672 | 74.864 | 74.242 | 1.00 | 20.00 |
| ATOM | 1854 | N | ASN | 554 | 60.057 | 72.005 | 70.285 | 1.00 | 20.00 |
| ATOM | 1855 | CA | ASN | 554 | 61.301 | 71.977 | 69.561 | 1.00 | 20.00 |
| ATOM | 1856 | C | ASN | 554 | 61.192 | 72.331 | 68.103 | 1.00 | 20.00 |
| ATOM | 1857 | O | ASN | 554 | 62.185 | 72.744 | 67.505 | 1.00 | 20.00 |
| ATOM | 1858 | CB | ASN | 554 | 62.017 | 70.621 | 69.675 | 1.00 | 20.00 |
| ATOM | 1859 | CG | ASN | 554 | 62.557 | 70.517 | 71.096 | 1.00 | 20.00 |
| ATOM | 1860 | OD1 | ASN | 554 | 62.766 | 71.528 | 71.762 | 1.00 | 20.00 |
| ATOM | 1861 | ND2 | ASN | 554 | 62.799 | 69.268 | 71.576 | 1.00 | 20.00 |
| ATOM | 1862 | N | CYS | 555 | 60.005 | 72.158 | 67.492 | 1.00 | 20.00 |
| ATOM | 1863 | CA | CYS | 555 | 59.774 | 72.307 | 66.076 | 1.00 | 20.00 |
| ATOM | 1864 | C | CYS | 555 | 60.501 | 73.479 | 65.475 | 1.00 | 20.00 |
| ATOM | 1865 | O | CYS | 555 | 60.788 | 74.475 | 66.138 | 1.00 | 20.00 |
| ATOM | 1866 | CB | CYS | 555 | 58.295 | 72.537 | 65.726 | 1.00 | 20.00 |
| ATOM | 1867 | SG | CYS | 555 | 57.153 | 71.342 | 66.478 | 1.00 | 20.00 |
| ATOM | 1868 | N | ILE | 556 | 60.926 | 73.314 | 64.200 | 1.00 | 20.00 |
| ATOM | 1869 | CA | ILE | 556 | 61.457 | 74.384 | 63.404 | 1.00 | 20.00 |
| ATOM | 1870 | C | ILE | 556 | 60.290 | 75.190 | 62.924 | 1.00 | 20.00 |
| ATOM | 1871 | O | ILE | 556 | 60.341 | 76.418 | 62.877 | 1.00 | 20.00 |
| ATOM | 1872 | CB | ILE | 556 | 62.242 | 73.889 | 62.210 | 1.00 | 20.00 |
| ATOM | 1873 | CG1 | ILE | 556 | 62.951 | 75.036 | 61.457 | 1.00 | 20.00 |
| ATOM | 1874 | CG2 | ILE | 556 | 61.312 | 73.038 | 61.328 | 1.00 | 20.00 |
| ATOM | 1875 | CD1 | ILE | 556 | 62.039 | 76.016 | 60.716 | 1.00 | 20.00 |
| ATOM | 1876 | N | GLN | 557 | 59.210 | 74.481 | 62.533 | 1.00 | 20.00 |
| ATOM | 1877 | CA | GLN | 557 | 58.009 | 75.077 | 62.030 | 1.00 | 20.00 |
| ATOM | 1878 | C | GLN | 557 | 56.885 | 74.165 | 62.400 | 1.00 | 20.00 |
| ATOM | 1879 | O | GLN | 557 | 57.118 | 73.059 | 62.886 | 1.00 | 20.00 |
| ATOM | 1880 | CB | GLN | 557 | 57.980 | 75.245 | 60.502 | 1.00 | 20.00 |
| ATOM | 1881 | CG | GLN | 557 | 58.907 | 76.347 | 59.987 | 1.00 | 20.00 |
| ATOM | 1882 | CD | GLN | 557 | 58.316 | 77.684 | 60.415 | 1.00 | 20.00 |
| ATOM | 1883 | OE1 | GLN | 557 | 58.218 | 77.983 | 61.604 | 1.00 | 20.00 |
| ATOM | 1884 | NE2 | GLN | 557 | 57.905 | 78.513 | 59.418 | 1.00 | 20.00 |

Figure 6A-55

| ATOM | 1885 | N | CYS | 558 | 55.629 | 74.610 | 62.174 | 1.00 | 20.00 |
|------|------|-----|-----|-----|--------|--------|--------|------|-------|
| ATOM | 1886 | CA | CYS | 558 | 54.560 | 73.819 | 62.573 | 1.00 | 20.00 |
| ATOM | 1887 | C | CYS | 558 | 53.792 | 73.313 | 61.357 | 1.00 | 20.00 |
| ATOM | 1888 | O | CYS | 558 | 53.817 | 73.939 | 60.300 | 1.00 | 20.00 |
| ATOM | 1889 | CB | CYS | 558 | 53.471 | 74.597 | 63.409 | 1.00 | 20.00 |
| ATOM | 1890 | SG | CYS | 558 | 54.165 | 75.235 | 64.962 | 1.00 | 20.00 |
| ATOM | 1891 | N | ALA | 559 | 53.193 | 72.110 | 61.481 | 1.00 | 20.00 |
| ATOM | 1892 | CA | ALA | 559 | 52.433 | 71.512 | 60.421 | 1.00 | 20.00 |
| ATOM | 1893 | C | ALA | 559 | 51.170 | 72.289 | 60.250 | 1.00 | 20.00 |
| ATOM | 1894 | O | ALA | 559 | 50.742 | 72.573 | 59.131 | 1.00 | 20.00 |
| ATOM | 1895 | CB | ALA | 559 | 52.042 | 70.055 | 60.721 | 1.00 | 20.00 |
| ATOM | 1896 | N | HIS | 560 | 50.557 | 72.673 | 61.384 | 1.00 | 20.00 |
| ATOM | 1897 | CA | HIS | 560 | 49.297 | 73.354 | 61.380 | 1.00 | 20.00 |
| ATOM | 1898 | C | HIS | 560 | 49.537 | 74.749 | 61.865 | 1.00 | 20.00 |
| ATOM | 1899 | O | HIS | 560 | 50.199 | 75.540 | 61.195 | 1.00 | 20.00 |
| ATOM | 1900 | CB | HIS | 560 | 48.260 | 72.703 | 62.312 | 1.00 | 20.00 |
| ATOM | 1901 | CG | HIS | 560 | 47.829 | 71.346 | 61.836 | 1.00 | 20.00 |
| ATOM | 1902 | ND1 | HIS | 560 | 48.565 | 70.196 | 62.010 | 1.00 | 20.00 |
| ATOM | 1903 | CD2 | HIS | 560 | 46.704 | 70.969 | 61.168 | 1.00 | 20.00 |
| ATOM | 1904 | CE1 | HIS | 560 | 47.856 | 69.187 | 61.443 | 1.00 | 20.00 |
| ATOM | 1905 | NE2 | HIS | 560 | 46.718 | 69.609 | 60.918 | 1.00 | 20.00 |
| ATOM | 1906 | N | TYR | 561 | 48.982 | 75.094 | 63.045 | 1.00 | 20.00 |
| ATOM | 1907 | CA | TYR | 561 | 49.080 | 76.440 | 63.536 | 1.00 | 20.00 |
| ATOM | 1908 | C | TYR | 561 | 49.975 | 76.468 | 64.736 | 1.00 | 20.00 |
| ATOM | 1909 | O | TYR | 561 | 49.969 | 75.545 | 65.548 | 1.00 | 20.00 |
| ATOM | 1910 | CB | TYR | 561 | 47.728 | 77.000 | 64.014 | 1.00 | 20.00 |
| ATOM | 1911 | CG | TYR | 561 | 46.778 | 76.861 | 62.878 | 1.00 | 20.00 |
| ATOM | 1912 | CD1 | TYR | 561 | 46.145 | 75.658 | 62.667 | 1.00 | 20.00 |
| ATOM | 1913 | CD2 | TYR | 561 | 46.518 | 77.912 | 62.029 | 1.00 | 20.00 |
| ATOM | 1914 | CE1 | TYR | 561 | 45.264 | 75.499 | 61.624 | 1.00 | 20.00 |
| ATOM | 1915 | CE2 | TYR | 561 | 45.637 | 77.759 | 60.984 | 1.00 | 20.00 |
| ATOM | 1916 | CZ | TYR | 561 | 45.010 | 76.553 | 60.780 | 1.00 | 20.00 |
| ATOM | 1917 | OH | TYR | 561 | 44.107 | 76.394 | 59.708 | 1.00 | 20.00 |
| ATOM | 1918 | N | ILE | 562 | 50.766 | 77.552 | 64.886 | 1.00 | 20.00 |
| ATOM | 1919 | CA | ILE | 562 | 51.630 | 77.640 | 66.027 | 1.00 | 20.00 |
| ATOM | 1920 | C | ILE | 562 | 50.986 | 78.554 | 67.021 | 1.00 | 20.00 |
| ATOM | 1921 | O | ILE | 562 | 50.464 | 79.608 | 66.661 | 1.00 | 20.00 |
| ATOM | 1922 | CB | ILE | 562 | 53.000 | 78.178 | 65.724 | 1.00 | 20.00 |
| ATOM | 1923 | CG1 | ILE | 562 | 53.943 | 77.938 | 66.915 | 1.00 | 20.00 |
| ATOM | 1924 | CG2 | ILE | 562 | 52.865 | 79.656 | 65.332 | 1.00 | 20.00 |
| ATOM | 1925 | CD1 | ILE | 562 | 55.414 | 78.191 | 66.591 | 1.00 | 20.00 |
| ATOM | 1926 | N | ASP | 563 | 50.977 | 78.148 | 68.306 | 1.00 | 20.00 |
| ATOM | 1927 | CA | ASP | 563 | 50.359 | 78.961 | 69.312 | 1.00 | 20.00 |
| ATOM | 1928 | C | ASP | 563 | 51.118 | 78.819 | 70.593 | 1.00 | 20.00 |
| ATOM | 1929 | O | ASP | 563 | 51.329 | 77.697 | 71.049 | 1.00 | 20.00 |
| ATOM | 1930 | CB | ASP | 563 | 48.917 | 78.525 | 69.625 | 1.00 | 20.00 |
| ATOM | 1931 | CG | ASP | 563 | 48.364 | 79.426 | 70.722 | 1.00 | 20.00 |
| ATOM | 1932 | OD1 | ASP | 563 | 48.956 | 80.511 | 70.959 | 1.00 | 20.00 |
| ATOM | 1933 | OD2 | ASP | 563 | 47.343 | 79.032 | 71.348 | 1.00 | 20.00 |
| ATOM | 1934 | N | GLY | 564 | 51.509 | 79.966 | 71.206 | 1.00 | 20.00 |
| ATOM | 1935 | CA | GLY | 564 | 52.211 | 79.995 | 72.467 | 1.00 | 20.00 |
| ATOM | 1936 | C | GLY | 564 | 53.301 | 78.980 | 72.392 | 1.00 | 20.00 |
| ATOM | 1937 | O | GLY | 564 | 53.162 | 77.898 | 72.958 | 1.00 | 20.00 |
| ATOM | 1938 | N | PRO | 565 | 54.393 | 79.407 | 71.797 | 1.00 | 20.00 |
| ATOM | 1939 | CA | PRO | 565 | 55.444 | 78.525 | 71.327 | 1.00 | 20.00 |
| ATOM | 1940 | C | PRO | 565 | 55.183 | 77.051 | 71.369 | 1.00 | 20.00 |
| ATOM | 1941 | O | PRO | 565 | 56.038 | 76.285 | 71.810 | 1.00 | 20.00 |
| ATOM | 1942 | CB | PRO | 565 | 56.737 | 78.955 | 72.028 | 1.00 | 20.00 |
| ATOM | 1943 | CG | PRO | 565 | 56.299 | 80.027 | 73.038 | 1.00 | 20.00 |
| ATOM | 1944 | CD | PRO | 565 | 54.984 | 80.559 | 72.457 | 1.00 | 20.00 |
| ATOM | 1945 | N | HIS | 566 | 54.017 | 76.632 | 70.833 | 1.00 | 20.00 |
| ATOM | 1946 | CA | HIS | 566 | 53.689 | 75.240 | 70.771 | 1.00 | 20.00 |
| ATOM | 1947 | C | HIS | 566 | 53.069 | 75.013 | 69.432 | 1.00 | 20.00 |
| ATOM | 1948 | O | HIS | 566 | 52.273 | 75.826 | 68.964 | 1.00 | 20.00 |
| ATOM | 1949 | CB | HIS | 566 | 52.668 | 74.807 | 71.837 | 1.00 | 20.00 |
| ATOM | 1950 | CG | HIS | 566 | 52.550 | 73.319 | 71.982 | 1.00 | 20.00 |
| ATOM | 1951 | ND1 | HIS | 566 | 53.361 | 72.562 | 72.797 | 1.00 | 20.00 |
| ATOM | 1952 | CD2 | HIS | 566 | 51.688 | 72.444 | 71.397 | 1.00 | 20.00 |
| ATOM | 1953 | CE1 | HIS | 566 | 52.953 | 71.274 | 72.668 | 1.00 | 20.00 |
| ATOM | 1954 | NE2 | HIS | 566 | 51.940 | 71.153 | 71.829 | 1.00 | 20.00 |
| ATOM | 1955 | N | CYS | 567 | 53.417 | 73.895 | 68.765 | 1.00 | 20.00 |
| ATOM | 1956 | CA | CYS | 567 | 52.825 | 73.660 | 67.483 | 1.00 | 20.00 |
| ATOM | 1957 | C | CYS | 567 | 51.523 | 72.988 | 67.727 | 1.00 | 20.00 |
| ATOM | 1958 | O | CYS | 567 | 51.485 | 71.875 | 68.251 | 1.00 | 20.00 |
| ATOM | 1959 | CB | CYS | 567 | 53.639 | 72.751 | 66.551 | 1.00 | 20.00 |
| ATOM | 1960 | SG | CYS | 567 | 55.046 | 73.611 | 65.799 | 1.00 | 20.00 |
| ATOM | 1961 | N | VAL | 568 | 50.416 | 73.658 | 67.340 | 1.00 | 20.00 |

Figure 6A-56

```
ATOM   1962  CA   VAL   568      49.128  73.100  67.619  1.00 20.00
ATOM   1963  C    VAL   568      48.478  72.735  66.317  1.00 20.00
ATOM   1964  O    VAL   568      48.734  73.341  65.278  1.00 20.00
ATOM   1965  CB   VAL   568      48.227  74.019  68.381  1.00 20.00
ATOM   1966  CG1  VAL   568      46.905  73.276  68.605  1.00 20.00
ATOM   1967  CG2  VAL   568      48.932  74.455  69.676  1.00 20.00
ATOM   1968  N    LYS   569      47.655  71.664  66.351  1.00 20.00
ATOM   1969  CA   LYS   569      46.930  71.150  65.220  1.00 20.00
ATOM   1970  C    LYS   569      45.838  72.095  64.828  1.00 20.00
ATOM   1971  O    LYS   569      45.511  72.223  63.648  1.00 20.00
ATOM   1972  CB   LYS   569      46.257  69.797  65.513  1.00 20.00
ATOM   1973  CG   LYS   569      45.478  69.230  64.323  1.00 20.00
ATOM   1974  CD   LYS   569      45.008  67.788  64.523  1.00 20.00
ATOM   1975  CE   LYS   569      44.141  67.257  63.377  1.00 20.00
ATOM   1976  NZ   LYS   569      43.723  65.865  63.661  1.00 20.00
ATOM   1977  N    THR   570      45.197  72.738  65.823  1.00 20.00
ATOM   1978  CA   THR   570      44.134  73.648  65.517  1.00 20.00
ATOM   1979  C    THR   570      44.127  74.693  66.581  1.00 20.00
ATOM   1980  O    THR   570      44.661  74.502  67.668  1.00 20.00
ATOM   1981  CB   THR   570      42.779  73.003  65.508  1.00 20.00
ATOM   1982  OG1  THR   570      42.471  72.494  66.798  1.00 20.00
ATOM   1983  CG2  THR   570      42.782  71.864  64.475  1.00 20.00
ATOM   1984  N    CYS   571      43.504  75.843  66.293  1.00 20.00
ATOM   1985  CA   CYS   571      43.476  76.920  67.234  1.00 20.00
ATOM   1986  C    CYS   571      42.741  76.508  68.472  1.00 20.00
ATOM   1987  O    CYS   571      41.757  75.772  68.441  1.00 20.00
ATOM   1988  CB   CYS   571      42.716  78.132  66.691  1.00 20.00
ATOM   1989  SG   CYS   571      43.685  79.164  65.569  1.00 20.00
ATOM   1990  N    PRO   572      43.235  77.006  69.573  1.00 20.00
ATOM   1991  CA   PRO   572      42.619  76.788  70.856  1.00 20.00
ATOM   1992  C    PRO   572      41.430  77.693  70.943  1.00 20.00
ATOM   1993  O    PRO   572      41.348  78.636  70.160  1.00 20.00
ATOM   1994  CB   PRO   572      43.697  77.075  71.902  1.00 20.00
ATOM   1995  CG   PRO   572      44.798  77.823  71.132  1.00 20.00
ATOM   1996  CD   PRO   572      44.649  77.315  69.690  1.00 20.00
ATOM   1997  N    ALA   573      40.498  77.433  71.881  1.00 20.00
ATOM   1998  CA   ALA   573      39.307  78.232  71.961  1.00 20.00
ATOM   1999  C    ALA   573      39.668  79.625  72.367  1.00 20.00
ATOM   2000  O    ALA   573      40.596  79.845  73.141  1.00 20.00
ATOM   2001  CB   ALA   573      38.277  77.700  72.974  1.00 20.00
ATOM   2002  N    GLY   574      38.937  80.611  71.805  1.00 20.00
ATOM   2003  CA   GLY   574      39.109  81.993  72.150  1.00 20.00
ATOM   2004  C    GLY   574      40.195  82.578  71.310  1.00 20.00
ATOM   2005  O    GLY   574      40.421  83.788  71.337  1.00 20.00
ATOM   2006  N    VAL   575      40.903  81.741  70.531  1.00 20.00
ATOM   2007  CA   VAL   575      41.961  82.289  69.736  1.00 20.00
ATOM   2008  C    VAL   575      41.649  81.875  68.326  1.00 20.00
ATOM   2009  O    VAL   575      41.123  80.787  68.100  1.00 20.00
ATOM   2010  CB   VAL   575      43.302  81.755  70.158  1.00 20.00
ATOM   2011  CG1  VAL   575      44.403  82.365  69.285  1.00 20.00
ATOM   2012  CG2  VAL   575      43.480  82.030  71.660  1.00 20.00
ATOM   2013  N    MET   576      41.928  82.748  67.334  1.00 20.00
ATOM   2014  CA   MET   576      41.583  82.424  65.978  1.00 20.00
ATOM   2015  C    MET   576      42.802  82.464  65.123  1.00 20.00
ATOM   2016  O    MET   576      43.766  83.166  65.416  1.00 20.00
ATOM   2017  CB   MET   576      40.556  83.382  65.350  1.00 20.00
ATOM   2018  CG   MET   576      40.195  83.020  63.907  1.00 20.00
ATOM   2019  SD   MET   576      38.885  84.044  63.171  1.00 20.00
ATOM   2020  CE   MET   576      37.528  83.205  64.039  1.00 20.00
ATOM   2021  N    GLY   577      42.786  81.678  64.030  1.00 20.00
ATOM   2022  CA   GLY   577      43.921  81.593  63.165  1.00 20.00
ATOM   2023  C    GLY   577      44.090  82.900  62.474  1.00 20.00
ATOM   2024  O    GLY   577      43.127  83.494  61.989  1.00 20.00
ATOM   2025  N    GLU   578      45.343  83.379  62.371  1.00 40.00
ATOM   2026  CA   GLU   578      45.547  84.629  61.705  1.00 40.00
ATOM   2027  C    GLU   578      45.290  84.395  60.256  1.00 40.00
ATOM   2028  O    GLU   578      45.577  83.321  59.729  1.00 40.00
ATOM   2029  CB   GLU   578      46.973  85.187  61.850  1.00 40.00
ATOM   2030  CG   GLU   578      47.160  86.558  61.196  1.00 40.00
ATOM   2031  CD   GLU   578      48.604  86.987  61.414  1.00 40.00
ATOM   2032  OE1  GLU   578      49.512  86.143  61.187  1.00 40.00
ATOM   2033  OE2  GLU   578      48.818  88.162  61.816  1.00 40.00
ATOM   2034  N    ASN   579      44.716  85.402  59.571  1.00 60.00
ATOM   2035  CA   ASN   579      44.440  85.235  58.178  1.00 60.00
ATOM   2036  C    ASN   579      45.210  86.275  57.439  1.00 60.00
ATOM   2037  O    ASN   579      45.442  87.373  57.943  1.00 60.00
ATOM   2038  CB   ASN   579      42.958  85.427  57.811  1.00 60.00
```

Figure 6A-57

| | | | | | | | | |
|---|---|---|---|---|---|---|---|---|
| ATOM | 2039 | CG | ASN | 579 | 42.172 | 84.264 | 58.397 | 1.00 60.00 |
| ATOM | 2040 | OD1 | ASN | 579 | 42.728 | 83.211 | 58.705 | 1.00 60.00 |
| ATOM | 2041 | ND2 | ASN | 579 | 40.834 | 84.454 | 58.548 | 1.00 60.00 |
| ATOM | 2042 | N | ASN | 580 | 45.637 | 85.936 | 56.210 | 1.00 60.00 |
| ATOM | 2043 | CA | ASN | 580 | 46.365 | 86.867 | 55.405 | 1.00 60.00 |
| ATOM | 2044 | C | ASN | 580 | 45.562 | 87.066 | 54.165 | 1.00 60.00 |
| ATOM | 2045 | O | ASN | 580 | 44.794 | 86.193 | 53.764 | 1.00 60.00 |
| ATOM | 2046 | CB | ASN | 580 | 47.759 | 86.367 | 54.990 | 1.00 60.00 |
| ATOM | 2047 | CG | ASN | 580 | 48.640 | 86.362 | 56.231 | 1.00 60.00 |
| ATOM | 2048 | OD1 | ASN | 580 | 48.848 | 87.397 | 56.864 | 1.00 60.00 |
| ATOM | 2049 | ND2 | ASN | 580 | 49.170 | 85.165 | 56.599 | 1.00 60.00 |
| ATOM | 2050 | N | THR | 581 | 45.706 | 88.244 | 53.532 | 1.00 60.00 |
| ATOM | 2051 | CA | THR | 581 | 44.944 | 88.510 | 52.352 | 1.00 60.00 |
| ATOM | 2052 | C | THR | 581 | 45.336 | 87.507 | 51.321 | 1.00 60.00 |
| ATOM | 2053 | O | THR | 581 | 44.483 | 86.912 | 50.665 | 1.00 60.00 |
| ATOM | 2054 | CB | THR | 581 | 45.206 | 89.875 | 51.789 | 1.00 60.00 |
| ATOM | 2055 | OG1 | THR | 581 | 46.569 | 90.000 | 51.416 | 1.00 60.00 |
| ATOM | 2056 | CG2 | THR | 581 | 44.852 | 90.922 | 52.860 | 1.00 60.00 |
| ATOM | 2057 | N | LEU | 582 | 46.653 | 87.277 | 51.164 | 1.00 60.00 |
| ATOM | 2058 | CA | LEU | 582 | 47.091 | 66.320 | 50.194 | 1.00 60.00 |
| ATOM | 2059 | C | LEU | 582 | 46.855 | 84.968 | 50.770 | 1.00 60.00 |
| ATOM | 2060 | O | LEU | 582 | 46.752 | 84.807 | 51.986 | 1.00 60.00 |
| ATOM | 2061 | CB | LEU | 582 | 48.588 | 86.413 | 49.847 | 1.00 60.00 |
| ATOM | 2062 | CG | LEU | 582 | 48.995 | 87.727 | 49.151 | 1.00 60.00 |
| ATOM | 2063 | CD1 | LEU | 582 | 48.324 | 87.865 | 47.776 | 1.00 60.00 |
| ATOM | 2064 | CD2 | LEU | 582 | 48.762 | 88.942 | 50.062 | 1.00 60.00 |
| ATOM | 2065 | N | VAL | 583 | 46.742 | 83.951 | 49.896 | 1.00 60.00 |
| ATOM | 2066 | CA | VAL | 583 | 46.540 | 82.620 | 50.376 | 1.00 60.00 |
| ATOM | 2067 | C | VAL | 583 | 47.867 | 81.945 | 50.317 | 1.00 60.00 |
| ATOM | 2068 | O | VAL | 583 | 48.581 | 82.039 | 49.319 | 1.00 60.00 |
| ATOM | 2069 | CB | VAL | 583 | 45.575 | 81.819 | 49.550 | 1.00 60.00 |
| ATOM | 2070 | CG1 | VAL | 583 | 46.137 | 81.681 | 48.124 | 1.00 60.00 |
| ATOM | 2071 | CG2 | VAL | 583 | 45.334 | 80.474 | 50.254 | 1.00 60.00 |
| ATOM | 2072 | N | TRP | 584 | 48.250 | 81.263 | 51.412 | 1.00 60.00 |
| ATOM | 2073 | CA | TRP | 584 | 49.530 | 80.628 | 51.419 | 1.00 60.00 |
| ATOM | 2074 | C | TRP | 584 | 49.379 | 79.268 | 50.829 | 1.00 60.00 |
| ATOM | 2075 | O | TRP | 584 | 48.339 | 78.624 | 50.967 | 1.00 60.00 |
| ATOM | 2076 | CB | TRP | 584 | 50.140 | 80.483 | 52.819 | 1.00 60.00 |
| ATOM | 2077 | CG | TRP | 584 | 50.459 | 81.808 | 53.468 | 1.00 60.00 |
| ATOM | 2078 | CD1 | TRP | 584 | 49.828 | 82.439 | 54.500 | 1.00 60.00 |
| ATOM | 2079 | CD2 | TRP | 584 | 51.521 | 82.679 | 53.047 | 1.00 60.00 |
| ATOM | 2080 | NE1 | TRP | 584 | 50.435 | 83.646 | 54.753 | 1.00 60.00 |
| ATOM | 2081 | CE2 | TRP | 584 | 51.476 | 83.808 | 53.865 | 1.00 60.00 |
| ATOM | 2082 | CE3 | TRP | 584 | 52.453 | 82.551 | 52.058 | 1.00 60.00 |
| ATOM | 2083 | CZ2 | TRP | 584 | 52.368 | 84.830 | 53.706 | 1.00 60.00 |
| ATOM | 2084 | CZ3 | TRP | 584 | 53.353 | 83.582 | 51.903 | 1.00 60.00 |
| ATOM | 2085 | CH2 | TRP | 584 | 53.311 | 84.699 | 52.710 | 1.00 60.00 |
| ATOM | 2086 | N | LYS | 585 | 50.430 | 78.812 | 50.126 | 1.00 60.00 |
| ATOM | 2087 | CA | LYS | 585 | 50.401 | 77.536 | 49.481 | 1.00 60.00 |
| ATOM | 2088 | C | LYS | 585 | 50.330 | 76.447 | 50.502 | 1.00 60.00 |
| ATOM | 2089 | O | LYS | 585 | 49.544 | 75.513 | 50.356 | 1.00 60.00 |
| ATOM | 2090 | CB | LYS | 585 | 51.648 | 77.271 | 48.620 | 1.00 60.00 |
| ATOM | 2091 | CG | LYS | 585 | 51.717 | 78.119 | 47.347 | 1.00 60.00 |
| ATOM | 2092 | CD | LYS | 585 | 50.561 | 77.861 | 46.378 | 1.00 60.00 |
| ATOM | 2093 | CE | LYS | 585 | 50.624 | 78.707 | 45.105 | 1.00 60.00 |
| ATOM | 2094 | NZ | LYS | 585 | 50.489 | 80.141 | 45.444 | 1.00 60.00 |
| ATOM | 2095 | N | TYR | 586 | 51.139 | 76.529 | 51.577 | 1.00 60.00 |
| ATOM | 2096 | CA | TYR | 586 | 51.131 | 75.411 | 52.473 | 1.00 60.00 |
| ATOM | 2097 | C | TYR | 586 | 51.541 | 75.835 | 53.848 | 1.00 60.00 |
| ATOM | 2098 | O | TYR | 586 | 51.345 | 76.975 | 54.267 | 1.00 60.00 |
| ATOM | 2099 | CB | TYR | 586 | 52.101 | 74.294 | 52.050 | 1.00 60.00 |
| ATOM | 2100 | CG | TYR | 586 | 51.639 | 73.778 | 50.731 | 1.00 60.00 |
| ATOM | 2101 | CD1 | TYR | 586 | 50.620 | 72.855 | 50.658 | 1.00 60.00 |
| ATOM | 2102 | CD2 | TYR | 586 | 52.227 | 74.214 | 49.565 | 1.00 60.00 |
| ATOM | 2103 | CE1 | TYR | 586 | 50.192 | 72.378 | 49.442 | 1.00 60.00 |
| ATOM | 2104 | CE2 | TYR | 586 | 51.804 | 73.741 | 48.346 | 1.00 60.00 |
| ATOM | 2105 | CZ | TYR | 586 | 50.784 | 72.822 | 48.283 | 1.00 60.00 |
| ATOM | 2106 | OH | TYR | 586 | 50.347 | 72.333 | 47.033 | 1.00 60.00 |
| ATOM | 2107 | N | ALA | 587 | 52.121 | 74.860 | 54.576 | 1.00 60.00 |
| ATOM | 2108 | CA | ALA | 587 | 52.573 | 74.951 | 55.933 | 1.00 60.00 |
| ATOM | 2109 | C | ALA | 587 | 53.640 | 75.987 | 56.000 | 1.00 60.00 |
| ATOM | 2110 | O | ALA | 587 | 53.895 | 76.560 | 57.057 | 1.00 60.00 |
| ATOM | 2111 | CB | ALA | 587 | 53.162 | 73.631 | 56.454 | 1.00 60.00 |
| ATOM | 2112 | N | ASP | 588 | 54.295 | 76.249 | 54.857 | 1.00 60.00 |
| ATOM | 2113 | CA | ASP | 588 | 55.344 | 77.220 | 54.795 | 1.00 60.00 |
| ATOM | 2114 | C | ASP | 588 | 54.762 | 78.493 | 55.316 | 1.00 60.00 |
| ATOM | 2115 | O | ASP | 588 | 55.465 | 79.320 | 55.896 | 1.00 60.00 |

Figure 6A-58

| | | | | | | | | |
|---|---|---|---|---|---|---|---|---|
| ATOM | 2116 | CB | ASP | 588 | 55.828 | 77.482 | 53.359 | 1.00 60.00 |
| ATOM | 2117 | CG | ASP | 588 | 56.540 | 76.233 | 52.853 | 1.00 60.00 |
| ATOM | 2118 | OD1 | ASP | 588 | 56.754 | 75.301 | 53.675 | 1.00 60.00 |
| ATOM | 2119 | OD2 | ASP | 588 | 56.872 | 76.190 | 51.639 | 1.00 60.00 |
| ATOM | 2120 | N | ALA | 589 | 53.442 | 78.671 | 55.134 | 1.00 60.00 |
| ATOM | 2121 | CA | ALA | 589 | 52.783 | 79.858 | 55.590 | 1.00 60.00 |
| ATOM | 2122 | C | ALA | 589 | 53.064 | 80.002 | 57.050 | 1.00 60.00 |
| ATOM | 2123 | O | ALA | 589 | 53.375 | 81.096 | 57.519 | 1.00 60.00 |
| ATOM | 2124 | CB | ALA | 589 | 51.255 | 79.775 | 55.450 | 1.00 60.00 |
| ATOM | 2125 | N | GLY | 590 | 52.983 | 78.897 | 57.812 | 1.00 60.00 |
| ATOM | 2126 | CA | GLY | 590 | 53.267 | 79.002 | 59.213 | 1.00 60.00 |
| ATOM | 2127 | C | GLY | 590 | 52.138 | 79.727 | 59.867 | 1.00 60.00 |
| ATOM | 2128 | O | GLY | 590 | 52.347 | 80.690 | 60.605 | 1.00 60.00 |
| ATOM | 2129 | N | HIS | 591 | 50.899 | 79.280 | 59.599 | 1.00 60.00 |
| ATOM | 2130 | CA | HIS | 591 | 49.751 | 79.919 | 60.168 | 1.00 60.00 |
| ATOM | 2131 | C | HIS | 591 | 49.902 | 79.896 | 61.655 | 1.00 60.00 |
| ATOM | 2132 | O | HIS | 591 | 50.347 | 78.908 | 62.237 | 1.00 60.00 |
| ATOM | 2133 | CB | HIS | 591 | 48.433 | 79.207 | 59.822 | 1.00 60.00 |
| ATOM | 2134 | CG | HIS | 591 | 48.187 | 79.128 | 58.346 | 1.00 60.00 |
| ATOM | 2135 | ND1 | HIS | 591 | 48.714 | 78.152 | 57.529 | 1.00 60.00 |
| ATOM | 2136 | CD2 | HIS | 591 | 47.455 | 79.938 | 57.532 | 1.00 60.00 |
| ATOM | 2137 | CE1 | HIS | 591 | 48.277 | 78.415 | 56.272 | 1.00 60.00 |
| ATOM | 2138 | NE2 | HIS | 591 | 47.509 | 79.490 | 56.224 | 1.00 60.00 |
| ATOM | 2139 | N | VAL | 592 | 49.535 | 81.017 | 62.305 | 1.00 40.00 |
| ATOM | 2140 | CA | VAL | 592 | 49.640 | 81.132 | 63.730 | 1.00 40.00 |
| ATOM | 2141 | C | VAL | 592 | 48.276 | 81.467 | 64.234 | 1.00 40.00 |
| ATOM | 2142 | O | VAL | 592 | 47.414 | 81.895 | 63.467 | 1.00 40.00 |
| ATOM | 2143 | CB | VAL | 592 | 50.554 | 82.238 | 64.164 | 1.00 40.00 |
| ATOM | 2144 | CG1 | VAL | 592 | 51.975 | 81.924 | 63.670 | 1.00 40.00 |
| ATOM | 2145 | CG2 | VAL | 592 | 49.999 | 83.563 | 63.620 | 1.00 40.00 |
| ATOM | 2146 | N | CYS | 593 | 48.030 | 81.264 | 65.544 | 1.00 20.00 |
| ATOM | 2147 | CA | CYS | 593 | 46.725 | 81.565 | 66.036 | 1.00 20.00 |
| ATOM | 2148 | C | CYS | 593 | 46.860 | 82.778 | 66.911 | 1.00 20.00 |
| ATOM | 2149 | O | CYS | 593 | 47.823 | 82.899 | 67.666 | 1.00 20.00 |
| ATOM | 2150 | CB | CYS | 593 | 46.131 | 80.416 | 66.864 | 1.00 20.00 |
| ATOM | 2151 | SG | CYS | 593 | 44.332 | 80.552 | 66.886 | 1.00 20.00 |
| ATOM | 2152 | N | HIS | 594 | 45.905 | 83.729 | 66.811 | 1.00 20.00 |
| ATOM | 2153 | CA | HIS | 594 | 45.983 | 84.931 | 67.595 | 1.00 20.00 |
| ATOM | 2154 | C | HIS | 594 | 44.693 | 85.136 | 68.325 | 1.00 20.00 |
| ATOM | 2155 | O | HIS | 594 | 43.649 | 84.625 | 67.926 | 1.00 20.00 |
| ATOM | 2156 | CB | HIS | 594 | 46.256 | 86.197 | 66.765 | 1.00 20.00 |
| ATOM | 2157 | CG | HIS | 594 | 47.645 | 86.226 | 66.200 | 1.00 20.00 |
| ATOM | 2158 | ND1 | HIS | 594 | 48.743 | 86.699 | 66.882 | 1.00 20.00 |
| ATOM | 2159 | CD2 | HIS | 594 | 48.109 | 85.821 | 64.986 | 1.00 20.00 |
| ATOM | 2160 | CE1 | HIS | 594 | 49.808 | 86.558 | 66.054 | 1.00 20.00 |
| ATOM | 2161 | NE2 | HIS | 594 | 49.473 | 86.031 | 64.892 | 1.00 20.00 |
| ATOM | 2162 | N | LEU | 595 | 44.747 | 85.910 | 69.426 | 1.00 20.00 |
| ATOM | 2163 | CA | LEU | 595 | 43.613 | 86.140 | 70.278 | 1.00 20.00 |
| ATOM | 2164 | C | LEU | 595 | 42.596 | 86.943 | 69.557 | 1.00 20.00 |
| ATOM | 2165 | O | LEU | 595 | 42.911 | 87.735 | 68.669 | 1.00 20.00 |
| ATOM | 2166 | CB | LEU | 595 | 43.970 | 86.903 | 71.565 | 1.00 20.00 |
| ATOM | 2167 | CG | LEU | 595 | 44.979 | 86.165 | 72.460 | 1.00 20.00 |
| ATOM | 2168 | CD1 | LEU | 595 | 45.296 | 86.970 | 73.730 | 1.00 20.00 |
| ATOM | 2169 | CD2 | LEU | 595 | 44.522 | 84.731 | 72.758 | 1.00 20.00 |
| ATOM | 2170 | N | CYS | 596 | 41.319 | 86.724 | 69.922 | 1.00 20.00 |
| ATOM | 2171 | CA | CYS | 596 | 40.264 | 87.490 | 69.344 | 1.00 20.00 |
| ATOM | 2172 | C | CYS | 596 | 39.852 | 88.447 | 70.418 | 1.00 20.00 |
| ATOM | 2173 | O | CYS | 596 | 39.751 | 88.078 | 71.586 | 1.00 20.00 |
| ATOM | 2174 | CB | CYS | 596 | 39.065 | 86.636 | 68.890 | 1.00 20.00 |
| ATOM | 2175 | SG | CYS | 596 | 37.811 | 87.561 | 67.948 | 1.00 20.00 |
| ATOM | 2176 | N | HIS | 597 | 39.630 | 89.722 | 70.048 | 1.00 20.00 |
| ATOM | 2177 | CA | HIS | 597 | 39.306 | 90.720 | 71.027 | 1.00 20.00 |
| ATOM | 2178 | C | HIS | 597 | 37.999 | 90.354 | 71.647 | 1.00 20.00 |
| ATOM | 2179 | O | HIS | 597 | 37.160 | 89.701 | 71.033 | 1.00 20.00 |
| ATOM | 2180 | CB | HIS | 597 | 39.201 | 92.134 | 70.430 | 1.00 20.00 |
| ATOM | 2181 | CG | HIS | 597 | 38.981 | 93.202 | 71.456 | 1.00 20.00 |
| ATOM | 2182 | ND1 | HIS | 597 | 39.845 | 93.457 | 72.497 | 1.00 20.00 |
| ATOM | 2183 | CD2 | HIS | 597 | 37.971 | 94.104 | 71.583 | 1.00 20.00 |
| ATOM | 2184 | CE1 | HIS | 597 | 39.319 | 94.493 | 73.196 | 1.00 20.00 |
| ATOM | 2185 | NE2 | HIS | 597 | 38.181 | 94.920 | 72.680 | 1.00 20.00 |
| ATOM | 2186 | N | PRO | 598 | 37.823 | 90.734 | 72.880 | 1.00 20.00 |
| ATOM | 2187 | CA | PRO | 598 | 36.602 | 90.420 | 73.560 | 1.00 20.00 |
| ATOM | 2188 | C | PRO | 598 | 35.445 | 91.195 | 73.019 | 1.00 20.00 |
| ATOM | 2189 | O | PRO | 598 | 34.314 | 90.732 | 73.154 | 1.00 20.00 |
| ATOM | 2190 | CB | PRO | 598 | 36.875 | 90.632 | 75.052 | 1.00 20.00 |
| ATOM | 2191 | CG | PRO | 598 | 38.248 | 91.329 | 75.109 | 1.00 20.00 |
| ATOM | 2192 | CD | PRO | 598 | 38.932 | 90.896 | 73.803 | 1.00 20.00 |

Figure 6A-59

| ATOM | 2193 | N | ASN | 599 | 35.692 | 92.399 | 72.448 | 1.00 | 20.00 |
|------|------|-----|-----|-----|--------|--------|--------|------|-------|
| ATOM | 2194 | CA | ASN | 599 | 34.620 | 93.172 | 71.902 | 1.00 | 20.00 |
| ATOM | 2195 | C | ASN | 599 | 34.122 | 92.537 | 70.643 | 1.00 | 20.00 |
| ATOM | 2196 | O | ASN | 599 | 32.917 | 92.417 | 70.434 | 1.00 | 20.00 |
| ATOM | 2197 | CB | ASN | 599 | 35.028 | 94.615 | 71.556 | 1.00 | 20.00 |
| ATOM | 2198 | CG | ASN | 599 | 35.318 | 95.347 | 72.859 | 1.00 | 20.00 |
| ATOM | 2199 | OD1 | ASN | 599 | 34.964 | 94.867 | 73.942 | 1.00 | 20.00 |
| ATOM | 2200 | ND2 | ASN | 599 | 35.951 | 96.546 | 72.755 | 1.00 | 20.00 |
| ATOM | 2201 | N | CYS | 600 | 35.043 | 92.082 | 69.771 | 1.00 | 20.00 |
| ATOM | 2202 | CA | CYS | 600 | 34.608 | 91.561 | 68.509 | 1.00 | 20.00 |
| ATOM | 2203 | C | CYS | 600 | 33.767 | 90.362 | 68.773 | 1.00 | 20.00 |
| ATOM | 2204 | O | CYS | 600 | 33.836 | 89.762 | 69.845 | 1.00 | 20.00 |
| ATOM | 2205 | CB | CYS | 600 | 35.743 | 91.107 | 67.573 | 1.00 | 20.00 |
| ATOM | 2206 | SG | CYS | 600 | 36.923 | 92.422 | 67.157 | 1.00 | 20.00 |
| ATOM | 2207 | N | THR | 601 | 32.911 | 90.007 | 67.797 | 1.00 | 20.00 |
| ATOM | 2208 | CA | THR | 601 | 32.099 | 88.846 | 67.972 | 1.00 | 20.00 |
| ATOM | 2209 | C | THR | 601 | 32.181 | 88.032 | 66.721 | 1.00 | 20.00 |
| ATOM | 2210 | O | THR | 601 | 32.335 | 88.561 | 65.620 | 1.00 | 20.00 |
| ATOM | 2211 | CB | THR | 601 | 30.652 | 89.158 | 68.217 | 1.00 | 20.00 |
| ATOM | 2212 | OG1 | THR | 601 | 30.095 | 89.826 | 67.095 | 1.00 | 20.00 |
| ATOM | 2213 | CG2 | THR | 601 | 30.549 | 90.046 | 69.469 | 1.00 | 20.00 |
| ATOM | 2214 | N | TYR | 602 | 32.100 | 86.700 | 66.886 | 1.00 | 20.00 |
| ATOM | 2215 | CA | TYR | 602 | 32.070 | 85.753 | 65.812 | 1.00 | 20.00 |
| ATOM | 2216 | C | TYR | 602 | 33.273 | 85.827 | 64.922 | 1.00 | 20.00 |
| ATOM | 2217 | O | TYR | 602 | 33.163 | 85.523 | 63.737 | 1.00 | 20.00 |
| ATOM | 2218 | CB | TYR | 602 | 30.813 | 85.878 | 64.933 | 1.00 | 20.00 |
| ATOM | 2219 | CG | TYR | 602 | 29.647 | 85.457 | 65.761 | 1.00 | 20.00 |
| ATOM | 2220 | CD1 | TYR | 602 | 29.350 | 84.122 | 65.912 | 1.00 | 20.00 |
| ATOM | 2221 | CD2 | TYR | 602 | 28.851 | 86.390 | 66.383 | 1.00 | 20.00 |
| ATOM | 2222 | CE1 | TYR | 602 | 28.277 | 83.722 | 66.672 | 1.00 | 20.00 |
| ATOM | 2223 | CE2 | TYR | 602 | 27.775 | 85.997 | 67.145 | 1.00 | 20.00 |
| ATOM | 2224 | CZ | TYR | 602 | 27.488 | 84.660 | 67.289 | 1.00 | 20.00 |
| ATOM | 2225 | OH | TYR | 602 | 26.385 | 84.253 | 68.070 | 1.00 | 20.00 |
| ATOM | 2226 | N | GLY | 603 | 34.459 | 86.213 | 65.434 | 1.00 | 20.00 |
| ATOM | 2227 | CA | GLY | 603 | 35.588 | 86.115 | 64.549 | 1.00 | 20.00 |
| ATOM | 2228 | C | GLY | 603 | 36.486 | 87.304 | 64.674 | 1.00 | 20.00 |
| ATOM | 2229 | O | GLY | 603 | 36.071 | 88.380 | 65.101 | 1.00 | 20.00 |
| ATOM | 2230 | N | CYS | 604 | 37.769 | 87.113 | 64.288 | 1.00 | 20.00 |
| ATOM | 2231 | CA | CYS | 604 | 38.732 | 88.176 | 64.298 | 1.00 | 20.00 |
| ATOM | 2232 | C | CYS | 604 | 39.680 | 87.981 | 63.155 | 1.00 | 20.00 |
| ATOM | 2233 | O | CYS | 604 | 40.163 | 86.875 | 62.911 | 1.00 | 20.00 |
| ATOM | 2234 | CB | CYS | 604 | 39.619 | 88.219 | 65.558 | 1.00 | 20.00 |
| ATOM | 2235 | SG | CYS | 604 | 38.876 | 89.016 | 67.014 | 1.00 | 20.00 |
| ATOM | 2236 | N | THR | 605 | 39.943 | 89.064 | 62.398 | 1.00 | 20.00 |
| ATOM | 2237 | CA | THR | 605 | 40.928 | 89.017 | 61.358 | 1.00 | 20.00 |
| ATOM | 2238 | C | THR | 605 | 42.250 | 88.915 | 62.047 | 1.00 | 20.00 |
| ATOM | 2239 | O | THR | 605 | 43.123 | 88.142 | 61.654 | 1.00 | 20.00 |
| ATOM | 2240 | CB | THR | 605 | 40.941 | 90.260 | 60.520 | 1.00 | 20.00 |
| ATOM | 2241 | OG1 | THR | 605 | 41.253 | 91.390 | 61.322 | 1.00 | 20.00 |
| ATOM | 2242 | CG2 | THR | 605 | 39.556 | 90.431 | 59.874 | 1.00 | 20.00 |
| ATOM | 2243 | N | GLY | 606 | 42.403 | 89.706 | 63.126 | 1.00 | 20.00 |
| ATOM | 2244 | CA | GLY | 606 | 43.605 | 89.745 | 63.903 | 1.00 | 20.00 |
| ATOM | 2245 | C | GLY | 606 | 43.221 | 90.378 | 65.198 | 1.00 | 20.00 |
| ATOM | 2246 | O | GLY | 606 | 42.042 | 90.614 | 65.456 | 1.00 | 20.00 |
| ATOM | 2247 | N | PRO | 607 | 44.177 | 90.654 | 66.036 | 1.00 | 20.00 |
| ATOM | 2248 | CA | PRO | 607 | 43.861 | 91.278 | 67.288 | 1.00 | 20.00 |
| ATOM | 2249 | C | PRO | 607 | 43.557 | 92.720 | 67.061 | 1.00 | 20.00 |
| ATOM | 2250 | O | PRO | 607 | 44.089 | 93.297 | 66.113 | 1.00 | 20.00 |
| ATOM | 2251 | CB | PRO | 607 | 45.058 | 91.024 | 68.209 | 1.00 | 20.00 |
| ATOM | 2252 | CG | PRO | 607 | 46.162 | 90.484 | 67.279 | 1.00 | 20.00 |
| ATOM | 2253 | CD | PRO | 607 | 45.383 | 89.851 | 66.116 | 1.00 | 20.00 |
| ATOM | 2254 | N | GLY | 608 | 42.698 | 93.320 | 67.908 | 1.00 | 20.00 |
| ATOM | 2255 | CA | GLY | 608 | 42.388 | 94.708 | 67.751 | 1.00 | 20.00 |
| ATOM | 2256 | C | GLY | 608 | 40.920 | 94.842 | 67.505 | 1.00 | 20.00 |
| ATOM | 2257 | O | GLY | 608 | 40.263 | 93.913 | 67.037 | 1.00 | 20.00 |
| ATOM | 2258 | N | LEU | 609 | 40.378 | 96.033 | 67.826 | 1.00 | 20.00 |
| ATOM | 2259 | CA | LEU | 609 | 38.991 | 96.344 | 67.647 | 1.00 | 20.00 |
| ATOM | 2260 | C | LEU | 609 | 38.726 | 96.337 | 66.177 | 1.00 | 20.00 |
| ATOM | 2261 | O | LEU | 609 | 37.661 | 95.926 | 65.719 | 1.00 | 20.00 |
| ATOM | 2262 | CB | LEU | 609 | 38.635 | 97.750 | 68.158 | 1.00 | 20.00 |
| ATOM | 2263 | CG | LEU | 609 | 38.904 | 97.960 | 69.660 | 1.00 | 20.00 |
| ATOM | 2264 | CD1 | LEU | 609 | 40.404 | 97.869 | 69.978 | 1.00 | 20.00 |
| ATOM | 2265 | CD2 | LEU | 609 | 38.271 | 99.269 | 70.161 | 1.00 | 20.00 |
| ATOM | 2266 | N | GLU | 610 | 39.720 | 96.803 | 65.404 | 1.00 | 20.00 |
| ATOM | 2267 | CA | GLU | 610 | 39.648 | 96.911 | 63.976 | 1.00 | 20.00 |
| ATOM | 2268 | C | GLU | 610 | 39.475 | 95.539 | 63.422 | 1.00 | 20.00 |
| ATOM | 2269 | O | GLU | 610 | 38.824 | 95.343 | 62.396 | 1.00 | 20.00 |

Figure 6A-60

| | | | | | | | |
|---|---|---|---|---|---|---|---|
| ATOM | 2270 | CB | GLU | 610 | 40.943 | 97.471 | 63.365 | 1.00 20.00 |
| ATOM | 2271 | CG | GLU | 610 | 41.251 | 98.915 | 63.761 | 1.00 20.00 |
| ATOM | 2272 | CD | GLU | 610 | 42.554 | 99.307 | 63.078 | 1.00 20.00 |
| ATOM | 2273 | OE1 | GLU | 610 | 42.743 | 98.912 | 61.897 | 1.00 20.00 |
| ATOM | 2274 | OE2 | GLU | 610 | 43.380 | 100.002 | 63.731 | 1.00 20.00 |
| ATOM | 2275 | N | GLY | 611 | 40.055 | 94.549 | 64.118 | 1.00 20.00 |
| ATOM | 2276 | CA | GLY | 611 | 40.073 | 93.186 | 63.684 | 1.00 20.00 |
| ATOM | 2277 | C | GLY | 611 | 38.677 | 92.696 | 63.492 | 1.00 20.00 |
| ATOM | 2278 | O | GLY | 611 | 38.460 | 91.787 | 62.690 | 1.00 20.00 |
| ATOM | 2279 | N | CYS | 612 | 37.717 | 93.255 | 64.254 | 1.00 20.00 |
| ATOM | 2280 | CA | CYS | 612 | 36.359 | 92.832 | 64.099 | 1.00 20.00 |
| ATOM | 2281 | C | CYS | 612 | 36.021 | 93.091 | 62.670 | 1.00 20.00 |
| ATOM | 2282 | O | CYS | 612 | 36.613 | 93.962 | 62.033 | 1.00 20.00 |
| ATOM | 2283 | CB | CYS | 612 | 35.328 | 93.660 | 64.892 | 1.00 20.00 |
| ATOM | 2284 | SG | CYS | 612 | 35.756 | 93.986 | 66.626 | 1.00 20.00 |
| ATOM | 2285 | N | PRO | 613 | 35.097 | 92.336 | 62.146 | 1.00 60.00 |
| ATOM | 2286 | CA | PRO | 613 | 34.670 | 92.528 | 60.790 | 1.00 60.00 |
| ATOM | 2287 | C | PRO | 613 | 34.223 | 93.951 | 60.698 | 1.00 60.00 |
| ATOM | 2288 | O | PRO | 613 | 33.656 | 94.455 | 61.666 | 1.00 60.00 |
| ATOM | 2289 | CB | PRO | 613 | 33.493 | 91.576 | 60.603 | 1.00 60.00 |
| ATOM | 2290 | CG | PRO | 613 | 32.874 | 91.515 | 62.012 | 1.00 60.00 |
| ATOM | 2291 | CD | PRO | 613 | 34.079 | 91.688 | 62.955 | 1.00 60.00 |
| ATOM | 2292 | N | THR | 614 | 34.478 | 94.629 | 59.564 | 1.00 60.00 |
| ATOM | 2293 | CA | THR | 614 | 34.068 | 95.997 | 59.486 | 1.00 60.00 |
| ATOM | 2294 | C | THR | 614 | 33.136 | 96.141 | 58.331 | 1.00 60.00 |
| ATOM | 2295 | O | THR | 614 | 33.362 | 95.585 | 57.258 | 1.00 60.00 |
| ATOM | 2296 | CB | THR | 614 | 35.205 | 96.950 | 59.259 | 1.00 60.00 |
| ATOM | 2297 | OG1 | THR | 614 | 36.143 | 96.856 | 60.322 | 1.00 60.00 |
| ATOM | 2298 | CG2 | THR | 614 | 34.639 | 98.378 | 59.179 | 1.00 60.00 |
| ATOM | 2299 | N | ASN | 615 | 32.040 | 96.892 | 58.544 | 1.00 60.00 |
| ATOM | 2300 | CA | ASN | 615 | 31.101 | 97.135 | 57.494 | 1.00 60.00 |
| ATOM | 2301 | C | ASN | 615 | 31.794 | 97.983 | 56.478 | 1.00 60.00 |
| ATOM | 2302 | O | ASN | 615 | 31.612 | 97.805 | 55.275 | 1.00 60.00 |
| ATOM | 2303 | CB | ASN | 615 | 29.831 | 97.862 | 57.973 | 1.00 60.00 |
| ATOM | 2304 | CG | ASN | 615 | 30.226 | 99.212 | 58.551 | 1.00 60.00 |
| ATOM | 2305 | OD1 | ASN | 615 | 31.259 | 99.344 | 59.205 | 1.00 60.00 |
| ATOM | 2306 | ND2 | ASN | 615 | 29.374 | 100.243 | 58.309 | 1.00 60.00 |
| ATOM | 2307 | N | GLY | 616 | 32.636 | 98.921 | 56.953 | 1.00 60.00 |
| ATOM | 2308 | CA | GLY | 616 | 33.362 | 99.779 | 56.061 | 1.00 60.00 |
| ATOM | 2309 | C | GLY | 616 | 32.429 | 100.789 | 55.469 | 1.00 60.00 |
| ATOM | 2310 | O | GLY | 616 | 32.488 | 101.060 | 54.270 | 1.00 60.00 |
| ATOM | 2311 | N | PRO | 617 | 31.571 | 101.360 | 56.274 | 1.00 60.00 |
| ATOM | 2312 | CA | PRO | 617 | 30.612 | 102.308 | 55.777 | 1.00 60.00 |
| ATOM | 2313 | C | PRO | 617 | 31.360 | 103.413 | 55.104 | 1.00 60.00 |
| ATOM | 2314 | O | PRO | 617 | 32.523 | 103.636 | 55.437 | 1.00 60.00 |
| ATOM | 2315 | CB | PRO | 617 | 29.906 | 102.846 | 57.013 | 1.00 60.00 |
| ATOM | 2316 | CG | PRO | 617 | 31.027 | 102.833 | 58.067 | 1.00 60.00 |
| ATOM | 2317 | CD | PRO | 617 | 31.897 | 101.629 | 57.667 | 1.00 60.00 |
| ATOM | 2318 | N | LYS | 618 | 30.717 | 104.103 | 54.145 | 1.00 60.00 |
| ATOM | 2319 | CA | LYS | 618 | 31.363 | 105.186 | 53.470 | 1.00 60.00 |
| ATOM | 2320 | C | LYS | 618 | 31.672 | 106.227 | 54.494 | 1.00 60.00 |
| ATOM | 2321 | O | LYS | 618 | 32.768 | 106.782 | 54.517 | 1.00 60.00 |
| ATOM | 2322 | CB | LYS | 618 | 30.470 | 105.844 | 52.405 | 1.00 60.00 |
| ATOM | 2323 | CG | LYS | 618 | 30.300 | 105.010 | 51.134 | 1.00 60.00 |
| ATOM | 2324 | CD | LYS | 618 | 31.607 | 104.810 | 50.364 | 1.00 60.00 |
| ATOM | 2325 | CE | LYS | 618 | 31.453 | 103.977 | 49.091 | 1.00 60.00 |
| ATOM | 2326 | NZ | LYS | 618 | 32.740 | 103.929 | 48.362 | 1.00 60.00 |
| ATOM | 2327 | N | ILE | 619 | 30.705 | 106.503 | 55.389 | 1.00 60.00 |
| ATOM | 2328 | CA | ILE | 619 | 30.930 | 107.501 | 56.390 | 1.00 60.00 |
| ATOM | 2329 | C | ILE | 619 | 32.013 | 107.002 | 57.281 | 1.00 60.00 |
| ATOM | 2330 | O | ILE | 619 | 32.155 | 105.803 | 57.518 | 1.00 60.00 |
| ATOM | 2331 | CB | ILE | 619 | 29.732 | 107.775 | 57.253 | 1.00 60.00 |
| ATOM | 2332 | CG1 | ILE | 619 | 28.558 | 108.285 | 56.401 | 1.00 60.00 |
| ATOM | 2333 | CG2 | ILE | 619 | 30.164 | 108.744 | 58.365 | 1.00 60.00 |
| ATOM | 2334 | CD1 | ILE | 619 | 28.868 | 109.573 | 55.641 | 1.00 60.00 |
| ATOM | 2335 | N | PRO | 620 | 32.809 | 107.922 | 57.744 | 1.00 60.00 |
| ATOM | 2336 | CA | PRO | 620 | 33.873 | 107.585 | 58.644 | 1.00 60.00 |
| ATOM | 2337 | C | PRO | 620 | 33.318 | 107.382 | 60.013 | 1.00 60.00 |
| ATOM | 2338 | O | PRO | 620 | 32.243 | 107.904 | 60.304 | 1.00 60.00 |
| ATOM | 2339 | CB | PRO | 620 | 34.892 | 108.725 | 58.549 | 1.00 60.00 |
| ATOM | 2340 | CG | PRO | 620 | 34.143 | 109.860 | 57.827 | 1.00 60.00 |
| ATOM | 2341 | CD | PRO | 620 | 33.099 | 109.120 | 56.978 | 1.00 60.00 |
| ATOM | 2342 | N | SER | 621 | 34.027 | 106.617 | 60.864 | 1.00 60.00 |
| ATOM | 2343 | CA | SER | 621 | 33.548 | 106.395 | 62.193 | 1.00 60.00 |
| ATOM | 2344 | C | SER | 621 | 33.779 | 107.684 | 62.974 | 1.00 60.00 |
| ATOM | 2345 | O | SER | 621 | 33.285 | 108.746 | 62.511 | 1.00 60.00 |
| ATOM | 2346 | CB | SER | 621 | 34.281 | 105.252 | 62.921 | 1.00 60.00 |

Figure 6A-61

```
ATOM   2347  OG   SER    621      35.659 105.566  63.074  1.00 60.00
ATOM   2348  OXT  SER    621      34.446 107.626  64.041  1.00 60.00
TER
```

Figure 6A-62

METHOD OF DESIGNING AGONISTS AND ANTAGONISTS TO EGF RECEPTOR FAMILY

FIELD OF THE INVENTION

This invention relates to the field of epidermal growth factor (EGF) receptor structure and EGF receptor/ligand interactions. In particular, it relates to the field of using the EGF receptor structure to select and screen for ligands of the EGF receptor.

BACKGROUND OF THE INVENTION

Epidermal growth factor is a small polypeptide cytokine that stimulates marked proliferation of epithelial tissues and is a member of a larger family of structurally related cytokines such as transforming growth factor α (TGFα), amphiregulin, betacellulin, heparin-binding EGF and some viral gene products. Abnormal EGF family signalling is a characteristic of certain cancers (Soler, C. & Carpenter, G., 1994 In Nicola, N. (ed) "Guidebook to Cytokines and their Receptors", Oxford Univ. Press, Oxford, pp 194–197; Walker, F. & Burgess, A. W., 1994, In Nicola, N. (ed) "Guidebook to Cytokines and their Receptors", Oxford Univ. Press, Oxford, pp 198–201).

The epidermal growth factor receptor (EGFR) is the cell membrane receptor for EGF (Ullrich, A., and Schlessinger, J. (1990) Cell 61, 203–212). The EGFR also binds other ligands that contain amino acid sequences classified as the EGF-like motif. Among these ligands, the three-dimensional structures of EGF and TGFα have been determined by NMR (Montelione, G. T.; Wuthrich, K.; Nice, E. C., Burgess, A. W. and Scheraga, H. A. (1986) PNAS 83(22): 8594–8; Campbell, I. D., Cooke, R. M., Baron, M., Harvey, T. S., and Tappin, M. J. (1989) Prog. Growth Factor Res. 1, 13–22). Upon binding of the ligand to the extracellular domain, the EGFR undergoes dimerization, which eventually leads to the activation of its cytoplasmic protein tyrosine kinase (Ullrich, A., and Schlessinger, J. (1990) Cell 61, 203–212). The EGFR is also known as the ErbB-1 receptor and belongs to the type I family of receptor tyrosine kinases (Ullrich, A., and Schlessinger, J. (1990) Cell 61, 203–212). This group also includes the ErbB-2, ErbB-3 and ErbB-4 receptors. The ligand of ErbB-2 is still unknown but it is clear that heregulin binds to ErbB-3 and ErbB-4 (Plowman, G. D., Green, J. M., Calouscou, J. M., Carlton, G. W., Rothwell, V. M., and Buckley, S. (1993) Nature 366, 473–475). One of the heregulins is known as neuregulin or NDF and contains an EGF-like sequence that was found to fold into an EGF-like fold by NMR (Nagata, K., Kohda, D., Hatanska, H., Ichikawa, S., Matsuda, S., Yamamoto, T., Suzuki, A., and Inagaki, F. (1994) EMBO J. 13, 3517–3523 and Jacobson, N. E., Abadl, N., Sliwkowski, M. X., Reilly, D., Skelton, N. J., and Fairbrother, W. J. (1996) Biochemistry 36, 3402–3417).

The type II family of receptor tyrosine kinases consists of the insulin receptor (INSR), the insulin-like growth factor I receptor (IGF-1), and the insulin receptor-related receptor (Ullrich, A., and Schlessinger, J. (1990) Cell 61, 203–212). Although the type II receptors consist of four chains ($\alpha_2\beta_2$), both the extracellular portions of the receptors from the two families, as well as the tyrosine kinase portions, share significant sequence homology, suggesting a common evolutionary origin (Ullrich, A., and Schlessinger, J. (1990) Cell 61, 203–212, and Bajaj, M., Waterfield, M. D., Schlessinger, J., Taylor, W. R., and Blundell, T. (1987) Biochim. Biophys. Acta 916, 220–226).

The 621 amino acid residues of the extracellular domain of the human EGFR (sEGFR) can be subdivided into four domains as follows: L1, S1, L2 and S2, where L and S stand for "large" and "small" domains, respectively (Bajaj, M., Waterfield, M. D., Schlessinger, J., Taylor, W. R., and Blundell, T. (1987) Biochim. Biophys. Acta 916, 220–226, see FIG. 2). The L1 and L2 domains are homologous, as are the S1 and S2 domains.

Ligand-induced dimerization was first reported for the EGF receptor (Schlessinger, J. (1980) Trends Biochem Sci 13, 443–447) and now is widely accepted as a general mechanism for the transmission of growth stimulatory a signals across the cell membrane. Although many biochemical experiments have been performed to reveal the molecular mechanism of receptor dimerization (Lemnon, M. A., Bu, Z., Ladbury, J. E., Zhou, M., Pinchasi, D., Lax, L., Engelman, D. M., and Schlessinger, J. (1997) EMBO J. 16, 281–294 and Tzabar, E., Pinkas-Kramarski, R., Moyer, J. D., Klapper, D. N., Alroy, L., Levkowitz, G., Shelly, M., Henis, S., Eisenstein, M., Ratzkin, B. J., Sela, M., Andrews, G. C., and Yarden, Y. (1997) EMBO J. 16, 4938–4950 and Lax, L., Mitra, A. K., Ravern, C., Hurwitz, D. R., Rubinstein, M., Ullrich, A., Stroud, R. M., and Schlessinger, J. (1991), J. Biol. Chem. 266, 13828–13833), the molecular mechanism by which monomeric ligands induce dimerization is still unknown for members of the EGFR family. Single particle averaging of electron microscopic images suggests that the overall shape of the sEGFR is four-lobed and doughnut-like (Lax, L., Mitra, A. K., Ravern, C., Hurwitz, D. R., Rubinstein, M., Ullrich, A., Stroud, R. M., and Schlessinger, J. (1991), J. Biol. Chem. 266, 13828–13833). Small angle x-ray scattering also indicates that the sEGFR is a flattened sphere with long diameters of 110 Å and a short diameter of 20 Å (Lemmon, M. A., Bu, Z., Ladbury, J. E., Zhou, M., Pinchasi, D., Lax, L., Engelman, D. M., and Schlessinger, J. (1997) EMBO J. 16, 281–294). The crystallization of sEGFR in complex with EGF has been published (Günther, N., Betzel, C., and Weber, W. (1990) J. Biol. Chem. 265, 22082–22085; Degenhardt M., Weber W., Eschenburg S. Dierks K., Funari S S., Rapp G. and Betzel C. (1998) Acta Crystallogr. D Biol. Crystallogr. 54:999–1001), but the structure has not yet been reported, despite a decade of effort by many groups.

One EGF receptor ligand, TGF-α has been observed to be overproduced in keratinocyte cells which are subject to psoriasis (Turbitt, M. L. et al., 1990, J. Invest. Dermatol. 95(2), 229–232; Higashimyama, M. et al., 1991, J. Dermatol., 18(2), 117–119; Elder, J. T. et al, 1990, 94(1), 19–25). The overproduction of at least one other EGF receptor ligand, amphiregulin, has also been implicated in psoriasis. (Piepkorn, M. 1996, Am. J. Dermatopath., 18(2), 165–171). Molecules that inhibit the EGF receptor have been shown to inhibit the proliferation of both normal keratinocytes (Dvir, A. et al, 1991, J. Cell Biol., 113(4), 857–865) and psoriatic keratinocytes. (Ben-Bassat, H. et al., 1995, Exp. Dermatol., 4(2), 82–88). These findings indicate that EGF receptor antagonists may be useful in the treatment of psoriasis.

Many cancer cells express constitutively active EGFR (Sandgreen, E. P., et al., 1990, Cell, 61:1121–135; Karnes, W. E. J., et al., 1992, Gastroenterology, 102:474–485) or other EGFR family members (Hynes, N. E., 1993, Semin. Cancer Biol. 4:19–26). Elevated levels of activated EGFR occur in bladder, breast, lung and brain tumours (Harris, A. L., et al., 1989, In Furth & Greaves (eds) The Molecular Diagnostics of human cancer. Cold Spring Harbor Lab. Press, CSH, NY, pp 353–357). Antibodies to EGFR can inhibit ligand activation of EGFR (Sato, J. D., et al., 1983

Mol. Biol. Med. 1:511–529) and the growth of many epithelial cell lines (Aboud-Pirak E., et al., 1988, J. Natl Cancer Inst. 85:1327–1331). Patients receiving repeated doses of a humanised chimeric anti-EGFR monoclonal antibody (Mab) showed signs of disease stabilization. The large doses required and the cost of production of humanised Mab is likely to limit the application of this type of therapy. These findings indicate that the development of EGF receptor antagonists will be attractive anticancer agents.

SUMMARY OF THE INVENTION

The present inventors have now obtained three-dimensional structural information concerning the epidermal growth factor receptor (EGFR). This structural information was obtained by comparative modelling based on the three-dimensional structure of the IGF-1 receptor as described in PCT/AU98/00998. The information presented in the present application can be used to predict the structure of related members of the EGF receptor family, and to develop specific ligands of members of the EGF receptor family for therapeutic applications.

Accordingly, in a first aspect the present invention provides a method of designing a compound which binds to a molecule of the EGF receptor family and modulates an activity mediated by the molecule, which method comprises the step of assessing the stereochemical complementarity between the compound and a topographic region of the molecule, wherein the molecule is characterised by (i) amino acids 1–621 of the EGF receptor positioned at atomic coordinates substantially as shown in FIG. 6;

(ii) one or more subsets of said amino acids related to the coordinates shown in FIG. 6 by whole body translations and/or rotations; or (iii) amino acids present in the amino acid sequence of a member of the EGF receptor family, which form an equivalent three-dimensional structure to that of the receptor site defined by amino acids 1–621 of the EGF receptor positioned at atomic coordinates substantially as shown in FIG. 6.

In a preferred embodiment of the first aspect, the topographic region of the molecule is defined by amino acids 1475 of the EGF receptor, or an amino acid sequence which forms an equivalent three-dimensional structure to that of the region defined by amino acids 1–475 of the EGF receptor positioned at atomic coordinates substantially as shown in FIG. 6.

In a further preferred embodiment of the first aspect, the topographic region of the molecule is defined by amino acids 313–621 of the EGF receptor, or an amino acid sequence which forms an equivalent three-dimensional structure to that of the region defined by amino acids 313–621 of the EGF receptor positioned at atomic coordinates substantially as shown in FIG. 6.

The phrase "EGF receptor family" includes, but is not limited to, the EGF receptor, ErbB2, ErbB3 and ErbB4. In general, EGF receptor family molecules show similar domain arrangements and share significant sequence identity, preferably at least 40% identity.

The EGF receptor molecule defined in the first aspect of the present invention is depicted in FIG. 5. The fragment comprising residues 1–475 of the receptor comprises the L1, S1 and L2 domains of the ectodomain of the EGF receptor. At the centre of this structure is a cavity, bounded by all three domains, of sufficient size to accommodate a ligand molecule.

The fragment comprising residues 313–621 comprises the L2 and S2 domains, which are positioned such that they form a "corner" structure. It is envisaged that this corner structure provides a further binding site for ligands of EGF receptor family members.

By "stereochemical complementarity" we mean that the substance or a portion thereof correlates, in the manner of the classic "lock-and-key" visualisation of ligand-receptor interaction, with the cavity in the receptor site.

In a preferred embodiment of the first aspect of the present invention, the method further involves selecting or designing a compound which has portions that match residues positioned on the surface of the receptor site as depicted in FIGS. 7, 8 and 9. By "match" we mean that the identified portions interact with the surface residues, for example, via hydrogen bonding or by enthalpy-reducing Van der Waals interactions which promote desolvation of the biologically active compound within the site, in such a way that retention of the compound within the cavity is favoured energetically.

In a further preferred embodiment of the first aspect of the present invention, the method includes screening for, or designing, a compound which possesses a stereochemistry and/or geometry which allows it to interact with both the L1 and L2 domains of the receptor site. It is believed that EGFR monomers may dimerise in nature in such a manner that the cavities of each monomer may face each other. Accordingly, the method of the first aspect of the present invention may involve screening for, or designing, a biologically active compound which interacts with the L1 domain of one monomer and the L2 domain of the other monomer.

In a further preferred embodiment of the first aspect of the present invention the compound interacts with a fragment in the region of the L1 domain-S1 domain interface, causing an alteration in the positions of the domains relative to each other. Preferably, the interaction of the compound causes the L1 and S1 domains to move away from each other. In a further preferred embodiment the compound interacts with the hinge region between the S1 domain and the L2 domain causing an alteration in the positions of these domains relative to each other. In a further preferred embodiment the compound interacts with the β sheet of the L1 domain causing an alteration in the position of the L1 domain relative to the position of the S1 domain or L2 domain.

In a further preferred embodiment, the compound binds to a lower face (according to orientations shown in FIGS. 3 and 4) containing the second α-sheet of the L1 and/or L2 domains, wherein the structure of the face is characterised by a plurality of solvent-exposed hydrophobic residues. Examples of these hydrophobic residues include Tyr64, Leu66, Tyr89, Tyr93 (see FIG. 7), Leu348, Phe380 and Phe412 (see FIG. 10).

In a further preferred embodiment the compound interacts with the hinge region between the L2 domain and S2 domains, causing an alteration in the positions of the L1 and L2 domains relative to each other. Preferably, the interaction of the compound causes the L1 and L2 domains to move away from each other.

In a further preferred embodiment the compound interacts with the β sheet of the L2 domain causing an alteration in the position of the L2 domain relative to the position of the L1 domain.

In a further preferred embodiment of the present invention, the stereochemical complementarity is such that the compound has a $K_d$ for the receptor site of less than $10^{-6}$M. More preferably, the $K_d$ value is less than $10^{-8}$M and more preferably less than $10^{-9}$M.

In preferred embodiments of the first aspect of the present invention, the compound is selected or modified from a known compound identified from a data base.

In one embodiment of the first aspect, the compound has the ability to increase an activity mediated by the molecule of the EGF receptor family.

In another embodiment, the compound has the ability to decrease an activity mediated by the molecule of the EGF receptor family. Preferably, the stereochemical interaction between the compound and the receptor site is adapted to prevent the binding of a natural ligand of the molecule of the EGF receptor family to the receptor site. Preferably, the compound has a K, of less than $10^{-6}$M, more preferably less than $10^{-8}$M and more preferably less than $10^{-9}$M.

In a second aspect the present invention provides computer-assisted method for identifying potential compounds able to bind to a molecule of the EGF receptor family and to modulate an activity mediated by the molecule, using a programmed computer comprising a processor, an input device, and an output device, comprising the steps of:
  (a) inputting into the programmed computer, through the input device, data comprising the atomic coordinates of the EGF receptor molecule as shown in FIG. 6, or a subset thereof;
  (b) generating, using computer methods, a set of atomic coordinates of a structure that possesses stereochemical complementarity to the atomic coordinates of the EGF receptor site as shown in FIG. 6, or a subset thereof, thereby generating a criteria data set;
  (c) comparing, using the processor, the criteria data set to a computer database of chemical structures;
  (d) selecting from the database, using computer methods, chemical structures which are similar to a portion of said criteria data set; and
  (e) outputting, to the output device, the selected chemical structures which are similar to a portion of the criteria data set.

In a preferred embodiment of the second aspect, the method is used to identify potential compounds which have the ability to decrease an activity mediated by the receptor.

In a further preferred embodiment of the second aspect, the method further comprises the step of selecting one or more chemical structures from step (e) which interact with the receptor site of the molecule in a manner which prevents the binding of natural ligands to the receptor site.

In a further preferred embodiment of the second aspect, the method further comprises the step of obtaining a compound with a chemical structure selected in steps (d) and (e), and testing the compound for the ability to decrease an activity mediated by the receptor.

In a further preferred embodiment of the second aspect, the method is used to identify potential compounds which have the ability to increase an activity mediated by the receptor molecule.

In a further preferred embodiment of the second aspect, the method further comprises the step of obtaining a molecule with a chemical structure selected in steps (d) and (e), and testing the compound for the ability to increase an activity mediated by the receptor molecule.

The present invention also provides a method of screening of a putative compound having the ability to modulate the activity of a molecule of the EGF receptor family, comprising the steps of identifying a putative compound by a method according to the first or second aspects, and testing the compound for the ability to increase or decrease an activity mediated by the molecule. In one embodiment, the test is carried out in vitro. Preferably, the in vitro test is a high throughput assay. In another embodiment, the test is carried out in vivo.

In a third aspect the present invention provides a compound able to bind to a molecule of the EGF receptor family and to modulate an activity mediated by the molecule, the compound being obtained by a method according to the present invention.

In a preferred embodiment of the third aspect, the compound is a mutant ligand of a molecule of the EGF receptor family, where at least one mutation occurs in the region of the ligand which interacts with residues on the surface of the receptor site facing toward the cavity. For example, the residues Arg 41 and Tyr 13 in EGF are conserved in other members of the EGF receptor family of ligands (a Phe residue may be substituted for Tyr 13). Structures of several EGF family members show the two residues to be in close proximity (Groenen, L. C., Nice, E. C., Burgess, A. W., 1994, Growth Factors 11:235–257). This portion of EGF may interact with a hydrophobic portion of the EGF receptor which contains one or more negatively charged residues such as the lower β sheet of the L1 domain. Mutants of EGF which show altered activity may be generated by introducing modifications to Arg 41 or Tyr 13 or other nearby residues. Alternatively, mutants of EGF may be generated by introducing modifications to residues on the opposite side of the ligand which may interact with a second receptor molecule in the unmodified ligand.

In a fourth aspect the present invention provides a compound which possesses stereochemical complementarity to a topographic region of a molecule of the EGF receptor family and modulates an activity mediated by the molecule, wherein the molecule is characterised by
  (i) amino acids 1–621 of the EGF receptor positioned at atomic coordinates substantially as shown in FIG. 6;
  (ii) one or more subsets of said amino acids, related to the coordinates shown in FIG. 6 by whole body translations and/or rotations; or
  (iii) amino acids present in the amino acid sequence of a member of the EGF receptor family, which form an equivalent three-dimensional structure to that of the receptor site defined by amino acids 1–621 of the EGF receptor positioned at atomic coordinates substantially as shown in FIG. 6;
  with the proviso that the compound is not a naturally occurring ligand of a molecule of the EGF receptor family or a mutant thereof.

By "mutant" we mean a ligand which has been modified by one or more point mutations, insertions of amino acids or deletions of amino acids.

In a preferred embodiment of the fourth aspect, the topographic region of the molecule is defined by amino acids 1–475 of the EGF receptor or an amino acid sequence which forms an equivalent three-dimensional structure to that of the region defined by amino acids 1–475 of the EGF receptor positioned at atomic coordinates substantially as shown in FIG. 6.

In a further preferred embodiment of the fourth aspect, the topographic region of the molecule is defined by amino acids 313–621 of the EGF receptor or an amino acid sequence which forms an equivalent three-dimensional structure to that of the region defined by amino acids 313–621 of the EGF receptor positioned at atomic coordinates substantially as shown in FIG. 6.

In preferred embodiments of the third and fourth aspects, the stereochemical complementarity between the compound and the receptor site is such that the compound has a $K_d$ for the receptor site of less than $10^{-6}M$, more preferably less than $10^{-8}M$.

In some embodiments of the third and fourth aspects, the compound increases an activity mediated by the EGF receptor.

In other embodiments of the third and fourth aspects, the compound decreases an activity mediated by the EGF receptor.

In a fifth aspect, the present invention provides a pharmaceutical composition for preventing or treating a disease which would benefit from increased signalling by a molecule of the EGF receptor family, which comprises a compound according to the third or fourth aspects of the present invention and a pharmaceutically acceptable carrier or diluent.

In a sixth aspect, the present invention provides a pharmaceutical composition for preventing or treating a disease associated with signalling by a molecule of the EGF receptor family which comprises a compound according to the third or fourth aspects of the present invention and a pharmaceutically acceptable carrier or diluent.

In a seventh aspect the present invention provides a method of preventing or treating a disease which would benefit from increased signalling by a molecule of the EGF receptor family which method comprises administering to a subject in need thereof a compound according to the third or fourth aspects of the present invention. Preferably, the disease is selected from wound healing and gastric ulcers.

In an eighth aspect the present invention provides a method of preventing or treating a disease associated with signalling by a molecule of the EGF receptor family which method comprises administering to a subject in need thereof a compound according to the third or fourth aspects of the present invention. Preferably, the disease is selected from psoriasis and tumour states comprising but not restricted to cancer of the breast, brain, ovary, cervix, pancreas, lung, head and neck, and melanoma, rhabdomyosarcoma, mesothelioma and glioblastoma.

Throughout this specification, the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF THE DRAWINGS

FIG. 1: Sequence alignment of human EGF receptor family proteins with IGF-1 receptor sequences and insulin receptor sequence for the first two domains of the EGF receptor. The alignment of the EGF receptor and the various IGF-1 receptor sequences were used by the MODELLER program to create a model of the EGF receptor domains L1 and S1. Residues which are underlined were used to create additional Cα-Cα restraints for the construction of the EGF receptor model. Disulfide bonds are also indicated by lines between cysteine residues. The modules of the EGF receptor S1 domain are numbered.

FIG. 2: Sequence alignment of human EGF receptor family proteins with IGF-1 receptor sequences and insulin receptor sequence for the third and fourth domains of the EGF receptor. Additional labels and lines are similar to those in FIG. 1.

FIG. 6: Coordinates of the two models of the EGF receptor extracellular domain. The first model (6A-1 through top half of 6A-31) consists of the domains L1 and S1. The second model (6A-31 (bottom half) through 6A-62) consists of the domains L2 and S2. The coordinates are in relation to a Cartesian set of orthogonal axes. The L1, S1 and L2 domains of the EGF receptor models have been superimposed on the crystal structure of the IGF-1 receptor domains L1, cysteine-rich domain and L2. The final column contains the number 20, 40 or 60, depending on whether the residue containing the atom is judged to be well-modeled, have a moderate possibility of error, or is likely to be inaccurate, respectively.

DETAILED DESCRIPTION OF PREFERRED EMBODIMENTS OF THE INVENTION

The present inventors have developed three dimensional structural information about the EGF receptor to enable a more accurate understanding of how the binding of ligand leads to signal transduction. Such information provides a rational basis for the development of ligands for specific therapeutic applications, something that heretofore could not have been predicted de novo from available sequence data.

The precise mechanisms underlying the binding of agonists and antagonists to the EGF receptor are not fully clarified. However, the binding of ligands to the receptor site, preferably with an affinity in the order of $10^{-8}M$ or higher, is understood to arise from enhanced stereochemical complementarity relative to naturally occurring EGF receptor ligands.

Figure 7:
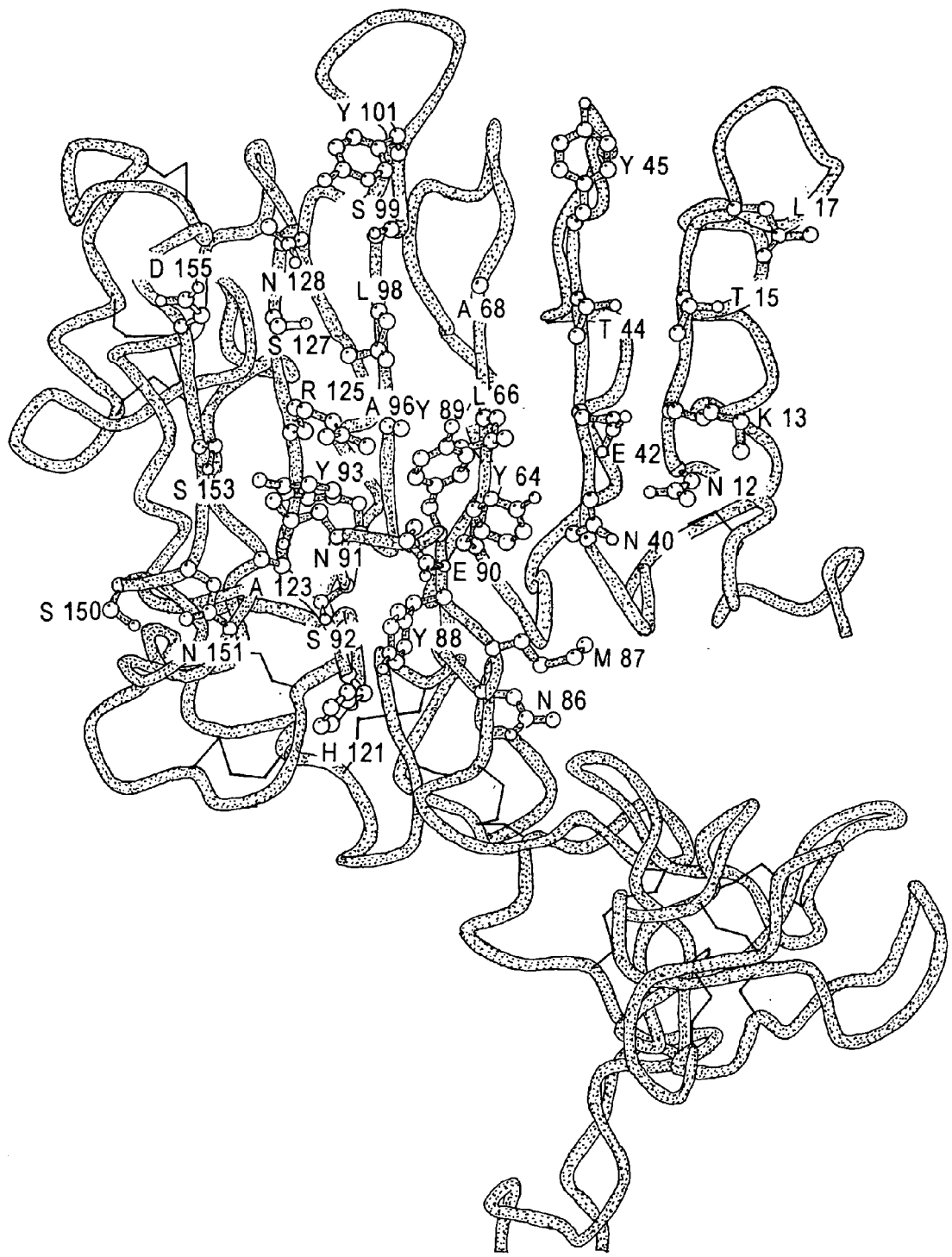
FIG. 7: Part of the model polypeptide fold of the L1 and S1 domains of the EGF receptor. Side chains of residues from the L1 domain which face towards the large cavity (shown in FIG. 5) are shown in ball and stick notation and labelled with residue number and the one letter code.
Figure 8:
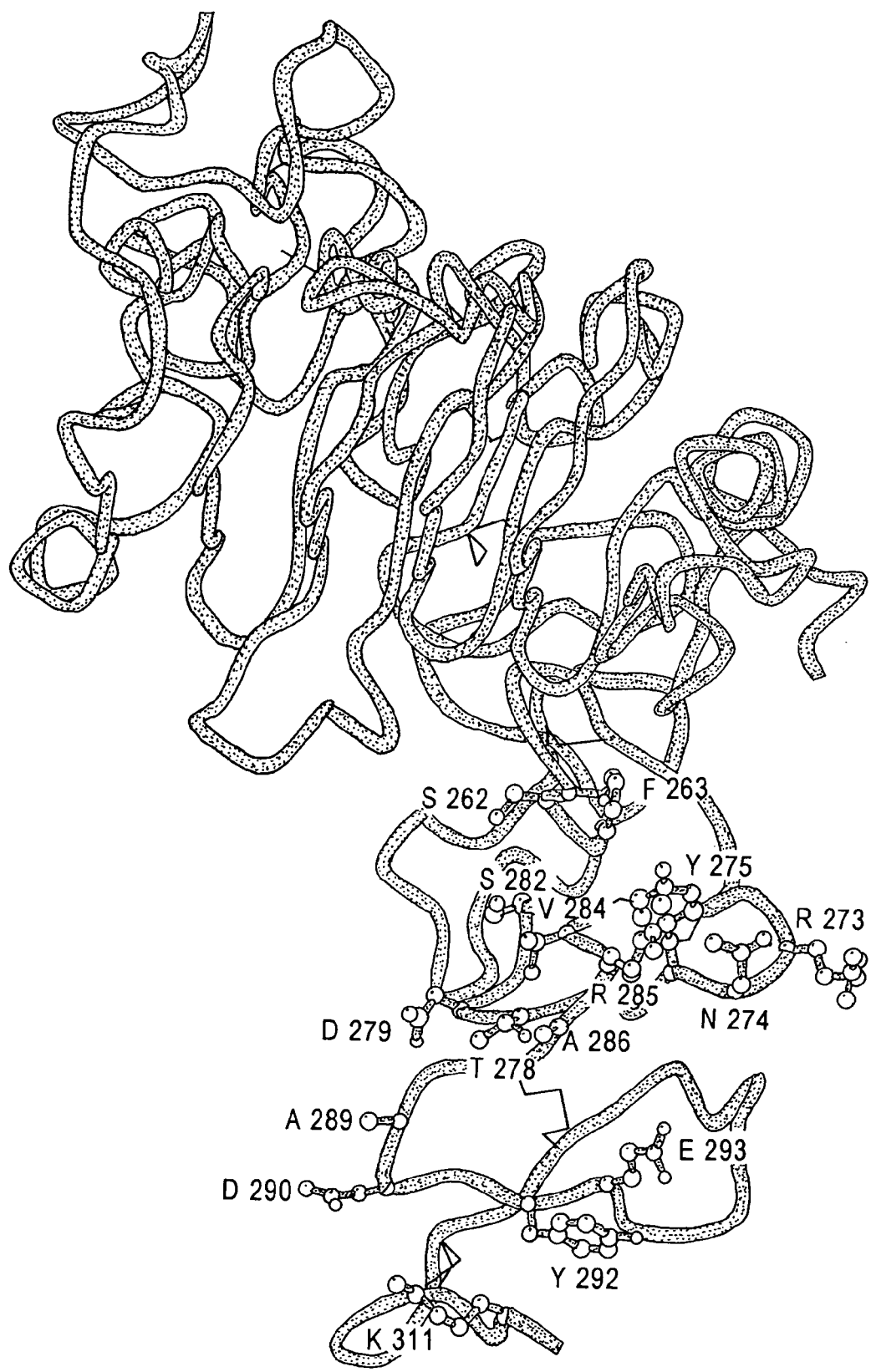
FIG. 8: Part of the model polypeptide fold of the L1 and S1 domains of the EGF receptor. Side chains of residues from the S1 domain which face towards the large cavity (shown in FIG. 5) are shown in ball and stick notation and labelled using the one letter code.
Figure 9:
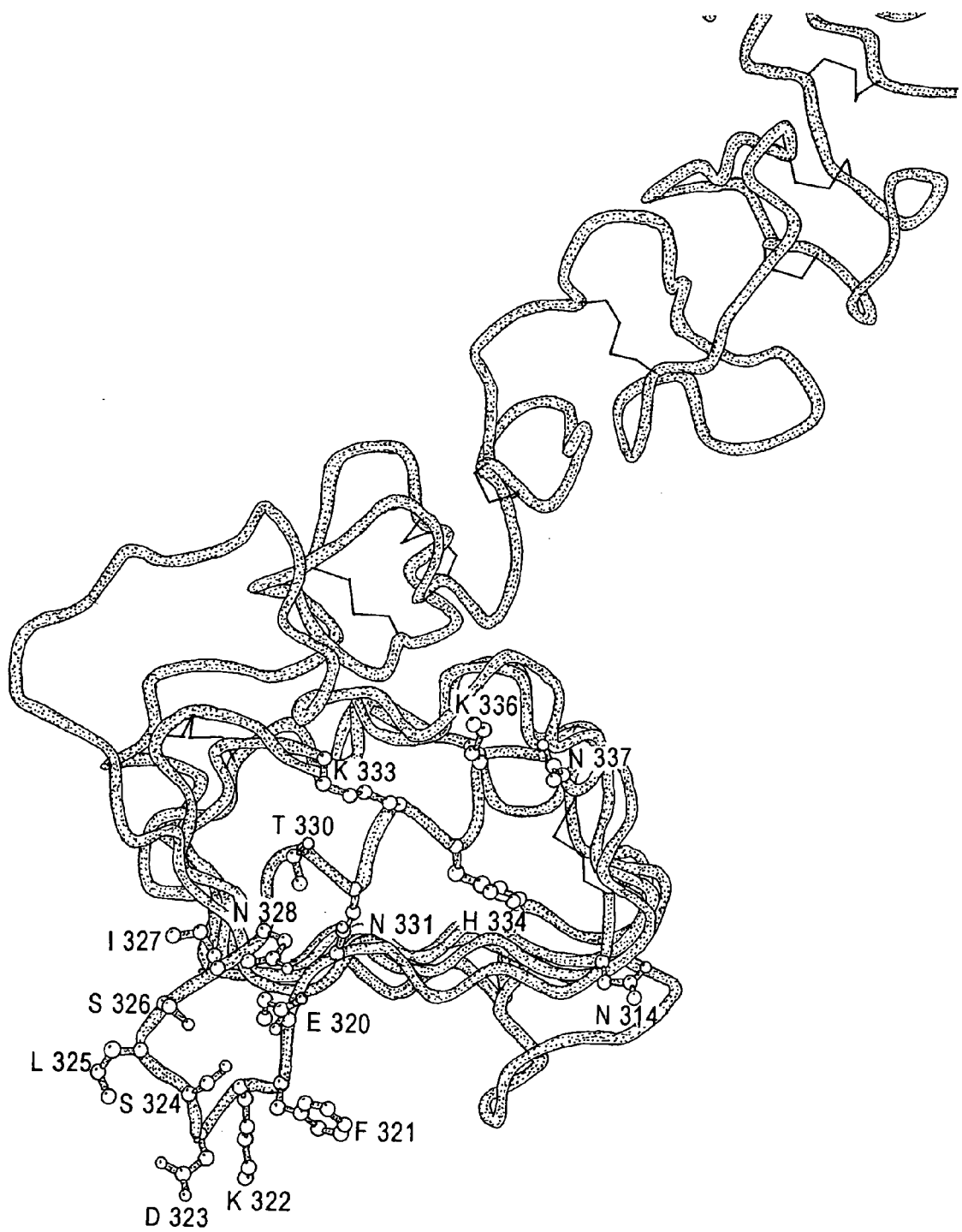
FIG. 9: Part of the model polypeptide fold of the L2 and S2 domains of the EGF receptor. Side chains of residues from the L2 domain which face towards the large cavity (shown in FIG. 5) are shown in ball and stick notation and labelled using the one letter code.

Such stereochemical complementarity, pursuant to the present invention, is characteristic of a molecule that matches intra-site surface residues lining the groove of the receptor site as enumerated by the coordinates set out in FIG. 6. The residues lining the groove are depicted in FIGS. 7, 8 and 9. By "match" we mean that the identified portions interact with the surface residues, for example, via hydrogen bonding or by enthalpy-reducing Van der Waals interactions which promote desolvation of the biologically active compound within the site, in such a way that retention of the biologically active compound within the groove is favoured energetically.

Substances which are complementary to the shape of the receptor site characterised by amino acids positioned at atomic coordinates set out in FIG. 6 may be able to bind to the receptor site and, when the binding is sufficiently strong, substantially prohibit binding of the naturally occurring ligands to the site.

It will be appreciated that it is not necessary that the complementarity between ligands and the receptor site extend over all residues lining the groove in order to inhibit binding of the natural ligand. Accordingly, agonists or antagonists which bind to a portion of the residues lining the groove are encompassed by the present invention.

In general, the design of a molecule possessing stereochemical complementarity can be accomplished by means of techniques that optimize, either chemically or geometrically, the "fit" between a molecule and a target receptor. Known techniques of this sort are reviewed by Sheridan and Venkataraghavan, Acc. Chem Res. 1987 20 322; Goodford, J. Med. Chem. 1984 27 557; Beddell, Chem. Soc. Reviews 1985, 279; Hol, Angew. Chem. 1986 25 767 and Verlinde C. L. M. J & Hol, W. G. J. Structure 1994, 2, 577, the respective contents of which are hereby incorporated by reference. See also Blundell et al., Nature 1987 326 347 (drug development based on information regarding receptor structure).

Thus, there are two preferred approaches to designing a molecule, according to the present invention, that complements the shape of the EGF receptor. By the geometric approach, the number of internal degrees of freedom (and the corresponding local minima in the molecular conformation space) is reduced by considering only the geometric (hard-sphere) interactions of two rigid bodies, where one body (the active site) contains "pockets" or "grooves" that form binding sites for the second body (the complementing molecule, as ligand). The second preferred approach entails an assessment of the interaction of respective chemical groups ("probes") with the active site at sample positions within and around the site, resulting in an array of energy values from which three-dimensional contour surfaces at selected energy levels can be generated.

The geometric approach is illustrated by Kuntz et al., J. Mol. Biol. 1982 161 269, the contents of which are hereby incorporated by reference, whose algorithm for ligand design is implemented in a commercial software package distributed by the Regents of the University of California and further described in a document, provided by the distributor, which is entitled "Overview of the DOCK Package, Version 1.0,", the contents of which are hereby incorporated by reference. Pursuant to the Kuntz algorithm, the shape of the cavity represented by the EGF receptor site is defined as a series of overlapping spheres of different radii. One or more extant databases of crystallographic data, such as the Cambridge Structural Database System maintained by Cambridge University (University Chemical Laboratory, Lensfield Road, Cambridge CB2 1EW, U.K.) and the Protein Data Bank maintained by Brookhaven National Laboratory (Chemistry Dept. Upton, N.Y. 11973, U.S.A.), is then searched for molecules which approximate the shape thus defined.

Molecules identified in this way, on the basis of geometric parameters, can then be modified to satisfy criteria associated with chemical complementarity, such as hydrogen bonding, ionic interactions and Van der Waals interactions.

The chemical-probe approach to ligand design is described, for example, by Goodford, J. Med. Chem. 1985 28 849, the contents of which are hereby incorporated by reference, and is implemented in several commercial software packages, such as GRID (product of Molecular Discovery Ltd., West Way House, Elms Parade, Oxford OX2 9LL, U.K.). Pursuant to this approach, the chemical prerequisites for a site-complementing molecule are identified at the outset, by probing the active site (as represented via the atomic coordinates shown in FIG. 1) with different chemical probes, e.g., water, a methyl group, an amine nitrogen, a carboxyl oxygen, and a hydroxyl. Favored sites for interaction between the active site and each probe are thus determined, and from the resulting three-dimensional pattern of such sites a putative complementary molecule can be generated.

Programs suitable for searching three-dimensional databases to identify molecules bearing a desired pharmacophore include: MACCS-3D and ISIS/3D (Molecular Design Ltd., San Leandro, Calif.), ChemDBS-3D (Chemical Design Ltd., Oxford, U.K.), and Sybyl/3 DB Unity (Tripos Associates, St Louis, Mo.).

Programs suitable for pharmacophore selection and design include: DISCO (Abbott Laboratories, Abbott Park, Ill.), Catalyst (Bio-CAD Corp., Mountain View, Calif.), and ChemDBS-3D (Chemical Design Ltd., Oxford, U.K.).

Databases of chemical structures are available from a number of sources including Cambridge Crystallographic Data Centre (Cambridge, U.K.) and Chemical Abstracts Service (Columbus, Ohio).

De novo design programs include Ludi (Biosym Technologies Inc., San Diego, Calif.), Sybyl (Tripos Associates) and Aladdin (Daylight Chemical Information Systems, Irvine, Calif.).

Those skilled in the art will recognize that the design of a mimetic may require slight structural alteration or adjustment of a chemical structure designed or identified using the methods of the invention.

The invention may be implemented in hardware or software, or a combination of both. However, preferably, the invention is implemented in computer programs executing on programmable computers each comprising a processor, a data storage system (including volatile and non-volatile memory and/or storage elements), at least one input device, and at least one output device. Program code is applied to input data to perform the functions described above and generate output information. The output information is applied to one or more output devices, in known fashion. The computer may be, for example, a personal computer, microcomputer, or workstation of conventional design.

Each program is preferably implemented in a high level procedural or object-oriented programming language to communicate with a computer system. However, the programs can be implemented in assembly or machine language, if desired. In any case, the language may be compiled or interpreted language.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

Compounds designed according to the methods of the present invention may be assessed by a number of in vitro and in vivo assays of hormone function. For example, the identification of EGF receptor antagonists of may be undertaken using a solid-phase receptor binding assay. Potential antagonists may be screened for their ability to inhibit the binding of europium-labelled EGF receptor ligands to soluble, recombinant EGF receptor in a microplate-based format. Europium is a lanthanide fluorophore, the presence of which can be measured using time-resolved fluorometry. The sensitivity of this assay matches that achieved by radioisotopes, measurement is rapid and is performed in a microplate format to allow high-sample throughput, and the approach is gaining wide acceptance as the method of choice in the development of screens for receptor agonists/antagonists (see Apell et. al. J. Biomolec. Screening 3:19–27, 1998 Inglese et. al. Biochemistry 37:2372–2377, 1998).

Binding affinity and inhibitor potency may be measured for candidate inhibitors using biosensor technology.

The EGF receptor antagonists may be tested for their ability to modulate receptor activity using a cell-based assay incorporating a stably transfected, EGF-responsive reporter gene (Souriau, C., Fort, P., Roux, P., Hartley, O., Lefranc, M-P., Weill, M., 1997, Nucleic Acids Res. 25:1585–1590). The assay addresses the ability of EGF to activate the reporter gene in the presence of novel ligands. It offers a rapid (results within 6–8 hours of hormone exposure), high-throughput (assay can be conducted in a 96-well format for automated counting) analysis using an extremely sensitive detection system (chemiluminescence). Once candidate compounds have been identified, their ability to antagonise signal transduction via the EGF-R can be assessed using a number of routine in vitro cellular assays such as inhibition of EGF-mediated cell proliferation. Ultimately, the efficiency of antagonist as a tumour therapeutic may be tested in vitro in animals beating tumour isografts and xenografts as described (Rockwell, P., O'Connor, W. J., King, K., Goldstein, N. I., Zhang, L. M., Stein, C. A., 1997, Proc Natl Acad Sci USA 94:6523–6528; Prewett, M., Rothman, M., Waksal, H., Feldman, M., Bander, N. H., Hicklin, D. J., 1998 Clin Cancer Res 4:2957–2966).

Tumour growth inhibition assays may be designed around a nude mouse xenograft model using a range of cell lines. The effects of the receptor antagonists and inhibitors may be tested on the growth of subcutaneous tumours.

Comparative Modelling

The comparative modelling method exploits the observation that proteins with more than 25% amino acid identity will almost always have a similar protein backbone (Sander, C. And Schneider, R., 1991, Proteins: Structure Function and Genetics, 9, 56–68). In some cases, proteins will have similar backbone structures with a lower proportion of identical amino acids. By aligning the sequence of a (target) protein which is to be modelled with the sequences with known structures (the templates), a model of the protein can be obtained. Where a region of the target sequence follows the sequences of a template, the backbone of the target is built to follow that of the template. Where the target sequence can not be aligned to a target sequence, the so-called insertion must be constructed by other means (Greer, J., 1991, Meth. Enzym. pp 239–252).

The MODELLER program ((Šali, A and Blundell, T. L., 1993, J. Mol. Biol. 234, 779–815) is a semi-automated approach to building models of proteins given the structures of one or more template structures and an alignment between the sequences of the target protein and the templates. Based on the sequence alignment and a set of rules derived from the analysis of sets of aligned structure, the program generates a series of restraints for variables such as Cα-Cα distances, main chain and side chain dihedral angles for the target structure. The restraints are expressed in terms of probability density functions (PDFs). The PDFs are combined to yield an expression for the most probable structure as a function of the variables (Cα-Cα distances etc). The program then attempts to find structures to maximise the value of this function. In effect, the program attempts to minimise a transformed version of this function.

While some comparative modelling approaches involve the explicit building of regions of the model for which there is no sequence alignment with a template, the MODELLER program constructs PDFs for these regions, thus including them in the consideration of constructing a comparative model. It is conceivable that once a comparative model has been constructed using MODELLER than an algorithm to build the structures of these regions is applied.

The MODELLER program was used to build the structures of the extracellular portion of the EGF receptor using the 3D structure of the IGF-1 receptor (as described in PCT/AU98/00998) as a template. The description of the generation of these models is outlined below.

Construction of the Alignment

The region of the IGF-1 receptor whose structure is known (Garrett, T. P., McKern, N. M., Lou, M., Frenkel, M. J., Bentley, J. D., Lovrecz, G. O., Elleman, T. C., Cosgrove, L. J., Ward, C. W., 1998 Nature 394:395–399) consists of three domains, the L1 domain, cysteine-rich domain (CRD) and the L2 domain (in order of increasing residue number). The L1 and L2 domains adopt similar folds, each consisting of a single-stranded right-hand β-helix. The helix contains three β-sheets which make up the left and right sides and the bottom of the β-helix. The top is less regular. This type of β-helix has been dubbed a "breadloaf". The cysteine-rich domain (CRD) consists of eight small modules, each of which has one or two disulfide bonds. The first three modules of the CRD contain two disulfide bonds which have a Cys1–Cys3 and Cys2–Cys4 disulfide pairing arrangement. The next four have a single disulfide bond with a so-called β-finger structure. The eighth module of the CRD contains one disulfide bond but is not a α-finger.

The sequence of the EGF receptor extracellular domain can be divided into four domains, L1, S1, L2 and S2 (in order of increasing residue number) on the basis of internal homology and homology with the insulin receptor family (Ward, C. W., Hoyne, P. A., Flegg, R. H., 1995, Proteins 22:141–153; Bajaj, M., Waterfield, M. D., Schlessinger, J., Taylor, W. R., Blundell, T., 1987, Biochim Biophys Acta 916:220–226). The L1 and L2 domains are similar in sequence to each other and to the L1 and L2 domains in the IGF-1 receptor. The S1 and S2 domains are similar in sequence and also similar to the CRD of the IGF-1 receptor. These three domains contain a large number of cysteine residues, although the S2 domain of the EGF receptor has two less cysteine residues than does the CRD of the IGF-1 receptor and the S1 domain of the EGF receptor.

Two important sequence motifs are found in the EGF receptor sequence which are conserved in other EGF receptor homologues. The first motif is the sequence CXXXXXXW which is found near the end of the sequences of the L1 and L2 domains of the EGF receptor and its homologues where C is cysteine and W is tryptophan. (The motif in the L1 domain of the EGF receptor consists of C133–W140 and in the L2 domain consists of C446–W453.) The second motif is the sequence CW which occurs near the start of the S1 and S2 domains of the EGF receptor (C175–W176 in the S1 domain and C491–W492 in the S2 domain). The two motifs also occur in the insulin receptor family (C120XXXXXXW127 and C175W176 in IGF-1 receptor) in the L1 domain and cysteine-rich domain respectively. In contrast to the EGF receptor and its homologues the first of these two motifs does not occur in the L2 domain of the insulin receptor family. Structurally, the first motif corresponds to part of the L1 domain which allows penetration of the tryptophan residue of the second motif into the β-helix. As the first sequence motif is absent from the L2 domain of the IGF-1 receptor, very little of the structure of this domain was used as a template in the modelling of the EGF receptor.

Construction of the Alignment of L1 and S1

Figure 1:
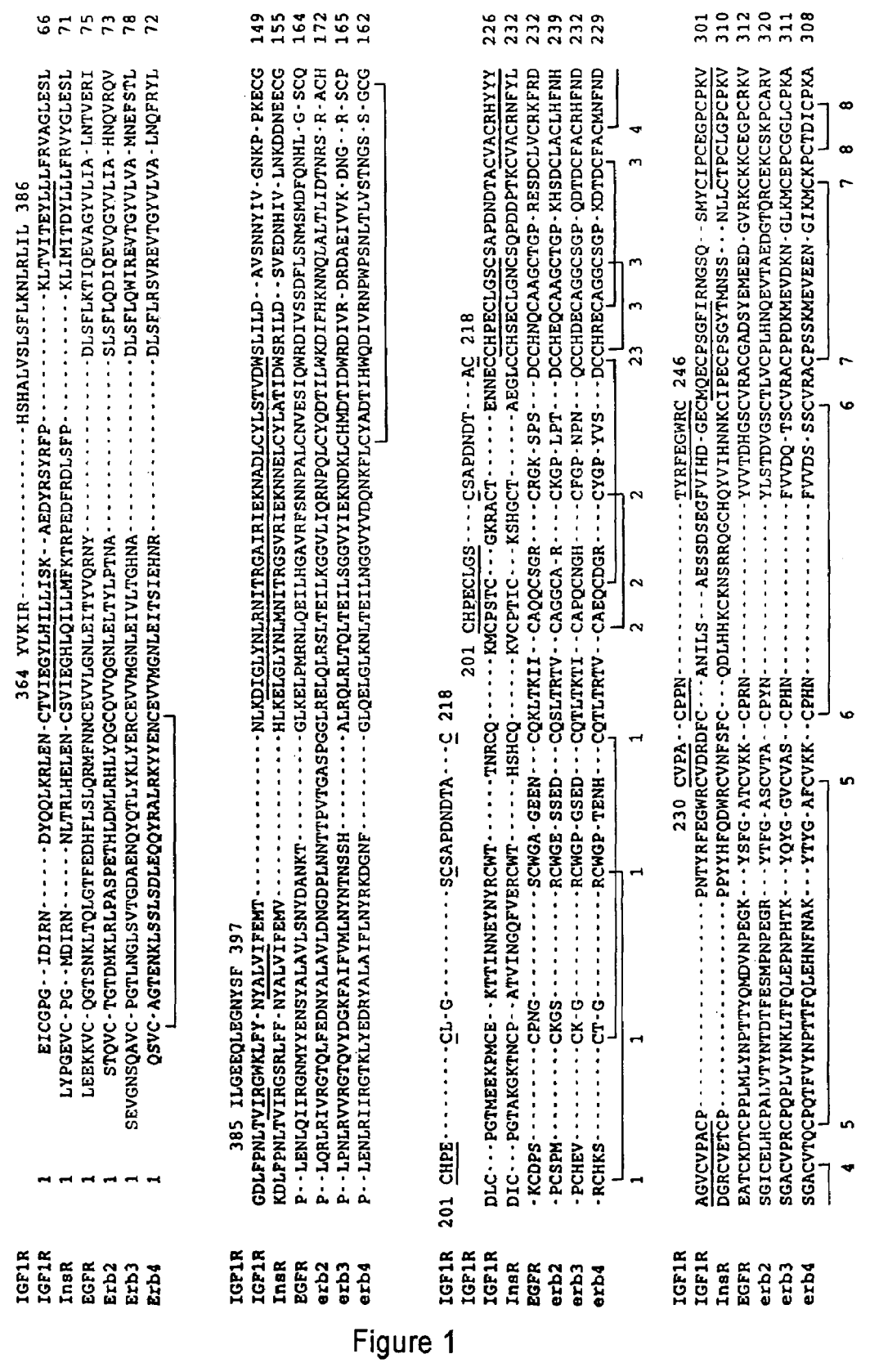

As the L1 domain of the IGF-1 receptor has a defined core, the sequence alignment was manually constructed with a view to placing most of the conserved hydrophobic residues of the EGF receptor such that their side chains point towards the β-helical core. Homologues of the EGF receptor were included in the alignment to assist with the identification of such residues (FIG. 1). Other IGF-1 receptor residues whose positions were conserved were the four cysteine residues in the L1 domain and the residues Arg 77, Trp 127, Trp 176 and Gln 182. Two small regions of the IGF-1 receptor were also included in the alignment. The first of these regions includes the sequence Ser 375–Lys 380 from the L2 domain of the IGF-1 receptor and is used as a template for modelling the EGF receptor residues Asp 51–Lys 56. Additional flanking residues were also used. Residues Ile 385–Phe 397 of the IGF-1 receptor were also used as a template to better model the EGF receptor residues Ile 83–Leu 95 (FIG. 1).

The alignment of the S1 domain of the EGF receptor to the cysteine-rich domain of the IGF-1 receptor used the same combination of modules. All of the putative modules of the EGF receptor S1 domain were aligned to part or all of the corresponding module of the CRD of the IGF-1 receptor. The third module of the IGF-1 receptor CRD (Cys 201–Cys 218) was used as an additional template to the first (Cys 166–Cys 183) and second (Cys 191–Cys 207) putative modules of the EGF receptor S1 domain. The residues Cys 230–Cys 246 of IGF-1 receptor, which include the protein's fifth module, were aligned to the EGF receptor residues Cys 267–Cys 283 (which include the EGF receptor S1 domain's putative sixth module).

Construction of the Alignment of L2 and S2

Figure 2:
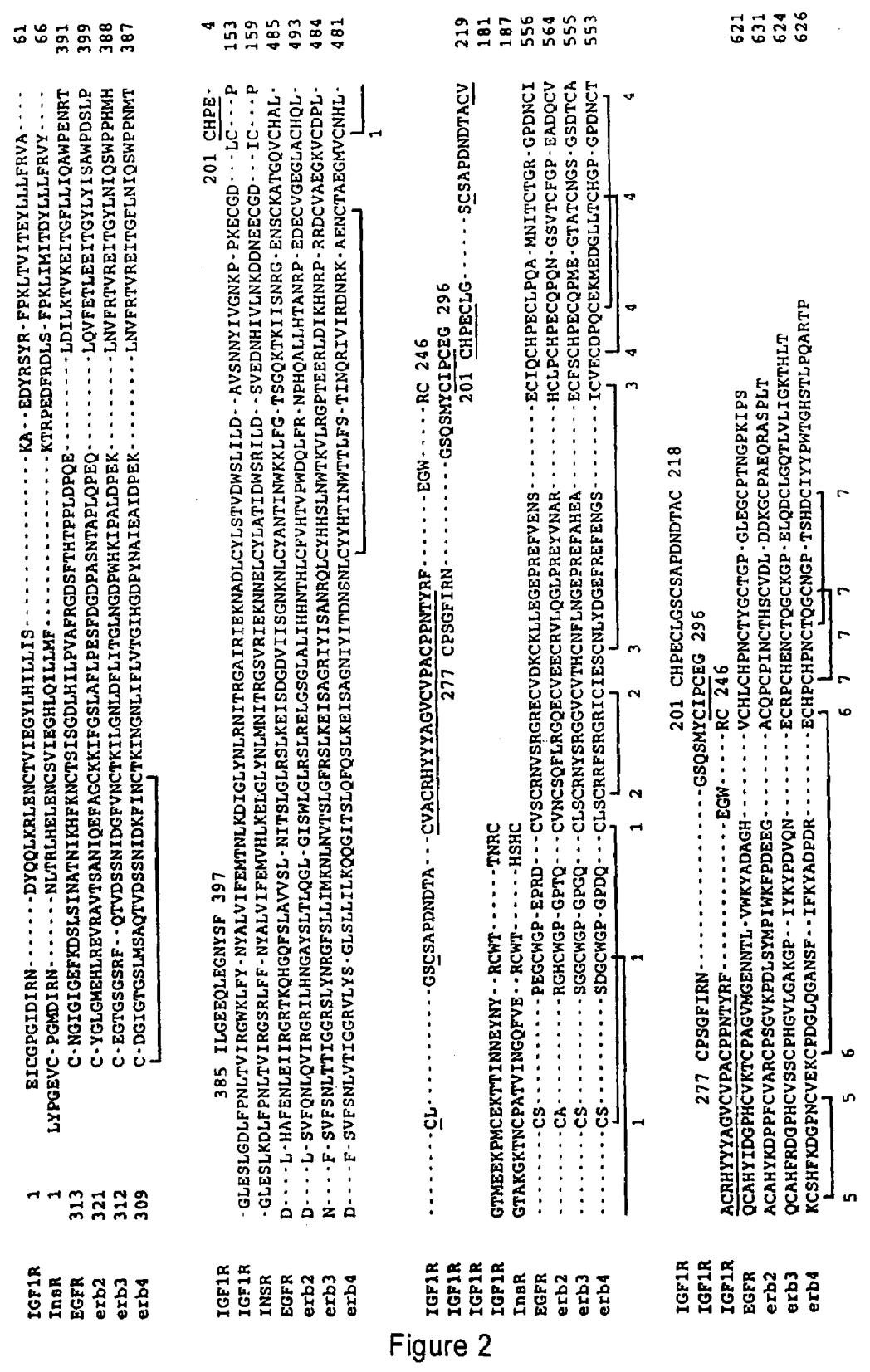

Construction of the alignment of the sequence of the L2 domain of the EGF receptor to the sequence of the L1 domain of the IGF-1 receptor followed similar principles to that of the alignment of the L1 domain of the EGF receptor. The region Ile 385–Phe 397 of the IGF-1 receptor served as an additional template and its sequence was aligned to Ile 402–Leu 414 of the EGF receptor (FIG. 2).

An analysis of α-finger modules in the IGF-1 receptor, TNF receptor and the laminin-γ structures revealed that these modules could be classified into three types exhibiting some structural and sequence conservation. Two of the structural types are relevant to the IGF-1 receptor and the EGF receptor. The first type of β-finger is characterised by structural conservation of the C-terminal part of the module and also of the linker region after the module. The signature sequence is C . . . CXXC where the third cysteine residue is the start of another β-finger module. The second type of β-finger is characterised by structural conservation of the N-terminal portion of the module and also of the linker region after the module. The signature sequence is C . . . CXXXC where the third cysteine is the start of a module whose disulfide bonding pattern has a Cys 1–Cys 3, Cys 2–Cys 4 arrangement.

Comparison of the sequences of the modules of the IGF-1 receptor CRD with the sequence of the EGF receptor S2 domains suggested that the arrangement of modules in the S2 domain were different from those of the IGF receptor CRD and the EGF receptor S1 domain. The residues of the third module in the CRD of the IGF-1 receptor, Cys 201–Cys 218, could be aligned with the segments of the EGF receptor S2 domain sequence: Cys 482–Cys 499; Cys 534–Cys 555 and Cys 596–Cys 612. These modules are the putative first, fourth and seventh modules of the S2 domain. The residues of the first EGF receptor module were also aligned to residues Cys 152–Cys 181 of the first module of the IGF-1 receptor CRD. The residues of the fourth module in the CRD of the IGF-1 receptor, Cys 221–Cys 230, a beta-finger module of the first type described above, could be aligned with the regions of sequence Cys 502–Cys 511 and Cys 558–Cys 567. These two regions of the EGF receptor S2 domain are the putative second and fifth modules. By elimination, the regions between the two sets of remaining cysteine residues (the putative third and sixth modules) were assigned as β-finger modules of the second type. These regions of sequence are followed by three residues and then a module containing four cysteine residues. The N-terminal regions of the fifth (Cys 234–Cys 246) and seventh modules (Cys 277–Cys 291) of the IGF-1 receptor CRD were both aligned to the N-terminal regions of the two modules (Cys 515–Cys 531 and Cys 571–Cys 593).

In the IGF-1 receptor CRD, there is no occurrence of a β-finger module being followed by a module containing four cysteine residues. Thus, the positioning of the fourth module in the EGF receptor S2 model relative to the third module is essentially arbitrary. The same applies to the positioning of the seventh module relative to the sixth module of the EGF receptor S2 domain model.

Construction of the Model

Version 3 of the MODELLER program (Modeler User Guide, October 1996, San Diego Molecular Simulations Inc) was used to build models of the EGF receptor. The various sequences of the IGF-1 receptor and the EGF receptor shown in FIG. 1 were used as the alignment for the construction of the model of the L1 and S1 domains of the EGF receptor. The coordinates of each of the IGF-1 receptor sequences (i.e. the templates) shown in FIG. 1 were also used as input for the MODELLER program. Additional distance restraints were generated between Cα atoms of selected residues. The restraints were generated as follows. The small IGF-1 receptor templates were superimposed into the structure of the first two domains of the IGF-1 receptor using the Cα atoms of the residues which are aligned in FIG. 1. Using the Homology module of the Insight II program (Homology User Guide, October 1995, San Diego BIO-SYM/MSI) coordinates were built for the EGF receptor residues which are aligned to the IGF-1 receptor coordinates which are in bold typeface. From these coordinates, distance restraints in the form of Gaussian curves were constructed for pairs of Cα atoms with a distance less than 50 Å. The sigma value of the Gaussian curves was set to be 2 Å. A MODELLER run was submitted using the alignment in FIG.

1. The built models of proteins attempt to satisfy these restraints in addition to the restraints the program derives from the alignment.

The aligned IGF-1 receptor and EGF receptor sequences of FIG. 2 were used as the alignment for creating the model of the L2 and S2 domains of the EGF receptor. The coordinates of the each of the IGF-1 receptor sequences shown in FIG. 2 were used as the structural templates. Two separate sets of additional restraints were used. The first set were based on the underlined IGF-1 receptor residues which are aligned to EGF receptor residues Cys 482–Cys 534 (the first module of the S2 domain to the first cysteine of the fourth module). From the coordinates of the Cα atoms of these residues, distance restraints in the form of Gaussian curves were constructed for pairs of Cα atoms with a distance less than 50 Å. The second set of additional restraints were based on the Cα atoms of the underlined IGF-1 residues which are aligned to EGF receptor residues Cys 534–Cys 596 (the fourth module of the S2 domain to the first cysteine of the seventh module). The signal value of the Gaussian curve used to construct the additional restraints was 1 Å.

For both sets of models, the MODELLER program constructed 20 models whose coordinates were perturbed from an initial structure by a random value of maximum distance 4 Å. The refinement level used was the 'refine1' option in the MODELLER program.

Most of the insertion regions of the EGF receptor models were constructed using the "loop" routine of version 4 of MODELLER (Modeler User Guide, June 1997, San Diego Molecular Simulations Inc). Coordinates for each insertion were built using one of the two models obtained in the previous section as a scaffold. The regions of sequence for which coordinates were built in this manner were 1–5, 8–12, 16–23, 46–51, 101–107, 145–148, 184–191, 241–262, 319–328, 522–530, 540–546, 578–600 and 612–621. Coordinates for residues 351–368 and 387–393 were constructed simultaneously due to the proximity of these regions in the model of the L2 domain. For each insertion, 50 models were constructed. In cases where the generated loops with the lowest scores had similar backbone structures, the loop building process was considered to have converged and the coordinates of the loop replaced those of the same residues on the refined model. Where the loop structures did not converge, the structures with the three lowest MODELLER loop scores were evaluated using Procheck (Laskowski R A, MacArthur M W, Moss D S, Thornton J M. (1993). J Appl. Crystallogr 26: 283–291), ProsaII (Hendlich M, Lackner P, Weitckus S, Floeckner H. Froschauer R, Gottsbacher K, Casari G, Sippl M J. (1990) J Mol Biol 216:167–180; Sippl M J. (1993) Proteins 17: 355–362.) and Profiles-3D (Bowie J U, Lüthy R, Eisenberg D. (1991) Science 253:164–170; Lüthy R, Bowie J U, Eisenberg D. 1992. Nature 356: 83–85.). For several of these loops, the one with the second lowest MODELLER score was selected as it had a more favorable Profiles3D and ProsaII plot.

In order to retain certain secondary structures, additional restraints were used in the construction of some of the loops. Restraints with the form of a right-handed half-Gaussian function with a s value of 0.05 Å were used to hold selected mainchain N-O distances to 3.0 Å or less. The atom pairs for which this additional restraint was added were: Gln 139.N–Gln 184.OE1, Val 268.N–Tyr 261.O, Val 268.O–Tyr 261.N, Ser 506.N–Ser 529, Ile 562.N–His 591.O and Glu 578.N–Val 592.

Structure of the EGF Receptor Model

Figure 3:
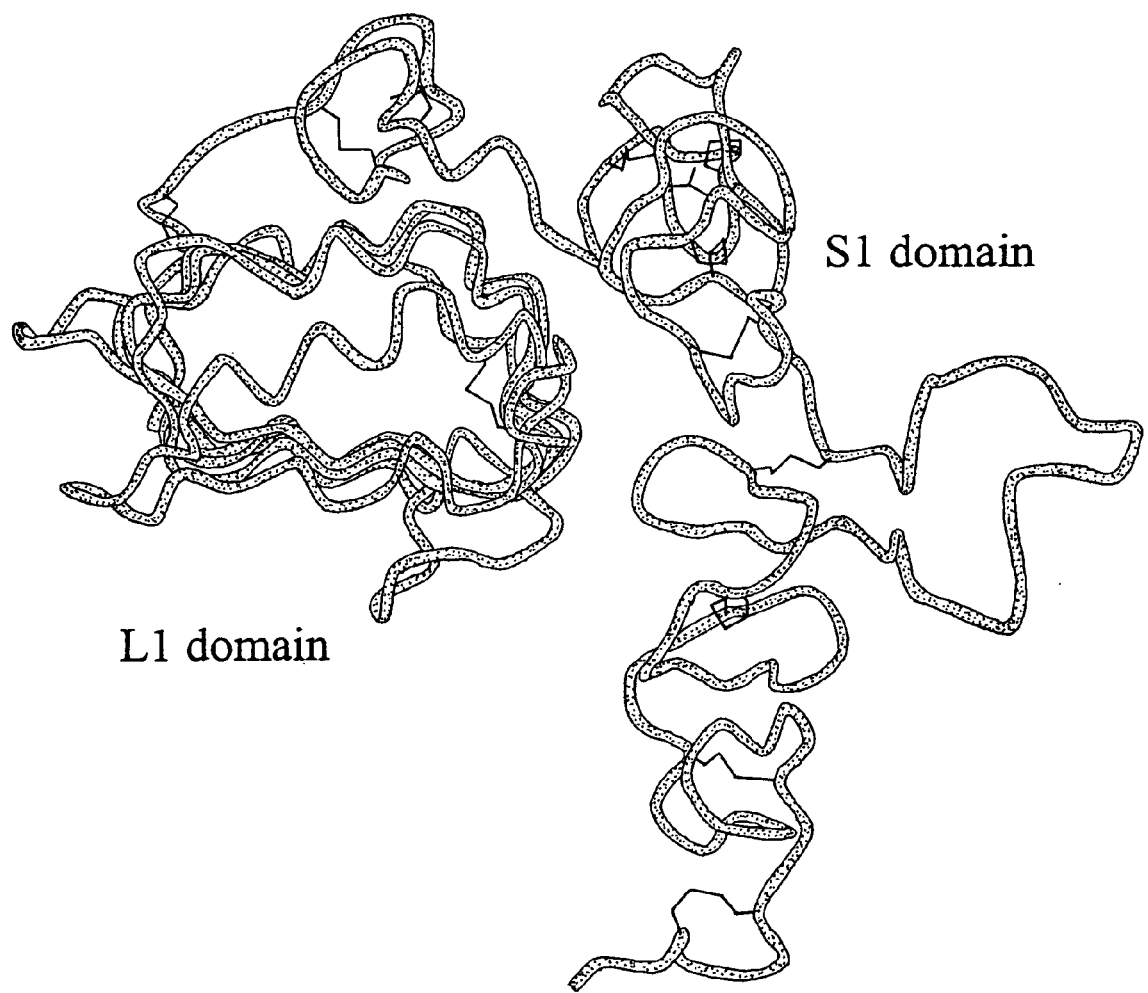
FIG. 3: Model polypeptide fold of the L1 and S1 domains of the EGF receptor. The L1 is at the left hand side of the structure with the N-terminus facing the front. Cysteine residue sidechains are depicted as sticks.
Figure 4:
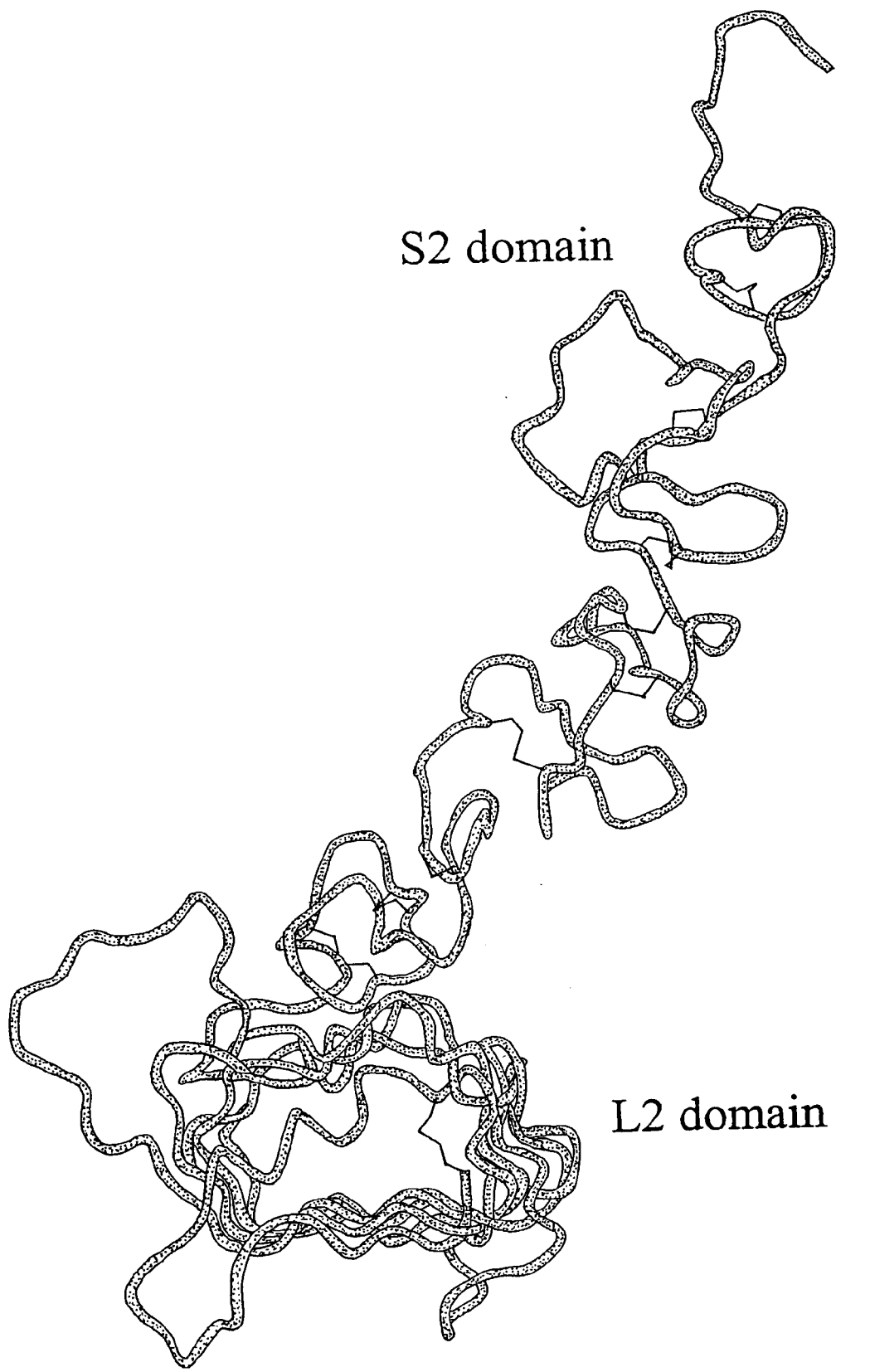
FIG. 4: Model polypeptide fold of the L2 and S2 domains of the EGF receptor. The L2 is at the bottom of the structure with the N-terminus facing the front. Cysteine residue sidechains are depicted as sticks.

The structure of the L1 and S1 domains of the EGF receptor as determined by the modelling described above is shown in FIG. 3, while the structure of the L2 and S2 domains is shown in FIG. 4. The superposition of these two models onto the structure of the extracellular domains of the IGF-1 receptor is shown in FIG. 5.

The coordinates of the EGF receptor domains L1, S1, L2 and S2 are shown in FIG. 6.

Figure 5:
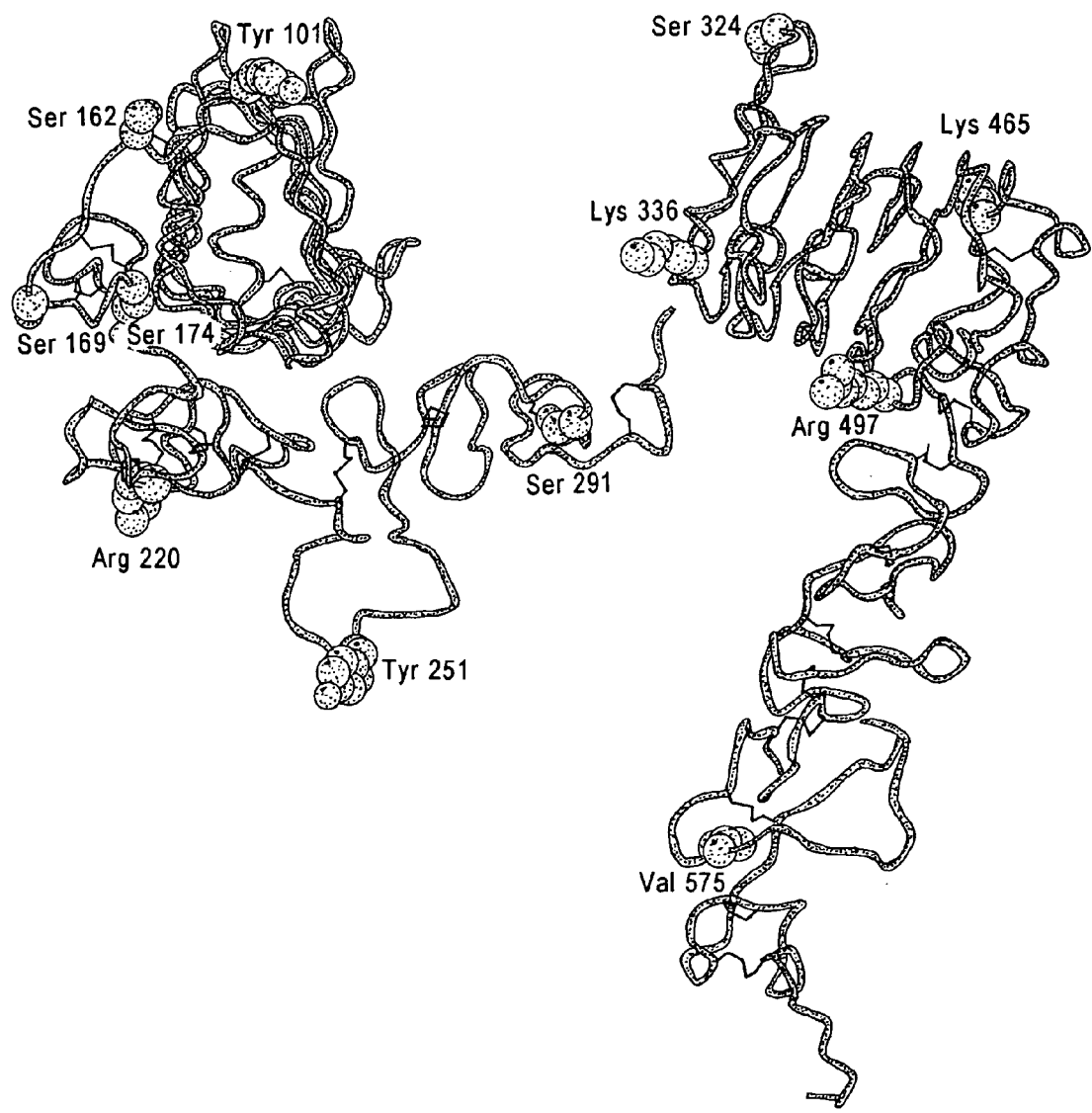
FIG. 5: Superposition of the two models (of the L1 and S1 domain and of L2 and S2 domains) onto the structure of the first three domains of the IGF-1 receptor. Cysteine residue sidechains are depicted as sticks. Selected residues are shown as spheres and labelled.
Figure 10:
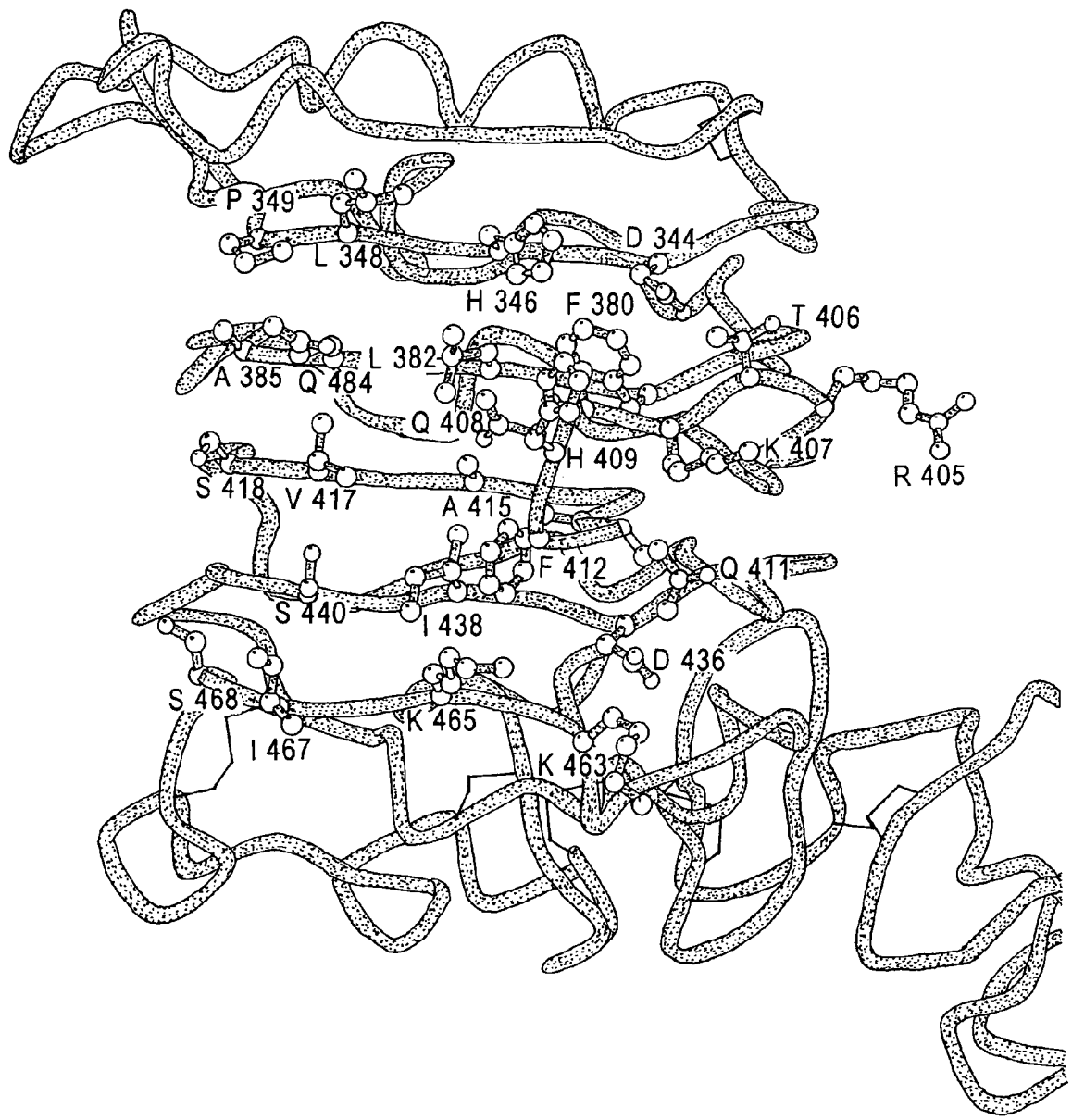
FIG. 10: Part of the model polypeptide fold of the L2 and S2 domains of the EGF receptor. Solvent exposed residues from the face of the L2 domain containing the large β sheet are shown in ball and stick representation.

FIGS. 7, 8 and 9 show the sidechains of residues of the EGF receptor models which face the large cavity as shown in FIG. 5. FIG. 10 shows the sidechains of residues of the face of the EGF receptor L2 domain which contains the second beta sheet (the lower face of the L2 domain using the orientation shown in FIG. 4).

The structures of the L1 and S1 domains are similar to those of the IGF-1 receptor structure, as expected. There are three major differences in the S1 domain of the EGF receptor model from the structure of the IGF-1 receptor cysteine-rich domain. The first module of the S1 domain is noticeably smaller than that of the IGF-1 receptor CRD. The sixth module (Cys 271–Cys 283) of the S1 domain is smaller than that of the IGF-1 receptor and occupies less of the region between the L1 and L2 domains. The fifth module (Cys 240–Cys 267) contains a large insertion which points away from the L1 domain. The eighth module of the EGF receptor S1 domain (Cys 305–Cys 309) and the linker region (Arg 310–Val 312) which follows it are similar in structure to the analogous regions of the IGF-1 receptor. Like the IGF-1 receptor, the linker region is postulated to be a hinge region about which the S1 domain and the L2 domain can reorient.

A region of the EGF receptor in the L2 domain which could not be aligned with the IGF-1 receptor includes the residues Trp 386–Pro 387 which are conserved across the EGF receptor family. This sequence motif is not found in the insulin receptor family and may represent a region of novel structure.

The amino acids 352–367 correspond to a large insertion in the L2 domain of the EGF receptor. The amino acids 351–364 have been identified as the epitope for several antibodies against the EGF receptor (Wu, D. G., Wang, L. H., Sato, G. H., West, K. A., Harris, W. R., Crabb, J. W., Sato, J. D., 1989, J. Biol. Chem. 264:17469–17475). This region forms a loop which sticks out of the surface is consistent with this region being accessible to antibodies. The structure itself is difficult to model accurately since its sequence does not correspond to any part of the IGF-1 receptor sequence. The position of this insertion is in approximately the same region as where the IGF 1 receptor differs in backbone structure.

The S2 domain model of the EGF receptor adopts a different arrangement of modules and consequently a different shape that of the CRD of the IGF-1 receptor and the S1 domain model of the EGF receptor. The disulfide bond arrangement is the same as that predicted by similarity to the tumour necrosis receptor (Ward, C. W., Hoyne, P. A., Flegg, R. H., 1995, Proteins 22:141–153) and has since been confirmed by mass spectroscopic analyses of proteolytically digested EGF receptor extracellular domain (Abe, Y., Odaka, M., Inagaki, F., Lax, I., Schlessinger, J., Kohda, D., 1998, J. Biol. Chem. 273:11150–11157). The only significant contact of the S2 domain with the L2 domain of the EGF receptor model is the intercalation of Trp 492 into the L2 domain, analogous to that made by Trp 176 in the S1 domain of the EGF receptor and Trp 176 in the CRD of the IGF-1 receptor to their respective L1 domains. Unlike the S1 domain of the EGF receptor, the rest of the S2 domain does not make any contacts with the L2 domain. The S2 domain is rod-like and points out from the L2 domain with a different geometry to the manner in which the S1 domain points out from the L1 domain.

Putative Binding Sites of the EGF Receptor

From the IGF-1 receptor structure and a number of insulin receptor mutants, one of the regions of insulin binding was proposed to the face of the L1 domain which contains the second β-sheet (Garrett, T. P., McKern, N. M., Lou, M., Frenkel, M. J., Bentley, J. D., Lovrecz, G. O., Elleman, T. C., Cosgrove, L. J., Ward, C. W., 1998 Nature 394:395–399). This surface is characterised by a number of hydrophobic residues which point out of the structure and also the presence of a structurally conserved loop. By analogy, we propose that the analogous β sheets of the L1 and L2 are potential binding sites. These sheets contain a number of hydrophobic residues, conserved amongst EGF receptor family members, which point away from the core of the β-helix structure. Residue 45 of a mutant EGF has been cross-linked to the residue Lysine 465 which is in the last strand of the lower β sheet of the L2 domain. (Summerfield, A E et al, J Biol Chem, 1996, 271(33), 19656–19659). Tyrosine 101 has been cross-linked to the N-terminus of EGF (Woltjer, R L et al, PNAS, 1992, 89(16), 7801–7805). This residue is in the portion of sequence which immediately follows a strand in the lower β sheet of L1.

The side chain of asparagine 1 of EGF has been cross-linked to lysine 336 of the EGF receptor (Wu, D G et al, PNAS, 1990, 87(8), 3151–3155). The latter residue is in the N-terminal helix of the L2 domain and points towards the cavity which is formed when the two halves of the EGF receptor are postioned in a similar arrangement to the first three domains of the IGF-1 receptor. Two nearby residues, Asn 328 and Asn 337 are glycosylated. This mutation is in a similar position to the insulin receptor mutant S323L which has aberrent insulin binding.

Several insertional mutants of the EGF receptor extracellular domain were constructed to probe the role of several regions of the receptor (Harte, M. T., Gentry, L. E., 1995, Arch Biochem Biophys 322:378–389). A number of these mutants were not detectably secreted by the cells producing them, suggesting that they did not fold to form stable proteins. Most of these insertions were in positions in the model structure where they would be unable to tolerate an insertion. In contrast, most of the other insertions were in loops or other positions which, according to the model, are able to tolerate insertions. EGF receptor extracellular domain mutants with insertions at residues 162, 169, 174 and 220 bound EGF with a similar affinity to the wild-type EGF receptor extracellular domain but bound TGF-α with a lower affinity. The first of these insertions was located one residue before the last cysteine residue of the L1 domain. The second and third insertions were present in the first module of the EGF receptor S1 domain and the fourth was present in the third module of the S1 domain. All of these positions are on a side of the molecule far removed from the large cavity as shown in FIG. 5. EGF receptor mutants with insertions at positions 251 (in the fifth module of the S1 domain) and 575 (in the sixth module of the S2 domain) appeared to bind twice as much ligand as the wild-type receptor. Two insertional mutants which showed reduced EGF receptor binding contained insertions at positions 291 (in the seventh module of the S1 domain) and 474 (one residue before the last cysteine of the L2 domain).

Another EGF receptor mutant which shows altered ligand binding behaviour is the R497K mutant. The site of this mutation in the first module of the S2 domain and faces the side of the L2 domain opposite to that containing residue 465. This mutant binds EGF in a similar fashion as wild-type receptor but abolishes the high affinity binding site for TGF-α (Moriai, T., Kobrin, M. S., Hope, C., Speck, L., Korc, M., 1994, Proc Natl Acad Sci USA 91:10217–10221).

On the faces containing the second β-sheet (the lower face according to the orientations shown in FIGS. 3 and 4) of the L1 and L2 domains are a number of solvent-exposed hydrophobic residues including Tyr 64, Leu 66, Tyr 89, Tyr 93, Leu 348, Phe 380 and Phe 412. According to a survey of protein-protein interfaces, tyrosine, phenylalanine and leucine are more likely to be involved in an interface than on the exterior of a protein complex (Tsai C-J, Lin S L, Wolfson, H J, Nussinov R (1997) Protein Sci 6: 53–64). Lys 465 is located on the lower face of the L2 domain and Tyr 101 is proximal to the lower face fo the L1 domain and are consistent with the lower faces of the domains having roles in ligand binding.

Strategies for Developing EGF Receptor Ligands

For several signalling systems, ligand analogues which have antagonist properties have been described. These ligand include the human growth hormone (Chen W Y, Chen N Y, Yun J, Wagner TE, Kopchick J J (1994) J Biol Chem 269:15892–15897), interleukin-6 (Savino R, Lahm A, Salvati A L, Ciapponi L, Sporeno E, Altamura S, Paonessa G, Toniatti C, Ciliberto G EMBO J. 1994 Mar. 15;13(6): 1357–67) and interleukin-4 (Kruse N, Tony H P, Sebald W (1992) EMBO J 11:3237–3244; Zurawski S M, Vega F Jr, Huyghe B, Zurawski G (1993) EMBO J 12:2663–2670). The function of these unmodified ligands is to bind their receptors and then subsequently recruit a second receptor molecule. The mutations of the ligands mentioned above are in positions which interfere with the binding of the second receptor (de Vos A M; Ultsch M, Kossiakoff A A (1992) Science 255:306–312; Brakenhoff J P, de Hon F D, Fontaine V, ten Boekel E, Schooltink H, Rose-John S. Heinrich P C, Content J, Aarden L A (1994) J Biol Chem 269:86–93; Davis I D, Treutlein H R, Friedrich K, Burgess A W (1995) Growth Factors 12:69–83).

To date, no analogues of EGF receptor ligands have been found which are purely antagonistic. Whether EGF and its homologues have sites of binding for two receptor molecules, like the proteins described above, has not been shown. Analysis of 1H NMR transferred nuclear Overhauser enhancement data for titration of TGF-α with the extracellular domain of the EGF receptor indicates that most parts of the ligand are in contact with the receptor upon binding (McInnes C, Hoyt D W, Harkins R N, Pagila R N, Debanne M T, O'Connor-McCourt M, Sykes B D (1996) J Biol Chem 271:32204–32211). However, the concentrations used in the experiment were such that the dominant receptor species was the ligand-receptor complex with 2:2 stiochiometry. However, even if the ligands of the EGF receptor are buried in the cleft formed by the first three domains of the receptor, it is difficult to envisage that such binding will lead to contact with most of the bound ligand when only one receptor binds the ligand. In an alternative scheme, at least two separate faces on EGF are required to bind into the large cleft of a single EGF receptor molecule which enacts a conformational change in the receptor which then allows it to dimerise. An antagonist may bind to the first binding site of the receptor and not the second, thus preventing dimerisation and subsequent signalling of the receptor. Thus, delineation of the parts of the ligand involved in the (putative) primary and secondary binding faces would greatly assist antagonist design.

Using the EGF receptor model and the known structures of EGF receptor ligands, it may be possible to construct a model, or a partial model, of ligand binding which could suggest which parts of bound ligand are involved in binding to the first and second EGF receptors of the ligand-receptor complex. There are several computer programs that can assist with the construction of such models. Programs such as Quilt (Lijnzaad P, Argos P (1997) Proteins 28:333–343; Lijnzaad P, Berendsen H J, Argos P (1996) Proteins 26:192–203; Lijnzaad P, Berendsen H J, Argos P 1996 Proteins 25:389–397) can be used to suggest sites on proteins involved in interactions with other proteins. Possible structures of protein complexes can be obtained by programs such as FT-DOCK (Gabb H A, Jackson R M, Sternberg M J (1997) J Mol Biol 272:106–120) and GRAM (Vakser I A (1996) Biopolymers 39:455–464; Katchalski-Katzir E, Shariv I, Eisenstein M, Friesem A A, Aflalo C, Vakser I A (1992) Proc Natl Acad Sci USA 89:2195–2199). The calculation of electrostatic potentials from the Poisson-Boltzmann equation has been used to investigate complexes made up of cytokines and growth factors and their receptors (Demchuk E, Mueller T, Oschkinat H, Sebald W, Wade R C (1994) Protein Sci 3:920–935) and may guide the construction of model complexes. The construction of models will suggest regions of the EGF receptor ligands which may be involved in receptor binding. With the model and supporting experiments, it is envisaged that mutants of EGF and TGF-α will be constructed which are potential antagonists.

The majority of targets for drugs which have made use of structural information are enzymes. One advantage of enzymes over other types of proteins is the presence of substrate-binding clefts whose normal function is to bind small molecule substrates or short lengths of peptides. In contrast, few small molecule inhibitors have been developed which inhibit protein-protein interactions.

Desolvation of protein surfaces appears to be an important factor in the formation of a protein-protein complex. Since, unlike the substrate-binding clefts of enzymes, protein-binding surfaces tend to be much less concave, a bound small molecule is unlikely to provide enough desolvation to enable tight binding. The lower surfaces of the L1 and L2 domains, which have been suggested to be involved in ligand binding, contain hydrophobic regions which suggest that they need to be buried for strong binding of a molecule to these surfaces to occur. We envisage that cyclic molecules, including cyclic peptides, may be able to bind to such surfaces. Hydrophobic functional groups may be chosen which, when bound to the hydrophobic regions of the relevent face, desolvate regions of the protein. Some of the functional groups which interact with the protein will be polar or charged to make favourable electrostatic interactions. Other parts in the cyclic molecule may be polar or charged to increase the aqueous solubility of the molecule. Cyclic molecules also have the advantages of having few possible conformations when unbound, providing a lower loss of entropy upon binding and thus greater binding as compared to a non-cyclic analogue. A degree of flexibility would exist and would allow the molecule to alter its conformation to better accommodate the protein it is binding to.

Algorithms such as LUDI (Bohm H J (1992) J Comput Aided Mol Des, 6: 593–606) can be used to search for functional groups and molecular moieties which may interact with a surface of the EGF receptor model. Algorithms such as CLIX (Lawrence M C, Davis P C (1992) Proteins 12:31–41) or DOCK (Kuntz I D, Blaney J M, Oatley S J, Langridge R, Ferrin T E (1982) J Mol Biol 161:269–88) can be used to search a database of molecular structures for those which have shape and/or chemical complementarity to the EGF receptor. Computational combinatorial design algorithms (Miranker A, Karplus M Proteins (1991) 11:29–34; Eisen M B, Wiley D C, Karplus M, Hubbard R E; Caflisch A (1994) Proteins 19:199–221) can also be tried. In one instance, a combinatorial approach has been used to design peptides to inhibit the interaction of the proteins Ras and Raf (Zeng, J, et al, Protein Engineering, to be published).

We envisage that as an alternative to a cyclic molecule, a small protein could be used as a scaffold for placing amino acids that will interact with the EGF receptor. At least one small protein (potato carboxypeptidase inhibitor) with a fold different to that of EGF receptor ligands has been identified which is a weak EGF antagonist (Blanco-Aparicio C, Molina M A. Fernandez-Salas E, Frazier M L, Mas J M, Querol E, Aviles F X, de Llorens R (1998) J Biol Chem 273:12370–12377). The use of a structural scaffold for proteins with diverse functions has been observed in Nature (Lin S L, Nussinov R 1995 Nat Struct Biol 2:835–837). Other molecular scaffolds such as dendrimers may also be considered which can be used to present the functional groups which will tightly interact with the EGF receptor.

At least two, non-exclusive modes of action can be envisaged. The first mode involves a molecule competing for binding sites with one of the EGF receptor's natural ligands. Most likely, the molecule will prevent the receptor dimerisation which is required for activation of the EGF receptor, thus acting as an antagonist. We do not rule out the possiblity that the binding may be activating and the molecule acts as an agonist. The second potential mode of action is for the molecule to bind to a site on the EGF receptor which is not necessarily a ligand binding site. Such a molecule may be physically large enough to hinder physical access of a second receptor to the receptor which binds the molecule in question. This would hinder dimerisation and subsequent activation of the receptor. If the molecule is sufficiently "sticky", it may attract a second EGF receptor and induce dimerisation, thereby acting as an agonist rather than an antagonist.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method of identifying a compound which modulates binding of a ligand to an EGF receptor comprising:

(A) designing or screening for a compound which binds to the structure formed by amino acids 1–475 or formed by amino acids 313–621 of a receptor having the atomic coordinates as shown in FIG. 6 for amino acids 1–621 of the EGF receptor, where binding of the compound to the structure is favored energetically, and (B) testing the compound designed or screened for in (A) for its ability to modulate binding of the ligand to the EGF receptor in vivo or in vitro, thereby identifying a compound that modulates binding to the EGF receptor.

2. The method according to claim 1, wherein the testing in step (B) is performed by a high-throughput assay.

3. The method of claim 1, wherein the testing in step (B) comprises testing the compound for the ability to modulate EGF receptor mediated cell proliferation.

4. The method of claim 1, wherein step (A) involves designing or screening for a compound which binds to a β-sheet of the L1 domain within the structure formed by amino acids 1–475 of a receptor having the atomic co-ordinates as shown in FIG. 6 for amino acids 1–621 of the EGF receptor.

5. The method of claim 1, wherein step (A) involves designing or screening for a compound which binds to a β-sheet of the L2 domain within the structure formed by amino acids 1–475 or formed by amino acids 313–621 of a receptor having the atomic co-ordinates shown in FIG. 6 for amino acids 1–621 of the EGF receptor.

6. The method of claim 1 in which the compound is identified from test compounds in a database.

7. The method of claim 1, wherein step (B) comprises testing the compound for its ability to increase signal transduction by binding to the EGF receptor.

8. The method of claim 1, wherein step (B) comprises testing the compound for its ability to decrease signal transduction by binding to the EGF receptor.

9. The method of claim 1, wherein step (B) comprises testing the compound for its ability to inhibit or prevent the binding of a ligand to the EGF receptor.

10. A method of selecting a compound which binds to the EGF receptor comprising:
(A) designing or screening for a compound which binds to the structure formed by amino acids 1–475 or formed by amino acids 313–621 of a receptor having the atomic coordinates as shown in FIG. 6 for amino acids 1–621 of the EGF receptor, where binding of the compound to the structure is favored energetically, and
(B) selecting a compound designed or screened for in (A) which has an experimentally determined $K_d$ or $K_I$ of less than $10^{-6}$M for the EGF receptor, thereby selecting a compound which binds to the EGF receptor.

11. The method as claimed in claim 10, wherein $K_d$ is less than $10^{-8}$M.

12. The method of claim 10, wherein $K_I$ is less than $10^{-8}$M.

* * * * *